United States Patent
Jorand-LeBrun et al.

(10) Patent No.: US 11,033,547 B2
(45) Date of Patent: Jun. 15, 2021

(54) CARBOXAMIDE-PYRIMIDINE DERIVATIVES AS SHP2 ANTAGONISTS

(71) Applicant: Merck Patent GmbH, Darmstadt (DE)

(72) Inventors: Catherine Jorand-LeBrun, Arlington, MA (US); Roch Boivin, North Chelmsford, MA (US); Igor Mochalkin, Westford, MA (US); Theresa Johnson, Salem, MA (US); Nina Linde, Frankfurt am Main (DE); Doreen Musch, Reinheim (DE); Deepak Kumar, Canton, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/813,192

(22) Filed: Mar. 9, 2020

(65) Prior Publication Data

US 2020/0281926 A1    Sep. 10, 2020

Related U.S. Application Data

(60) Provisional application No. 62/879,597, filed on Jul. 29, 2019.

(30) Foreign Application Priority Data

Mar. 7, 2019  (EP) .................................. 19161323

(51) Int. Cl.
| | | |
|---|---|---|
| A61K 31/506 | (2006.01) | |
| A61K 31/497 | (2006.01) | |
| A61K 39/395 | (2006.01) | |
| A61K 45/06 | (2006.01) | |
| C07D 401/04 | (2006.01) | |
| C07D 491/107 | (2006.01) | |
| C07D 513/10 | (2006.01) | |

(52) U.S. Cl.
CPC .......... *A61K 31/506* (2013.01); *A61K 31/497* (2013.01); *A61K 39/3955* (2013.01); *A61K 45/06* (2013.01); *C07D 401/04* (2013.01); *C07D 491/107* (2013.01); *C07D 513/10* (2013.01)

(58) Field of Classification Search
CPC ................ A61K 31/497; A61K 31/506; A61K 39/3955; A61K 45/06; A61P 35/00; C07D 239/42; C07D 401/04; C07D 403/04; C07D 405/14; C07D 413/04; C07D 451/14; C07D 491/107; C07D 513/10
See application file for complete search history.

(56) References Cited

U.S. PATENT DOCUMENTS

| | | |
|---|---|---|
| 4,125,828 A | 11/1978 | Resnick et al. |
| 4,207,554 A | 6/1980 | Resnick et al. |

FOREIGN PATENT DOCUMENTS

| | | | |
|---|---|---|---|
| WO | WO97/22596 A1 | 6/1997 | |
| WO | WO97/30035 A1 | 8/1997 | |
| WO | WO97/32856 A1 | 9/1997 | |
| WO | WO98/13354 A1 | 4/1998 | |
| WO | WO99/02166 A1 | 1/1999 | |
| WO | WO00/40529 A1 | 7/2000 | |
| WO | WO00/41669 A2 | 7/2000 | |
| WO | WO01/92224 A1 | 12/2001 | |
| WO | WO02/04434 A1 | 1/2002 | |
| WO | WO02/08213 A1 | 1/2002 | |
| WO | WO 2015/107493 A1 | 7/2015 | |
| WO | WO 2015/107494 A1 | 7/2015 | |
| WO | WO 2015/107495 A1 | 7/2015 | |
| WO | WO 2016/120355 * | 8/2016 | ............ A01N 43/54 |
| WO | WO 2016/203404 A1 | 12/2016 | |
| WO | WO 2016/203405 A1 | 12/2016 | |
| WO | WO 2016/203406 A1 | 12/2016 | |
| WO | WO 2017/216706 A1 | 12/2017 | |
| WO | WO2017211303 A1 | 12/2017 | |
| WO | WO2018/013597 A1 | 1/2018 | |
| WO | WO2018/057884 A1 | 3/2018 | |
| WO | WO2018/081091 A1 | 5/2018 | |
| WO | WO2018/130928 A1 | 7/2018 | |
| WO | WO2018/136264 A1 | 7/2018 | |
| WO | WO2018/136265 A1 | 7/2018 | |
| WO | WO2018/172984 A1 | 9/2018 | |

(Continued)

OTHER PUBLICATIONS

N. Aceto et al., Nature Medicine, 2012, 28, 529-538.

(Continued)

*Primary Examiner* — Erich A Leeser

(74) *Attorney, Agent, or Firm* — Kathryn M. Bishop; EMD Serono Research and Development Institute Inc.

(57) ABSTRACT

The invention relates to carboxamide-pyrimidine derivatives of the general formula I,

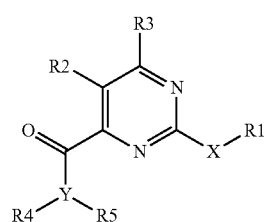

or a pharmaceutically acceptable salt thereof, and the use of the compounds of the present invention for the treatment of hyperproliferative diseases and disorders in mammals, especially humans, and pharmaceutical compositions containing such compound.

24 Claims, 1 Drawing Sheet

(56) References Cited

FOREIGN PATENT DOCUMENTS

| WO | WO2019/051084 A1 | | 3/2019 | |
|----|----|----|----|----|
| WO | WO2019/051469 A1 | | 3/2019 | |
| WO | WO2019/067843 A1 | | 4/2019 | |
| WO | WO2019/118909 A1 | | 6/2019 | |
| WO | WO 20109/121373 | * | 6/2019 | ........... C07D 403/04 |
| WO | WO2019/165073 A1 | | 8/2019 | |
| WO | WO2019/83364 A1 | | 9/2019 | |
| WO | WO2019/183367 A1 | | 9/2019 | |
| WO | WO 2020/058062 | * | 3/2020 | ........... C07D 403/12 |

OTHER PUBLICATIONS

M. Bentires-Alj et al., in Cancer Res. 2004, 64, 8816-8820.
Cai et al., Biomedicine & Pharmacotherapy 2014, 68, 285-29.
Chen et al., Nature, 2016, doi. 10.1038/nature/18621.
J. G. Fortanet et al., J. Med. Chem. 2016, doi: 10.1021/acs.jmedchem.6b00600.
P.J. Fraker et al., Proc. Nat. Acad. Sci. USA, vol. 75, No. 11, 1978, 5660-5664.
CM Furcht, Oncogene, 2013, 32, 2346-2355.
K. S. Grossman et al., Adv. Cancer Res., 2010, 106, 53-89.
J. Schaffer et al., Journal of Pharmaceutical Sciences, 1999, vol. 88, No. 3, 313-318.
V. E. Schneeberger et al., Oncotarget, 2015, 6, 6191-6202.
P. Tyle, Pharmaceutical Research, 1986, vol. 3, No. 6, 318-326.
J. Wang et al., J. Clin. Invest., 2016, 126, 6, 2077-2092.
M. Yosida et al., International Journal of Pharmaceutics, 1995, 115, 61-67.

* cited by examiner

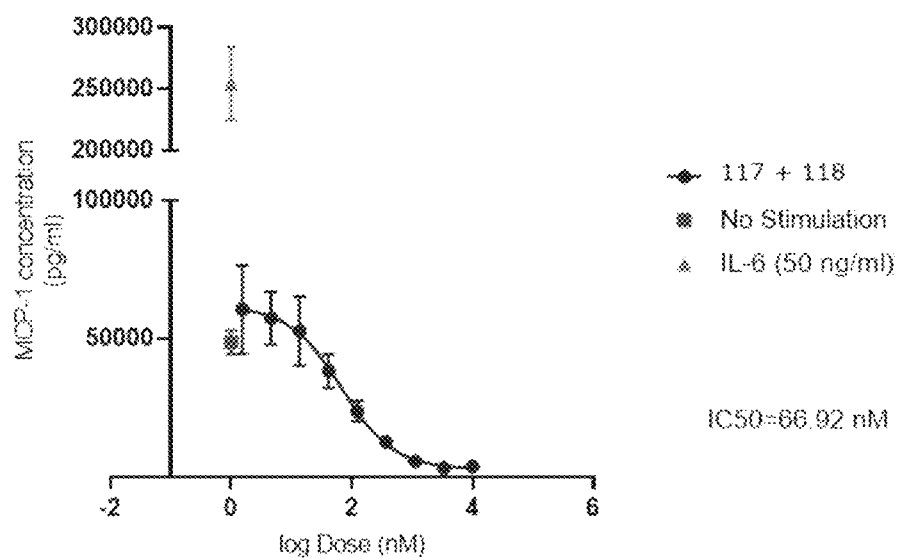

CARBOXAMIDE-PYRIMIDINE DERIVATIVES AS SHP2 ANTAGONISTS

REFERENCE TO RELATED APPLICATIONS

This application claims the benefit of priority to European Application Number 19161323.1, filed on Mar. 7, 2019, and U.S. Provisional Application No. 62/879,597, filed Jul. 29, 2019. All of the above-referenced applications are incorporated by reference herein.

The invention relates to carboxamide-pyrimidine derivatives of the general Formula I,

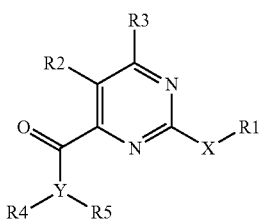

I and the use of the compounds of the present invention for the treatment and/or prevention of hyperproliferative diseases and disorders in mammals, especially humans, and pharmaceutical compositions containing such compounds.

BACKGROUND OF THE INVENTION

Src homology region 2 (SH2) containing protein tyrosine phosphatase 2 (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways. SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors leads to exposure of the catalytic site resulting in enzymatic activation of SHP2.

SHP2 is ubiquitously expressed in various tissues and cell types. It plays an important role in diverse signaling pathways to regulate cellular biological processes and is involved in the signaling pathways of a variety of growth factors and cytokines. Within a single signaling pathway, SHP2 can play both positive (signal enhancing) and negative (signal diminishing) roles intracellular signaling processes. SHP2 is believed to function by dephosphorylating its associated signaling molecules, thereby attenuating the local signaling flow. However, the main effect of SHP2 action in most signaling pathways (e.g. growth factor, cytokine and extracellular matrix receptors) is to enhance signal transduction. For example, SHP2 is a positive regulator of the ERK/MAPK signaling pathway, playing a key role in regulating cellular proliferation and survival (K. S. Grossman et al., Adv. Cancer Res., 2010, 106, 53-89 and references cited therein).

Mutations in the PTPN11 gene that affect the N-SH2 or PTP domain residues involved in basal inhibition of SHP2 result in more readily activatable forms of SHP2 protein, which can lead to unregulated or increased SHP2 activity. Such activated mutants of SHP2 have been associated with developmental disorders such as Noonan syndrome, where nearly all mutated forms of SHP2 demonstrate increased PTP activity. Activating SHP2 mutations have also been detected in juvenile myelomonocytic leukemia (e.g. Q506P), chronic myelomonocytic leukemia (e.g. Y63C), neuroblastoma (e.g. T507K), melanoma (e.g R138Q), acute myeloid leukemia (e.g, G503V), breast cancer, lung cancer (e.g. E76V) and colorectal cancer (e.g. E76G) (M. Bentires-Alj er al., in Cancer Res. 2004, 64, 8816-8820; and references cited therein). Additional PTPN1 mutations associated with cancers are disclosed in WO 2015/107495 and references cited therein.

Mutations in the PTPN11 gene and subsequently in SHP2 have been identified in several human diseases, such as Noonan Syndrome (NS), Leopard Syndrome, diabetes, neutropenia (Kostmann's syndrome), systemic lupus erythematosus, neuroblastoma, melanoma, juvenile myelomonocytic leukemia, acute myeloid leukemia, juvenile leukemia, chronic myelomonocytic leukemia and other cancers associated with SHP2 deregulation such as cancers of the lung, colon and breast such as HER2-positive breast cancer, triple-negative breast cancer, ductal carcinoma of the breast, invasive ductal carcinoma of the breast, non-small cell lung cancer (including adenocarcinoma of the lung), esophageal cancer, gastric cancer, squamous-cell carcinoma of hhe head and neck (SCCHN) and colon cancer. (N. Aceto et al., Nature Medicine, 2012, 28, 529-538; C. M. Furcht et al., Oncogene, 2013, 32, 2346-2355; V. E. Schneeberger et al., Oncotarget, 2015, 6, 6191-6202; P. Cai et al., Biomedicine & Pharmacotherapy 2014, 6, 285-290; and references cited therein).

Therefore, SHP2 represents a highly attractive target for the development of novel therapies for the treatment of various diseases. The compounds of the present disclosure fulfill the need for small molecules to that inhibit the activity of SHP2.

SHP2 phosphatase inhibitors are disclosed e.g. in WO 2015/107493, WO 2015/107494, WO 2015/107495, WO 2016/203404, WO 2016/203405, WO 2016/203406, WO2017/216706, WO2018/013597, WO2018/136264, WO2018/136265, WO2018/057884, WO2018/081091 and J. G. Fortanet et al., J. Med. Chem. 2016, doi: 10.1021/acs.jmedchem.6b00600 and references cited therein. The effects of SHP2 phsophatase inhibition are described e.g. in Y.-N. P. Chen et al., Nature, 2016, doi. 10.1038/nature/18621; J. Wang et al., J. Clin. Invest., 2016, 126, 2077-2092 and references cited therein. SHP2 phosphatase inhibitors include e.g. 8-Hydroxy-7-[(6-sulfo-2-naphthyl)azo]-5-quinolinesulfonic acid (NSC 87077) and SHP099.

However, known compounds such as SHP099 (or the compounds of the WO2015/107493) and/or RMC-4550 (the compounds of the WO2018/013597) do not show a high selectivity over hErg which is very important for the safety of compounds which are intended to be used for the prevention or treatment of diseases.

Furthermore, the compounds of the present invention show superior pharmacokinetic properties (e.g., low clearance and/or high exposure) as compared to known compounds such as SHP099 (or the compounds of the WO2015/107493) or RMC-4550 (the compounds of WO2018/013597).

Thus, there remains a need for highly effective SHP2 inhibitors which do not show the described disadvantages. It was a specific object of the invention to provide improved methods of preventing or treating hyperproliferative diseases and disorders in a host, especially to provide effective SHP2 antagonists for the treatment and prevention of such diseases.

SUMMARY OF THE INVENTION

Surprisingly, it has been found that the carboxamide-pyrimidine derivatives according to the invention are highly effective inhibitors of SHP2 and thus they can be used for the treatment of hyperproliferative diseases and disorders such as cancer.

Additionally, the compounds of the present invention are highly effective inhibitors of ERK1 2, a target downstream form SHP2 in the signaling pathway (as mentioned above SHP2 is a positive regulator of the ERK/MAPK signaling pathway, ERK phosphorylation depends on SHP2 activation), which is playing a key role in regulating cellular proliferation and survival. This also confirms that the compounds of the present invention can be used for the treatment of hyperproliferative diseases and disorders such as cancer.

At the same time, the compounds of the present invention in comparison with the known SHP2 antagonists SHP099, RMC-4550 and similar pyrimidine derivatives surprisingly have a much higher selectivity over hErg (the ion channel Kv11.1). The high hErg inhibitory activity of SHP099, RMC-4550 and similar pyrimidine derivatives clearly point to a potential cardiotoxicity risk, which is avoided by the compounds of the present invention. This improved safety profile of the compounds of the present invention is combined with the more desirable pharmacokinetic properties and enhanced target engagement (lower IC50s). The surprising properties of the compounds of the present invention show a significant needed advancement in the field of SHP2 inhibitors.

The invention relates to carboxamide-pyrimidine derivatives of the general Formula I*,

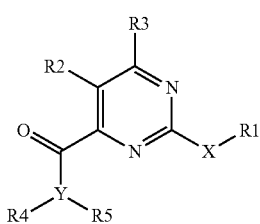

wherein
R1 is mono- or bicyclic alkyl, heterocyclyl, heteroaryl or bicyclic alkylaryl, containing 3 to 14 carbon atoms and 0-4 heteroatoms, independently selected from N, O and S, which is unsubstituted or mono-, di- or trisubstituted by $(CH_2)_nNH_2$, $(CH_2)_nOH$, $(CH_2)_nCH_3$ or Hal,
X is a single bond, —NH— or —N(CH$_3$)—, $(CH_2)_n$ or O,
R2 is aryl or heteroaryl, S-aryl or S-heteroaryl which is unsubstituted or mono-, di- or trisubstituted by $(CH_2)_n$ NH$_2$, $(CH_2)_n$OH, COOH, CONH$_2$, alkyl, =S, =O, =NH, CN or Hal,
R3 is H, NH$_2$, OH, Hal or alkyl,
Y is N or O,
R4, R5 are both H or one of R4 and R5 is OH, COOH, NH$_2$, CONH$_2$ or methyl or ethyl which is unsubstituted or substituted by =S, =O, OH, COOH, =NH, NH$_2$, CONH$_2$,
Hal is F, Cl, Br, or I,
n is 0, 1, 2 or 3,
and physiologically acceptable salts, derivatives, solvates, prodrugs, stereoisomers and atropisomers thereof, including mixtures thereof in all ratios.

BRIEF DESCRIPTIONS OF DRAWINGS

FIG. 1 depicts the mixture of compounds (117+118) suppressed MCP-1 production in U937 cells stimulated with IL-6.

DETAILED DESCRIPTION OF THE INVENTION

The invention preferably relates to carboxamide-pyrimidine derivatives of the general formula I,

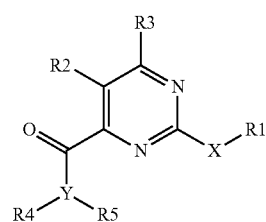

or a pharmaceutically acceptable salt thereof, wherein
R1 is a monocycloalkyl, bicycloalkyl, monoheterocyclyl or biheterocyclyl any of which is optionally spiro connected to a monocycloalkyl, bicycloalkyl, monoheterocyclyl, or biheterocyclyl, each of which mono- or bi-cycloalkyl and heterocyclyl may be each optionally and independently substituted with 1-3 groups selected from $C_1$-$C_6$ alkyl, —F, —Cl, —CF$_3$, —NH$_2$, $C_1$-$C_3$ aminoalkyl, —OH, $C_1$-$C_3$ alkoxy, $C_1$-$C_3$ hydroxyalkyl and phenyl;
X is a bond, —NH— or —N(Me)—;
R2 is an aryl or heteroaryl which is substituted with 1-3 groups selected from —F, —Cl, —CF$_3$, $C_1$-$C_3$ alkoxy and $C_1$-$C_3$ alkyl;
R3 is —H, —NH$_2$, —OH, —Cl, —F, —Br, or —CH$_3$;
Y is —N—; and
R4 and R5 are independently —H, —NH$_2$, —OH, $C_1$-$C_3$ alkyl, or $C_1$-$C_3$ hydroxyalkyl.

The invention preferably relates to carboxamide-pyrimidine derivatives of the general Formula Ia,

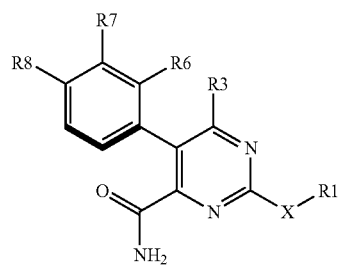

or a pharmaceutically acceptable salt thereof, wherein each of R6, R7 and R8 are independently selected from —H, —F, —Cl, —CF₃, C₁-C₃ alkoxy and C₁-C₃ alkyl, and the rest of the variables are as described for compounds of Formula I.

The invention preferably relates to carboxamide-pyrimidine derivatives of the general formula Ib,

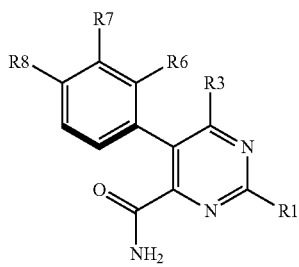

Ib or a pharmaceutically acceptable salt thereof, wherein R1 is

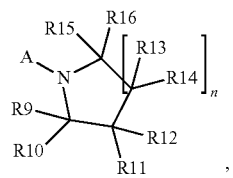

when A is the point of attachment to the pyrimidine ring of Formula Ib;

each of R6, R7 and R8 are independently selected from —H, —F, —Cl, —CF₃, C₁-C₃ alkoxy and C₁-C₃ alkyl;

n is 0, 1, 2, or 3; and each of R9, R10, R11, R12, R13, R14, R15 and R16, when present, are independently selected from —H, C₁-C₃ alkyl, —NH₂, —OH, —Cl, —F, —Br, C₁-C₃ aminoalkyl, C₁-C₃ hydroxyalkyl, C₁-C₃ alkoxy, and phenyl; or two of R9, R11, R13 and R16 are taken together to form a bridged bicyclic heterocyclic system which is optionally substituted with 1-3 substituents selected from C₁-C₃ alkyl, —NH₂, —OH, —Cl, —F, —Br, C₁-C₃ aminoalkyl, C₁-C₃ hydroxyalkyl, C₁-C₃ alkoxy, and phenyl; or two of R9, R10, R11, R12, R13, R14, R15, and R16, which are attached to the same carbon atom, are taken together to form a monocyclic or bicyclic spirocyclyl, which is optionally substituted with 1-3 substituents selected from C₁-C₃ alkyl, —NH₂, —OH, —Cl, —F, —Br, C₁-C₃ aminoalkyl, C₁-C₃ hydroxyalkyl, C₁-C₃ alkoxy, and phenyl; or two of R9, R10, R11, R12, R13, R14, R15, and R16, which are attached to adjacent carbon atoms, are taken together to form a fused carbocyclyl or heterocyclyl, which is optionally substituted with 1-3 substituents selected from C₁-C₃ alkyl, —NH₂, —OH, —Cl, —F, —Br, C₁-C₃ aminoalkyl, C₁-C₃ hydroxyalkyl, C₁-C₃ alkoxy, and phenyl; and the rest of the variables have the meanings as described for Formula I above.

The invention preferably relates to carboxamide-pyrimidine derivatives of the general Formula Ic,

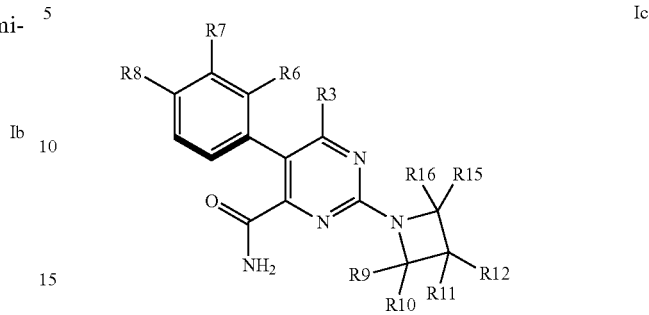

Ic and wherein the rest of the variables have the meanings as described for Formula I above.

The invention preferably relates to carboxamide-pyrimidine derivatives of the general Formula Id,

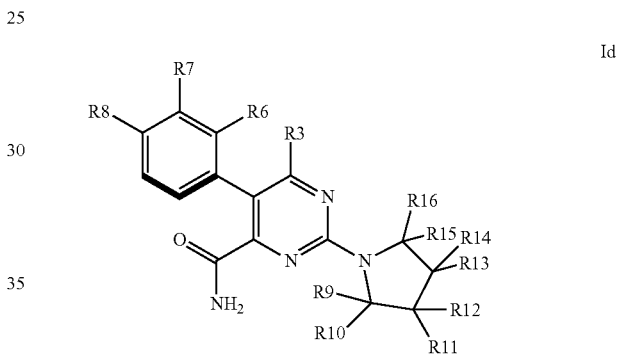

Id wherein the rest of the variables have the meanings as described for Formula I above.

The invention preferably relates to carboxamide-pyrimidine derivatives of the general Formula Ie,

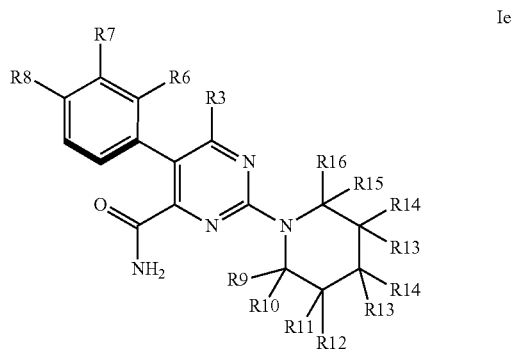

Ie wherein the rest of the variables have the meanings as described for Formula I above.

The invention preferably relates to carboxamide-pyrimidine derivatives of the general Formula If,

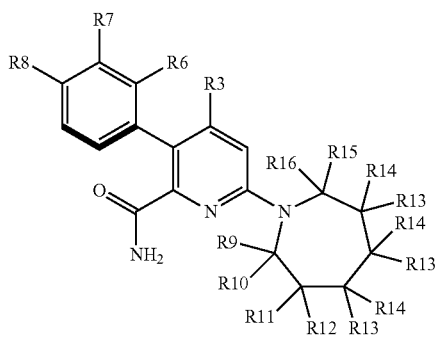
wherein the rest of the variables have the meanings as described for Formula I above.
The invention preferably relates to a compound according to Formula I or Formula Ia, wherein R1 is one of the following structures:
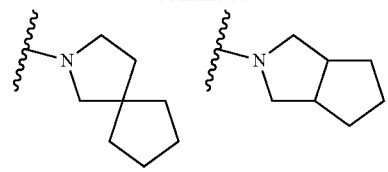
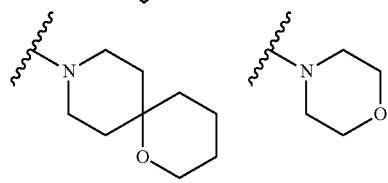
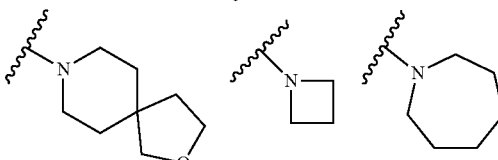
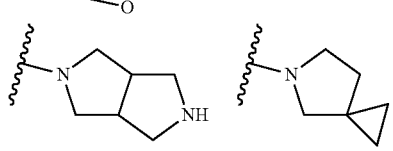
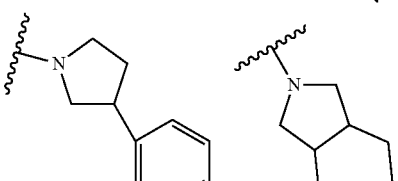
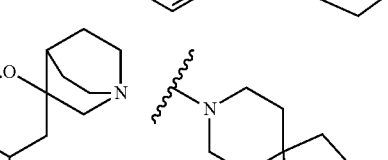
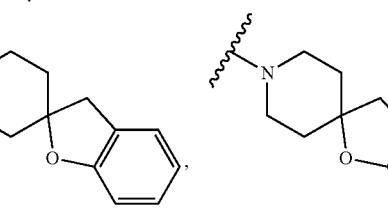
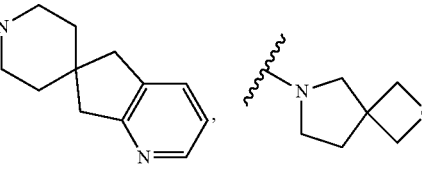
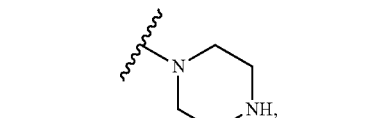
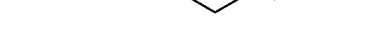
which is unsubstituted or mono-, di- or trisubstituted by $C_1$-$C_6$ alkyl, —F, —Cl, —CF$_3$, —NH$_2$, $C_1$-$C_3$ aminoalkyl, —OH, $C_1$-$C_3$ alkoxy, or $C_1$-$C_3$ hydroxyalkyl, and wherein X, R2, R3, Y, R4 and R5 have the meanings as disclosed above.
The invention more preferably relates to a compound according to Formula I or Formula Ia, wherein X—R1 is one of the following structures:
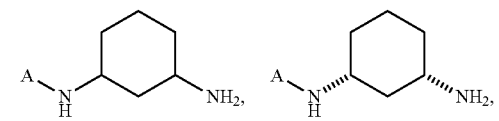
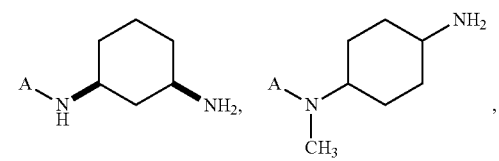
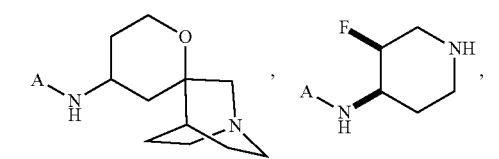
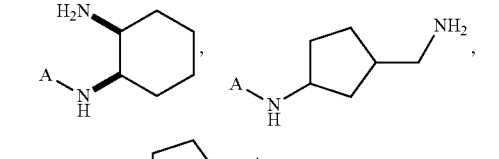
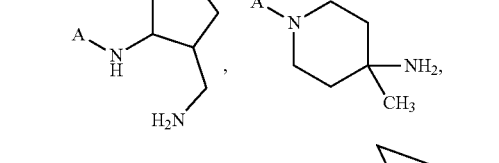
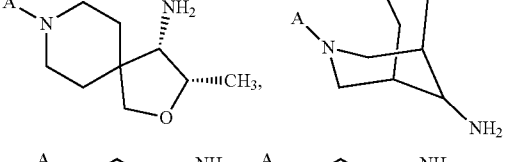
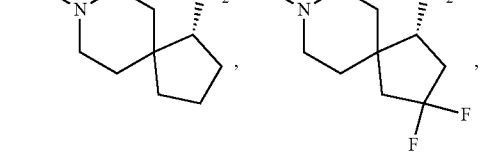
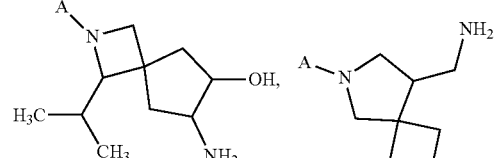
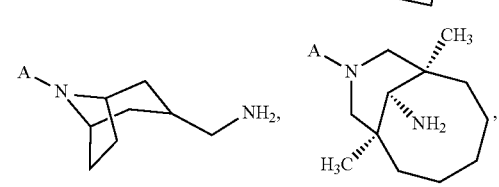
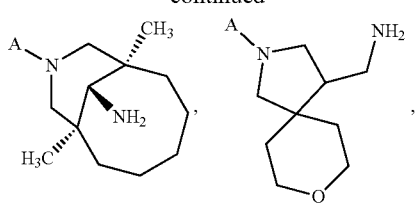
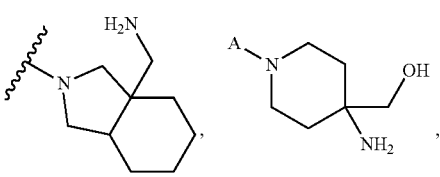
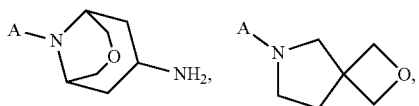
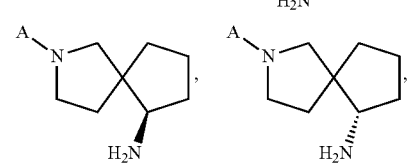
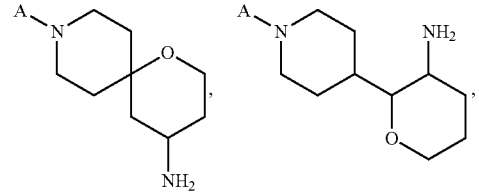
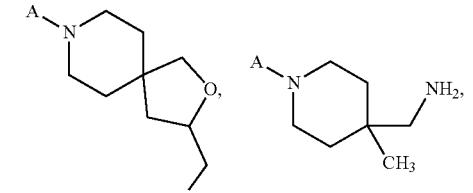
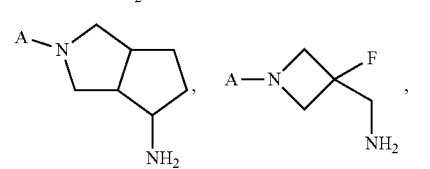
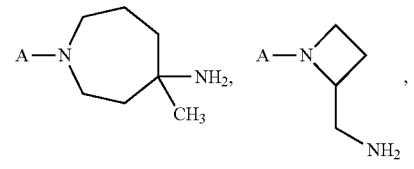
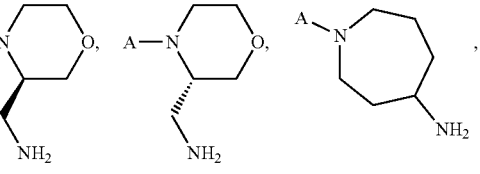

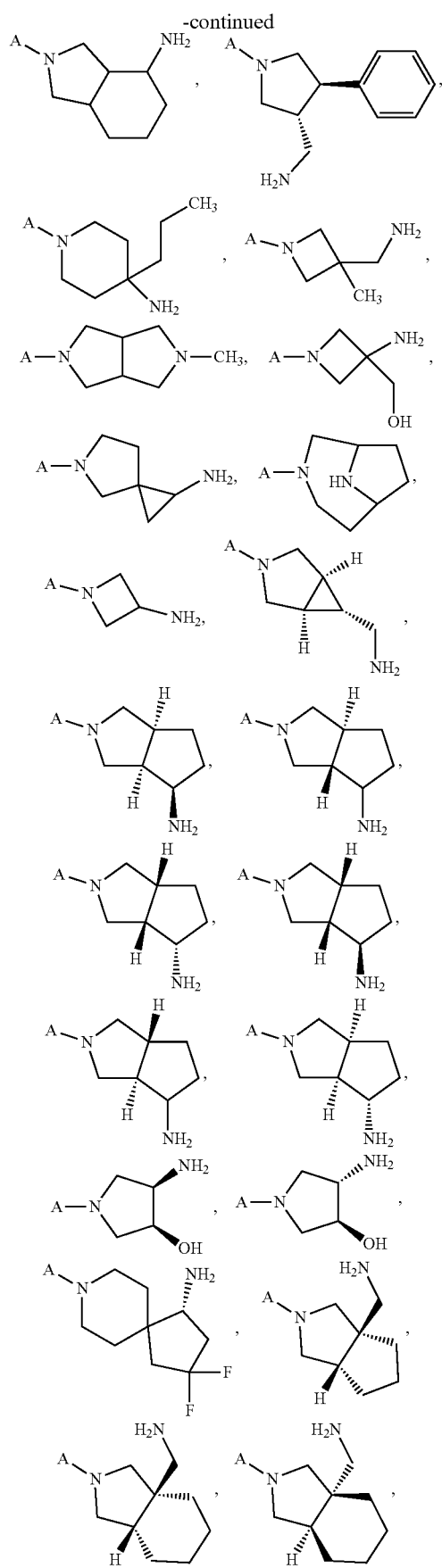
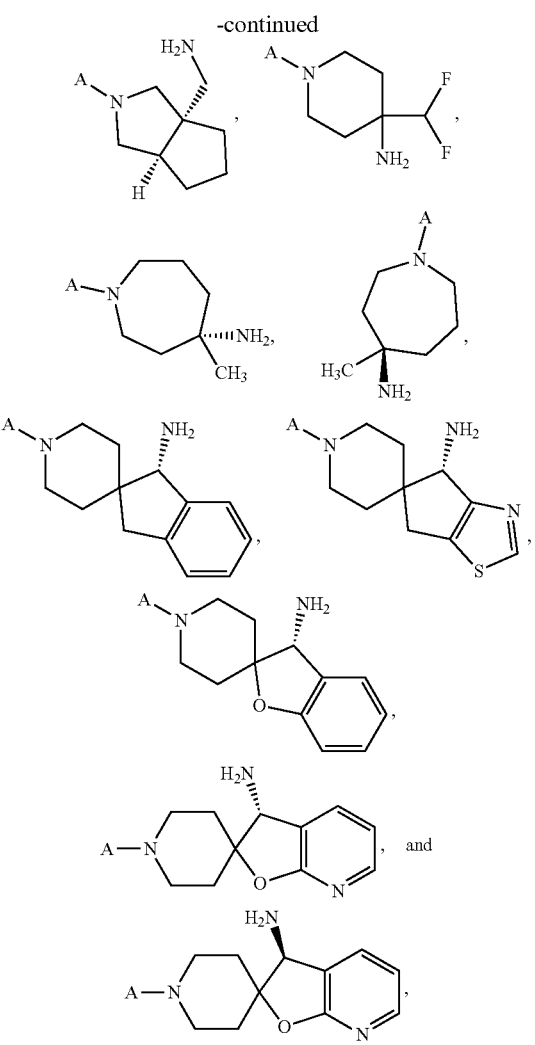

wherein A represents the point of attachment to the pyrimidine ring, and wherein the rest of the variables have the meanings as described for the formulae.

In one aspect of the present invention, for Formula I or Formula Ia, X—R1 is selected from the group consisting of:

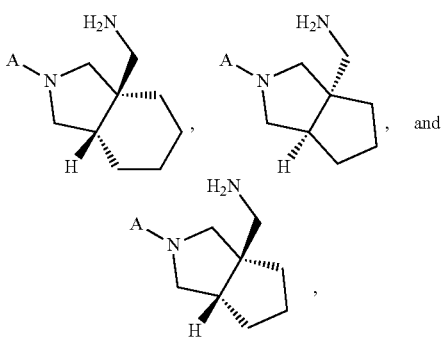

wherein A represents the point of attachment to the pyrimidine ring.

In one aspect of the present invention, for Formula I or Formula Ia, X—R1 is selected from the group consisting of:

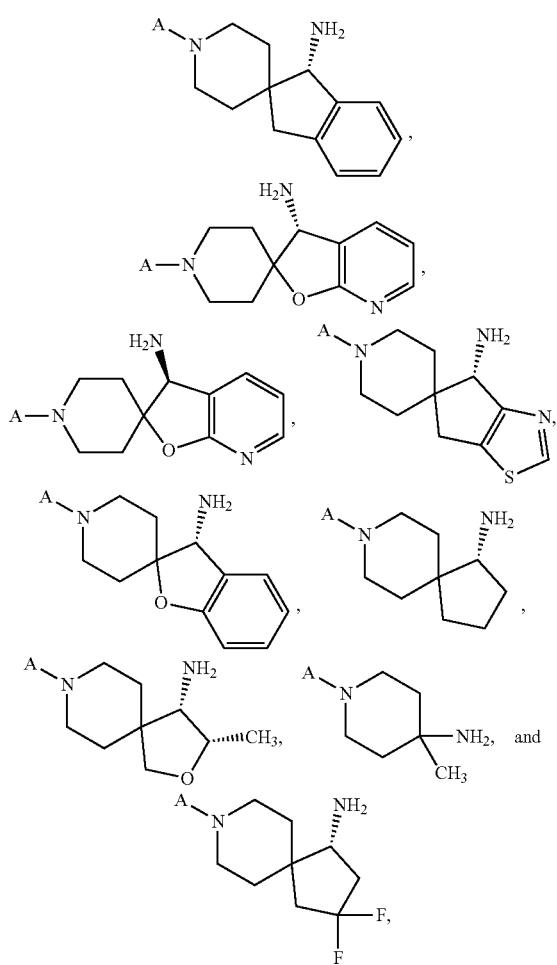

wherein A represents the point of attachment to the pyrimidine ring.

In one aspect of the present invention, for Formula I or Formula Ia, X—R1 is selected from the group consisting of:

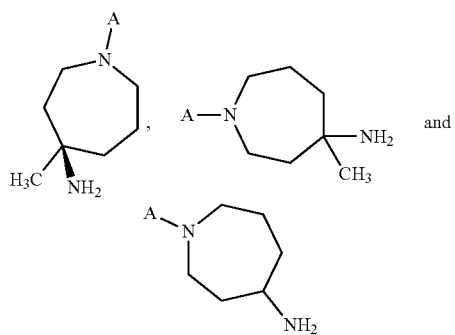

wherein A represents the point of attachment to the pyrimidine ring.

The invention preferably relates to a compound according to Formula I, or a pharmaceutically acceptable salt thereof, wherein R2 is phenyl which is unsubstituted or mono-, di- or trisubstituted by —F, —Cl and/or —Br, and wherein X, R1, R3, Y, R4 and R5 have the meanings as disclosed above.

The invention preferably relates to a compound according to Formula I, or a pharmaceutically acceptable salt thereof, wherein R2 is one of the following structures:

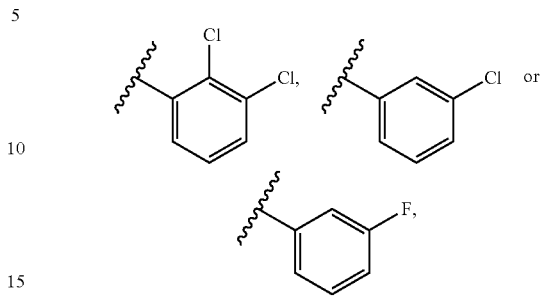

and wherein X, R1, R3, Y, R4 and R5 have the meanings as disclosed above.

The invention preferably relates to a compound according to Formula I, or a pharmaceutically acceptable salt thereof, wherein R3 is —NH$_2$, and wherein X, R1, R2, Y, R4 and R5 have the meanings as disclosed above.

The invention preferably relates to a compound according to Formula I, or a pharmaceutically acceptable salt thereof, wherein R3 is —CH$_3$, and wherein X, R1, R2, Y, R4 and R5 have the meanings as disclosed above.

The invention preferably relates to a compound according to Formula I, or a pharmaceutically acceptable salt thereof, wherein R3 is —H, and wherein X, R1, R2, Y, R4 and R5 have the meanings as disclosed above.

The invention preferably relates to a compound according to Formula I, or a pharmaceutically acceptable salt thereof, wherein R3 is —Cl, and wherein X, R1, R2, Y, R4 and R5 have the meanings as disclosed above.

The invention preferably relates to a compound according to Formula I, or a pharmaceutically acceptable salt thereof, wherein X is a single bond, —NH— or —N(CH$_3$)—, and wherein Y, R1, R2, R3, R4 and R5 have the meanings as disclosed above.

In one aspect of the present invention is a compound according to Formula Ib, or a pharmaceutically acceptable salt thereof, wherein R1 is

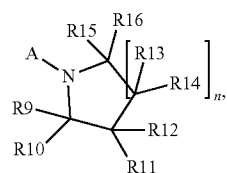

when A is the point of attachment to the pyrimidine ring of Formula Ib;
each of R6, R7 and R8 are independently selected from —H, —F, —Cl, —CF$_3$, C$_1$-C$_3$ alkoxy and C$_1$-C$_3$ alkyl;
n is 0, 1, 2, or 3; and
each of R9, R10, R11, R12, R13, R14, R15 and R16, when present, are independently selected from —H, C$_1$-C$_3$ alkyl, —NH$_2$, —OH, —Cl, —F, —Br, C$_1$-C$_3$ aminoalkyl, C$_1$-C$_3$ hydroxyalkyl, C$_1$-C$_3$ alkoxy, and phenyl; or
two of R9, R11, R13 and R16 are taken together to form a bridged bicyclic heterocyclic system which is optionally substituted with 1-3 substituents selected from C$_1$-C$_3$ alkyl, —NH$_2$, —OH, —Cl, —F, —Br, C$_1$-C$_3$ aminoalkyl, C$_1$-C$_3$ hydroxyalkyl, C$_1$-C$_3$ alkoxy, and phenyl; or
two of R9, R10, R11, R12, R13, R14, R15, and R16, which are attached to the same carbon atom, are taken together to form a monocyclic or bicyclic spirocyclyl, which is optionally substituted with 1-3 substituents selected from $C_1$-$C_3$ alkyl, —$NH_2$, —OH, —Cl, —F, —Br, $C_1$-$C_3$ aminoalkyl, $C_1$-$C_3$ hydroxyalkyl, $C_1$-$C_3$ alkoxy, and phenyl; or two of R9, R10, R11, R12, R13, R14, R15, and R16, which are attached to adjacent carbon atoms, are taken together to form a fused carbocyclyl or heterocyclyl, which is optionally substituted with 1-3 substituents selected from $C_1$-$C_3$ alkyl, —$NH_2$, —OH, —Cl, —F, —Br, $C_1$-$C_3$ aminoalkyl, $C_1$-$C_3$ hydroxyalkyl, $C_1$-$C_3$ alkoxy, and phenyl.

The invention particularly preferably relates to a compound selected from the group consisting of:

| No. | | IUPAC-Name |
|---|---|---|
| 1 | *(structure)* | 2-(4-amino-4-methylpiperidin-1-yl)-5-(2,3-dichlorophenyl)-pyrimidine-4-carboxamide |
| 2 | *(structure)* | 6-Amino-2-(4-amino-4-methylpiperidin-1-yl)-5-(3-chlorophenyl)-pyrimidine-4-carboxylic acid amide |
| 3 | *(structure)* | 6-Amino-2-(4-amino-4-methylpiperidin-1-yl)-5-(2,3-dichlorophenyl)-pyrimidine-4-carboxylic acid amide |

-continued

| No. | | IUPAC-Name |
|---|---|---|
| 4 | 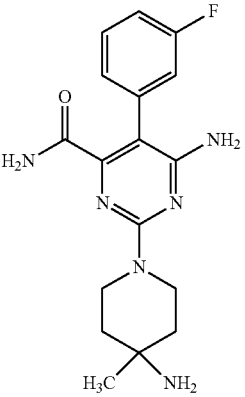 [SMILES: CC1(N)CCN(c2nc(N)c(-c3cccc(F)c3)c(C(N)=O)n2)CC1] | 6-Amino-2-(4-amino-4-methylpiperidin-1-yl)-5-(3-fluorophenyl)-pyrimidine-4-carboxylic acid amide |
| 5 | 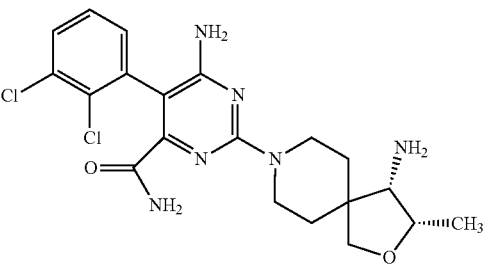 [SMILES: C[C@@H]1OCC2(CCN(c3nc(N)c(-c4cccc(Cl)c4Cl)c(C(N)=O)n3)CC2)[C@@H]1N] | 6-amino-2-[(3S,4S)-4-amino-3-methyl-2-oxa-8-azaspiro[4.5]decan-8-yl]-5-(2,3-dichlorophenyl)pyrimidine-4-carboxamide |
| 6 | 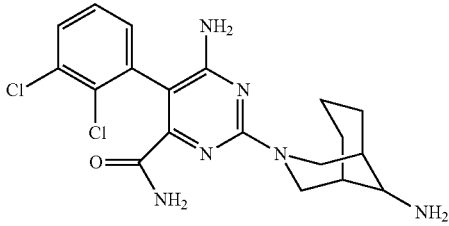 [SMILES: NC(=O)c1nc(N2CC3CCCC(C2)C3N)nc(N)c1-c1cccc(Cl)c1Cl] | 6-amino-2-{9-amino-3-azabicyclo[3.3.1]nonan-3-yl}-5-(2,3-dichlorophenyl)pyrimidine-4-carboxamide |
| 7 | 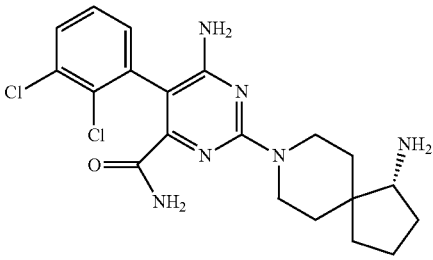 [SMILES: NC(=O)c1nc(N2CCC3(CCC[C@H]3N)CC2)nc(N)c1-c1cccc(Cl)c1Cl] | 6-amino-2-[(1R)-1-amino-8-azaspiro[4.5]decan-8-yl]-5-(2,3-dichlorophenyl)pyrimidine-4-carboxamide |
| 8 | 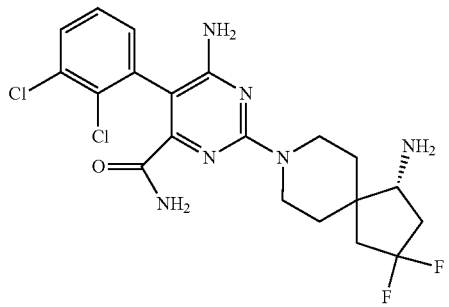 [SMILES: NC(=O)c1nc(N2CCC3(CC2)CC(F)(F)C[C@H]3N)nc(N)c1-c1cccc(Cl)c1Cl] | 6-amino-2-[(1R)-1-amino-3,3-difluoro-8-azaspiro[4.5]decan-8-yl]-5-(2,3-dichlorophenyl)pyrimidine-4-carboxamide |

| No. | | IUPAC-Name |
|---|---|---|
| 9 | | 6-Amino-2-(4-amino-4-methylpiperidin-1-yl)-5-(2,3-dichlorophenyl)-pyrimidine-4-carboxylic acid methylamide |
| 10 | | 6-amino-2-[6-amino-7-hydroxy-1-(propan-2-yl)-2-azaspiro[3.4]octan-2-yl]-5-(2,3-dichlorophenyl)pyrimidine-4-carboxamide |
| 11 | | 6-amino-2-[8-(aminomethyl)-6-azaspiro[3.4]octan-6-yl]-5-(2,3-dichlorophenyl)pyrimidine-4-carboxamide |
| 12 | | 6-amino-2-[3-(aminomethyl)-8-azabicyclo[3.2.1]octan-8-yl]-5-(2,3-dichlorophenyl)pyrimidine-4-carboxamide |
| 13 | | 6-amino-5-(2,3-dichlorophenyl)-2-[(1R,7S,11s)-11-amino-1,7-dimethyl-9-azabicyclo[5.3.1]undecan-9-yl]pyrimidine-4-carboxamide |

-continued

| No. | | IUPAC-Name |
|---|---|---|
| 14 | 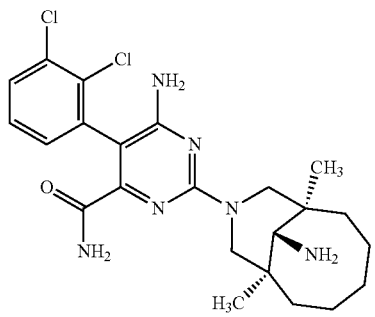 [SMILES: C[C@]12CCCCC[C@](C)(CN(c3nc(N)c(-c4cccc(Cl)c4Cl)c(C(N)=O)n3)C1)[C@@H]2N] | 6-amino-5-(2,3-dichlorophenyl)-2-[(1R,7S,11r)-11-amino-1,7-dimethyl-9-azabicyclo[5.3.1]undecan-9-yl]pyrimidine-4-carboxamide |
| 15 | 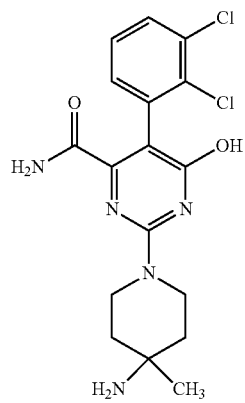 [SMILES: CC1(N)CCN(c2nc(O)c(-c3cccc(Cl)c3Cl)c(C(N)=O)n2)CC1] | 2-(4-Amino-4-methylpiperidin-1-yl)-5-(2,3-dichlorophenyl)-6-hydroxypyrimidine-4-carboxylic acid amide |
| 16 | 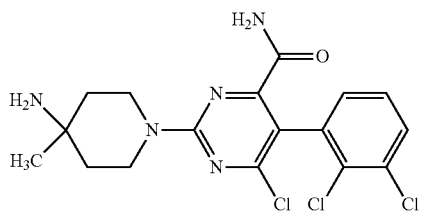 [SMILES: CC1(N)CCN(c2nc(Cl)c(-c3cccc(Cl)c3Cl)c(C(N)=O)n2)CC1] | 2-(4-Amino-4-methylpiperidin-1-yl)-6-chloro-5-(2,3-dichlorophenyl)-pyrimidine-4-carboxylic acid amide |
| 17 | 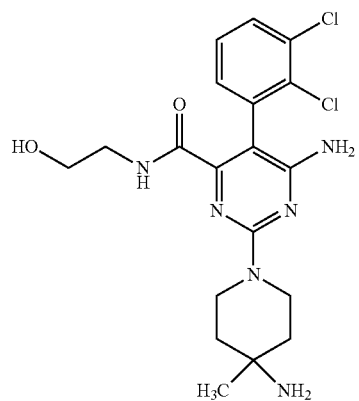 [SMILES: CC1(N)CCN(c2nc(N)c(-c3cccc(Cl)c3Cl)c(C(=O)NCCO)n2)CC1] | 6-Amino-2-(4-amino-4-methylpiperidin-1-yl)-5-(2,3-dichlorophenyl)-pyrimidine-4-carboxylic acid (2-hydroxyethyl)-amide |

-continued

| No. | | IUPAC-Name |
|---|---|---|
| 18 | 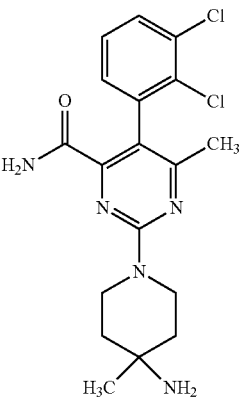 | 2-(4-Amino-4-methylpiperidin-1-yl)-5-(2,3-dichlorophenyl)-6-methylpyrimidine-4-carboxylic acid amide |
| 19 | 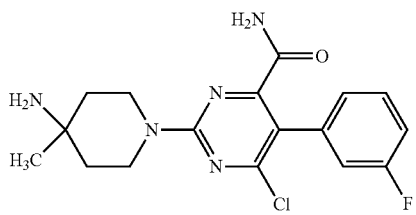 [SMILES: CC1(N)CCN(c2nc(Cl)c(-c3cccc(F)c3)c(C(N)=O)n2)CC1] | 2-(4-Amino-4-methylpiperidin-1-yl)-6-chloro-5-(3-fluorophenyl)-pyrimidine-4-carboxylic acid amide |
| 20 | 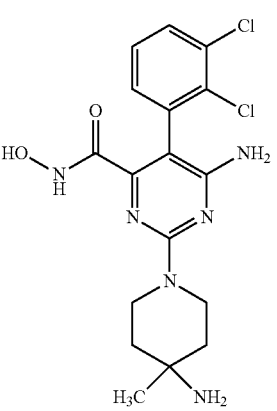 [SMILES: CC1(N)CCN(c2nc(N)c(-c3cccc(Cl)c3Cl)c(C(=O)NO)n2)CC1] | 6-Amino-2-(4-amino-4-methylpiperidin-1-yl)-5-(2,3-dichlorophenyl)-pyrimidine-4-carboxylic acid hydroxyamide |
| 21 | 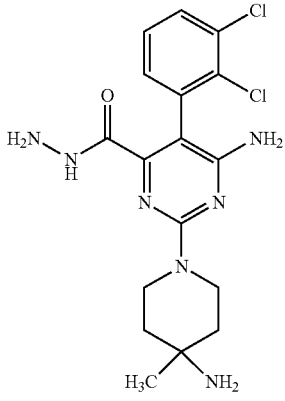 [SMILES: CC1(N)CCN(c2nc(N)c(-c3cccc(Cl)c3Cl)c(C(=O)NN)n2)CC1] | 6-Amino-2-(4-amino-4-methylpiperidin-1-yl)-5-(2,3-dichlorophenyl)-pyrimidine-4-carboxylic acid hydrazide |

-continued

| No. | | IUPAC-Name |
|---|---|---|
| 22 | 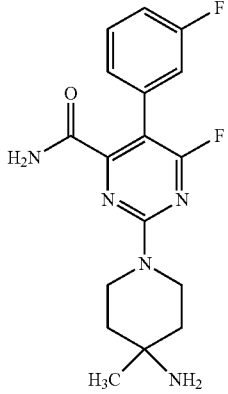 | 2-(4-Amino-4-methylpiperidin-1-yl)-6-fluoro-5-(3-fluorophenyl)-pyrimidine-4-carboxylic acid amide |
| 23 | 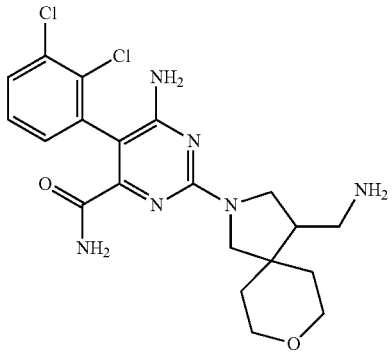 [SMILES: NCC1CN(c2nc(N)c(-c3cccc(Cl)c3Cl)c(C(N)=O)n2)CC12CCOCC2] | 6-amino-2-[4-(aminomethyl)-8-oxa-2-azaspiro[4.5]decan-2-yl]-5-(2,3-dichlorophenyl)pyrimidine-4-carboxamide |
| 24 | 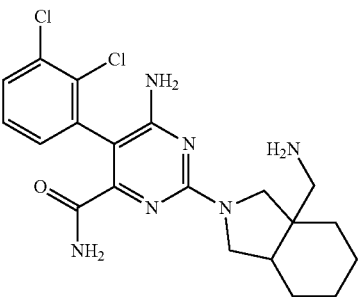 [SMILES: NCC12CCCCC1CN(c1nc(N)c(-c3cccc(Cl)c3Cl)c(C(N)=O)n1)C2] | 2-[3a-(aminomethyl)-octahydro-1H-isoindol-2-yl]-6-amino-5-(2,3-dichlorophenyl)pyrimidine-4-carboxamide |
| 25 | 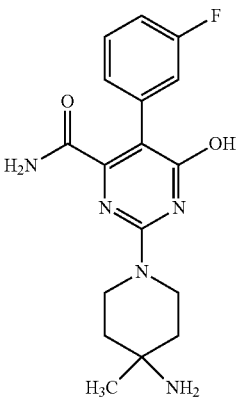 | 2-(4-Amino-4-methylpiperidin-1-yl)-5-(3-fluorophenyl)-6-hydroxypyrimidine-4-carboxylic acid amide |

-continued

| No. | | IUPAC-Name |
|---|---|---|
| 26 | | (4M)-6-amino-2-(4-amino-4-methylpiperidin-1-yl)-5-(2,3-dichlorophenyl)pyrimidine-4-carboxamide |
| 27 | | (4P)-6-amino-2-(4-amino-4-methylpiperidin-1-yl)-5-(2,3-dichlorophenyl)pyrimidine-4-carboxamide |
| 28 | | 2-(3-Aminocyclohexylamino)-5-(2,3-dichlorophenyl)-6-methylpyrimidine-4-carboxylic acid amide |
| 29 | | 6-amino-2-[4-amino-4-(hydroxymethyl)piperidin-1-yl]-5-(2,3-dichlorophenyl)pyrimidine-4-carboxamide |
| 30 | | (4M)-2-(4-amino-4-methylpiperidin-1-yl)-5-(2,3-dichlorophenyl)-6-methylpyrimidine-4-carboxamide |
| 31 | | (4P)-2-(4-amino-4-methylpiperidin-1-yl)-5-(2,3-dichlorophenyl)-6-methylpyrimidine-4-carboxamide |

| No. | | IUPAC-Name |
|---|---|---|
| 32 | | 2-[(4-Aminocyclohexyl)-methylamino]-5-(2,3-dichlorophenyl)-6-methylpyrimidine-4-carboxylic acid amide |
| 33 | | 2-(7-Amino-3-oxa-9-azabicyclo[3.3.1]non-9-yl)-5-(2,3-dichlorophenyl)-6-methylpyrimidine-4-carboxylic acid amide |
| 34 | | 6-amino-2-[8-(aminomethyl)-2-oxa-6-azaspiro[3.4]octan-6-yl]-5-(2,3-dichlorophenyl)pyrimidine-4-carboxamide |
| 35 | | 2-((R)-6-Amino-2-azaspiro[4.4]non-2-yl)-5-(2,3-dichlorophenyl)-6-methylpyrimidine-4-carboxylic acid amide |
| 36 | | 2-(3-Aminomethylcyclopentylamino)-5-(2,3-dichlorophenyl)-6-methylpyrimidine-4-carboxylic acid amide |
| 37 | | 2-((S)-6-Amino-2-azaspiro[4.4]non-2-yl)-5-(2,3-dichlorophenyl)-6-methylpyrimidine-4-carboxylic acid amide |

| No. | | IUPAC-Name |
|---|---|---|
| 38 | 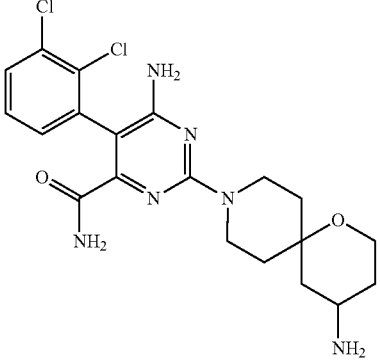 [SMILES: NC(=O)c1nc(N2CCC3(CC2)CC(N)CCO3)nc(N)c1-c1cccc(Cl)c1Cl] | 6-amino-2-{4-amino-1-oxa-9-azaspiro[5.5]undecan-9-yl}-5-(2,3-dichlorophenyl)pyrimidine-4-carboxamide |
| 39 | 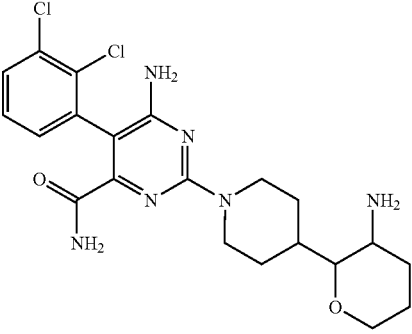 [SMILES: NC(=O)c1nc(N2CCC(C3OCCCC3N)CC2)nc(N)c1-c1cccc(Cl)c1Cl] | 6-amino-2-[4-(3-aminooxan-2-yl)piperidin-1-yl]-5-(2,3-dichlorophenyl)pyrimidine-4-carboxamide |
| 40 | 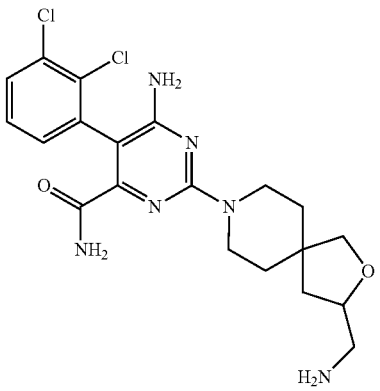 [SMILES: NCC1CC2(CCN(c3nc(N)c(-c4cccc(Cl)c4Cl)c(C(N)=O)n3)CC2)CO1] | 6-amino-2-[3-(aminomethyl)-2-oxa-8-azaspiro[4.5]decan-8-yl]-5-(2,3-dichlorophenyl)pyrimidine-4-carboxamide |
| 41 | 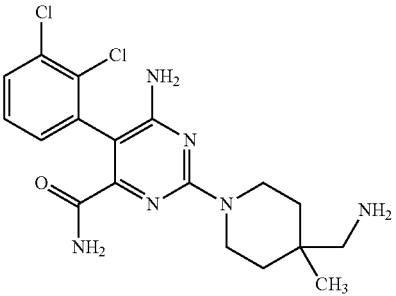 [SMILES: CC1(CN)CCN(c2nc(N)c(-c3cccc(Cl)c3Cl)c(C(N)=O)n2)CC1] | 6-amino-2-[4-(aminomethyl)-4-methylpiperidin-1-yl]-5-(2,3-dichlorophenyl)pyrimidine-4-carboxamide |

-continued

| No. | | IUPAC-Name |
|---|---|---|
| 42 | 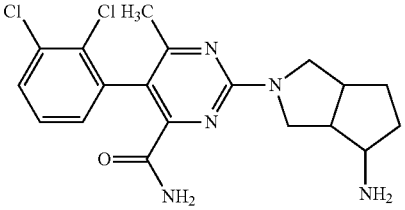 [SMILES: Cc1nc(N2CC3CCC(N)C3C2)nc(C(N)=O)c1-c1cccc(Cl)c1Cl] | 2-(4-Aminohexahydrocyclopenta[c]pyrrol-2-yl)-5-(2,3-dichlorophenyl)-6-methylpyrimidine-4-carboxylic acid amide hydrochloride |
| 43 | 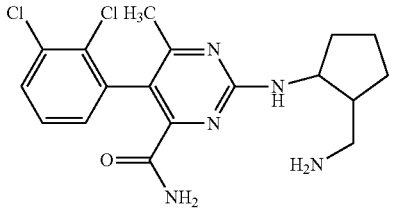 [SMILES: Cc1nc(NC2CCCC2CN)nc(C(N)=O)c1-c1cccc(Cl)c1Cl] | 2-(2-Aminomethylcyclopentylamino)-5-(2,3-dichlorophenyl)-6-methylpyrimidine-4-carboxylic acid amide |
| 44 | 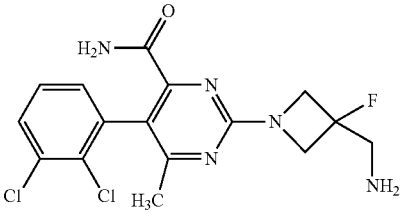 [SMILES: Cc1nc(N2CC(F)(CN)C2)nc(C(N)=O)c1-c1cccc(Cl)c1Cl] | 2-(3-Aminomethyl-3-fluoroazetidin-1-yl)-5-(2,3-dichlorophenyl)-6-methylpyrimidine-4-carboxylic acid amide |
| 45 | 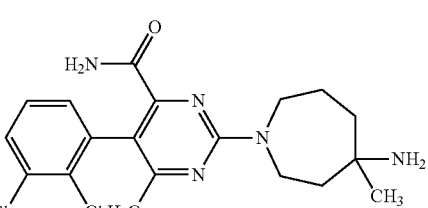 | 2-(4-Amino-4-methylazepan-1-yl)-5-(2,3-dichlorophenyl)-6-methylpyrimidine-4-carboxylic acid amide |
| 46 | 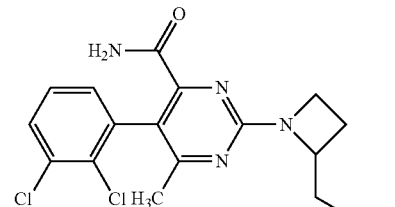 | 2-(2-Aminomethylazetidin-1-yl)-5-(2,3-dichlorophenyl)-6-methylpyrimidine-4-carboxylic acid amide |
| 47 | 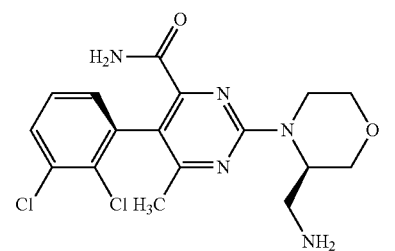 | (4P)-2-[(3R)-3-(aminomethyl)morpholin-4-yl]-5-(2,3-dichlorophenyl)-6-methylpyrimidine-4-carboxamide hydrochloride |

-continued

| No. | | IUPAC-Name |
|---|---|---|
| 48 | 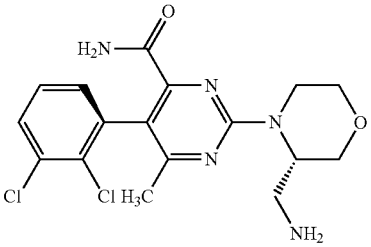 | (4P)-2-[(3S)-3-(aminomethyl)morpholin-4-yl]-5-(2,3-dichlorophenyl)-6-methylpyrimidine-4-carboxamide hydrochloride |
| 49 | 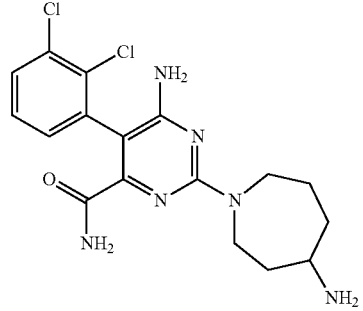 [SMILES: NC(=O)c1nc(N2CCCC(N)CC2)nc(N)c1-c1cccc(Cl)c1Cl] | 6-amino-2-(4-aminoazepan-1-yl)-5-(2,3-dichlorophenyl)-pyrimidine-4-carboxamide |
| 50 | 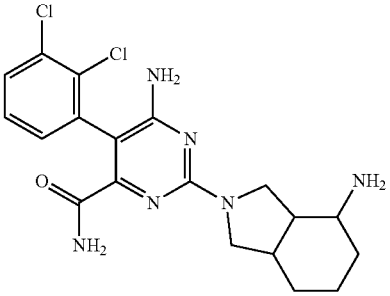 [SMILES: NC(=O)c1nc(N2CC3CCCC(N)C3C2)nc(N)c1-c1cccc(Cl)c1Cl] | 6-amino-2-(4-aminooctahydro-1H-isoindol-2-yl)-5-(2,3-dichlorophenyl)pyrimidine-4-carboxamide |
| 51 | 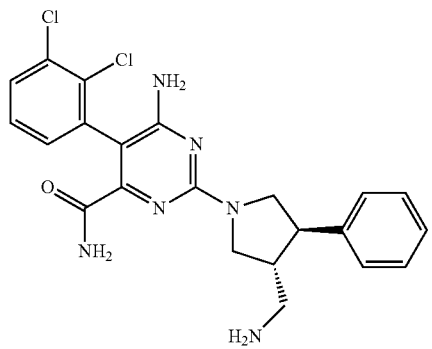 [SMILES: NC[C@@H]1CN(c2nc(N)c(-c3cccc(Cl)c3Cl)c(C(N)=O)n2)C[C@H]1c1ccccc1] | 6-amino-2-[(3R,4R)-3-(aminomethyl)-4-phenylpyrrolidin-1-yl]-5-(2,3-dichlorophenyl)pyrimidine-4-carboxamide |
| 52 | 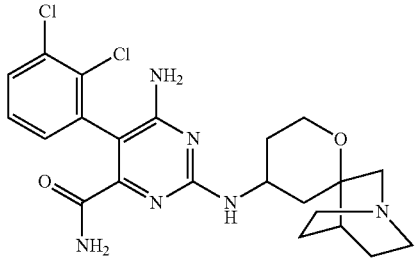 [SMILES: NC(=O)c1nc(NC2CCOC3(C2)CN2CCC3CC2)nc(N)c1-c1cccc(Cl)c1Cl] | 6-amino-2-({4-azaspiro[bicyclo[2.2.2]octane-2,2'-oxan]-4'-yl}amino)-5-(2,3-dichlorophenyl)pyrimidine-4-carboxamide |

-continued

| No. | | IUPAC-Name |
|---|---|---|
| 53 | 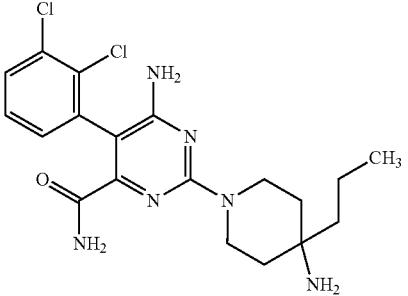 [SMILES: CCCC1(N)CCN(c2nc(N)c(-c3cccc(Cl)c3Cl)c(C(N)=O)n2)CC1] | 6-amino-2-(4-amino-4-propylpiperidin-1-yl)-5-(2,3-dichlorophenyl)pyrimidine-4-carboxamide |
| 54 | 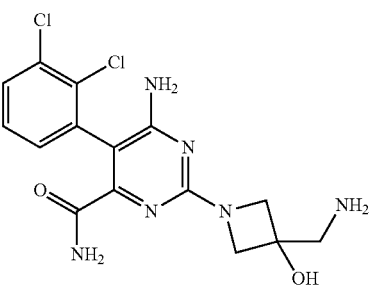 [SMILES: NCC1(O)CN(c2nc(N)c(-c3cccc(Cl)c3Cl)c(C(N)=O)n2)C1] | 6-amino-2-[3-(aminomethyl)-3-hydroxyazetidin-1-yl]-5-(2,3-dichlorophenyl)pyrimidine-4-carboxamide |
| 55 | 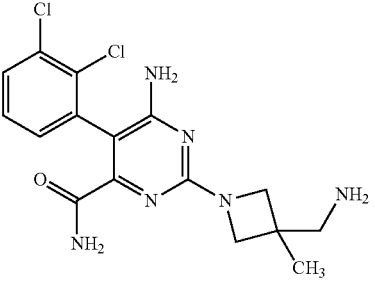 [SMILES: CC1(CN)CN(c2nc(N)c(-c3cccc(Cl)c3Cl)c(C(N)=O)n2)C1] | 6-amino-2-[3-(aminomethyl)-3-methylazetidin-1-yl]-5-(2,3-dichlorophenyl)pyrimidine-4-carboxamide |
| 56 | 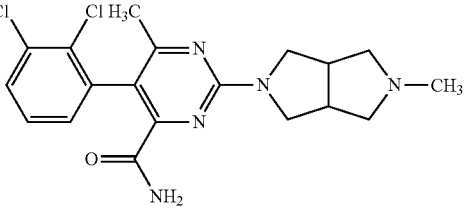 | 5-(2,3-Dichlorophenyl)-6-methyl-2-(5-methylhexahydropyrrolo[3,4-c]pyrrol-2-yl)-pyrimidine-4-carboxylic acid amide |
| 57 | 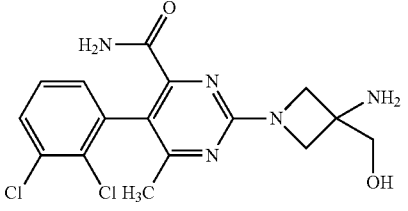 [SMILES: Cc1nc(N2CC(N)(CO)C2)nc(C(N)=O)c1-c1cccc(Cl)c1Cl] | 2-(3-Amino-3-hydroxymethylazetidin-1-yl)-5-(2,3-dichlorophenyl)-6-methylpyrimidine-4-carboxylic acid amide |
| 58 | 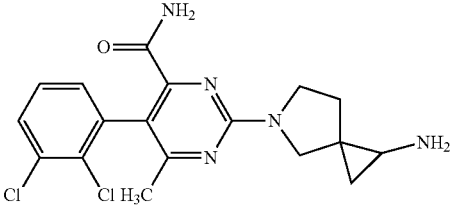 | 2-(1-Amino-5-azaspiro[2.4]hept-5-yl)-5-(2,3-dichlorophenyl)-6-methylpyrimidine-4-carboxylic acid amide |

-continued

| No. | | IUPAC-Name |
|---|---|---|
| 60 | | 2-(4-Amino-4-methylpiperidin-1-yl)-5-(1H-benzoimidazol-4-yl)-pyrimidine-4-carboxylic acid amide |
| 61 | | 2-(4-Amino-4-methylpiperidin-1-yl)-5-benzo[1,2,5]oxadiazol-4-ylpyrimidine-4-carboxylic acid amide |
| 62 | | 6-Amino-2-(4-amino-4-methylpiperidin-1-yl)-5-(7-chloro-1H-indazol-6-yl)-pyrimidine-4-carboxylic acid amide |
| 63 | | 5-(2,3-Dichlorophenyl)-6-methyl-2-(5-methylhexahydropyrrolo[3,4-c]pyrrol-2-yl)-pyrimidine-4-carboxylic acid amide |
| 64 | | (5M)-6-amino-5-(2,3-dichlorophenyl)-2-{[(3S,4R)-3-fluoropiperidin-4-yl]amino}-pyrimidine-4-carboxamide |

-continued

| No. | | IUPAC-Name |
|---|---|---|
| 65 | 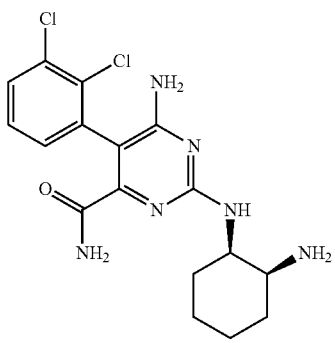 [SMILES: NC(=O)c1nc(N[C@@H]2CCCC[C@@H]2N)nc(N)c1-c1cccc(Cl)c1Cl] | 6-amino-2-{[(1R,2S)-2-aminocyclohexyl]amino}-5-(2,3-dichlorophenyl)-pyrimidine-4-carboxamide |
| 66 | 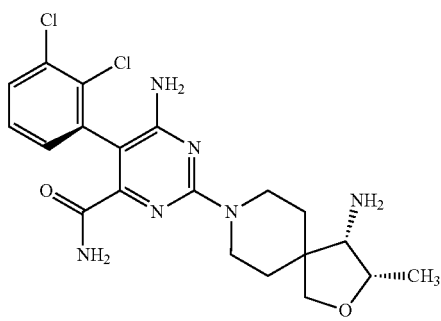 | (5P)-6-amino-2-[(3S,4S)-4-amino-3-methyl-2-oxa-8-azaspiro[4.5]decan-8-yl]-5-(2,3-dichlorophenyl)-pyrimidine-4-carboxamide |
| 67 | 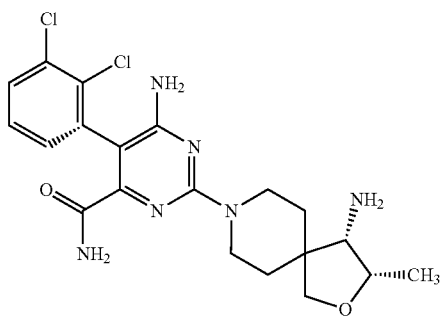 | (5M)-6-amino-2-[(3S,4S)-4-amino-3-methyl-2-oxa-8-azaspiro[4.5]decan-8-yl]-5-(2,3-dichlorophenyl)-pyrimidine-4-carboxamide |
| 68 | 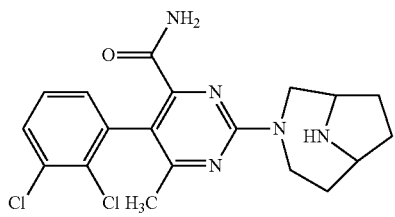 [SMILES: Cc1nc(N2CCC3CCC(C2)N3)nc(C(N)=O)c1-c1cccc(Cl)c1Cl] | 2-(3,9-Diazabicyclo[4.2.1]non-3-yl)-5-(2,3-dichlorophenyl)-6-methylpyrimidine-4-carboxylic acid amide |
| 69 | 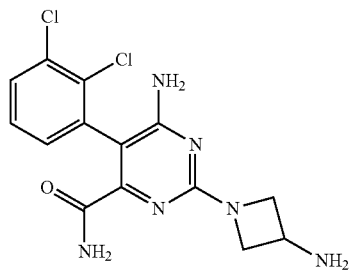 [SMILES: NC(=O)c1nc(N2CC(N)C2)nc(N)c1-c1cccc(Cl)c1Cl] | 6-amino-2-(3-aminoazetidin-1-yl)-5-(2,3-dichlorophenyl)-pyrimidine-4-carboxamide |

-continued

| No. | | IUPAC-Name |
|---|---|---|
| 70 | 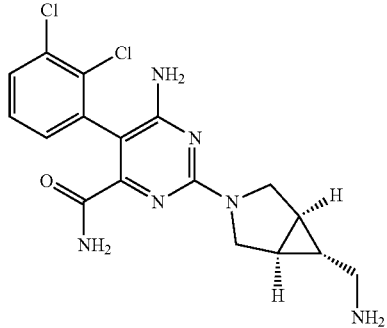 [SMILES: NC[C@@H]1[C@H]2CN(c3nc(N)c(-c4cccc(Cl)c4Cl)c(C(N)=O)n3)C[C@@H]12] | 6-amino-2-[(1R,5S,6R)-6-(aminomethyl)-3-azabicyclo[3.1.0]hexan-3-yl]-5-(2,3-dichlorophenyl)pyrimidine-4-carboxamide |
| 71 | 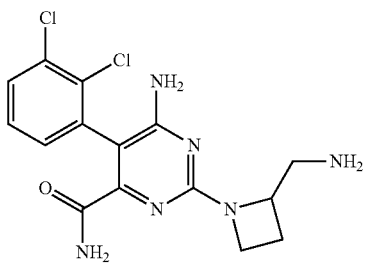 [SMILES: NCC1CCN1c1nc(N)c(-c2cccc(Cl)c2Cl)c(C(N)=O)n1] | 6-amino-2-[2-(aminomethyl)-azetidin-1-yl]-5-(2,3-dichlorophenyl)pyrimidine-4-carboxamide |
| 72 | 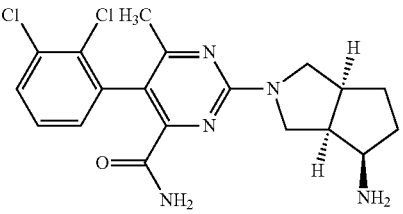 [SMILES: Cc1nc(N2C[C@H]3CC[C@@H](N)[C@H]3C2)nc(C(N)=O)c1-c1cccc(Cl)c1Cl] | 2-((3aR,4R,6aS)-4-Aminohexahydrocyclopenta[c]pyrrol-2-yl)-5-(2,3-dichlorophenyl)-6-methylpyrimidine-4-carboxylic acid amide |
| 73 | 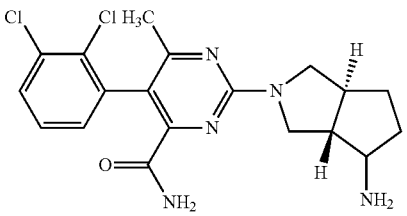 [SMILES: Cc1nc(N2C[C@H]3CCC(N)[C@@H]3C2)nc(C(N)=O)c1-c1cccc(Cl)c1Cl] | 2-((3aS,6aS)-4-Aminohexahydrocyclopenta[c]pyrrol-2-yl)-5-(2,3-dichlorophenyl)-6-methylpyrimidine-4-carboxylic acid amide |
| 74 | 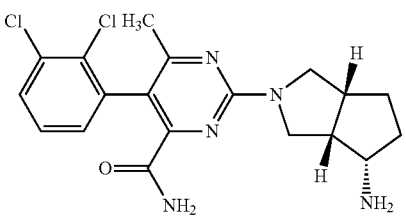 [SMILES: Cc1nc(N2C[C@@H]3CC[C@H](N)[C@@H]3C2)nc(C(N)=O)c1-c1cccc(Cl)c1Cl] | 2-((3aS,4S,6aR)-4-Aminohexahydrocyclopenta[c]pyrrol-2-yl)-5-(2,3-dichlorophenyl)-6-methylpyrimidine-4-carboxylic acid amide |
| 75 | 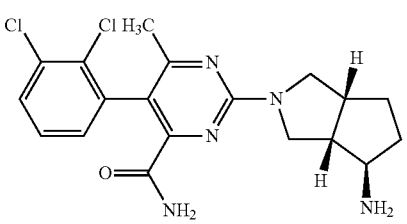 [SMILES: Cc1nc(N2C[C@@H]3CC[C@@H](N)[C@@H]3C2)nc(C(N)=O)c1-c1cccc(Cl)c1Cl] | 2-((3aS,4R,6aR)-4-Aminohexahydrocyclopenta[c]pyrrol-2-yl)-5-(2,3-dichlorophenyl)-6-methylpyrimidine-4-carboxylic acid amide |

-continued

| No. | IUPAC-Name |
|---|---|
| 76 | 2-((3aR,6aR)-4-Aminohexahydrocyclopenta[c]pyrrol-2-yl)-5-(2,3-dichlorophenyl)-6-methylpyrimidine-4-carboxylic acid amide |
| 77 | 2-((3aR,4S,6aS)-4-Aminohexahydrocyclopenta[c]pyrrol-2-yl)-5-(2,3-dichlorophenyl)-6-methylpyrimidine-4-carboxylic acid amide |
| 78 | (4M)-2-(4-amino-4-methylpiperidin-1-yl)-6-chloro-5-(2,3-dichlorophenyl)-pyrimidine-4-carboxamide |
| 79 | (4P)-2-(4-amino-4-methylpiperidin-1-yl)-6-chloro-5-(2,3-dichlorophenyl)-pyrimidine-4-carboxamide |
| 80 | 2-((3R,4S)-3-Amino-4-hydroxypyrrolidin-1-yl)-5-(2,3-dichlorophenyl)-6-methylpyrimidine-4-carboxylic acid amide |
| 81 | 2-(4-Amino-4-methylpiperidin-1-yl)-5-(5-(2,3-dichloropyridin-4-yl)-6-methylpyrimidine-4-carboxylic acid amide |

-continued

| No. | | IUPAC-Name |
|---|---|---|
| 82 | 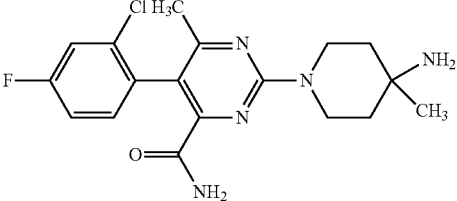 [SMILES: Cc1nc(N2CCC(C)(N)CC2)nc(C(N)=O)c1-c1ccc(F)cc1Cl] | 2-(4-Amino-4-methylpiperidin-1-yl)-5-(2-chloro-4-fluorophenyl)-6-methylpyrimidine-4-carboxylic acid amide |
| 83 | 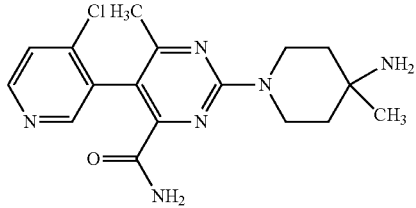 [SMILES: Cc1nc(N2CCC(C)(N)CC2)nc(C(N)=O)c1-c1cnccc1Cl] | 2-(4-Amino-4-methylpiperidin-1-yl)-5-(4-chloropyridin-3-yl)-6-methylpyrimidine-4-carboxylic acid amide |
| 84 | 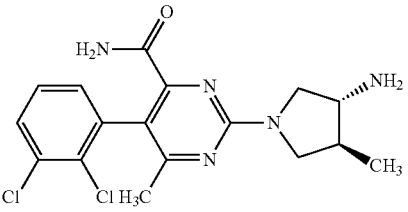 | 2-((3S,4S)-3-Amino-4-hydroxypyrrolidin-1-yl)-5-(2,3-dichlorophenyl)-6-methylpyrimidine-4-carboxylic acid amide |
| 85 | 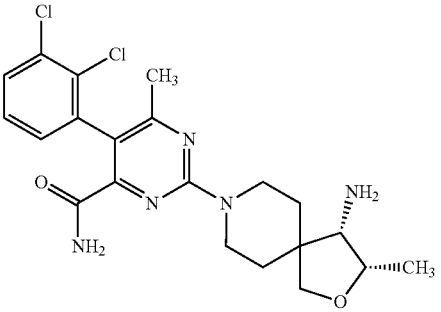 [SMILES: Cc1nc(N2CCC3(CC2)CO[C@@H](C)[C@H]3N)nc(C(N)=O)c1-c1cccc(Cl)c1Cl] | 2-[(3S,4S)-4-amino-3-methyl-2-oxa-8-azaspiro[4.5]decan-8-yl]-5-(2,3-dichlorophenyl)-6-methylpyrimidine-4-carboxamide |
| 86 | 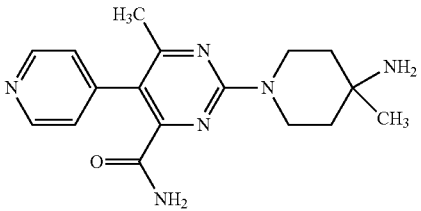 | 2-(4-Amino-4-methylpiperidin-1-yl)-6-methyl-5-pyridin-4-ylpyrimidine-4-carboxylic acid amide |
| 87 | 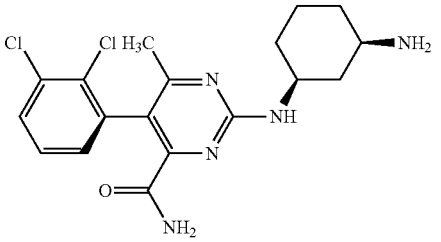 | (4M)-2-{[(1S,3R)-3-aminocyclohexyl]amino}-5-(2,3-dichlorophenyl)-6-methylpyrimidine-4-carboxamide |

-continued

| No. | IUPAC-Name |
|-----|------------|
| 88 | (4M)-2-{[(1R,3S)-3-aminocyclohexyl]amino}-5-(2,3-dichlorophenyl)-6-methylpyrimidine-4-carboxamide |
| 89 | (4P)-2-{[(1R,3S)-3-aminocyclohexyl]amino}-5-(2,3-dichlorophenyl)-6-methylpyrimidine-4-carboxamide |
| 90 | (4P)-2-{[(1S,3R)-3-aminocyclohexyl]amino}-5-(2,3-dichlorophenyl)-6-methylpyrimidine-4-carboxamide |
| 91 | 6-Amino-2-(4-amino-4-methylazepan-1-yl)-5-(2,3-dichlorophenyl)-pyrimidine-4-carboxylic acid amide |
| 92 | 2-(4-Amino-4-methylpiperidin-1-yl)-5-(1H-indol-3-yl)-6-methylpyrimidine-4-carboxylic acid amide |

| No. | IUPAC-Name |
|---|---|
| 93 | 2-(4-Aminocyclohexylamino)-5-(2,3-dichlorophenyl)-6-methylpyrimidine-4-carboxylic acid amide |
| 94 | (5P)-2-[(3S,4S)-4-amino-3-methyl-2-oxa-8-azaspiro[4.5]decan-8-yl]-5-(2,3-dichlorophenyl)-6-methylpyrimidine-4-carboxamide |
| 95 | (5M)-2-[(3S,4S)-4-amino-3-methyl-2-oxa-8-azaspiro[4.5]decan-8-yl]-5-(2,3-dichlorophenyl)-6-methylpyrimidine-4-carboxamide |
| 96 | (5M)-2-[(1R)-1-amino-3,3-difluoro-8-azaspiro[4.5]decan-8-yl]-5-(2,3-dichlorophenyl)-6-methylpyrimidine-4-carboxamide |
| 97 | (5P)-2-[(1R)-1-amino-3,3-difluoro-8-azaspiro[4.5]decan-8-yl]-5-(2,3-dichlorophenyl)-6-methylpyrimidine-4-carboxamide |

-continued

| No. | IUPAC-Name |
|---|---|
| 98 | (5P)-2-[(3aR,6aS)-3a-(aminomethyl)-octahydrocyclopenta[c]pyrrol-2-yl]-6-amino-5-(2,3-dichlorophenyl)-pyrimidine-4-carboxamide |
| 99 | (5M)-2-[(3aR,6aS)-3a-(aminomethyl)-octahydrocyclopenta[c]pyrrol-2-yl]-6-amino-5-(2,3-dichlorophenyl)-pyrimidine-4-carboxamide |
| 100 | (5P)-2-[(3aR,7aS)-3a-(aminomethyl)-octahydro-1H-isoindol-2-yl]-6-amino-5-(2,3-dichlorophenyl)pyrimidine-4-carboxamide |
| 101 | (5P)-2-[(3aS,7aR)-3a-(aminomethyl)-octahydro-1H-isoindol-2-yl]-6-amino-5-(2,3-dichlorophenyl)pyrimidine-4-carboxamide |
| 102 | (5M)-2-[(3aR,7aS)-3a-(aminomethyl)-octahydro-1H-isoindol-2-yl]-6-amino-5-(2,3-dichlorophenyl)pyrimidine-4-carboxamide |

-continued

| No. | | IUPAC-Name |
|---|---|---|
| 103 | | (5M)-2-[(3aS,7aR)-3a-(aminomethyl)-octahydro-1H-isoindol-2-yl]-6-amino-5-(2,3-dichlorophenyl)pyrimidine-4-carboxamide |
| 104 | | (5P)-2-[(3aS,6aR)-3a-(aminomethyl)-octahydrocyclopenta[c]pyrrol-2-yl]-6-amino-5-(2,3-dichlorophenyl)-pyrimidine-4-carboxamide |
| 105 | | (5M)-2-[(3aS,6aR)-3a-(aminomethyl)-octahydrocyclopenta[c]pyrrol-2-yl]-6-amino-5-(2,3-dichlorophenyl)-pyrimidine-4-carboxamide |
| 106 | | (5P)-6-amino-2-[4-amino-4-(difluoromethyl)piperidin-1-yl]-5-(2,3-dichlorophenyl)-pyrimidine-4-carboxamide |
| 107 | | (5M)-6-amino-2-[4-amino-4-(difluoromethyl)piperidin-1-yl]-5-(2,3-dichlorophenyl)-pyrimidine-4-carboxamide |

-continued
| No. | | IUPAC-Name |
|---|---|---|
| 108 | 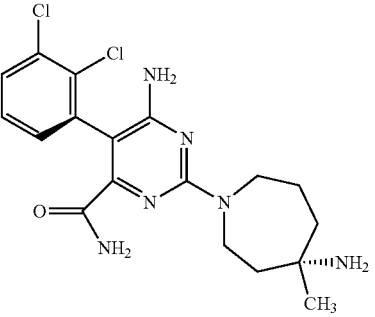 | (5P)-6-amino-2-[(4S)-4-amino-4-methylazepan-1-yl]-5-(2,3-dichlorophenyl)-pyrimidine-4-carboxamide |
| 109 | 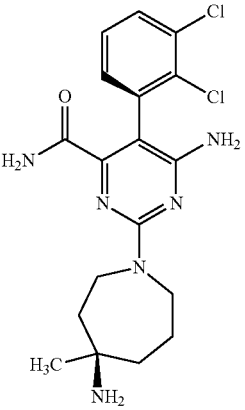 | (5P)-6-amino-2-[(4R)-4-amino-4-methylazepan-1-yl]-5-(2,3-dichlorophenyl)-pyrimidine-4-carboxamide |
| 110 | 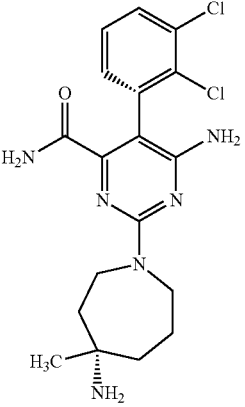 | (5M)-6-amino-2-[(4S)-4-amino-4-methylazepan-1-yl]-5-(2,3-dichlorophenyl)-pyrimidine-4-carboxamide |
| 111 | 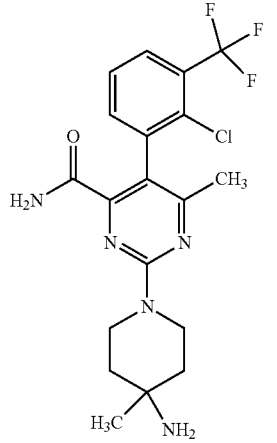 [SMILES: Cc1nc(N2CCC(C)(N)CC2)nc(C(N)=O)c1-c1cccc(C(F)(F)F)c1Cl] | 2-(4-Amino-4-methylpiperidin-1-yl)-5-(2-chloro-3-trifluoromethylphenyl)-6-methylpyrimidine-4-carboxylic acid amide |

| No. | | IUPAC-Name |
|---|---|---|
| 112 | 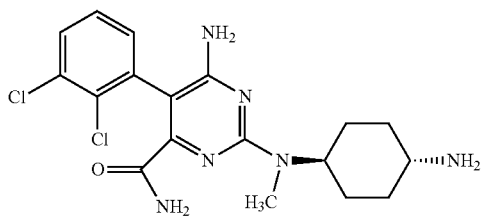 [SMILES: CN(c1nc(N)c(-c2cccc(Cl)c2Cl)c(C(N)=O)n1)[C@H]1CC[C@H](N)CC1] | 6-Amino-2-[(4-aminocyclohexyl)-methylamino]-5-(2,3-dichlorophenyl)-pyrimidine-4-carboxylic acid amide |
| 113 | 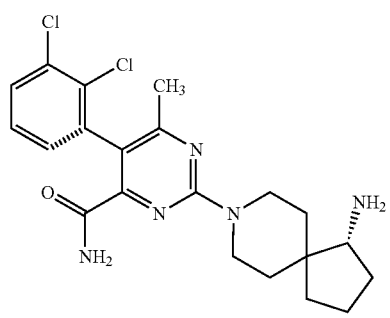 | (5P)-2-[(1R)-1-amino-8-azaspiro[4.5]decan-8-yl]-5-(2,3-dichlorophenyl)-6-methylpyrimidine-4-carboxamide |
| 114 | 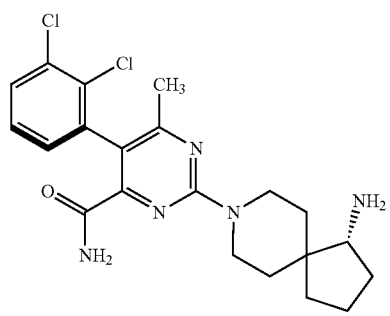 | (5M)-2-[(1R)-1-amino-8-azaspiro[4.5]decan-8-yl]-5-(2,3-dichlorophenyl)-6-methylpyrimidine-4-carboxamide |
| 115 | 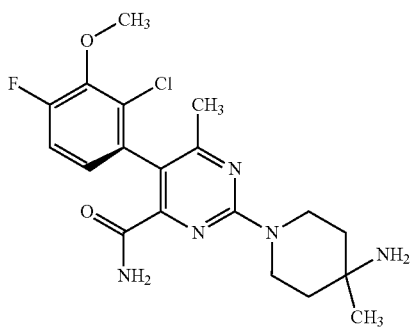 | (4M)-2-(4-amino-4-methylpiperidin-1-yl)-5-(2-chloro-4-fluoro-3-methoxyphenyl)-6-methylpyrimidine-4-carboxamide |
| 116 | 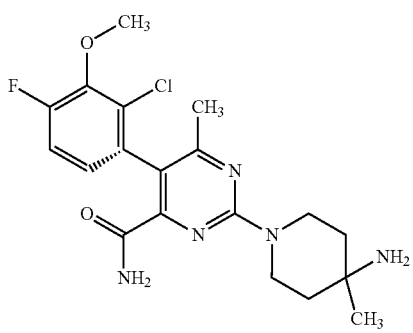 | (4P)-2-(4-amino-4-methylpiperidin-1-yl)-5-(2-chloro-4-fluoro-3-methoxyphenyl)-6-methylpyrimidine-4-carboxamide |

-continued

| No. | | IUPAC-Name |
|---|---|---|
| 117 | 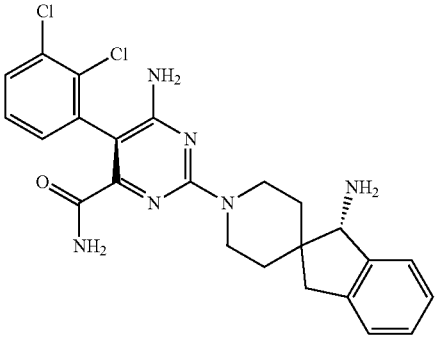 | (5P)-6-amino-2-[(1S)-1-amino-1,3-dihydrospiro[indene-2,4'-piperidin]-1'-yl]-5-(2,3-dichlorophenyl)pyrimidine-4-carboxamide |
| 118 | 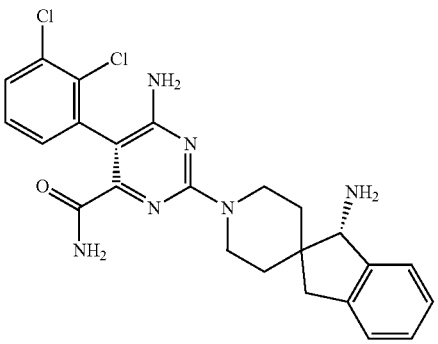 | (5M)-6-amino-2-[(1S)-1-amino-1,3-dihydrospiro[indene-2,4'-piperidin]-1'-yl]-5-(2,3-dichlorophenyl)pyrimidine-4-carboxamide |
| 119 | 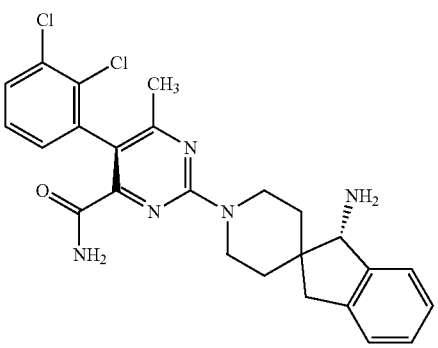 | (5M)-2-[(1S)-1-amino-1,3-dihydrospiro[indene-2,4'-piperidin]-1'-yl]-5-(2,3-dichlorophenyl)-6-methylpyrimidine-4-carboxamide |
| 120 | 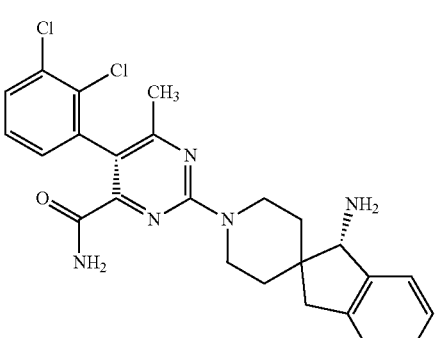 | (5P)-2-[(1S)-1-amino-1,3-dihydrospiro[indene-2,4'-piperidin]-1'-yl]-5-(2,3-dichlorophenyl)-6-methylpyrimidine-4-carboxamide |

| No. | | IUPAC-Name |
|---|---|---|
| 121 | 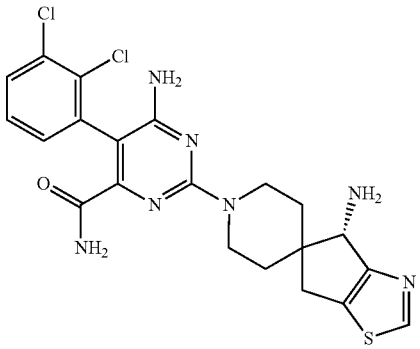 [SMILES: NC(=O)c1nc(N2CCC3(CC2)Cc2scnc2[C@H]3N)nc(N)c1-c1cccc(Cl)c1Cl] | 6-amino-2-[(4S)-4-amino-4,6-dihydrospiro[cyclopenta[d][1,3]thiazole-5,4'-piperidin]-1'-yl]-5-(2,3-dichlorophenyl)pyrimidine-4-carboxamide |
| 122 | 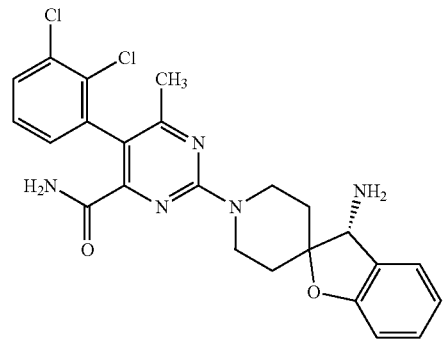 [SMILES: Cc1nc(N2CCC3(CC2)Oc2ccccc2[C@H]3N)nc(C(N)=O)c1-c1cccc(Cl)c1Cl] | 2-[(3R)-3-amino-3H-spiro[1-benzofuran-2,4'-piperidin]-1'-yl]-5-(2,3-dichlorophenyl)-6-methylpyrimidine-4-carboxamide |
| 123 | 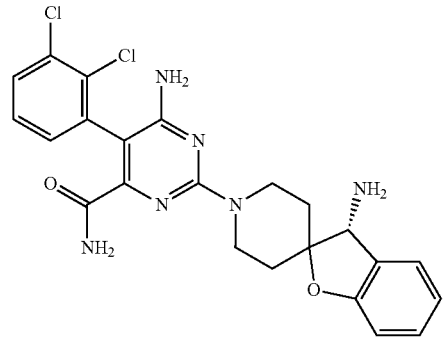 [SMILES: NC(=O)c1nc(N2CCC3(CC2)Oc2ccccc2[C@H]3N)nc(N)c1-c1cccc(Cl)c1Cl] | 6-amino-2-[(3R)-3-amino-3H-spiro[1-benzofuran-2,4'-piperidin]-1'-yl]-5-(2,3-dichlorophenyl)pyrimidine-4-carboxamide |
| 124 | 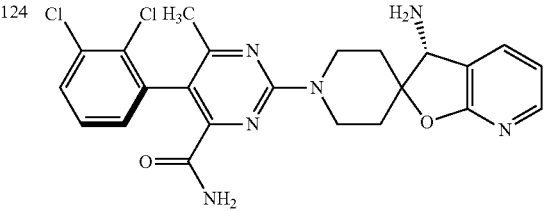 | (4M)-2-[(3R)-3-amino-3H-spiro[furo[2,3-b]pyridine-2,4'-piperidin]-1'-yl]-5-(2,3-dichlorophenyl)-6-methylpyrimidine-4-carboxamide |
| 125 | 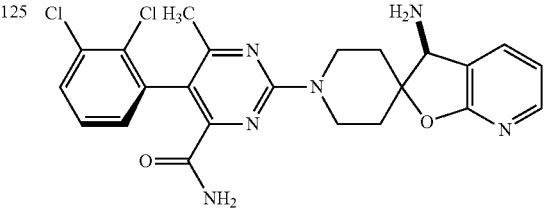 | (4M)-2-[(3S)-3-amino-3H-spiro[furo[2,3-b]pyridine-2,4'-piperidin]-1'-yl]-5-(2,3-dichlorophenyl)-6-methylpyrimidine-4-carboxamide |

-continued

| No. | IUPAC-Name |
|---|---|
| 126 | (4P)-2-[(3R)-3-amino-3H-spiro[furo[2,3-b]pyridine-2,4'-piperidin]-1'-yl]-5-(2,3-dichlorophenyl)-6-methylpyrimidine-4-carboxamide |
| 127 | (4P)-2-[(3S)-3-amino-3H-spiro[furo[2,3-b]pyridine-2,4'-piperidin]-1'-yl]-5-(2,3-dichlorophenyl)-6-methylpyrimidine-4-carboxamide |
| 128 | (4P)-6-amino-2-[(3R)-3-amino-3H-spiro[furo[2,3-b]pyridine-2,4'-piperidin]-1'-yl]-5-(2,3-dichlorophenyl)pyrimidine-4-carboxamide |
| 129 | (4P)-6-amino-2-[(3S)-3-amino-3H-spiro[furo[2,3-b]pyridine-2,4'-piperidin]-1'-yl]-5-(2,3-dichlorophenyl)pyrimidine-4-carboxamide |
| 130 | (4M)-6-amino-2-[(3R)-3-amino-3H-spiro[furo[2,3-b]pyridine-2,4'-piperidin]-1'-yl]-5-(2,3-dichlorophenyl)pyrimidine-4-carboxamide |
| 131 | (4M)-6-amino-2-[(3S)-3-amino-3H-spiro[furo[2,3-b]pyridine-2,4'-piperidin]-1'-yl]-5-(2,3-dichlorophenyl)pyrimidine-4-carboxamide | and pharmaceutically acceptable salts and atropisomers thereof, including mixtures thereof in all ratios.

All above-mentioned embodiments of the above definitions of the variables, when present, of the compounds of any one of Formula I, Ia, Ib, Ic, Id, Ie and If, it should be understood in such a way that any of these specific embodiments can be combined with one another in any possible embodiment in combination to give compounds of the invention.

Alkyl is a saturated unbranched or branched hydrocarbon chain and has 1, 2, 3, 4, 5, 6, 7, 8, 9 or 10 C atoms. Examples of "alkyl" groups include methyl, ethyl, propyl, isopropyl, butyl, isobutyl, sec-butyl or tert-butyl, and the like.

Aminoalkyl is an alkyl as described above, which is substituted with an —NH$_2$ group.

Hydroxyalkyl is an alkyl as described above, which is substituted with an —OH group.

Alkoxy is a saturated unbranched or branched hydrocarbon chain which has 1-10 C atoms, according to the formula —O(CH$_2$)$_n$CH$_3$, wherein n is 0-9. Examples of an alkoxy include methoxy, ethoxy, isopropoxy, and the like.

Cyclic alkyl or cycloalkyl is a saturated cyclic hydrocarbon chain which has 3-15 carbon atoms and can be in the form of a bridged ring system, a mono-cyclic ring system, a bicyclic ring system and/or a spiro-connected ring system. Monocyclic cycloalkyl groups are preferably 3-7 C atoms and preferably denotes cyclopropyl, cyclobutyl, cyclopentyl, cyclohexyl or cycloheptyl. Cycloalkyl may also denote a partially unsaturated cyclic akyl, such as, for example, cyclohexenyl or cyclohexynyl. When the cycloalkyl group is a part of a bicyclic ring system, at least one of the rings is a 3-7 membered cycloalkyl group, which may be fused to a 5 or 6 membered heteroaryl, phenyl group, a 5-7 membered heterocyclyl, or a 5-7 membered cycloalkyl group. Examples of bicyclic ring systems that are embodied in the definition of cycloalkyl include, for example, 2,3-dihydro-1H-indenyl, 4H,5H,6H-cyclopenta[d][1,3]thiazolyl, 1,2,3,4-tetrahydronaphthalenyl, 5,6,7,8-tetrahydroquinolinyl, 5,6,7,8-tetrahydroisoquinolinyl, 5H,6H,7H-cyclopenta(b)pyridinyl, 5H,6H,7H-cyclopenta(c)pyridinyl, and the like.

Aryl, Ar or aromatic ring denotes a mono- or polycyclic aromatic or fully unsaturated cyclic hydrocarbon chain, for example unsubstituted phenyl, naphthyl or biphenyl, furthermore preferably phenyl, naphthyl or biphenyl, each of which is mono-, di- or trisubstituted, for example, by fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, and/or amidyl.

Heterocycle and heterocyclyl refer to saturated or unsaturated non-aromatic monocyclic rings, or partially or fully non-aromatic ring systems which may be bridged, bicyclic ("fused") and/or spiro-connected. Heterocyclyls contain at least one heteroatom selected from O, S and N, and further may include the oxidized forms of sulfur, namely SO and SO$_2$. Monocyclic heterocyclyl groups are preferably 3-7 atoms and includes azetidine, tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, oxolane, oxane, azepane, and the like. When the heterocyclyl group is a part of a bicyclic ring system, at least one of the rings is a 3-7 membered heterocyclic group, which may be fused to a 5 or 6 membered heteroaryl, phenyl group, a 5-7 membered heterocyclyl, or a 5-7 membered cycloalkyl group. Examples of bicyclic ring systems that are embodied in the definition of heterocyclyl include, for example, 2H,3H-furo[2,3-b]pyridine, 2H,3H-furo[2,3-c]pyridine, 2H,3H-furo[2,3-d]pyridine, 2,3-dihydrobenzofuran, octahydro-1H-isoindole, octahydrocyclopenta[c]pyrrole, octahydropyrrolo[3,4-c]pyrrole, 3-azabicyclo[3.1.0]hexane, 3,9-diazabicyclo[4.2.1]non-3-yl, and the like.

Heteroaryl means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoxazolyl, isoindolyl, dihydrobenzothienyl, indolizinyl, cinnolinyl, phthalazinyl, quinazolinyl, naphthyridinyl, carbazolyl, benzdioxinyl, benzodioxolyl, quinoxalinyl, purinyl, furazanyl, thiophenyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

Spiro connected cyclic moieties denote those in which two rings, or ring systems, are connected through a single, common, carbon atom. Spiro compounds may be fully carbocyclic (all carbon) or heterocyclic (having one or more non-carbon atom). Spiro connected cyclic moieties which include two cycles are considered bicyclic; spiro connected cyclic moieties which connect a monocycle with a bicyclic moiety are considered tricyclic moieties. Examples of spiro connected bicyclic moieties include 8-azaspiro[4.5]decane, 2-oxa-8-azaspiro[4.5]decane, 2-azaspiro[3.4]octane, 6-azaspiro[3.4]octane, 2-oxa-6-azaspiro[3.4]octane, 2-azaspiro[4.4]nonane, 1-oxa-9-azaspiro[5.5]undecane, 5-azaspiro[2.4]heptane, 1,3-dihydrospiro-[indene-2,4'-piperidine], 5,7-dihydrospiro[cyclopenta[b]pyridine-6,4'-piperidine], 3H-spiro[furo[2,3-b]pyridine-2,4'-piperidine], 3H-spiro[1-benzofuran-2,4'-piperidine], 4,6-dihydrospiro[cyclopenta[d][1,3]thiazole-5,4'-piperidine], and the like.

Compounds of the present invention may form atropisomers, which are conformational isomers in relation to the pyrimidine moiety present in Formulae I, Ia, Ib, Ic, Id, Ie and If. Atropisomers are stereoisomers arising because of hindered rotation about a single bond, where energy differences due to steric strain or other contributors create a barrier to rotation that is high enough to allow for isolation of individual conformers. There are two different atropisomers that were observed in the compounds of the present invention, which are shown, for example below when R2 is a phenyl substituted with R6, R7 and R8:

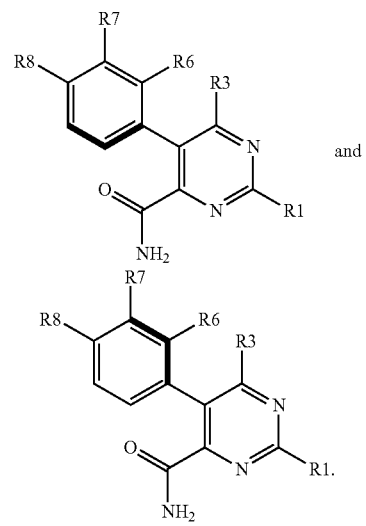

These forms are denoted in the nomenclature of the compounds as being of the M or P forms, depending on the orientation of the aryl or heteroaryl group and the substituent R3 on the pyrimidine ring. Examples of the M and P forms are provided in the examples. Particularly preferred compounds are those with the orientation:

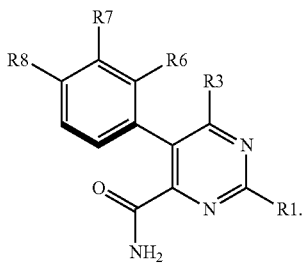

The invention also relates to a pharmaceutical preparation comprising the compound according to the present invention and/or one of its physiologically acceptable salts.

The invention also relates to a pharmaceutical preparation according to the invention of this type, comprising further excipients and/or adjuvants.

In addition, the invention relates to an above pharmaceutical preparation according to the invention, further comprising one or more additional therapeutic agent.

The compound of the present invention can be used in its freebase form. On the other hand, the present invention also encompasses the use of the compounds of the present invention in the form of their pharmaceutically acceptable salts, which can be derived from various organic and inorganic bases by procedures known in the art. The term pharmaceutical salt is used to refer to an ionisable drug that has been combined with a counter-ion to form a neutral complex. Converting a drug into a salt through this process can increase its chemical stability, render the complex easier to administer and allow manipulation of the agent's pharmacokinetic profile. Salt selection is now a common standard operation performed with small ionisable molecules during drug development, and in many cases the drug salts display preferential properties as compared with the parent molecule. Pharmaceutically acceptable salt forms of the compounds of the present invention are for the most part prepared by conventional methods.

In one embodiment, the pharmaceutically acceptable salt of the compound of the invention may be selected from hydrochloride, sodium, sulfate, acetate, phosphate or diphosphate, chloride, potassium, maleate, calcium, citrate, mesylate, nitrate, tartrate, aluminium, gluconate, benzoate, besylate, and edisylate. In one aspect of this embodiment, the pharmaceutically acceptable salt is benzoate, besylate, or edisylate.

A pharmaceutically acceptable salt of the compound of the present invention includes solvates of said salts. The term solvate is taken to mean adductions of inert solvent molecules of the compounds of the present invention which form owing to their mutual attractive force. Solvates are, for example, hydrates, such as monohydrates or dihydrates, or alcoholates, i.e. addition compounds with alcohols, such as, for example, with methanol or ethanol.

Compounds of the general formula I may contain one or more centres of chirality, so that all stereoisomers, enantiomers, diastereomers, etc., of the compounds of the general formula I are also claimed in the present invention Thus, the invention also relates to the optically active forms (stereoisomers), the enantiomers, the racemates, the diastereomers and hydrates and solvates of these compounds.

It is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, or a pharmaceutically acceptable salt thereof, which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^{3}H$ or $^{14}C$, has been incorporated is suitable for medicament and/or substrate tissue distribution assays. These radioisotopes, i.e. tritium ($^{3}H$) and carbon-14 ($^{14}C$), are particularly preferred owing to their simple preparation and excellent detectability. Incorporation of heavier isotopes, for example deuterium ($^{2}H$), into a compound of the formula I has therapeutic advantages owing to the higher metabolic stability of this isotope-labelled compound. Higher metabolic stability translates directly into an increased in-vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant with a readily available isotope-labelled reactant.

In order to manipulate the oxidative metabolism of the compound by way of the primary kinetic isotope effect, deuterium ($^{2}H$) can also be incorporated into a compound of the formula I. The primary kinetic isotope effect is a change in the rate of a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom in a non-exchangeable position, rate differences of $k_M/k_D=2-7$ are typical. If this rate difference is successfully applied to a compound of the formula I that is susceptible to oxidation, the profile of this compound in vivo can thereby be drastically modified and result in improved pharmacokinetic properties.

The replacement of hydrogen by deuterium in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the undesired metabolite, even if the particular oxidation is not a rate-determining step. Further information on the state of the art with respect to deuterium-hydrogen exchange is given, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al., Biochemistry 33(10), 2927-2937, 1994, and Jarman et al., Carcinogenesis 16(4), 683-688, 1993.

The invention also relates to mixtures of the compounds of the formula I according to the invention, for example mixtures of two atropisomers and/or two or more diastereomers, for example in the ratio 1:1, 1:2, 1:3, 1:4, 1:5, 1:10, 1:100 or 1:1000. These are particularly preferably mixtures of two stereoisomeric compounds. In one embodiment of the present invention, mixtures of atropisomers and/or diastereomers contain at least 80% of the desired conformation. In one aspect of this embodiment, the mixture of atropisomers and/or diastereomers contain at least 85% of the desired conformation. In another aspect of this embodiment, the mixture of atropisomers and/or diastereomers contain at least 90% of the desired conformation. In one aspect of this embodiment, the mixture of atropisomers and/or diastereomers contain at least 95% of the desired conformation. In one aspect of this embodiment, the mixture of atropisomers and/or diastereomers contain at least 98% of the desired conformation.

If desired, the starting materials can also be formed in situ by not isolating them from the reaction mixture, but instead immediately converting them further into the compounds of the formula I.

The compounds of the formula I are preferably obtained by liberating them from their functional derivatives by solvolysis, in particular by hydrolysis, or by hydrogenolysis. Preferred starting materials for the solvolysis or hydrogenolysis are those which contain correspondingly protected amino, carboxyl and/or hydroxyl groups instead of one or more free amino, carboxyl and/or hydroxyl groups, preferably those which carry an amino-protecting group instead of an H atom which is connected to an N atom. Preference is furthermore given to starting materials which carry a hydroxyl-protecting group instead of the H atom of a hydroxyl group. Preference is also given to starting materials which carry a protected carboxyl group instead of a free carboxyl group. It is also possible for a plurality of identical or different protected amino, carboxyl and/or hydroxyl groups to be present in the molecule of the starting material. If the protecting groups present are different from one another, they can in many cases be cleaved off selectively.

The term "amino-protecting group" is generally known and relates to groups which are suitable for protecting (blocking) an amino group against chemical reactions, but which can easily be removed after the desired chemical reaction has been carried out elsewhere in the molecule. Typical of such groups are, in particular, unsubstituted or substituted acyl groups, furthermore unsubstituted or substituted aryl (for example 2,4-dinitrophenyl) or aralkyl groups (for example benzyl, 4-nitrobenzyl, triphenylmethyl). Since the amino-protecting groups are removed after the desired reaction or reaction sequence, their type and size is, in addition, not crucial, but preference is given to those having 1-20, in particular 1-8, C atoms. The term "acyl group" is to be understood in the broadest sense in connection with the present process. It encompasses acyl groups derived from aliphatic, araliphatic, aromatic or heterocyclic carboxylic acids or sulfonic acids and, in particular, alkoxycarbonyl, aryloxycarbonyl and especially aralkoxycarbonyl groups. Examples of such acyl groups are alkanoyl, such as acetyl, propionyl, buturyl, aralkanoyl, such as phenylacetyl, aroyl, such as benzoyl or toluyl, aryoxyaklkanoyl, such as phenoxyacetyl, alkyoxycarbonyyl, such as methoxycarbonyl, ethoxycarbonyl, 2,2,2-trichloroethoxycarbonyl, BOC, 2-iodoethoxycaronyl, aralkoxycarbonyl. such as CBZ, 4-methoxybenzyloxycarbonyl or FMOC. Preferred acyl groups are CBZ, FMOC, benzyl and acetyl.

The term "acid-protecting group" or "carboxyl-protecting group" is likewise generally known and relates to groups which are suitable for protecting a —COOH group against chemical reactions, but which can easily be removed after the desired chemical reaction has been carried out elsewhere in the molecule. The use of esters instead of the free acids, for example of substituted and unsubstituted alkyl esters (such as methyl, ethyl, tert-butyl and substituted derivatives thereof), of substituted and unsubstituted benzyl esters or silyl esters, is typical. The type and size of the acid-protecting groups is not crucial, but preference is given to those having 1-20, in particular 1-10, C atoms.

The term "hydroxyl-protecting group" is likewise generally known and relates to groups which are suitable for protecting a hydroxyl group against chemical reactions, but which can easily be removed after the desired chemical reaction has been carried out elsewhere in the molecule. Typical of such groups are the above-mentioned unsubstituted or substituted aryl, aralkyl or acyl groups, furthermore also alkyl groups. Their type and size of the hydroxyl-protecting groups is not crucial, but preference is given to those having 1-20, in particular 1-10, C atoms. Examples of hyrdoxyl-protecting groups are, inter alia, benzyl, p-nitrobenzoyl, p-toluenesulfonyl and acetyl, where benzyl and acetyl are preferred.

Further typical examples of amino-, acid- and hydroxyl-protecting groups are found, for example, in "Greene's Protective Groups in Organic Synthesis", fourth edition, Wiley-Interscience, 2007.

The resultant compounds according to the invention can be separated from the corresponding solution in which they are prepared (for example by centrifugation and washing) and can be stored in another composition after separation, or they can remain directly in the preparation solution. The resultant compounds according to the invention can also be taken up in desired solvents for the particular use.

Conventional work-up steps, such as, for example, addition of water to the reaction mixture and extraction, enable the compounds to be obtained after removal of the solvent. It may be advantageous, for further purification of the product, to follow this with a distillation or crystallisation or to carry out a chromatographic purification.

It has been surprisingly found that the compounds of the formula I may have advantageous efficacy, selectivity, pharmacokinetic properties, dosing schedule, lower toxicity, and/or physical properties as compared to prior art compounds.

The invention furthermore relates to the use of compounds according to the invention for the preparation of a medicament for the treatment of diseases which are caused, promoted and/or propagated by SHP2 or its agonists.

The invention thus also relates, in particular, to a medicament comprising at least one compound according to the invention and/or one of its pharmaceutically acceptable salts, for use in the treatment of physiological and/or pathophysiological states. Particular preference is given, in particular, to physiological and/or pathophysiological states which are connected to SHP2. Physiological and/or pathophysiological states are taken to mean physiological and/or pathophysiological states which are medically relevant, such as, for example, diseases or illnesses and medical disorders, complaints, symptoms or complications and the like, in particular diseases.

The invention furthermore relates to a medicament comprising at least one compound according to the invention and/or one of its pharmaceutically acceptable salts, for use in the treatment of physiological and/or pathophysiological states selected from the group consisting of hyperproliferative diseases and disorders. in one embodiment, the hyperproliferative disease or disorder is cancer.

The invention thus particularly relates to a medicament comprising at least one compound according to the invention and/or one of its pharmaceutically acceptable salts, wherein the cancer is selected from the group consisting of acute and chronic lymphocytic leukemia, acute granulocytic leukemia, adrenal cortex cancer, bladder cancer, brain cancer, breast cancer, cervical cancer, cervical hyperplasia, chorio cancer, colon cancer, endometrial cancer, esophageal cancer, essential thrombocytosis, genitourinary carcinoma, glioma, glioblastoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid and lymphocytic leukemia, neuroblastoma, non-Hodgkin's lymphoma, non-small cell lung cancer, osteogenic sarcoma, ovarian carcinoma, pancreatic carcinoma, polycythemia vera, primary brain carcinoma, primary macroglobulinemia, prostatic cancer, renal cell cancer, rhabdomyosarcoma, skin cancer, small-cell lung cancer, soft-tissue sarcoma, squamous cell cancer, stomach cancer, testicular cancer, thyroid cancer and Wilms' tumor. In one embodiment of the invention, the cancer is selected from non-small cell lung cancer, small cell lung cancer, head and neck carcinoma, breast cancer, esophageal cancer, gastric cancer, colorectal cancer, glioblastoma, pancreatic cancer, osteosarcoma, melanoma and kidney cancer. In one aspect of this embodiment, the cancer is head and neck carcinoma. In another aspect of this embodiment, the cancer is lung cancer. In one aspect of this embodiment, the lung cancer is non-small cell lung cancer. In another aspect of this embodiment, the lung cancer is small cell lung cancer. In another aspect of this embodiment, the cancer is colorectal cancer. In a further aspect of this embodiment, the cancer is esophageal cancer. In another aspect of this embodiment, the cancer is gastric cancer.

The invention further relates to a medicament comprising at least one compound according to the invention and/or one of its pharmaceutically acceptable salts, for use in the treatment of physiological and/or pathophysiological states selected from the group consisting of hyperproliferative and infectious diseases and disorders, wherein the hyperproliferative disease or disorder is selected from the group consisting of age-related macular degeneration, Crohn's disease, cirrhosis, chronic inflammatory-related disorders, proliferative diabetic retinopathy, proliferative vitreoretinopathy, retinopathy of prematurity, granulomatosis, immune hyperproliferation associated with organ or tissue transplantation and an immunoproliferative disease or disorder selected from the group consisting of inflammatory bowel disease, psoriasis, rheumatoid arthritis, systemic lupus erythematosus (SLE), vascular hyperproliferation secondary to retinal hypoxia and vasculitis.

It is intended that the medicaments disclosed above include a corresponding use of the compounds according to the invention for the preparation of a medicament for the treatment of the above physiological and/or pathophysiological states.

It is additionally intended that the medicaments disclosed above include a corresponding method for the treatment of the above physiological and/or pathophysiological states in which at least one compound according to the invention is administered to a patient in need of such a treatment.

The compounds according to the invention preferably exhibit an advantageous biological activity which can easily be demonstrated in enzyme assays and animal experiments, as described in the examples. In such enzyme-based assays, the compounds according to the invention preferably exhibit and cause an inhibiting effect, which is usually documented by $IC_{50}$ values in a suitable range, preferably in the micromolar range and more preferably in the nanomolar range.

The compounds according to the invention can be administered to humans or animals, in particular mammals, such as apes, dogs, cats, rats or mice, and can be used in the therapeutic treatment of the human or animal body and in the combating of the above-mentioned diseases. They can furthermore be used as diagnostic agents or as reagents.

Furthermore, compounds according to the invention can be used for the isolation and investigation of the activity or expression of SHP2. In addition, they are particularly suitable for use in diagnostic methods for diseases in connection with disturbed SHP2 activity. The invention therefore furthermore relates to the use of the compounds according to the invention for the isolation and investigation of the activity or expression of SHP2 or as binders and inhibitors of SHP2.

For diagnostic purposes, the compounds according to the invention can, for example, be radioactively labelled. Examples of radioactive labels are $^{3}H$, $^{14}C$, $^{231}I$ and $^{125}I$. A preferred labelling method is the iodogen method (Fraker et al., 1978). In addition, the compounds according to the invention can be labelled by enzymes, fluorophores and chemophores. Examples of enzymes are alkaline phosphatase, β-galactosidase and glucose oxidase, an example of a fluorophore is fluorescein, an example of a chemophore is luminol, and automated detection systems, for example for fluorescent colorations, are described, for example, in U.S. Pat. Nos. 4,125,828 and 4,207,554.

The invention therefore furthermore relates to pharmaceutical preparations comprising at least one compound of the formula I and/or pharmaceutically acceptable salts thereof. In particular, the invention also relates to pharmaceutical preparations which comprise further excipients and/or adjuvants, and also to pharmaceutical preparations which comprise at least one further medicament active compound.

In particular, the invention also relates to a process for the preparation of a pharmaceutical preparation, characterised in that a compound of the formula I and/or one of its pharmaceutically acceptable salts, is brought into a suitable dosage form together with a solid, liquid or semi-liquid excipient or adjuvant and optionally with one or more additional therapeutic agent.

The pharmaceutical preparations according to the invention can be used as medicaments in human or veterinary medicine. The patient or host can belong to any mammal species, for example a primate species, particularly humans; rodents, including mice, rats and hamsters; rabbits; horses, cattle, dogs, cats, etc. Animal models are of interest for experimental investigations, where they provide a model for the treatment of a human disease.

Suitable carrier substances are organic or inorganic substances which are suitable for enteral (for example oral), parenteral or topical administration and do not react with the novel compounds, for example water, vegetable oils (such as sunflower oil or cod-liver oil), benzyl alcohols, polyethylene glycols, gelatine, carbohydrates, such as lactose or starch, magnesium stearate, talc, lanolin or Vaseline. Owing to his expert knowledge, the person skilled in the art is familiar with which adjuvants are suitable for the desired medicament formulation. Besides solvents, for example water, physiological saline solution or alcohols, such as, for example, ethanol, propanol or glycerol, sugar solutions, such as glucose or mannitol solutions, or a mixture of the said solvents, gel formers, tablet assistants and other active-ingredient carriers, it is also possible to use, for example, lubricants, stabilisers and/or wetting agents, emulsifiers, salts for influencing the osmotic pressure, antioxidants, dispersants, antifoams, buffer substances, flavours and/or aromas or flavour correctants, preservatives, solubilisers or dyes. If desired, preparations or medicaments according to the invention may comprise one or more further active compounds, for example one or more vitamins.

If desired, preparations or medicaments according to the invention may comprise one or more further active compounds and/or one or more action enhancers (adjuvants).

The terms "pharmaceutical formulation" and "pharmaceutical preparation" are used as synonyms for the purposes of the present invention.

As used here, "pharmaceutically acceptable" relates to medicaments, precipitation reagents, excipients, adjuvants, stabilisers, solvents and other agents which facilitate the administration of the pharmaceutical preparations obtained therefrom to a mammal without undesired physiological side effects, such as, for example, nausea, dizziness, digestion problems or the like.

In pharmaceutical preparations for parenteral administration, there is a requirement for isotonicity, euhydration and tolerability and safety of the formulation (low toxicity), of the adjuvants employed and of the primary packaging. Surprisingly, the compounds according to the invention preferably have the advantage that direct use is possible and further purification steps for the removal of toxicologically unacceptable agents, such as, for example, high concentrations of organic solvents or other toxicologically unacceptable adjuvants, are thus unnecessary before use of the compounds according to the invention in pharmaceutical formulations.

The invention particularly preferably also relates to pharmaceutical preparations comprising at least one compound according to the invention in precipitated noncrystalline, precipitated crystalline or in dissolved or suspended form, and optionally excipients and/or adjuvants and/or further pharmaceutical active compounds.

The compounds according to the invention preferably enable the preparation of highly concentrated formulations without unfavourable, undesired aggregation of the compounds according to the invention occurring. Thus, ready-to-use solutions having a high active-ingredient content can be prepared with the aid of compounds according to the invention with aqueous solvents or in aqueous media.

The compounds and/or physiologically acceptable salts and solvates thereof can also be lyophilised and the resultant lyophilisates used, for example, for the preparation of injection preparations.

Pharmaceutical preparations according to the invention may also comprise mixtures of a plurality of compounds according to the invention.

The preparations according to the invention are physiologically well tolerated, easy to prepare, can be dispensed precisely and are preferably stable with respect to assay, decomposition products and aggregates throughout storage and transport and during multiple freezing and thawing processes. They can preferably be stored in a stable manner over a period of at least three months to two years at refrigerator temperature (2-8° C.) and at room temperature (23-27° C.) and 60% relative atmospheric humidity (R.H.).

For example, the compounds according to the invention can be stored in a stable manner by drying and when necessary converted into a ready-to-use pharmaceutical preparation by dissolution or suspension. Possible drying methods are, for example, without being restricted to these examples, nitrogen-gas drying, vacuum-oven drying, lyophilisation, washing with organic solvents and subsequent air drying, liquid-bed drying, fluidised-bed drying, spray drying, roller drying, layer drying, air drying at room temperature and further methods.

The term "effective amount" denotes the amount of a compound of Formula I, or a pharmaceutically acceptable salt thereof, which causes in a tissue, system, animal or human a biological or medical response which is sought or desired, for example, by a researcher or physician.

In addition, the term "therapeutically effective amount" denotes an amount which, compared with a corresponding subject who has not received this amount, has the following consequence: improvement of one or more symptoms, healing, or elimination of a disease, syndrome, disease state, complaint, disorder or prevention of side effects. "Therapeutically effective amount" also encompasses a reduction in the progress of a disease, complaint or disorder. In the context of cancer treatment, a "therapeutically effective amount" can lead to lessening the tumor burden of a subject, delaying the progression of disease ("progression-free survival"), prolonging the life expectancy of the subject (improving the overall survival), slowing or preventing the metastasis of the primary tumor to other tissues and/or improving the quality of life of the subject undergoing treatment. The term "therapeutically effective amount" also encompasses the amounts which are effective for increasing normal physiological function.

One embodiment of the present invention is the use of preparations or medicaments consisting of compounds according to the invention, and/or pharmaceutically acceptable salts thereof, for preparations in dosages of between 0.1 and 500 mg, in particular 1 and 300 mg, per use unit. The daily dose is preferably between 0.001 and 250 mg/kg, in particular 0.01 and 100 mg/kg, of body weight. The preparation can be administered one or more times per day, for example two, three or four times per day. However, the individual dose for a patient depends on a large number of individual factors, such as, for example, on the efficacy of the particular compound used, on the age, body weight, general state of health, sex, nutrition, on the time and method of administration, on the excretion rate, on the combination with other medicaments and on the severity and duration of the particular disease.

A measure of the uptake of a medicament active compound in an organism is its bioavailability. If the medicament active compound is delivered to the organism intravenously in the form of an injection solution, its absolute bioavailability, i.e. the proportion of the pharmaceutical which reaches the systemic blood, i.e. the major circulation, in unchanged form, is 100%. In the case of oral administration of a therapeutic active compound, the active compound is generally in the form of a solid in the formulation and must therefore first be dissolved in order that it is able to overcome the entry barriers, for example the gastrointestinal tract, the oral mucous membrane, nasal membranes or the skin, in particular the stratum corneum, or can be absorbed by the body. Data on the pharmacokinetics, i.e. on the bioavailability, can be obtained analogously to the method of J. Shaffer et al., J. Pharm. Sciences, 88 (1999), 313-318.

Furthermore, medicaments of this type can be prepared by means of one of the processes generally known in the pharmaceutical art.

Medicaments can be adapted for administration via any desired suitable route, for example by the oral (including buccal or sublingual), rectal, pulmonary, nasal, topical (including buccal, sublingual or transdermal), vaginal or parenteral (including subcutaneous, intramuscular, intravenous, intradermal and in particular intraarticular) routes. Medicaments of this type can be prepared by means of all processes known in the pharmaceutical art by, for example, combining the active compound with the excipient(s) or adjuvant(s).

Suitable for enteral administration (oral or rectal) are, in particular, tablets, dragees, capsules, syrups, juices, drops or suppositories, and suitable for topical use are ointments, creams, pastes, lotions, gels, sprays, foams, aerosols, solutions (for example solutions in alcohols, such as ethanol or isopropanol, acetonitrile, DMF, dimethylacetamide, 1,2-propanediol or mixtures thereof with one another and/or with water) or powders. Also, particularly suitable for topical uses are liposomal preparations.

It goes without saying that, besides the constituents particularly mentioned above, the medicaments according to the invention may also comprise other agents usual in the art with respect to the particular type of pharmaceutical formulation.

The invention also relates to a set (kit) consisting of separate packs of a) an effective amount of a compound of the formula I and/or physiologically acceptable salts, derivatives, solvates, prodrugs, stereoisomers and atropisomers thereof, including mixtures thereof in all ratios, and b) an effective amount of a further medicament active compound.

The set comprises suitable containers, such as boxes or cartons, individual bottles, bags or ampoules. The set may, for example, comprise separate ampoules each containing an effective amount of a compound of the formula I and/or pharmaceutically acceptable salts thereof, and an effective amount of one or more additional therapeutic agents in dissolved or lyophilised form.

Furthermore, the medicaments according to the invention can be used in order to provide additive or synergistic effects in certain known therapies and/or can be used in order to restore the efficacy of certain existing therapies.

Besides the compounds according to the invention, the pharmaceutical preparations according to the invention may also comprise one or more additional therapeutic agents, for example for use in the treatment of cancer, other anti-tumor medicaments. For the treatment of the other diseases mentioned, the pharmaceutical preparations according to the invention may also, besides the compounds according to the invention, comprise further medicament active compounds which are known to the person skilled in the art in the treatment thereof.

In one embodiment, a compound of the present invention, or a pharmaceutically acceptable salt thereof, is administered in combination with one or more additional therapeutic agent. In one aspect of this invention, the one or more additional therapeutic agent is an EGFR inhibitor, MET inhibitor, PD-L1 inhibitor, MEK 1/2 inhibitor, TGF-βR pathway inhibitor, or a combination thereof. In another aspect of this embodiment, the one or more additional therapeutic agent is Erbitux, tepotinib, avelumab, Muc1-TGFβR2 Nb, EGFR-Muc1-ADC, pimasertib, pembrolizumab, nivolumab, cemiplimab, atezolizumab, durvalumab, or a combination thereof. In one aspect of this embodiment, the one or more additional therapeutic agents is Erbitux, tepotinib, avelumab, pimasertib or a combination thereof.

In one principal embodiment, methods are provided for enhancing an immune response in a host in need thereof. The immune response can be enhanced by reducing T cell tolerance, including by increasing IFN-γ release, by decreasing regulatory T cell production or activation, or by increasing antigen-specific memory T cell production in a host. In one embodiment, the method comprises administering a compound of the present invention to a host in combination or alternation with an antibody. In one aspect of this embodiment, the antibody is a therapeutic antibody. In one particular embodiment, a method of enhancing efficacy of passive antibody therapy is provided comprising administering a compound of the present invention in combination or alternation with one or more passive antibodies. This method can enhance the efficacy of antibody therapy for treatment of abnormal cell proliferative disorders such as cancer or can enhance the efficacy of therapy in the treatment or prevention of infectious diseases. The compound of the present invention can be administered in combination or alternation with antibodies such as rituximab, herceptin or erbitux, for example.

In another principal embodiment, a method of treating or preventing abnormal cell proliferation is provided comprising administering a compound of the present invention to a host in need thereof substantially in the absence of another anti-cancer agent.

In another principal embodiment, a method of treating or preventing abnormal cell proliferation in a host in need thereof is provided, comprising administering a first a compound of the present invention substantially in combination with a first anti-cancer agent to the host and subsequently administering a second SHP2 antagonist. In one aspect of this embodiment, the second antagonist is administered substantially in the absence of another anti-cancer agent. In another principal embodiment, a method of treating or preventing abnormal cell proliferation in a host in need thereof is provided, comprising administering a compound of the present invention substantially in combination with a first anti-cancer agent to the host and subsequently administering a second anti-cancer agent in the absence of the antagonist.

Thus, the cancer treatment disclosed here can be carried out as therapy with a compound of the present invention or in combination with an operation, irradiation or chemotherapy. Chemotherapy of this type can include the use of one or more additional therapeutic agents selected from the group consisting of:

(i) antiproliferative/antineoplastic/DNA-damaging active compounds and combinations thereof, as used in medical oncology, such as alkylating active compounds (for example cis-platin, parboplatin, cyclophosphamide, nitrogen mustard, melphalan, chlorambucil, busulphan and nitrosoureas); antimetabolites (for example antifolates such as fluoropyrimidines such as 5-fluorouracil and tegafur, raltitrexed, methotrexate, cytosine arabinoside, hydroxyurea and gemcitabine); antitumour antibiotics (for example anthracyclines, such as adriamycin, bleomycin, doxorubicin, daunomycin, epirubicin, idarubicin, mitomycin-C, dactinomycin and mithramycin); antimitotic active compounds (for example vinca alkaloids, such as vincristine, vinblastine, vindesine and vinorelbine, and taxoids, such as taxol and taxotere); topoisomerase inhibitors (for example epipodophyllotoxins, such as etoposide and teniposide, amsacrine, topotecan, irinotecan and camptothecin) and cell-differentiating active compounds (for example all-trans-retinoic acid, 13-cis-retinoic acid and fenretinide);

(ii) cytostatic active compounds, such as anti-oestrogens (for example tamoxifen, toremifene, raloxifene, droloxifene and iodoxyfene), oestrogen receptor regulators (for example fulvestrant), anti-androgens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example anastrozole, letrozole, vorazole and exemestane) and inhibitors of 5α-reductase, such as finasteride;

(iii) active compounds which inhibit cancer invasion including for example metalloproteinase inhibitors, like marimastat, and inhibitors of urokinase plasminogen activator receptor function;

(iv) inhibitors of growth factor function, for example growth factor antibodies, growth factor receptor antibodies, for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033), for example inhibitors of the platelet-derived growth factor family and, for example, inhibitors of the hepatocyte growth factor family;

(v) anti-angiogenic active compounds, such as bevacizumab, angiostatin, endostatin, linomide, batimastat, captopril, cartilage derived inhibitor, genistein, interleukin 12, lavendustin, medroxypregesterone acetate, recombinant human platelet factor 4, tecogalan, thrombospondin, TNP-470, anti-VEGF monoclonal antibody, soluble VEGF-receptor chimaeric protein, anti-VEGF receptor antibodies, anti-PDGF receptors, inhibitors of integrins, tyrosine kinase inhibitors, serine/threonine kinase inhibitors, antisense oligonucleotides, antisense oligodexoynucleotides, siRNAs, anti-VEGF aptamers, pigment epithelium derived factor and compounds which have been published in the international patent applications WO 97/22596, WO 97/30035, WO 97/32856 and WO 98/13354);

(vi) vessel-destroying agents, such as combretastatin A4 and compounds which have been published in the international patent applications WO 99/02166, WO 00/40529, WO 00/41669, WO 01/92224, WO 02/04434 and WO 02/08213;

(vii) antisense therapies, for example those directed to the targets mentioned above, such as ISIS 2503, an anti-Ras antisense;

(viii) gene therapy approaches, including, for example, approaches for replacement of abnormal, modified genes, such as abnormal p53 or abnormal BRCA1 or BRCA2, GDEPT approaches (gene-directed enzyme pro-drug therapy), such as those which use cytosine deaminase, thymidine kinase or a bacterial nitroreductase enzyme, and approaches which increase the tolerance of a patient to chemotherapy or radiotherapy, such as multi-drug resistance therapy; and (ix) immunotherapy approaches, including, for example, ex-vivo and in-vivo approaches for increasing the immunogenicity of tumour cells of a patient, such as transfection with cytokines, such as interleukin 2, interleukin 4 or granulocyte macrophage colony stimulating factor, approaches for decreasing T-cell anergy, approaches using transfected immune cells, such as cytokine-transfected dendritic cells, approaches for use of cytokine-transfected tumour cells and approaches for use of anti-idiotypic antibodies (x) chemotherapeutic agents including foor example abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, epirubicin, epoetin alfa, estramustine, etoposide, exemestane, filgrastim, floxuridine, fludarabine, fluorouracil, fulvestrant and gemcitabine.

Additional therapeutic agents from table 1 can preferably, but not exclusively, be combined with the compounds of the formula I.

TABLE 1

| | | |
|---|---|---|
| Alkylating active compounds | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum active compounds | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 |
| | Ormiplatin | (Hoffmann-La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |

TABLE 1-continued

| | | |
|---|---|---|
| | 5-Fluorouracil | Fludarabine |
| | Floxuridine | Pentostatin |
| | 2-Chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-Fluorodesoxycytidine | Irofulven (MGI Pharrna) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma- Tau) |
| | Irinotecan (CPT-11) | Diflomotecan |
| | 7-ethyl-10-hydroxycamptothecin | (Beaufour-Ipsen) |
| | Topotecan | TAS-103 (Taiho) |
| | Dexrazoxanet (TopoTarget) | Elsamitrucin (Spectrum) |
| | Pixantrone (Novuspharrna) | J-107088 (Merck & Co) |
| | Rebeccamycin analogue | BNP-1350 (BioNumerik) |
| | (Exelixis) | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxorubicin | |
| | Mitoxantron (Novantron) | |
| Antimitotic active compounds | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B |
| | RPR 109881A (Aventis) | (PharmaMar) |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | IDN-5109 (Indena) |
| | Cryptophycin 52 (Eli Lilly) | AVLB (Prescient |
| | Vinflunine (Fabre) | NeuroPharma) |
| | Auristatin PE (Teikoku Hormone) | Azaepothilon B (BMS) |
| | BMS 247550 (BMS) | BNP- 7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate Synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (isotope solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Lonafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | Biricodar dicitrate (Vertex) |
| | MS-209 (Schering AG) | |

TABLE 1-continued

| | | |
|---|---|---|
| Histone acetyl transferase inhibitors | Tacedinaline (Pfizer) SAHA (Aton Pharma) MS-275 (Schering AG) | Pivaloyloxymethyl butyrate (Titan) Depsipeptide (Fujisawa) |
| Metalloproteinase inhibitors | Neovastat (Aeterna Laboratories) Marimastat (British Biotech) | CMT -3 (CollaGenex) BMS-275291 (Celltech) |
| Ribonucleoside reductase inhibitors | Gallium maltolate (Titan) Triapin (Vion) | Tezacitabine (Aventis) Didox (Molecules for Health) |
| TNF-alpha agonists/ antagonists | Virulizin (Lorus Therapeutics) CDC-394 (Celgene) | Revimid (Celgene) |
| Endothelin-A receptor antagonists | Atrasentan (Abbot) ZD-4054 (AstraZeneca) | YM-598 (Yamanouchi) |
| Retinoic acid receptor agonists | Fenretinide (Johnson & Johnson) LGD-1550 (ligand) | Alitretinoin (Ligand) |
| Immunomodulators | Interferon Oncophage (Antigenics) GMK (Progenics) Adenocarcinoma vaccine (Biomira) CTP-37 (AVI BioPharma) JRX-2 (Immuno-Rx) PEP-005 (Peplin Biotech) Synchrovax vaccines (CTL Immuno) Melanoma vaccines (CTL Immuno) p21-RAS vaccine (GemVax) | Dexosome therapy (Anosys) Pentrix (Australian Cancer Technology) JSF-154 (Tragen) Cancer vaccine (Intercell) Norelin (Biostar) BLP-25 (Biomira) MGV (Progenics) I3-Alethin (Dovetail) CLL-Thera (Vasogen) |
| Hormonal and antihormonal active compounds | Oestrogens Conjugated oestrogens Ethynyloestradiol Chlorotrianisene Idenestrol Hydroxyprogesterone caproate Medroxyprogesterone Testosterone Testosterone propionate Fluoxymesterone Methyltestosterone Diethylstilbestrol Megestrol Tamoxifen Toremofin Dexamethasone | Prednisone Methylprednisolone Prednisolone Aminoglutethimide Leuprolide Goserelin Leuporelin Bicalutamide Flutamide Octreotide Nilutamide Mitotan P-04 (Novogen) 2-Methoxyoestradiol (En_-treMed) Arzoxifen (Eli Lilly) |
| Photodynamic active compounds | Talaporfin (Light Sciences) Theralux (Theratechnologies) Motexafin-Gadolinium (Pharmacyclics) | Pd bacteriopheophorbide (Yeda) Lutetium texaphyrin (Pharmacyclics) Hypericin |
| Tyrosine kinase inhibitors | Imatinib (Novartis) Leflunomide(Sugen/Pharmacia) ZDI839 (AstraZeneca) Erlotinib (Oncogene Science) Canertjnib (Pfizer) Squalamine (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmithKline) EKB-509 (Wyeth) EKB-569 (Wyeth) | Kahalide F (PharmaMar) CEP- 701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) |
| Various other active compounds | SR-27897 (CCK-A inhibitor, Sanofi-Synthelabo) Tocladesine (cyclic AMP agonist, Ribapharm) Alvocidib (CDK inhibitor, Aventis) CV-247 (COX-2 inhibitor, Ivy Medical) P54 (COX-2 inhibitor, Phytopharm) CapCell ™ (CYP450 stimulant, Bavarian Nordic) GCS-IOO (gal3 antagonist, GlycoGenesys) | BCX-1777 (PNP inhibitor, BioCryst) Ranpirnase (ribonuclease stimulant, Alfacell) Galarubicin (RNA synthesis inhibitor, Dong-A) Tirapazamine (reducing agent, SRI International) N-Acetylcysteine (reducing agent, Zambon) R-Flurbiprofen (NF-kappaB inhibitor, Encore) 3CPA (NF-kappaB inhibitor, |

TABLE 1-continued

| | |
|---|---|
| G17DT immunogen (gastrin inhibitor, Aphton) | Active Biotech) |
| Efaproxiral (oxygenator, Allos Therapeutics) | Seocalcitol (vitamin D receptor agonist, Leo) |
| PI-88 (heparanase inhibitor, Progen) | 131-I-TM-601 (DNA antagonist, TransMolecular) |
| Tesmilifen (histamine antagonist, YM BioSciences) | Eflornithin (ODC inhibitor, ILEX Oncology) |
| Histamine (histamine H2 receptor agonist, Maxim) | Minodronic acid (osteoclast inhibitor, Yamanouchi) |
| Tiazofurin (IMPDH inhibitor, Ribapharm) | Indisulam (p53 stimulant, Eisai) |
| Cilengitide (integrin antagonist, Merck KGaA) | Aplidin (PPT inhibitor, PharmaMar) |
| SR-31747 (IL-1 antagonist, Sanofi-Synthelabo) | Rituximab (CD20 antibody, Genentech) |
| CCI-779 (mTOR kinase inhibitor, Wyeth) | Gemtuzumab (CD33 antibody, Wyeth Ayerst) |
| Exisulind (PDE-V inhibitor, Cell Pathways) | PG2 (haematopoiesis promoter, Pharmagenesis) |
| CP-461 (PDE-V inhibitor, Cell Pathways) | Immunol ™ (triclosan mouthwash, Endo) |
| AG-2037 (GART inhibitor, Pfizer) | Triacetyluridine (uridine prodrug, Wellstat) |
| WX-UK1 (plasminogen activator inhibitor, Wilex) | SN-4071 (sarcoma agent, Signature BioScience) |
| PBI-1402 (PMN stimulant, ProMetic LifeSciences) | TransMID-107 ™ (immunotoxin, KS Biomedix) |
| Bortezomib (proteasome inhibitor, Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) |
| PT-100 (growth factor agonist, Point Therapeutics) | trans-Retinoic acid (differentiator, NIH) |
| Midostaurin (PKC inhibitor, Novartis) | MX6 (apoptosis promoter, MAXIA) |
| Bryostatin-1 (PKC stimulant, GPC Biotech) | Apomine (apoptosis promoter, ILEX Oncology) |
| CDA-II (apoptosis promoter, Everlife) | Urocidin (apoptosis promoter, Bioniche) |
| SDX-101 (apoptosis promoter, Salmedix) | Ro-31-7453 (apoptosis promoter, La Roche) |
| Ceflatonin (apoptosis promoter, ChemGenex) | Brostallicin (apoptosis promoter, Pharmacia) |

Even without further embodiments, it is assumed that a person skilled in the art will be able to use the above description in the broadest scope. The preferred embodiments should therefore merely be regarded as descriptive disclosure which is absolutely not limiting in any way.

The following examples are thus intended to explain the invention without limiting it. Unless indicated otherwise, percent data denote percent by weight. All temperatures are indicated in degrees Celsius. "Conventional work-up": water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, filtered and evaporated, and the product is purified by chromatography on silica gel and/or by crystallisation.

LIST OF ABBREVIATIONS

AUC Area under the plasma drug concentration-time curve
$C_{max}$ Maximum plasma concentration
CL Clearance
CV Coefficient of variation
CYP Cytochrome P450
DMSO Dimethyl sulfoxide
% F Bioavailability
$f_a$ Fraction absorbed
iv Intravenous
LC-MS/MS Liquid chromatography tandem mass spectrometry
LLOQ Lower limit of quantification
NC Not calculated
NT Not tested
PEG Polyethylene glycol
Pgp Permeability glycoprotein
PK Pharmacokinetic(s)
po Per os (oral)
$t_{1/2}$ Half-life
$t_{max}$ Time at which maximum plasma concentration of drug is reached
UPLC Ultra performance liquid chromatography
$V_{ss}$ Volume of distribution (at steady state)
v/v Volume to volume Example 1: Examples of Compounds of the Present Invention The invention especially relates to the compounds of Table 2 and physiologically acceptable salts, derivatives, solvates, prodrugs, stereoisomers and atropisomers thereof, including mixtures thereof in all ratios.

TABLE 2 examples of compounds of the present invention

| No. | Structure | IUPAC-Name |
|---|---|---|
| 1 | 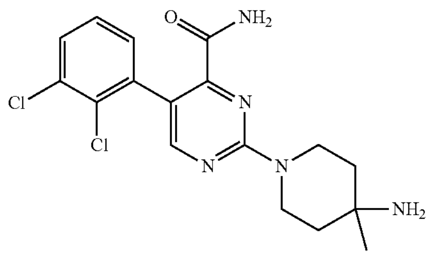 [SMILES: CC1(N)CCN(c2ncc(-c3cccc(Cl)c3Cl)c(C(N)=O)n2)CC1] | 2-(4-amino-4-methylpiperidin-1-yl)-5-(2,3-dichloro-phenyl)-pyrimidine-4-carboxamide |
| 2 | 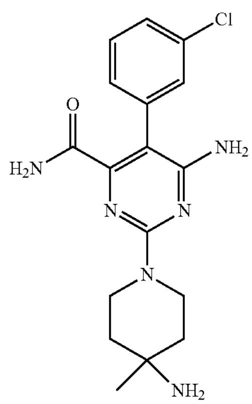 [SMILES: CC1(N)CCN(c2nc(N)c(-c3cccc(Cl)c3)c(C(N)=O)n2)CC1] | 6-Amino-2-(4-amino-4-methyl-piperidin-1-yl)-5-(3-chloro-phenyl)-pyrimidine-4-carboxylic acid amide |
| 3 | 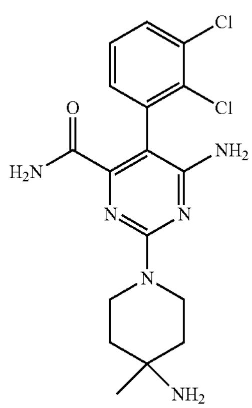 [SMILES: CC1(N)CCN(c2nc(N)c(-c3cccc(Cl)c3Cl)c(C(N)=O)n2)CC1] | 6-Amino-2-(4-amino-4-methyl-piperidin-1-yl)-5-(2,3-dichloro-phenyl)-pyrimidine-4-carboxylic acid amide |
| 4 | 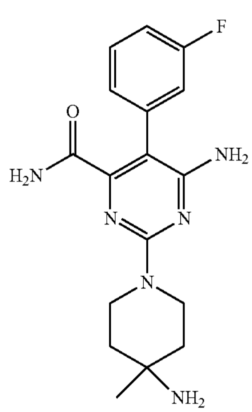 [SMILES: CC1(N)CCN(c2nc(N)c(-c3cccc(F)c3)c(C(N)=O)n2)CC1] | 6-Amino-2-(4-amino-4-methyl-piperidin-1-yl)-5-(3-fluoro-phenyl)-pyrimidine-4-carboxylic acid amide |

TABLE 2-continued examples of compounds of the present invention

| No. | Structure | IUPAC-Name |
|---|---|---|
| 5 | 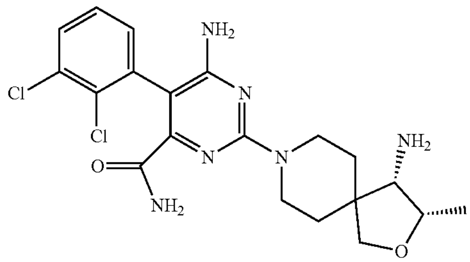 [SMILES: C[C@@H]1OCC2(CCN(c3nc(N)c(-c4cccc(Cl)c4Cl)c(C(N)=O)n3)CC2)[C@@H]1N] | 6-amino-2-[(3S,4S)-4-amino-3-methyl-2-oxa-8-azaspiro-[4.5]decan-8-yl]-5-(2,3-dichlorophenyl)pyrimidine-4-carboxamide |
| 6 | 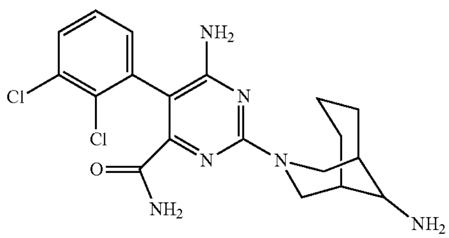 [SMILES: NC(=O)c1nc(N2CC3CCCC(C2)C3N)nc(N)c1-c1cccc(Cl)c1Cl] | 6-amino-2-{9-amino-3-azabicyclo[3.3.1]nonan-3-yl}-5-(2,3-dichlorophenyl)-pyrimidine-4-carboxamide |
| 7 | 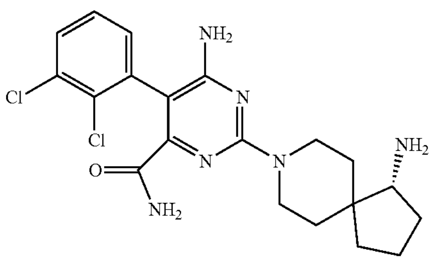 [SMILES: NC(=O)c1nc(N2CCC3(CCC[C@H]3N)CC2)nc(N)c1-c1cccc(Cl)c1Cl] | 6-amino-2-[(1R)-1-amino-8-azaspiro[4.5]decan-8-yl]-5-(2,3-dichlorophenyl)-pyrimidine-4-carboxamide |
| 8 | 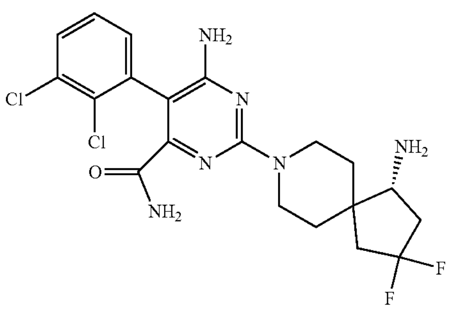 [SMILES: NC(=O)c1nc(N2CCC3(CC2)CC(F)(F)C[C@H]3N)nc(N)c1-c1cccc(Cl)c1Cl] | 6-amino-2-[(1R)-1-amino-3,3-difluoro-8-azaspiro[4.5]-decan-8-yl]-5-(2,3-dichloro-phenyl)-pyrimidine-4-carboxamide |
| 9 | 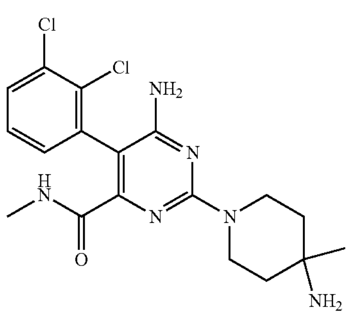 [SMILES: CNC(=O)c1nc(N2CCC(C)(N)CC2)nc(N)c1-c1cccc(Cl)c1Cl] | 6-Amino-2-(4-amino-4-methyl-piperidin-1-yl)-5-(2,3-dichloro-phenyl)-pyrimidine-4-carboxylic acid methylamide |

TABLE 2-continued examples of compounds of the present invention

| No. | Structure | IUPAC-Name |
|---|---|---|
| 10 | 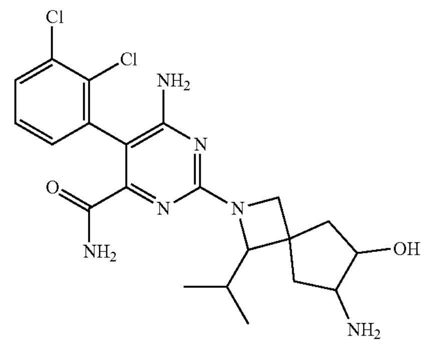 [SMILES: CC(C)C1N(c2nc(N)c(-c3cccc(Cl)c3Cl)c(C(N)=O)n2)CC12CC(N)C(O)C2] | 6-amino-2-[6-amino-7-hydroxy-1-(propan-2-yl)-2-azaspiro[3.4]octan-2-yl]-5-(2,3-dichlorophenyl)-pyrimidine-4-carboxamide |
| 11 | 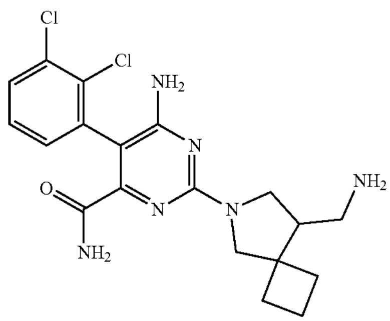 [SMILES: NCC1CN(c2nc(N)c(-c3cccc(Cl)c3Cl)c(C(N)=O)n2)CC12CCC2] | 6-amino-2-[8-(aminomethyl)-6-azaspiro[3.4]octan-6-yl]-5-(2,3-dichlorophenyl)-pyrimidine-4-carboxamide |
| 12 | 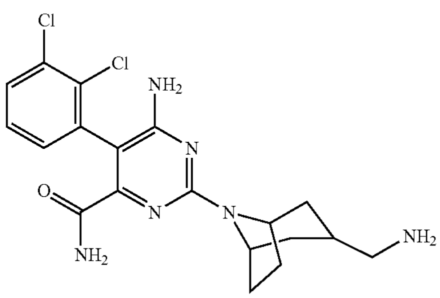 [SMILES: NCC1CC2CCC(C1)N2c1nc(N)c(-c2cccc(Cl)c2Cl)c(C(N)=O)n1] | 6-amino-2-[3-(aminomethyl)-8-azabicyclo[3.2.1]octan-8-yl]-5-(2,3-dichlorophenyl)-pyrimidine-4-carboxamide |
| 13 | 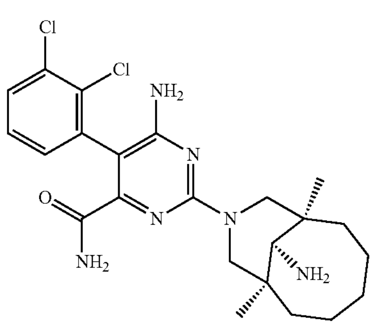 [SMILES: C[C@]12CCCCC[C@](C)(CN(c3nc(N)c(-c4cccc(Cl)c4Cl)c(C(N)=O)n3)C1)[C@H]2N] | 6-amino-5-(2,3-dichlorophenyl)-2-[(1R,7S,11s)-11-amino-1,7-dimethyl-9-azabicyclo[5.3.1]-undecan-9-yl]pyrimidine-4-carboxamide |

TABLE 2-continued examples of compounds of the present invention

| No. | Structure | IUPAC-Name |
|---|---|---|
| 14 | 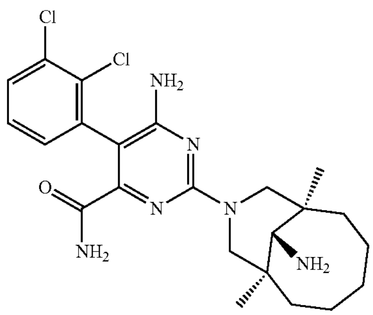 [SMILES: C[C@]12CCCCC[C@](C)(CN(c3nc(N)c(-c4cccc(Cl)c4Cl)c(C(N)=O)n3)C1)[C@@H]2N] | 6-amino-5-(2,3-dichlorophenyl)-2-[(1R,7S,11r)-11-amino-1,7-dimethyl-9-azabicyclo[5.3.1]-undecan-9-yl]pyrimidine-4-carboxamide |
| 15 | 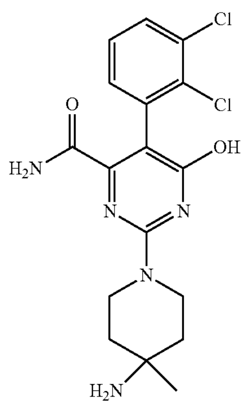 [SMILES: CC1(N)CCN(c2nc(O)c(-c3cccc(Cl)c3Cl)c(C(N)=O)n2)CC1] | 2-(4-Amino-4-methyl-piperidin-1-yl)-5-(2,3-dichloro-phenyl)-6-hydroxy-pyrimidine-4-carboxylic acid amide |
| 16 | 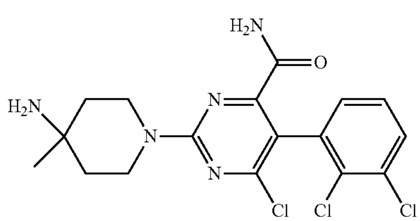 [SMILES: CC1(N)CCN(c2nc(Cl)c(-c3cccc(Cl)c3Cl)c(C(N)=O)n2)CC1] | 2-(4-Amino-4-methyl-piperidin-1-yl)-6-chloro-5-(2,3-dichloro-phenyl)-pyrimidine-4-carboxylic acid amide |
| 17 | 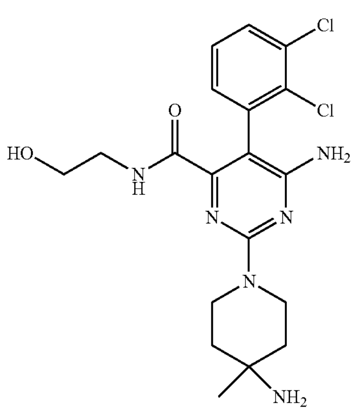 [SMILES: CC1(N)CCN(c2nc(N)c(-c3cccc(Cl)c3Cl)c(C(=O)NCCO)n2)CC1] | 6-Amino-2-(4-amino-4-methyl-piperidin-1-yl)-5-(2,3-dichloro-phenyl)-pyrimidine-4-carboxylic-acid-(2-hydroxy-ethyl)-amide |

TABLE 2-continued examples of compounds of the present invention

| No. | Structure | IUPAC-Name |
|---|---|---|
| 18 | 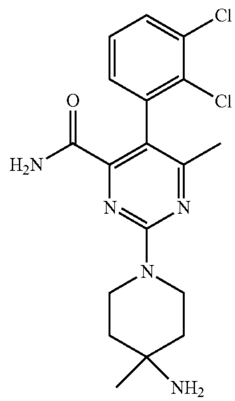 [SMILES: Cc1nc(N2CCC(C)(N)CC2)nc(C(N)=O)c1-c1cccc(Cl)c1Cl] | 2-(4-Amino-4-methyl-piperidin-1-yl)-5-(2,3-dichlorophenyl)-6-methyl-pyrimidine-4-carboxylic acid amide |
| 19 | 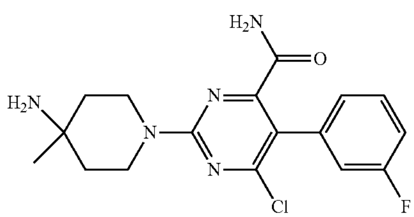 [SMILES: CC1(N)CCN(c2nc(Cl)c(-c3cccc(F)c3)c(C(N)=O)n2)CC1] | 2-(4-Amino-4-methyl-piperidin-1-yl)-6-chloro-5-(3-fluoro-phenyl)-pyrimidine-4-carboxylic acid amide |
| 20 | 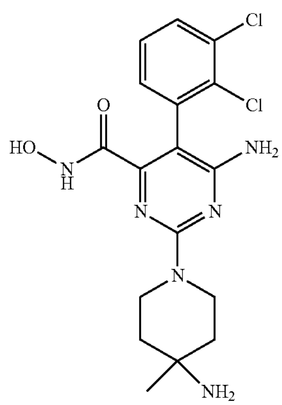 [SMILES: CC1(N)CCN(c2nc(N)c(-c3cccc(Cl)c3Cl)c(C(=O)NO)n2)CC1] | 6-Amino-2-(4-amino-4-methyl-piperidin-1-yl)-5-(2,3-dichloro-phenyl)-pyrimidine-4-carboxylic acid hydroxyamide |
| 21 | 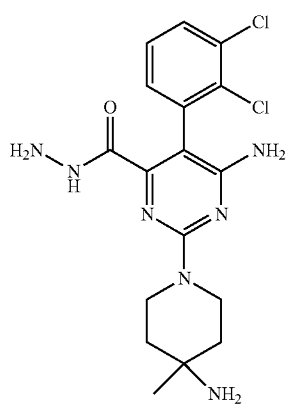 [SMILES: CC1(N)CCN(c2nc(N)c(-c3cccc(Cl)c3Cl)c(C(=O)NN)n2)CC1] | 6-Amino-2-(4-amino-4-methyl-piperidin-1-yl)-5-(2,3-dichloro-phenyl)-pyrimidine-4-carboxylic acid hydrazide |

TABLE 2-continued examples of compounds of the present invention

| No. | Structure | IUPAC-Name |
|---|---|---|
| 22 | 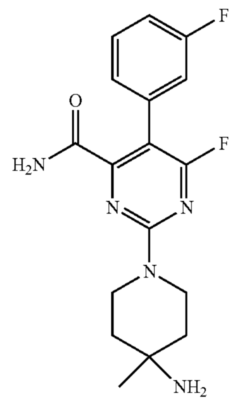 [SMILES: CC1(N)CCN(c2nc(F)c(-c3cccc(F)c3)c(C(N)=O)n2)CC1] | 2-(4-Amino-4-methyl-piperidin-1-yl)-6-fluoro-5-(3-fluoro-phenyl)-pyrimidine-4-carboxylic acid amide |
| 23 | 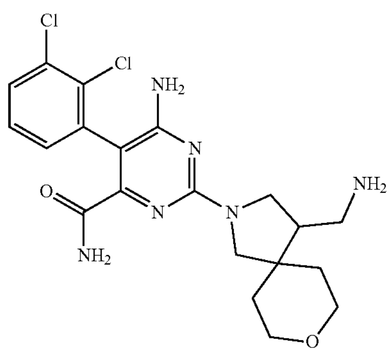 [SMILES: NCC1CN(c2nc(N)c(-c3cccc(Cl)c3Cl)c(C(N)=O)n2)CC12CCOCC2] | 6-amino-2-[4-(aminomethyl)-8-oxa-2-azaspiro[4.5]decan-2-yl]-5-(2,3-dichlorophenyl)-pyrimidine-4-carboxamide |
| 24 | 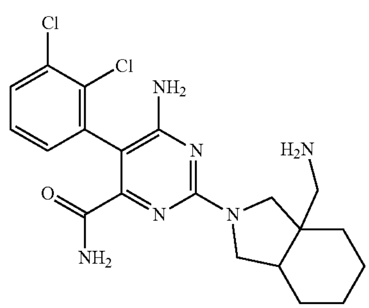 [SMILES: NCC12CCCCC1CN(c1nc(N)c(-c3cccc(Cl)c3Cl)c(C(N)=O)n1)C2] | 2-[3a-(aminomethyl)-octahydro-1H-isoindol-2-yl]-6-amino-5-(2,3-dichlorophenyl)-pyrimidine-4-carboxamide |
| 25 | 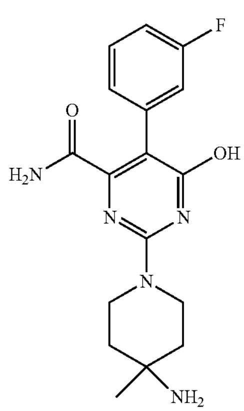 [SMILES: CC1(N)CCN(c2nc(O)c(-c3cccc(F)c3)c(C(N)=O)n2)CC1] | 2-(4-Amino-4-methyl-piperidin-1-yl)-5-(3-fluoro-phenyl)-6-hydroxy-pyrimidine-4-carboxylic acid amide |

TABLE 2-continued examples of compounds of the present invention

| No. | Structure | IUPAC-Name |
|---|---|---|
| 26 | 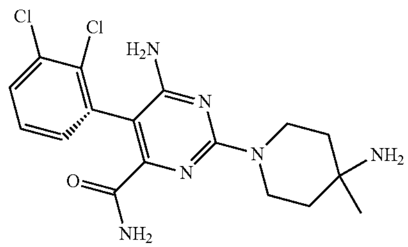 | (4M)-6-amino-2-(4-amino-4-methylpiperidin-1-yl)-5-(2,3-dichlorophenyl)pyrimidine-4-carboxamide |
| 27 | 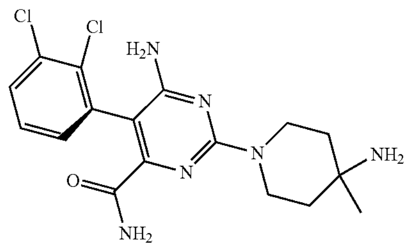 | (4P)-6-amino-2-(4-amino-4-methylpiperidin-1-yl)-5-(2,3-dichlorophenyl)pyrimidine-4-carboxamide |
| 28 | 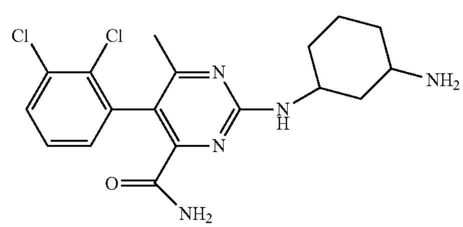 [SMILES: Cc1nc(NC2CCCC(N)C2)nc(C(N)=O)c1-c1cccc(Cl)c1Cl] | 2-(3-Amino-cyclohexyl-amino)-5-(2,3-dichloro-phenyl)-6-methyl-pyrimidine-4-carboxylic acid amide |
| 29 | 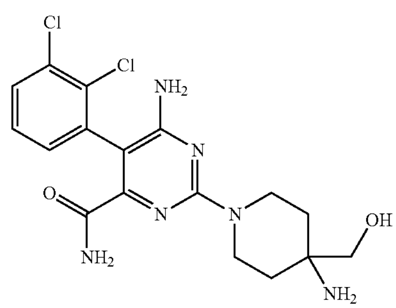 [SMILES: NC(=O)c1nc(N2CCC(N)(CO)CC2)nc(N)c1-c1cccc(Cl)c1Cl] | 6-amino-2-[4-amino-4-(hydroxymethyl)piperidin-1-yl]-5-(2,3-dichlorophenyl)-pyrimidine-4-carboxamide |
| 30 | 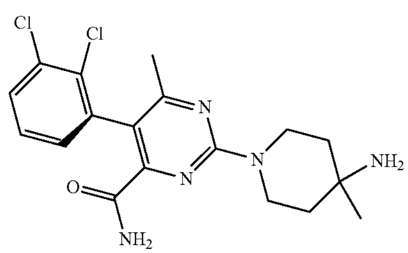 | (4M)-2-(4-amino-4-methyl-piperidin-1-yl)-5-(2,3-dichloro-phenyl)-6-methylpyrimidine-4-carboxamide |
| 31 | 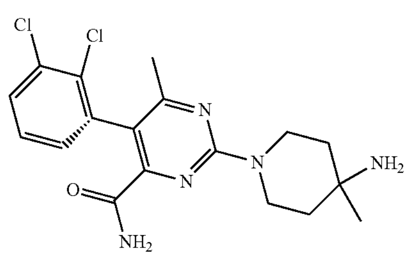 | (4P)-2-(4-amino-4-methyl-piperidin-1-yl)-5-(2,3-dichloro-phenyl)-6-methylpyrimidine-4-carboxamide |

TABLE2-continued examples of compounds of the present invention

| No. | Structure | IUPAC-Name |
|---|---|---|
| 32 | 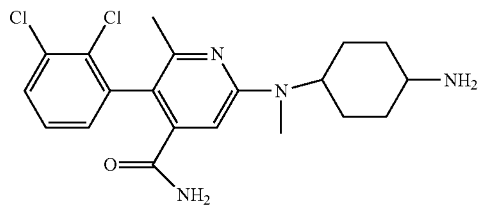 [SMILES: Cc1nc(N(C)C2CCC(N)CC2)cc(C(N)=O)c1-c1cccc(Cl)c1Cl] | 2-[(4-Amino-cyclohexyl)-methyl-amino]-5-(2,3-dichlorophenyl)-6-methyl-pyrimidine-4-carboxylic acid amide |
| 33 | 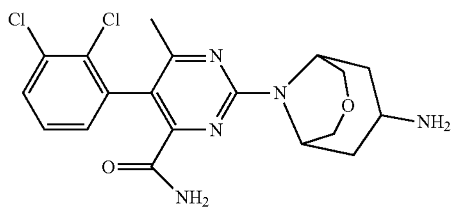 [SMILES: Cc1nc(N2C3COCC2CC(N)C3)nc(C(N)=O)c1-c1cccc(Cl)c1Cl] | 2-(7-Amino-3-oxa-9-aza-bicyclo[3.3.1]non-9-yl)-5-(2,3-dichlorophenyl)-6-methyl-pyrimidine-4-carboxylic acid amide |
| 34 | 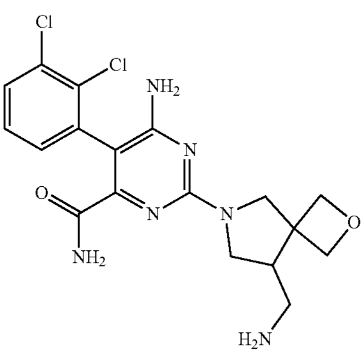 [SMILES: NCC1CN(c2nc(N)c(-c3cccc(Cl)c3Cl)c(C(N)=O)n2)CC12COC2] | 6-amino-2-[8-(aminomethyl)-2-oxa-6-azaspiro[3.4]octan-6-yl]-5-(2,3-dichloro-phenyl)pyrimidine-4-carboxamide |
| 35 | 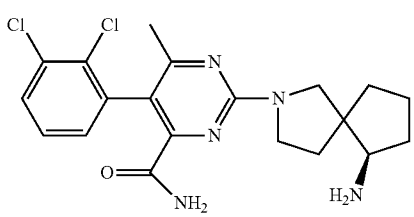 [SMILES: Cc1nc(N2CCC3(CCC[C@H]3N)C2)nc(C(N)=O)c1-c1cccc(Cl)c1Cl] | 2-((R)-6-Amino-2-aza-spiro[4.4]non-2-yl)-5-(2,3-dichloro-phenyl)-6-methyl-pyrimidine-4-carboxylic acid amide |
| 36 | 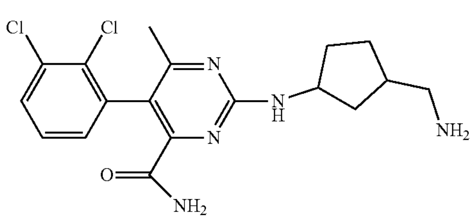 [SMILES: Cc1nc(NC2CCC(CN)C2)nc(C(N)=O)c1-c1cccc(Cl)c1Cl] | 2-(3-Aminomethyl-cyclopentylamino)-5-(2,3-dichloro-phenyl)-6-methyl-pyrimidine-4-carboxylic acid amide |
| 37 | 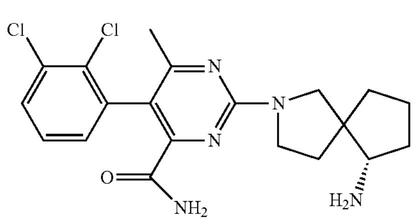 [SMILES: Cc1nc(N2CCC3(CCC[C@@H]3N)C2)nc(C(N)=O)c1-c1cccc(Cl)c1Cl] | 2-((S)-6-Amino-2-aza-spiro[4.4]non-2-yl)-5-(2,3-dichloro-phenyl)-6-methyl-pyrimidine-4-carboxylic acid amide |

TABLE2-continued examples of compounds of the present invention

| No. | Structure | IUPAC-Name |
| --- | --- | --- |
| 38 | 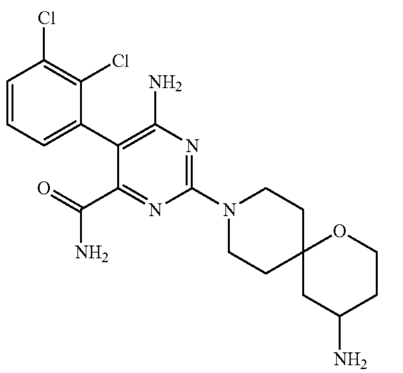 [SMILES: NC(=O)c1nc(N2CCC3(CC2)CC(N)CCO3)nc(N)c1-c1cccc(Cl)c1Cl] | 6-amino-2-{4-amino-1-oxa-9-azaspiro[5.5]undecan-9-yl}-5-(2,3-dichlorophenyl)pyrimidine-4-carboxamide |
| 39 | 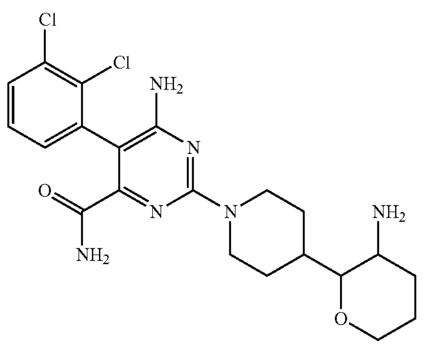 [SMILES: NC(=O)c1nc(N2CCC(C3OCCCC3N)CC2)nc(N)c1-c1cccc(Cl)c1Cl] | 6-amino-2-[4-(3-aminooxan-2-yl)piperidin-1-yl]-5-(2,3-dichlorophenyl)pyrimidine-4-carboxamide |
| 40 | 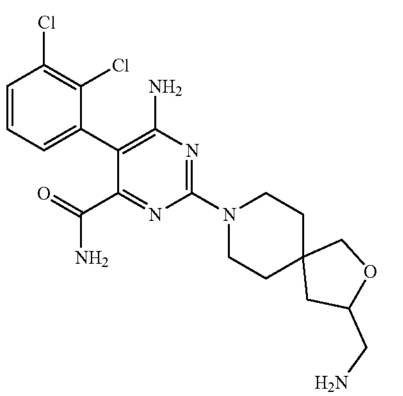 [SMILES: NCC1CC2(CCN(c3nc(N)c(-c4cccc(Cl)c4Cl)c(C(N)=O)n3)CC2)CO1] | 6-amino-2-[3-(aminomethyl)-2-oxa-8-azaspiro[4.5]decan-8-yl]-5-(2,3-dichlorophenyl)pyrimidine-4-carboxamide |
| 41 | 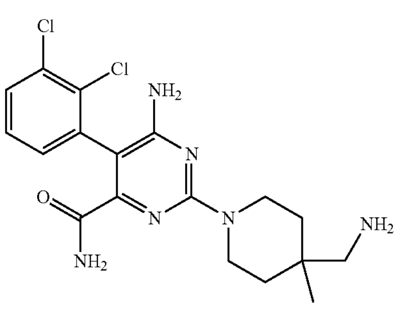 [SMILES: CC1(CN)CCN(c2nc(N)c(-c3cccc(Cl)c3Cl)c(C(N)=O)n2)CC1] | 6-amino-2-[4-(aminomethyl)-4-methylpiperidin-1-yl]-5-(2,3-dichlorophenyl)pyrimidine-4-carboxamide |

TABLE 2-continued examples of compounds of the present invention

| No. | Structure | IUPAC-Name |
|---|---|---|
| 42 | 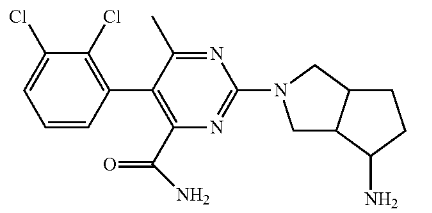 [SMILES: Cc1nc(N2CC3CCC(N)C3C2)nc(C(N)=O)c1-c1cccc(Cl)c1Cl] | 2-(4-Amino-hexahydro-cyclopenta[c]pyrrol-2-yl)-5-(2,3-dichloro-phenyl)-6-methyl-pyrimidine-4-carboxylic acid amide |
| 43 | 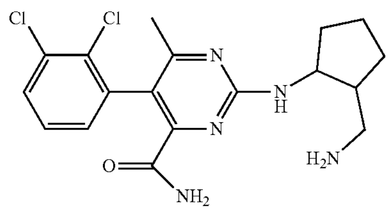 [SMILES: Cc1nc(NC2CCCC2CN)nc(C(N)=O)c1-c1cccc(Cl)c1Cl] | 2-(2-Aminomethyl-cyclopentylamino)-5-(2,3-dichloro-phenyl)-6-methyl-pyrimidine-4-carboxylic acid amide |
| 44 | 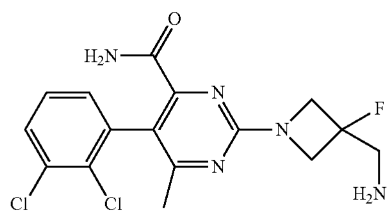 [SMILES: Cc1nc(N2CC(F)(CN)C2)nc(C(N)=O)c1-c1cccc(Cl)c1Cl] | 2-(3-Aminomethyl-3-fluoro-azetidin-1-yl)-5-(2,3-dichloro-phenyl)-6-methyl-pyrimidine-4-carboxylic acid amide |
| 45 | 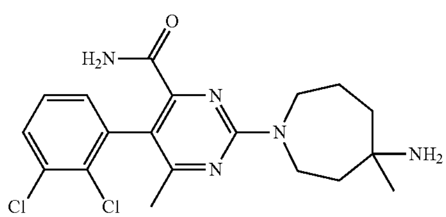 [SMILES: Cc1nc(N2CCCC(C)(N)CC2)nc(C(N)=O)c1-c1cccc(Cl)c1Cl] | 2-(4-Amino-4-methyl-azepan-1-yl)-5-(2,3-dichloro-phenyl)-6-methyl-pyrimidine-4-carboxylic acid amide |
| 46 | 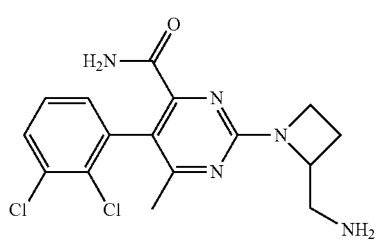 [SMILES: Cc1nc(N2CCC2CN)nc(C(N)=O)c1-c1cccc(Cl)c1Cl] | 2-(2-Aminomethyl-azetidin-1-yl)-5-(2,3-dichloro-phenyl)-6-methyl-pyrimidine-4-carboxylic acid amide |
| 47 | 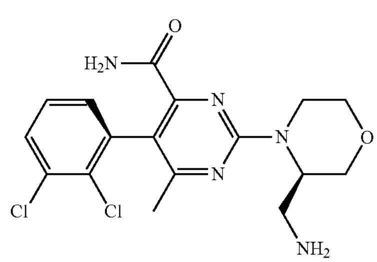 | (4P)-2-[(3R)-3-(aminomethyl)morpholin-4-yl]-5-(2,3-dichlorophenyl)-6-methylpyrimidine-4-carboxamide |

TABLE2-continued examples of compounds of the present invention

| No. | Structure | IUPAC-Name |
| --- | --- | --- |
| 48 | 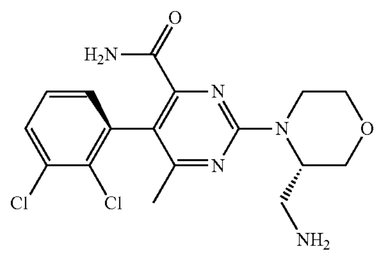 | (4P)-2-[(3S)-3-(aminomethyl)morpholin-4-yl]-5-(2,3-dichlorophenyl)-6-methylpyrimidine-4-carboxamide |
| 49 | 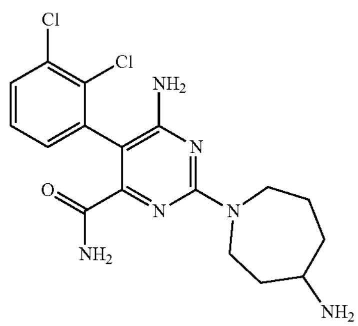 [SMILES: NC(=O)c1nc(N2CCCC(N)CC2)nc(N)c1-c1cccc(Cl)c1Cl] | 6-amino-2-(4-aminoazepan-1-yl)-5-(2,3-dichlorophenyl)-pyrimidine-4-carboxamide |
| 50 | 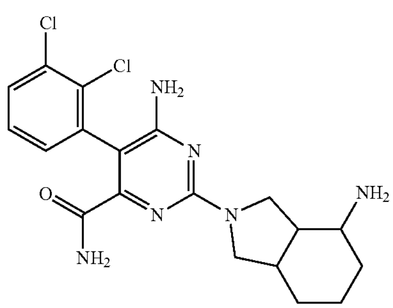 [SMILES: NC(=O)c1nc(N2CC3CCCC(N)C3C2)nc(N)c1-c1cccc(Cl)c1Cl] | 6-amino-2-(4-amino-octahydro-1H-isoindol-2-yl)-5-(2,3-dichlorophenyl)pyrimidine-4-carboxamide |
| 51 | 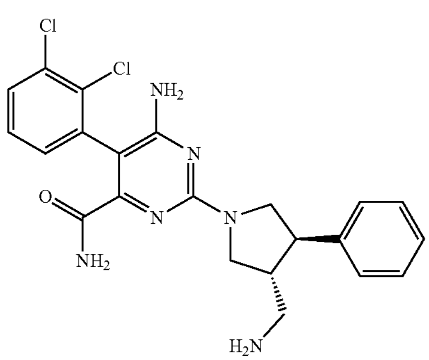 [SMILES: NC[C@@H]1CN(c2nc(N)c(-c3cccc(Cl)c3Cl)c(C(N)=O)n2)C[C@H]1c1ccccc1] | 6-amino-2-[(3R,4R)-3-(aminomethyl)-4-phenylpyrrolidin-1-yl]-5-(2,3-dichlorophenyl)pyrimidine-4-carboxamide |
| 52 | | 6-amino-2-({4-azaspiro[bicyclo[2.2.2]octane-2,2'-oxan]-4'-yl}amino)-5-(2,3-dichlorophenyl)pyrimidine-4-carboxamide |

## TABLE 2-continued examples of compounds of the present invention

| No. | Structure | IUPAC-Name |
|---|---|---|
| 53 | 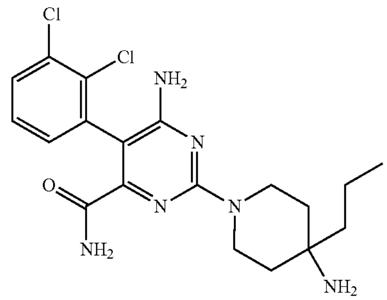 [SMILES: CCCC1(N)CCN(c2nc(N)c(-c3cccc(Cl)c3Cl)c(C(N)=O)n2)CC1] | 6-amino-2-(4-amino-4-propylpiperidin-1-yl)-5-(2,3-dichloro-phenyl)pyrimidine-4-carboxamide |
| 54 | 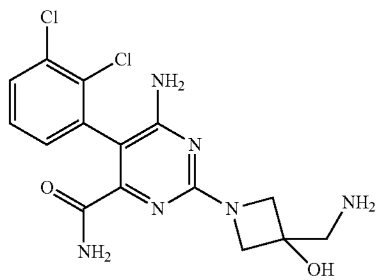 [SMILES: NCC1(O)CN(c2nc(N)c(-c3cccc(Cl)c3Cl)c(C(N)=O)n2)C1] | 6-amino-2-[3-(aminomethyl)-3-hydroxyazetidin-1-yl]-5-(2,3-dichlorophenyl)-pyrimidine-4-carboxamide |
| 55 | 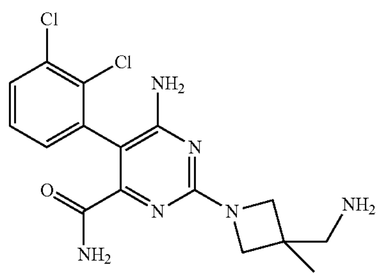 [SMILES: CC1(CN)CN(c2nc(N)c(-c3cccc(Cl)c3Cl)c(C(N)=O)n2)C1] | 6-amino-2-[3-(aminomethyl)-3-methylazetidin-1-yl]-5-(2,3-dichlorophenyl)pyrimidine-4-carboxamide |
| 56 | 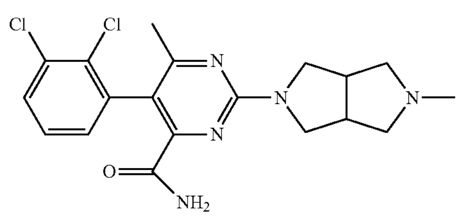 [SMILES: Cc1nc(N2CC3CN(C)CC3C2)nc(C(N)=O)c1-c1cccc(Cl)c1Cl] | 5-(2,3-Dichloro-phenyl)-6-methyl-2-(5-methyl-hexahydro-pyrrolo[3,4-c]pyrrol-2-yl)-pyrimidine-4-carboxylic acid amide |
| 57 | 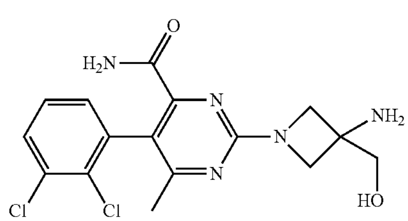 [SMILES: Cc1nc(N2CC(N)(CO)C2)nc(C(N)=O)c1-c1cccc(Cl)c1Cl] | 2-(3-Amino-3-hydroxymethyl-azetidin-1-yl)-5-(2,3-dichloro-phenyl)-6-methyl-pyrimidine-4-carboxylic acid amide |
| 58 | 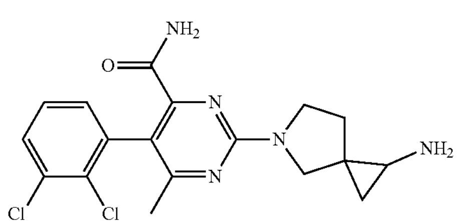 [SMILES: Cc1nc(N2CCC3(CC3N)C2)nc(C(N)=O)c1-c1cccc(Cl)c1Cl] | 2-(1-Amino-5-aza-spiro[2.4]hept-5-yl)-5-(2,3-dichloro-phenyl)-6-methyl-pyrimidine-4-carboxylic acid amide |

TABLE 2-continued examples of compounds of the present invention

| No. | Structure | IUPAC-Name |
|---|---|---|
| 60 | 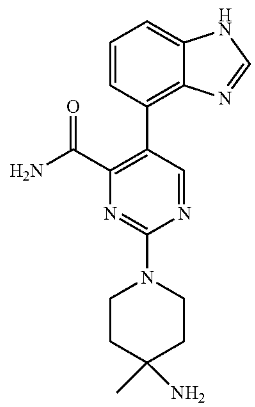 [SMILES: CC1(N)CCN(c2ncc(-c3cccc4[nH]cnc34)c(C(N)=O)n2)CC1] | 2-(4-Amino-4-methyl-piperidin-1-yl)-5-(1H-benzoimidazol-4-yl)-pyrimidine-4-carboxylic acid amide |
| 61 | 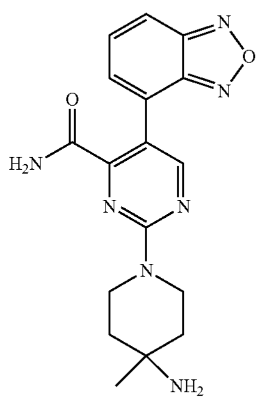 [SMILES: CC1(N)CCN(c2ncc(-c3cccc4nonc34)c(C(N)=O)n2)CC1] | 2-(4-Amino-4-methyl-piperidin-1-yl)-5-benzo[1,2,5]-oxadiazol-4-yl-pyrimidine-4-carboxylic acid amide |
| 62 | 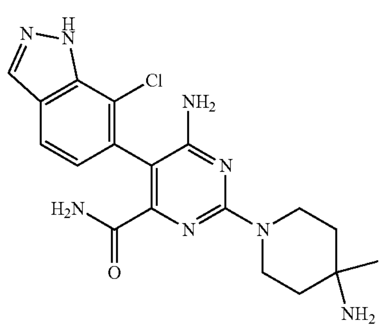 [SMILES: CC1(N)CCN(c2nc(N)c(-c3ccc4cn[nH]c4c3Cl)c(C(N)=O)n2)CC1] | 6-Amino-2-(4-amino-4-methyl-piperidin-1-yl)-5-(7-chloro-1H-indazol-6-yl)-pyrimidine-4-carboxylic acid amide |
| 63 | 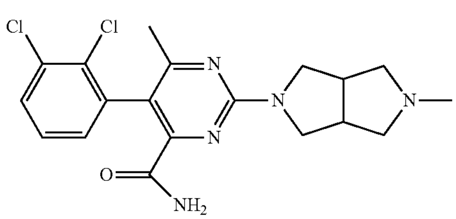 [SMILES: Cc1nc(N2CC3CN(C)CC3C2)nc(C(N)=O)c1-c1cccc(Cl)c1Cl] | 5-(2,3-Dichloro-phenyl)-6-methyl-2-(5-methyl-hexahydro-pyrrolo[3,4-c]pyrrol-2-yl)-pyrimidine-4-carboxylic acid amide |

TABLE 2-continued examples of compounds of the present invention

| No. | Structure | IUPAC-Name |
|---|---|---|
| 64 | 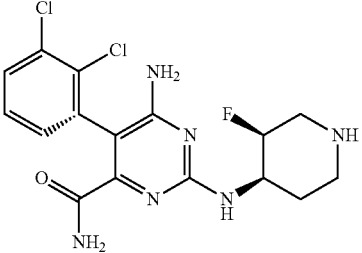 | (5M)-6-amino-5-(2,3-dichlorophenyl)-2-{[(3S,4R)-3-fluoropiperidin-4-yl]amino}-pyrimidine-4-carboxamide |
| 65 | 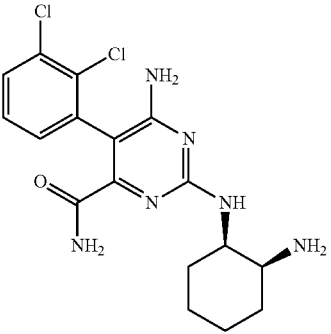 [SMILES: NC(=O)c1nc(N[C@@H]2CCCC[C@@H]2N)nc(N)c1-c1cccc(Cl)c1Cl] | 6-amino-2-{[(1R,2S)-2-aminocyclohexyl]amino}-5-(2,3-dichlorophenyl)-pyrimidine-4-carboxamide |
| 66 | 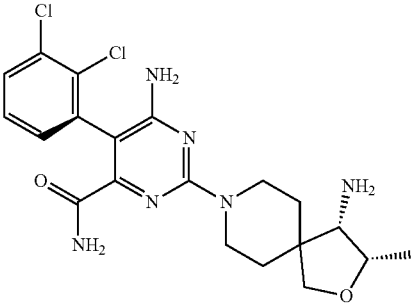 | (5P)-6-amino-2-[(3S,4S)-4-amino-3-methyl-2-oxa-8-azaspiro[4.5]decan-8-yl]-5-(2,3-dichlorophenyl)-pyrimidine-4-carboxamide |
| 67 | 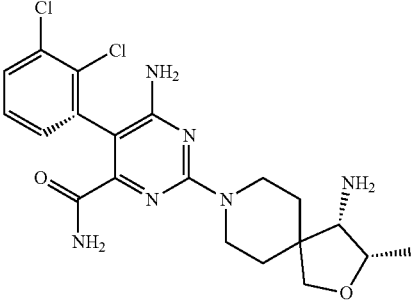 | (5M)-6-amino-2-[(3S,4S)-4-amino-3-methyl-2-oxa-8-azaspiro[4.5]decan-8-yl]-5-(2,3-dichlorophenyl)-pyrimidine-4-carboxamide |
| 68 | 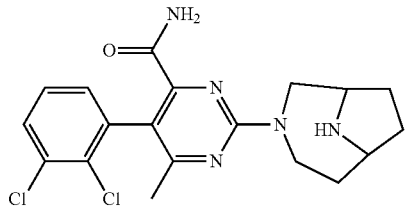 [SMILES: Cc1nc(N2CCC3CCC(C2)N3)nc(C(N)=O)c1-c1cccc(Cl)c1Cl] | 2-(3,9-Diaza-bicyclo[4.2.1]-non-3-yl)-5-(2,3-dichloro-phenyl)-6-methyl-pyrimidine-4-carboxylic acid amide |

TABLE 2-continued examples of compounds of the present invention

| No. | Structure | IUPAC-Name |
|---|---|---|
| 69 | 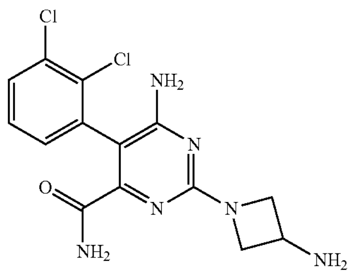 [SMILES: NC(=O)c1nc(N2CC(N)C2)nc(N)c1-c1cccc(Cl)c1Cl] | 6-amino-2-(3-aminoazetidin-1-yl)-5-(2,3-dichlorophenyl)-pyrimidine-4-carboxamide |
| 70 | 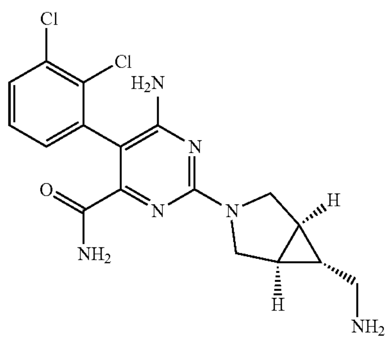 [SMILES: NC[C@@H]1[C@H]2CN(c3nc(N)c(-c4cccc(Cl)c4Cl)c(C(N)=O)n3)C[C@@H]12] | 6-amino-2-[(1R,5S,6R)-6-(aminomethyl)-3-azabicyclo-[3.1.0]hexan-3-yl]-5-(2,3-dichlorophenyl)pyrimidine-4-carboxamide |
| 71 | 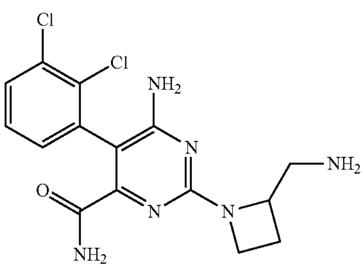 [SMILES: NCC1CCN1c1nc(N)c(-c2cccc(Cl)c2Cl)c(C(N)=O)n1] | 6-amino-2-[2-(aminomethyl)-azetidin-1-yl]-5-(2,3-dichlorophenyl)pyrimidine-4-carboxamide |
| 72 | 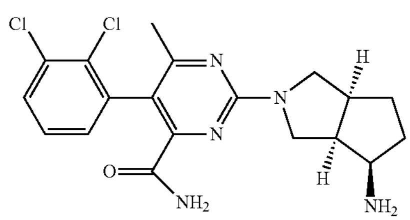 [SMILES: Cc1nc(N2C[C@H]3CC[C@@H](N)[C@H]3C2)nc(C(N)=O)c1-c1cccc(Cl)c1Cl] | 2-((3aR,4R,6aS)-4-Amino-hexahydro-cyclopenta-[c]pyrrol-2-yl)-5-(2,3-dichloro-phenyl)-6-methyl-pyrimidine-4-carboxylic acid amide |
| 73 | 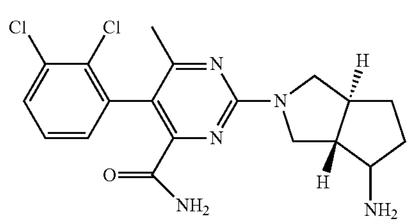 [SMILES: Cc1nc(N2C[C@H]3CCC(N)[C@@H]3C2)nc(C(N)=O)c1-c1cccc(Cl)c1Cl] | 2-((3aS,6aS)-4-Amino-hexahydro-cyclopenta-[c]pyrrol-2-yl)-5-(2,3-dichloro-phenyl)-6-methyl-pyrimidine-4-carboxylic acid amide |
| 74 | 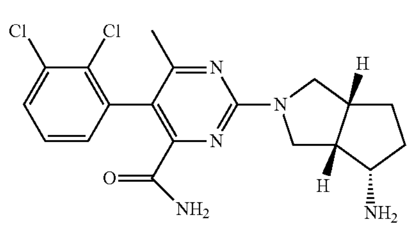 [SMILES: Cc1nc(N2C[C@@H]3CC[C@H](N)[C@@H]3C2)nc(C(N)=O)c1-c1cccc(Cl)c1Cl] | 2-((3aS,4S,6aR)-4-Amino-hexahydro-cyclopenta-[c]pyrrol-2-yl)-5-(2,3-dichloro-phenyl)-6-methyl-pyrimidine-4-carboxylic acid amide |

TABLE 2-continued examples of compounds of the present invention

| No. | Structure | IUPAC-Name |
|---|---|---|
| 75 | 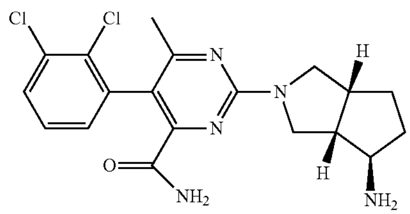 [SMILES: Cc1nc(N2C[C@@H]3CC[C@@H](N)[C@@H]3C2)nc(C(N)=O)c1-c1cccc(Cl)c1Cl] | 2-((3aS,4R,6aR)-4-Amino-hexahydro-cyclopenta[c]pyrrol-2-yl)-5-(2,3-dichloro-phenyl)-6-methyl-pyrimidine-4-carboxylic acid amide |
| 76 | 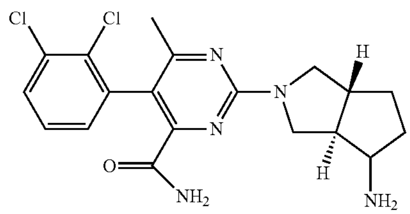 [SMILES: Cc1nc(N2C[C@@H]3CCC(N)[C@H]3C2)nc(C(N)=O)c1-c1cccc(Cl)c1Cl] | 2-((3aR,6aR)-4-Amino-hexahydro-cyclopenta-[c]pyrrol-2-yl)-5-(2,3-dichloro-phenyl)-6-methyl-pyrimidine-4-carboxylic acid amide |
| 77 | 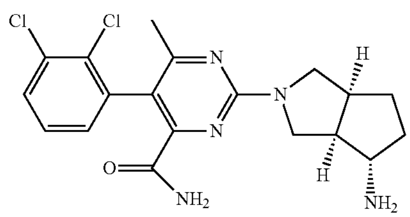 [SMILES: Cc1nc(N2C[C@H]3CC[C@H](N)[C@H]3C2)nc(C(N)=O)c1-c1cccc(Cl)c1Cl] | 2-((3aR,4S,6aS)-4-Amino-hexahydro-cyclopenta-[c]pyrrol-2-yl)-5-(2,3-dichloro-phenyl)-6-methyl-pyrimidine-4-carboxylic acid amide |
| 78 | 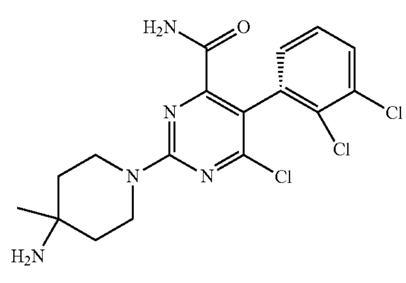 | (4M)-2-(4-amino-4-methylpiperidin-1-yl)-6-chloro-5-(2,3-dichlorophenyl)-pyrimidine-4-carboxamide |
| 79 | 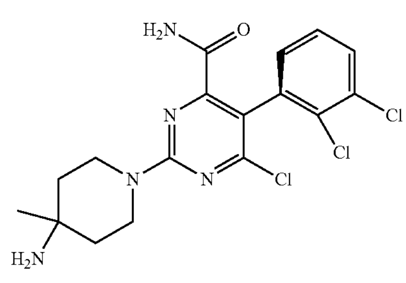 | (4P)-2-(4-amino-4-methylpiperidin-1-yl)-6-chloro-5-(2,3-dichlorophenyl)-pyrimidine-4-carboxamide |
| 80 | 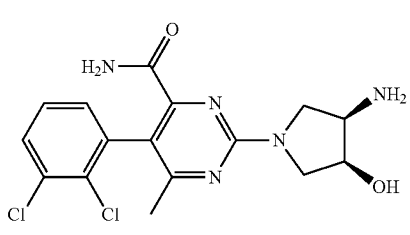 [SMILES: Cc1nc(N2C[C@@H](N)[C@@H](O)C2)nc(C(N)=O)c1-c1cccc(Cl)c1Cl] | 2-((3R,4S)-3-Amino-4-hydroxy-pyrrolidin-1-yl)-5-(2,3-dichloro-phenyl)-6-methyl-pyrimidine-4-carboxylic acid amide |

TABLE 2-continued examples of compounds of the present invention

| No. | Structure | IUPAC-Name |
|---|---|---|
| 81 | 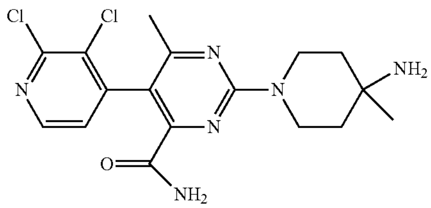 [SMILES: Cc1nc(N2CCC(C)(N)CC2)nc(C(N)=O)c1-c1ccnc(Cl)c1Cl] | 2-(4-Amino-4-methyl-piperidin-1-yl)-5-(2,3-dichloro-pyridin-4-yl)-6-methyl-pyrimidine-4-carboxylic acid amide |
| 82 | 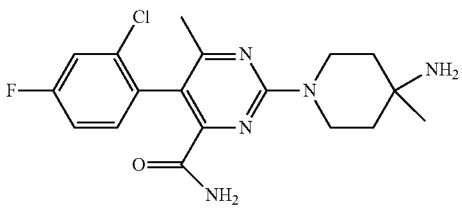 [SMILES: Cc1nc(N2CCC(C)(N)CC2)nc(C(N)=O)c1-c1ccc(F)cc1Cl] | 2-(4-Amino-4-methyl-piperidin-1-yl)-5-(2-chloro-4-fluoro-phenyl)-6-methyl-pyrimidine-4-carboxylic acid amide |
| 83 | 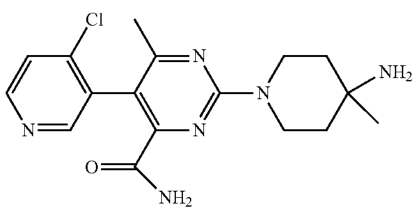 [SMILES: Cc1nc(N2CCC(C)(N)CC2)nc(C(N)=O)c1-c1cnccc1Cl] | 2-(4-Amino-4-methyl-piperidin-1-yl)-5-(4-chloro-pyridin-3-yl)-6-methyl-pyrimidine-4-carboxylic acid amide |
| 84 | 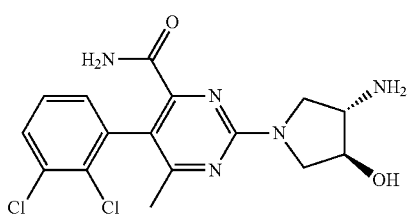 [SMILES: Cc1nc(N2C[C@H](N)[C@@H](O)C2)nc(C(N)=O)c1-c1cccc(Cl)c1Cl] | 2-((3S,4S)-3-Amino-4-hydroxy-pyrrolidin-1-yl)-5-(2,3-dichloro-phenyl)-6-methyl-pyrimidine-4-carboxylic acid amide |
| 85 | 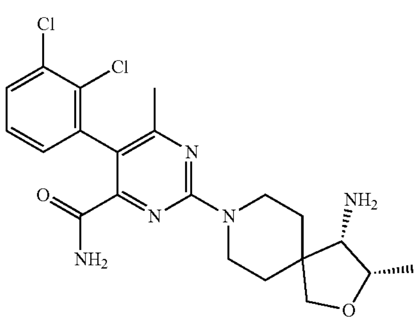 [SMILES: Cc1nc(N2CCC3(CC2)CO[C@@H](C)[C@H]3N)nc(C(N)=O)c1-c1cccc(Cl)c1Cl] | 2-[(3S,4S)-4-amino-3-methyl-2-oxa-8-azaspiro[4.5]decan-8-yl]-5-(2,3-dichlorophenyl)-6-methylpyrimidine-4-carboxamide |
| 86 | 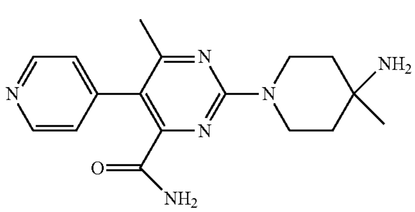 [SMILES: Cc1nc(N2CCC(C)(N)CC2)nc(C(N)=O)c1-c1ccncc1] | 2-(4-Amino-4-methyl-piperidin-1-yl)-6-methyl-5-pyridin-4-yl-pyrimidine-4-carboxylic acid amide |

TABLE 2-continued examples of compounds of the present invention

| No. | Structure | IUPAC-Name |
| --- | --- | --- |
| 87 | 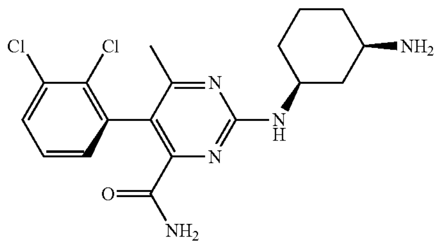 | (4M)-2-{[(1S,3R)-3-aminocyclohexyl]amino}-5-(2,3-dichlorophenyl)-6-methylpyrimidine-4-carboxamide |
| 88 | 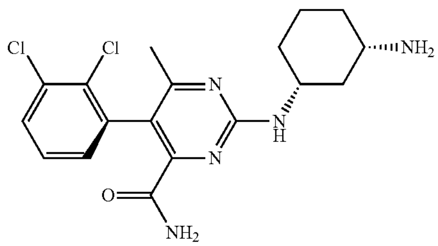 | (4M)-2-{[(1R,3S)-3-aminocyclohexyl]amino}-5-(2,3-dichlorophenyl)-6-methylpyrimidine-4-carboxamide |
| 89 | 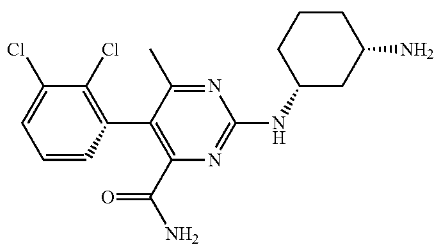 | (4P)-2-{[(1R,3S)-3-aminocyclohexyl]amino}-5-(2,3-dichlorophenyl)-6-methylpyrimidine-4-carboxamide |
| 90 | 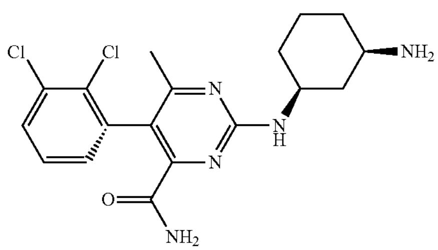 | (4P)-2-{[(1S,3R)-3-aminocyclohexyl]amino}-5-(2,3-dichlorophenyl)-6-methylpyrimidine-4-carboxamide |
| 91 | 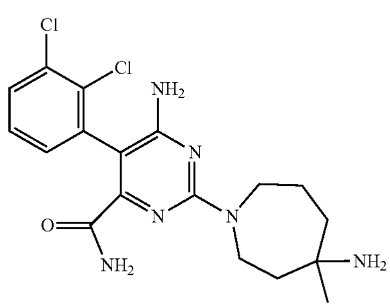 [SMILES: CC1(N)CCCN(c2nc(N)c(-c3cccc(Cl)c3Cl)c(C(N)=O)n2)CC1] | 6-Amino-2-(4-amino-4-methyl-azepan-1-yl)-5-(2,3-dichloro-phenyl)-pyrimidine-4-carboxylic acid amide |
| 92 | 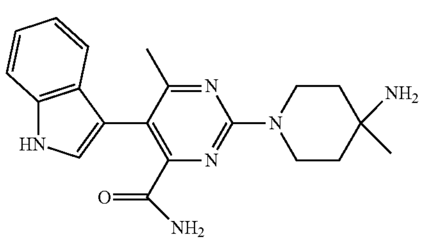 [SMILES: Cc1nc(N2CCC(C)(N)CC2)nc(C(N)=O)c1-c1c[nH]c2ccccc12] | 2-(4-Amino-4-methyl-piperidin-1-yl)-5-(1H-indol-3-yl)-6-methyl-pyrimidine-4-carboxylic acid amide |

TABLE 2-continued examples of compounds of the present invention

| No. | Structure | IUPAC-Name |
|---|---|---|
| 93 | 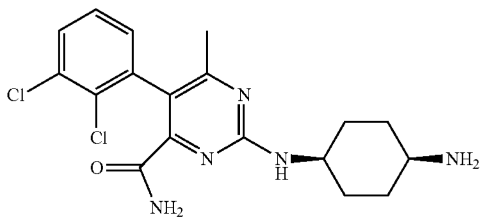 [SMILES: Cc1nc(N[C@H]2CC[C@@H](N)CC2)nc(C(N)=O)c1-c1cccc(Cl)c1Cl] | 2-(4-Amino-cyclohexyl-amino)-5-(2,3-dichloro-phenyl)-6-methyl-pyrimidine-4-carboxylic acid amide |
| 94 | 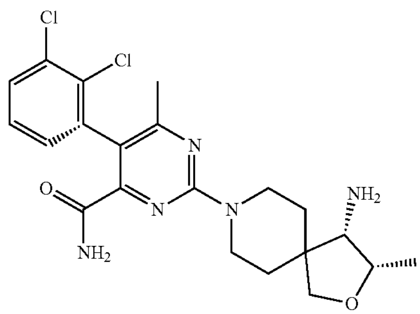 | (5P)-2-[(3S,4S)-4-amino-3-methyl-2-oxa-8-azaspiro[4.5]-decan-8-yl]-5-(2,3-dichloro-phenyl)-6-methylpyrimidine-4-carboxamide |
| 95 | 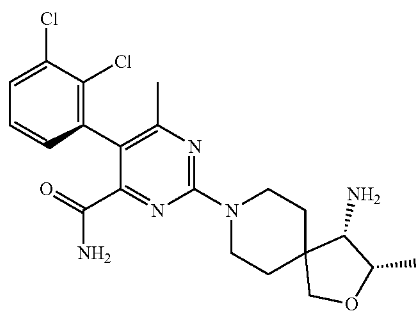 | (5M)-2-[(3S,4S)-4-amino-3-methyl-2-oxa-8-azaspiro[4.5]-decan-8-yl]-5-(2,3-dichloro-phenyl)-6-methylpyrimidine-4-carboxamide |
| 96 | 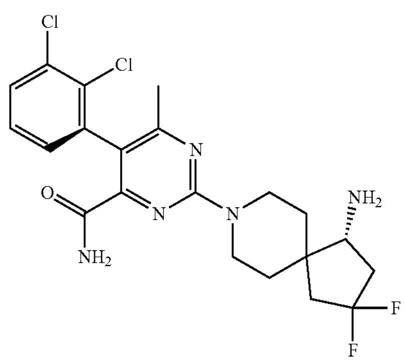 | (5M)-2-[(1R)-1-amino-3,3-difluoro-8-azaspiro[4.5]-decan-8-yl]-5-(2,3-dichloro-phenyl)-6-methylpyrimidine-4-carboxamide |
| 97 | 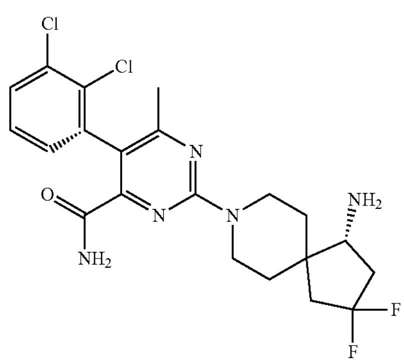 | (5P)-2-[(1R)-1-amino-3,3-difluoro-8-azaspiro[4.5]-decan-8-yl]-5-(2,3-dichlorophenyl)-6-methylpyrimidine-4-carboxamide |

TABLE 2-continued examples of compounds of the present invention

| No. | Structure | IUPAC-Name |
|---|---|---|
| 98 | 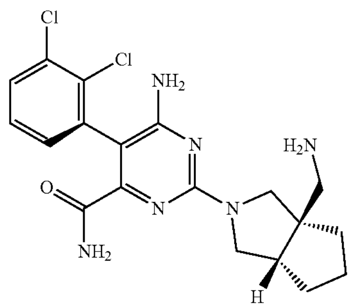 | (5P)-2-[(3aR,6aS)-3a-(aminomethyl)-octahydro-cyclopenta[c]pyrrol-2-yl]-6-amino-5-(2,3-dichlorophenyl)-pyrimidine-4-carboxamide |
| 99 | 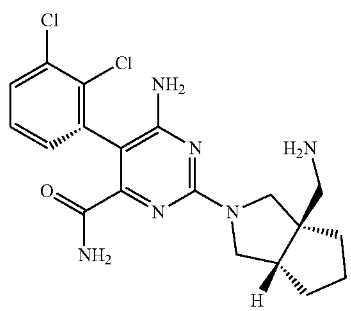 | (5M)-2-[(3aR,6aS)-3a-(aminomethyl)-octahydro-cyclopenta[c]pyrrol-2-yl]-6-amino-5-(2,3-dichlorophenyl)-pyrimidine-4-carboxamide |
| 100 | 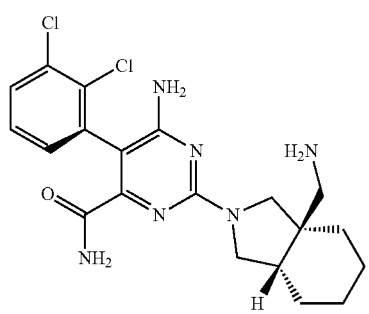 | (5P)-2-[(3aR,7aS)-3a-(aminomethyl)-octahydro-1H-isoindol-2-yl]-6-amino-5-(2,3-dichlorophenyl)pyrimidine-4-carboxamide |
| 101 | 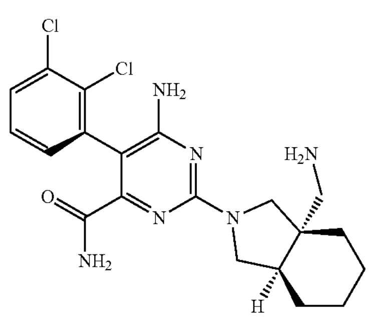 | (5P)-2-[(3aS,7aR)-3a-(aminomethyl)-octahydro-1H-isoindol-2-yl]-6-amino-5-(2,3-dichlorophenyl)pyrimidine-4-carboxamide |
| 102 | 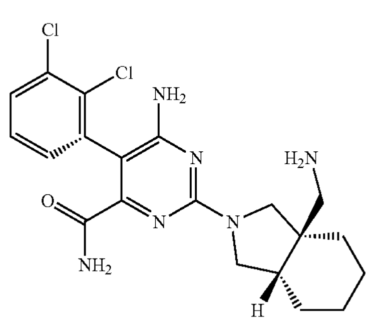 | (5M)-2-[(3aR,7aS)-3a-(aminomethyl)-octahydro-1H-isoindol-2-yl]-6-amino-5-(2,3-dichlorophenyl)pyrimidine-4-carboxamide |

TABLE 2-continued examples of compounds of the present invention

| No. | Structure | IUPAC-Name |
|---|---|---|
| 103 | 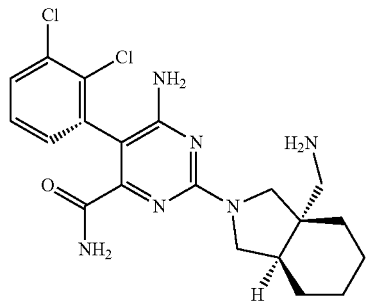 | (5M)-2-[(3aS,7aR)-3a-(aminomethyl)-octahydro-1H-isoindol-2-yl]-6-amino-5-(2,3-dichlorophenyl)pyrimidine-4-carboxamide |
| 104 | 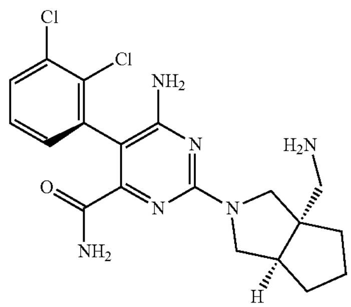 | (5P)-2-[(3aS,6aR)-3a-(aminomethyl)-octahydro-cyclopenta[c]pyrrol-2-yl]-6-amino-5-(2,3-dichlorophenyl)-pyrimidine-4-carboxamide |
| 105 | 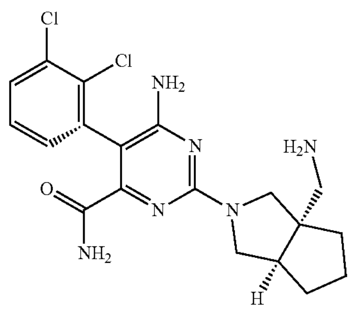 | (5M)-2-[(3aS,6aR)-3a-(aminomethyl)-octahydro-cyclopenta[c]pyrrol-2-yl]-6-amino-5-(2,3-dichlorophenyl)-pyrimidine-4-carboxamide |
| 106 | 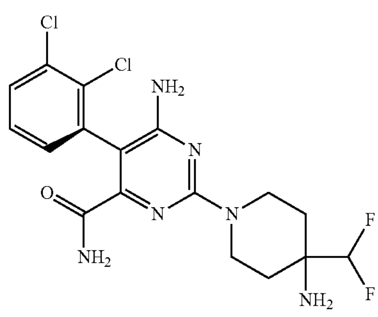 | (5P)-6-amino-2-[4-amino-4-(difluoromethyl)piperidin-1-yl]-5-(2,3-dichlorophenyl)-pyrimidine-4-carboxamide |
| 107 | 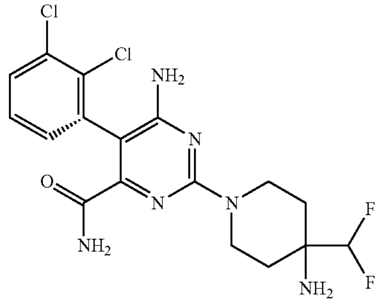 | (5M)-6-amino-2-[4-amino-4-(difluoromethyl)piperidin-1-yl]-5-(2,3-dichlorophenyl)-pyrimidine-4-carboxamide |

TABLE 2-continued examples of compounds of the present invention

| No. | Structure | IUPAC-Name |
|---|---|---|
| 108 | 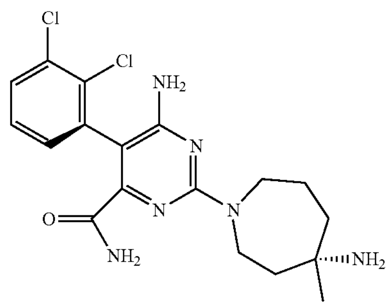 | (5P)-6-amino-2-[(4S)-4-amino-4-methylazepan-1-yl]-5-(2,3-dichlorophenyl)-pyrimidine-4-carboxamide |
| 109 | 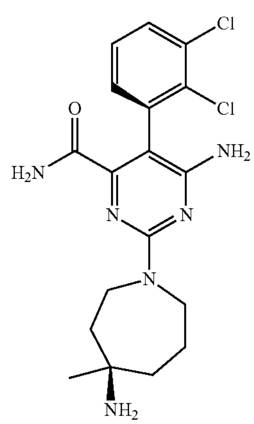 | (5P)-6-amino-2-[(4R)-4-amino-4-methylazepan-1-yl]-5-(2,3-dichlorophenyl)-pyrimidine-4-carboxamide |
| 110 | 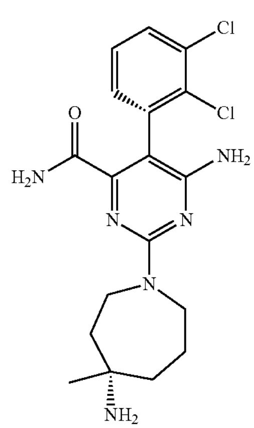 | (5M)-6-amino-2-[(4S)-4-amino-4-methylazepan-1-yl]-5-(2,3-dichlorophenyl)-pyrimidine-4-carboxamide |

TABLE 2-continued examples of compounds of the present invention

| No. | Structure | IUPAC-Name |
|-----|-----------|------------|
| 111 | 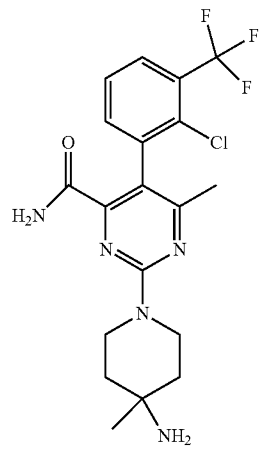 [SMILES: Cc1nc(N2CCC(C)(N)CC2)nc(C(N)=O)c1-c1cccc(C(F)(F)F)c1Cl] | 2-(4-Amino-4-methyl-piperidin-1-yl)-5-(2-chloro-3-trifluoromethyl-phenyl)-6-methyl-pyrimidine-4-carboxylic acid amide |
| 112 | 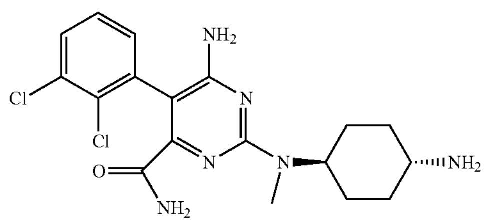 [SMILES: CN(c1nc(N)c(-c2cccc(Cl)c2Cl)c(C(N)=O)n1)[C@H]1CC[C@H](N)CC1] | 6-Amino-2-[(4-amino-cyclohexyl)-methyl-amino]-5-(2,3-dichloro-phenyl)-pyrimidine-4-carboxylic acid amide |
| 113 | 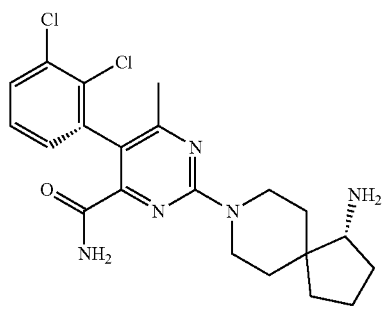 | (5P)-2-[(1R)-1-amino-8-azaspiro[4.5]decan-8-yl]-5-(2,3-dichlorophenyl)-6-methylpyrimidine-4-carboxamide |
| 114 | 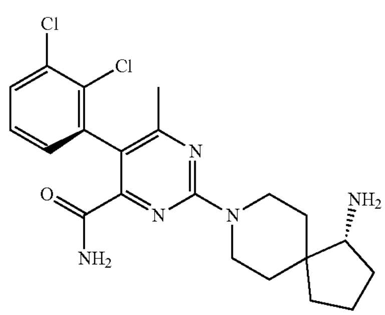 | (5M)-2-[(1R)-1-amino-8-azaspiro[4.5]decan-8-yl]-5-(2,3-dichlorophenyl)-6-methylpyrimidine-4-carboxamide |
| 115 | | (4M)-2-(4-amino-4-methylpiperidin-1-yl)-5-(2-chloro-4-fluoro-3-methoxyphenyl)-6-methylpyrimidine-4-carboxamide |
| 116 | | (4P)-2-(4-amino-4-methylpiperidin-1-yl)-5-(2-chloro-4-fluoro-3-methoxyphenyl)-6-methylpyrimidine-4-carboxamide |

TABLE 2-continued examples of compounds of the present invention

| No. | Structure | IUPAC-Name |
|---|---|---|
| 117 | 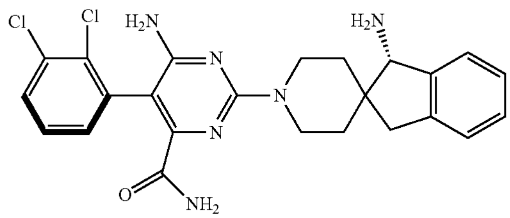 | (5P)-6-amino-2-[(1S)-1-amino-1,3-dihydrospiro[indene-2,4'-piperidin]-1'-yl]-5-(2,3-dichlorophenyl)pyrimidine-4-carboxamide |
| 118 | 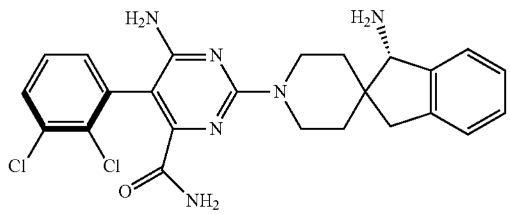 | (5M)-6-amino-2-[(1S)-1-amino-1,3-dihydrospiro[indene-2,4'-piperidin]-1'-yl]-5-(2,3-dichlorophenyl)pyrimidine-4-carboxamide |
| 119 | 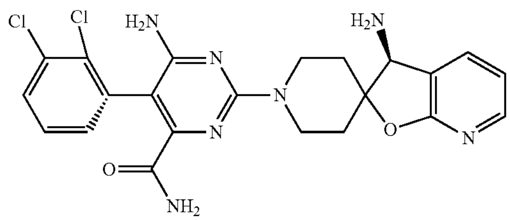 | (5M)-2-[(1S)-1-amino-1,3-dihydrospiro[indene-2,4'-piperidin]-1'-yl]-5-(2,3-dichlorophenyl)-6-methylpyrimidine-4-carboxamide |
| 120 | 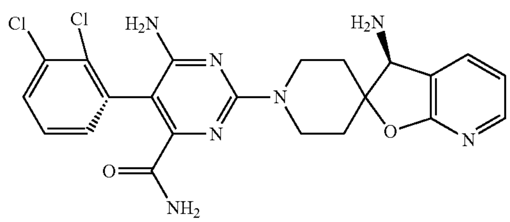 | (5P)-2-[(1S)-1-amino-1,3-dihydrospiro[indene-2,4'-piperidin]-1'-yl]-5-(2,3-dichlorophenyl)-6-methylpyrimidine-4-carboxamide |
| 121 | 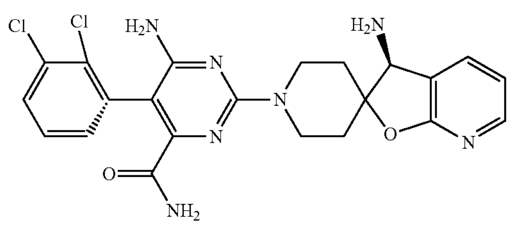 | 6-amino-2-[(4S)-4-amino-4,6-dihydrospiro[cyclopenta[d][1,3]thiazole-5,4'-piperidin]-1'-yl]-5-(2,3-dichlorophenyl)pyrimidine-4-carboxamide |
| 122 | 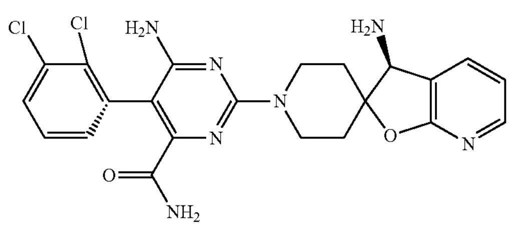 | 2-[(3R)-3-amino-3H-spiro[1-benzofuran-2,4'-piperidin]-1'-yl]-5-(2,3-dichlorophenyl)-6-methylpyrimidine-4-carboxamide |
| 123 | 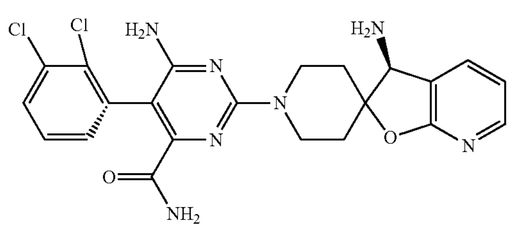 | 6-amino-2-[(3R)-3-amino-3H-spiro[1-benzofuran-2,4'-piperidin]-1'-yl]-5-(2,3-dichlorophenyl)pyrimidine-4-carboxamide |

TABLE2-continued examples of compounds of the present invention

| No. | Structure | IUPAC-Name |
|---|---|---|
| 124 | 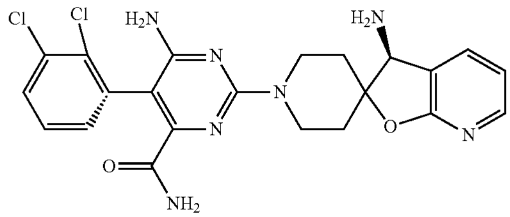 | (4M)-2-[(3R)-3-amino-3H-spiro[furo[2,3-b]pyridine-2,4'-piperidin]-1'-yl]-5-(2,3-dichlorophenyl)-6-methylpyrimidine-4-carboxamide |
| 125 | 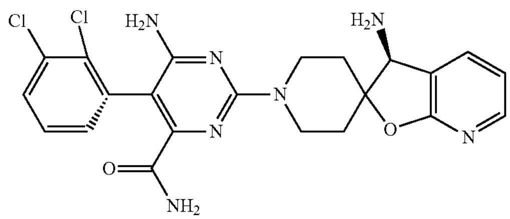 | (4M)-2-[(3S)-3-amino-3H-spiro[furo[2,3-b]pyridine-2,4'-piperidin]-1'-yl]-5-(2,3-dichlorophenyl)-6-methylpyrimidine-4-carboxamide |
| 126 | 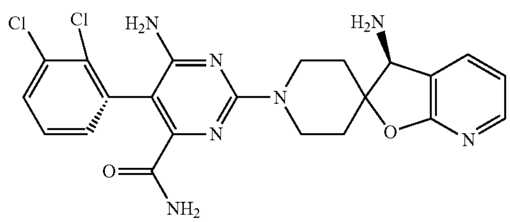 | (4P)-2-[(3R)-3-amino-3H-spiro[furo[2,3-b]pyridine-2,4'-piperidin]-1'-yl]-5-(2,3-dichlorophenyl)-6-methylpyrimidine-4-carboxamide |
| 127 | 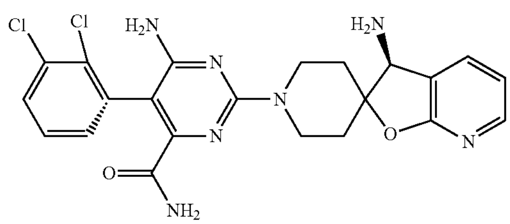 | (4P)-2-[(3S)-3-amino-3H-spiro[furo[2,3-b]pyridine-2,4'-piperidin]-1'-yl]-5-(2,3-dichlorophenyl)-6-methylpyrimidine-4-carboxamide |
| 128 | 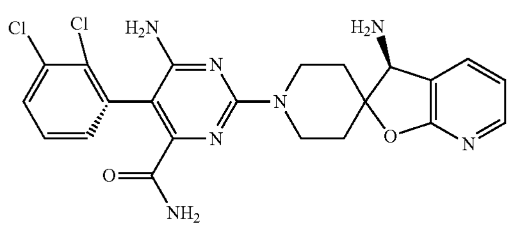 | (4P)-6-amino-2-[(3R)-3-amino-3H-spiro[furo[2,3-b]pyridine-2,4'-piperidin]-1'-yl]-5-(2,3-dichlorophenyl)pyrimidine-4-carboxamide |
| 129 | 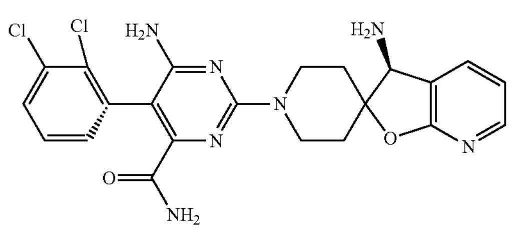 | (4P)-6-amino-2-[(3S)-3-amino-3H-spiro[furo[2,3-b]pyridine-2,4'-piperidin]-1'-yl]-5-(2,3-dichlorophenyl)pyrimidine-4-carboxamide |

TABLE 2-continued examples of compounds of the present invention

| No. | Structure | IUPAC-Name |
|---|---|---|
| 130 | 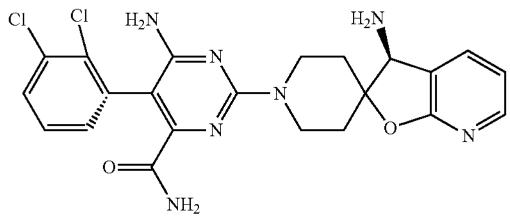 | (4M)-6-amino-2-[(3R)-3-amino-3H-spiro[furo[2,3-b]pyridine-2,4'-piperidin]-1'-yl]-5-(2,3-dichlorophenyl)pyrimidine-4-carboxamide |
| 131 | 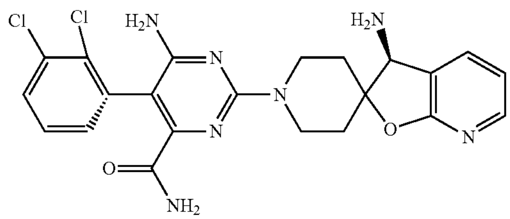 | (4M)-6-amino-2-[(3S)-3-amino-3H-spiro[furo[2,3-b]pyridine-2,4'-piperidin]-1'-yl]-5-(2,3-dichlorophenyl)pyrimidine-4-carboxamide |

Example 2: Preparation of the Compounds of the Present Invention and Analytical Methods The abbreviations below have the following meanings:
Boc ter-butoxycarbonyl
CBZ benzyloxycarbonyl
DNP 2,4-dinitrophenyl
FMOC 9-fluorenylmethoxycarbonyl
imi-DNP 2,4-dinitrophenyl in the 1-position of the imidazole ring
OMe methyl ester
POA phenoxyacetyl
DCC dicyclohexylcarbodiimide
HOBt 1-hydroxybenzotriazole In general, the compounds according to Formula (I) and related formulae of this invention can be prepared from readily available starting materials. If such starting materials are not commercially available, they may be prepared by standard synthetic techniques. In general, the synthesis pathways for any individual compound of Formula(I) and related formulae will depend on the specific substituents of each molecule, such factors being appreciated by those of ordinary skilled in the art. The following general methods and procedures described hereinafter in the examples may be employed to prepare compounds of Formula (I) and related formulae. Those methods are illustrative and are not meant to limit the possible methods one skilled in the art may use to prepare compounds disclosed herein. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups inOrganic Synthesis", Wiley Interscience, 3rd Edition 1999.

Depending on the nature of R1, R2, R3, R4, R5, X and Y different synthetic strategies may be selected for the synthesis of compounds of Formula (I). In the process illustrated in the following schemes, R1, R2, R3, R4, R5, X and Y are as above defined in the description unless otherwise mentioned.

According to one process, pyrimidine derivatives according to the general formula 4 wherein R2 and R3 are as above described, R20 and R21 are H, substituted alkyl, heteroalkyl or can combine to form a monocyclic or polycyclic alkyl or heteroalkyl which may or may not be substituted and R8 is COYR4R5 wherein Y, R4 and R5 are as above described or CN can be prepared following reaction scheme described in scheme 1.

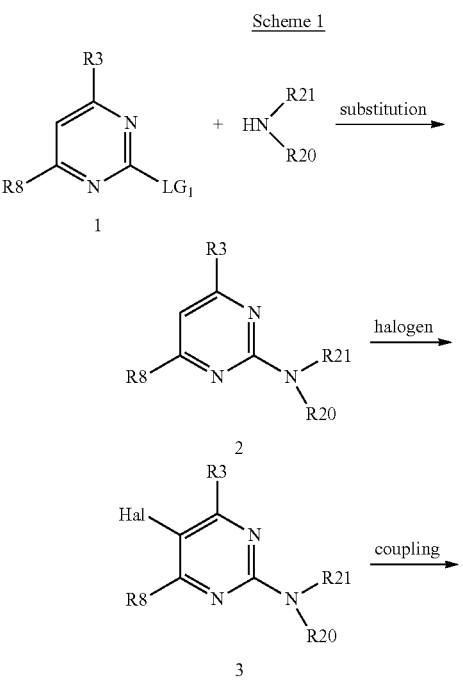

Scheme 1

-continued

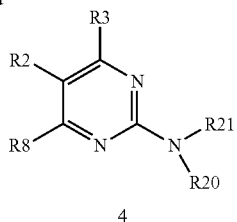

4

Pyrimidine 1 wherein R3 and R8 are as above described and LG1 is a leaving group such as a halogen or OMs, OTs, OTf undergoes a substitution reaction with an amine NHR20R21 wherein R20 and R21 are as above described by heating in a solvent such as, but not limited to MeOH, EtOH, DMF, DMSO in the presence or absence of a base such as TEA, DIEA, $Cs_2CO_3$ or $K_2CO_3$ to give a pyrimidine of general formula 2 wherein R3, R20, R21 and R8 are as above defined. Pyridine 2 is then submitted to halogenation conditions using for example NBS, NCS or NIS to give an intermediate of general formula 3 wherein R3, R20, R21 and R8 are as above describe and Hal is a halogen atom such as Cl, Br or I. Finally, pyrimidine 3 undergoes a cross coupling reaction to give pyrimidine 4 using standard conditions well known to one skilled in the art. In some embodiments, the cross-coupling reaction is a Suzuki reaction, but other cross coupling reactions may be employed. Alternatively, pyrimidine derivatives according to the general formula 4 wherein R2, R3, R20, R21, R8 are as above defined can be prepared following reaction scheme described in scheme 2.

In this reaction sequence, thiomethyl compound 5 wherein R3 and R8 are as above defined is first submitted to halogenation and then cross coupling conditions to give intermediate compound 7 wherein R2, R3, R8 are as above defined. Thiomethyl group is then oxidized to $SO_2Me$ using standard conditions well known to one skilled in the art such as e.g. mCPBA or $H_2O_2$ to give intermediate 8 wherein R2, R3 and R8 are as above defined. Finally, Intermediate 8 undergoes a substitution reaction with NHR20R21 wherein R20 and R21 are as above defined.

To obtain final compounds of general formula Ia, a last transformation of R8 may be required.

When R8 is COOR19 wherein R19 is H, alkyl, cycloalkyl, final compounds of general formula I are produced when COOR19 is reacted with an amine HNR4R5 wherein R4 and R5 are as above described using conditions well known to one skilled in the art to prepare an amide from an amine and a carboxylic acid or a carboxylic acid derivative with standard coupling agents such as e.g. DIC, EDC, TBTU, DECP, or others as depicted in scheme 3.

Scheme 3

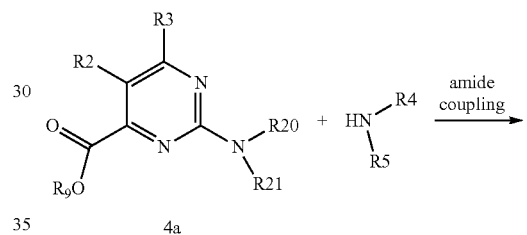

Scheme 2

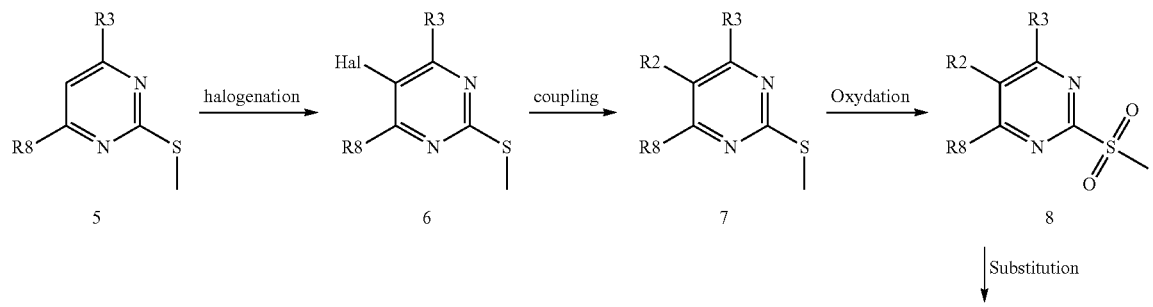

Substitution

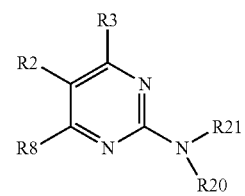

4

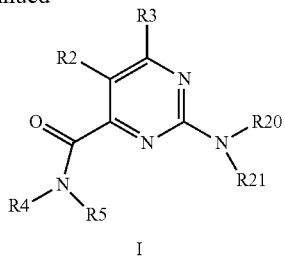

When R8 is CN, final compounds of general formula I wherein R2, R3, R4, R20 and R21 are as above defined may be obtained by hydrolysis of a compound of general formula 4b wherein R2, R3, R5 and R7 are as above defined to an acid of general formula 9 wherein R2, R3, R5 and R7 followed by an amide coupling reaction as depicted in scheme 4. Alternatively, compounds of general formula Ib may be obtained by direct hydrolysis of a compound of general formula 4b wherein R2, R3, R5 and R7 using condition well known from the one skilled in the art such as e.g. heating in presence of NaOH and $H_2O_2$ in DMF or DMSO.

were used as a reference signal, as per published guidelines (J. Org. Chem., Vol. 62, No. 21, 1997). Chemical shifts are expressed in parts per million (ppm, b units). Coupling constants are in units of hertz (Hz). Splitting patterns describe apparent multiplicities and are designated as s (singlet), d (doublet), t (triplet), q (quartet), m (multiplet), qt (quintuplet) or brs (broad singlet).

The following abbreviations refer to the abbreviations used below: Ac (acetyl); ACN (acetonitrile); atm (atmosphere); DIEA (Di-isopropyl ethylamine); ° C. (degrees centigrade); DMF (dimethylformamide); DMSO (dimethylsulfoxide); dppf (1,1'-bis-diphenyl phosphine ferrocene); EtOAc (Ethylacetate); g (gram); h (hour); HATU (N-[(Dimethylamino)(3H-[1,2,3]triazolo[4,5-b]pyridin-3-yloxy)methylene]-N-methylmethanaminiumhexafluoro phosphate); HOBt (Hydroxybenzotriazole); HPLC (High Performance Liquid Chromatography); h (hour); LC (liquid Chromatography); LDA (lithium diisopropylamine); MeOH (methanol); min (minute); mL (milliliter); mmol (millimole); MS (Mass spectroscopy); NBS (N-bromosuccinimide); NMR (Nuclear Magnetic Resonance); O/N (overnight); PE (Petroleum Ether); RT (room temperature); TBDMS (tert-Butyldimethylsilyl); TEA (triethylamine); TFA (trifluoroacetic acid); THF (tetrahydofurane); TMS (trimethylsilyl).

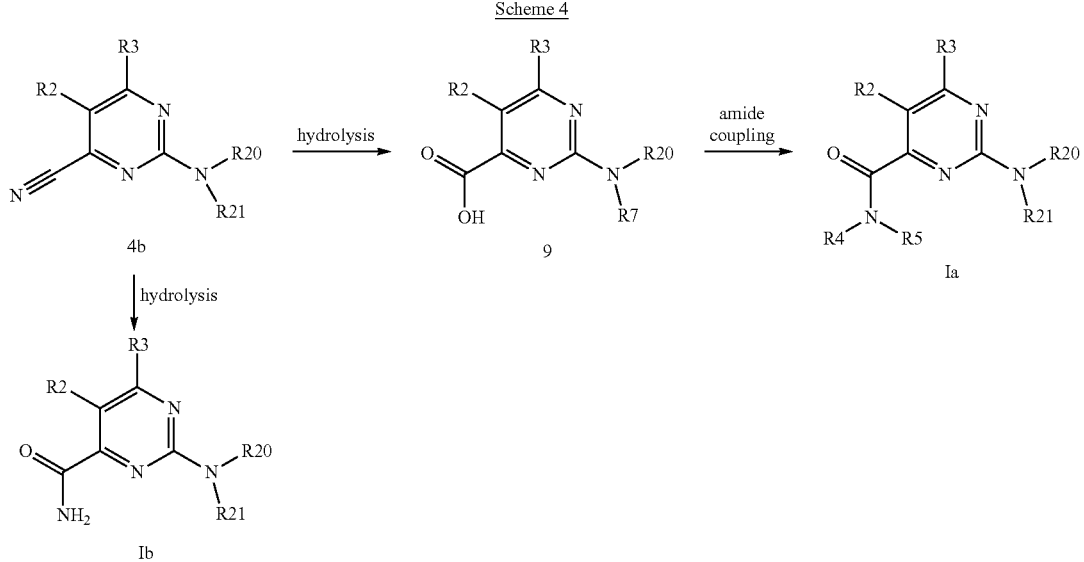

Scheme 4

For the synthesis of other compounds of general formula I, similar synthetic schemes should be applied with suitable modifications adapted to specific substituent of each molecules, such factors being appreciated by those of ordinary skilled in the art.

According to a further general process, compounds of formula I can be converted to alternative compounds of formula I, employing suitable interconversion techniques such as hereinafter described in the Examples.

All NMR experiments were recorded on Bruker Avance III 400 NMR Spectrometer equipped with a Bruker PABBO BB-1H/D Z GRD probe at 400 MHz for proton NMR or a Bruker DPX-300 MHz. Most deuterated solvents contained typically 0.03% to 0.05% v/v tetramethylsilane, which was used as the reference signal (set at 0.00 for both $^1H$ and $^{13}C$). In cases where the deuterated solvents did not contain tetramethylsilane, the residual non-deuterated solvent peaks UPLC/MS analyses were performed on a Waters AquityH with SQ detector (ESI) and LC/MS on an Agilent 1200 Series with a quadupole detector or a SHIMADZU LC-MS machine consisting of an UFLC 20-AD system and a LCMS 2020 MS detector.

The microwave reactions were conducted using Biotage Initiator Microwave Synthesizer using standard protocols that are known in the art.

The compounds of the invention were prepared from readily available starting materials by several synthetic approaches. Examples of synthetic pathways are described below in the examples. Unless otherwise stated, compounds of the invention obtained as a racemic mixture can be separated to provide an enantiomerically enriched mixture or a pure enantiomer.

The commercially available starting materials used in the following experimental description were purchased from Sigma-Aldrich or Fisher unless otherwise reported.

Intermediate 1: tert-butyl (1-(5-bromo-4-cyanopyrimidin-2-yl)-4-methylpiperidin-4-yl)carbamate Step 1: tert-butyl (1-(4-cyanopyrimidin-2-yl)-4-methylpiperidin-4-yl)carbamate

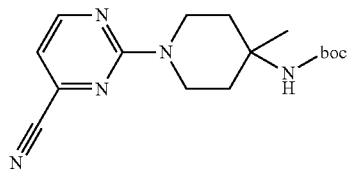

A solution of 2-chloropyrimidine-4-carbonitrile (2 g, 14.3 mmol), cesium carbonate (11.62 g, 35.7 mol) and tert-butyl (4-methylpiperidin-4-yl)carbamate (3.38 g, 15.8 mmol) in DMF (30 mL) was stirred overnight at 110° C. The reaction mixture was filtered through a celite pad. The pad was washed with EtOAc (50 mL) and filtrate was washed with brine. Organic layer was dried over magnesium sulfate, filtered and concentrated. Purification by flash chromatography over silica (PE: EtOAc, gradient from 100:0 to 50:50) afforded the title compound as a white solid (2 g, 66%). 1H NMR (400 MHz, DMSO-d6): 8.61 (s, 1H), 7.10 (s, 1H), 6.60 (brs, 1H), 4.06 (m, 2H), 3.38 (m, 2H), 2.07 (m, 2H), 1.42 (m, 2H), 1.39 (s, 9H), 1.25 (s, 3H).

Step 2: tert-butyl (1-(5-bromo-4-cyanopyrimidin-2-yl)-4-methylpiperidin-4-yl)carbamate

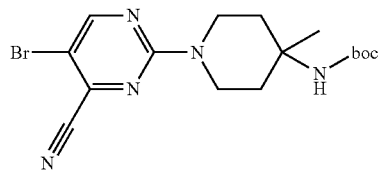

To a solution of tert-butyl (1-(4-cyanopyrimidin-2-yl)-4-methylpiperidin-4-yl)carbamate (2 g, 6.31 mmol) in anhydrous acetonitrile (30 mL) was added N-bromo-succinimide (1.2 g, 6.93 mmol) portion wise at 0° C. The reaction mixture was stirred at room temperature for 1 h then quenched with ice and extracted with EtOAc (50 mL). The organic layer was dried over sodium sulphate, filtered and concentrated. Purification by flash chromatography over silica (PE: EtOAc, gradient from 100:0 to 85:15) afforded the title compound as a white solid (2 g, 80%). 1H NMR (400 MHz, DMSO-d6): 8.75 (s, 1H), 6.66 (brs, 1H), 4.01 (m, 2H), 3.35 (m, 2H), 2.08 (m, 2H), 1.43 (m, 2H), 1.39 (s, 9H), 1.22 (s, 3H).

Intermediate 2: tert-butyl N-[1-(4-amino-5-bromo-6-carbamoylpyrimidin-2-yl)-4-methylpiperidin-4-yl]carbamate Step 1: tert-butyl N-[1-(4-amino-6-carbamoylpyrimidin-2-yl)-4-methylpiperidin-4-yl]carbamate

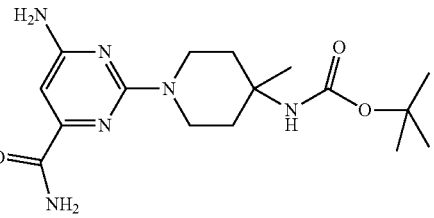

A mixture of 6-amino-2-chloropyrimidine-4-carboxamide (700 mg, 3.20 mmol), tert-butyl N-(4-methylpiperidin-4-yl)carbamate (1.3 g, 5.76 mmol), TEA (822 mg, 7.72 mmol) in acetonitrile (11 mL) was heated at 80° C. for 18 h in a sealed tube. Solvent was then removed under reduced pressure and the crude was directly purified by flash chromatography on silica (PE:EtOAc, 90:10) to give the title compound as a yellow solid (1.2 g, 100%). LC/MS (M+1): 351.2.

Step 2: tert-butyl N-[1-(4-amino-5-bromo-6-carbamoylpyrimidin-2-yl)-4-methylpiperidin-4-yl]carbamate

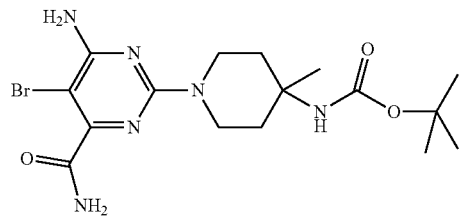 [SMILES: CC1(NC(=O)OC(C)(C)C)CCN(c2nc(N)c(Br)c(C(N)=O)n2)CC1]

NBS (243 mg, 1.30 mmol) was added portion wise to a solution of tert-butyl N-[1-(4-amino-6-carbamoylpyrimidin-2-yl)-4-methylpiperidin-4-yl]carbamate (400 mg, 1.14 mmol) in DMF (6 mL) maintained at 0° C. The reaction mixture was stirred at room temperature for 1 h then quenched with ice and extracted with EtOAc. The organic layer was dried over sodium sulfate, filtered and concentrated to give the title compound as yellow solid (420 mg, 80%). LC/MS (M+1): 429.2.

Intermediate 3: Methyl 5-bromo-2-(4-{[(tert-butoxy)carbonyl]amino}-4-methylpiperidin-1-yl)pyrimidine-4-carboxylate

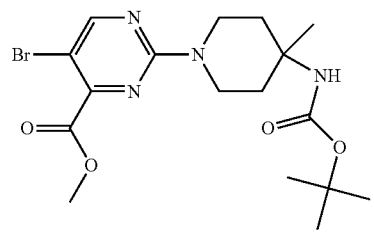 [SMILES: COC(=O)c1nc(N2CCC(C)(NC(=O)OC(C)(C)C)CC2)ncc1Br]

A mixture of methyl 5-bromo-2-chloropyrimidine-4-carboxylate (300 mg, 1.13 mmol), tert-butyl N-(4-methylpiperidin-4-yl)carbamate (307 mg, 1.36 mmol) and TEA (0.2 mL) in ACN (3 mL) was stirred for 2 h at 80° C. in a sealed tube. Solvent was then removed under reduced pressure and the crude was purified by flash chromatography on silica (PE:EtOAc, 73:27) to give the title compound as a yellow solid (495 mg, 96%). LC/MS (M+1): 429.2.

Intermediate 4: 6-Amino-5-(2,3-dichloro-phenyl)-2-methanesulfonyl-pyrimidine-4-carbonitrile Step 1: 6-amino-2-(methylsulfanyl)pyrimidine-4-carbonitrile

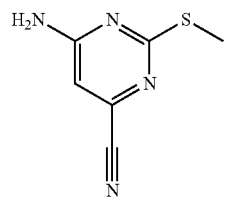

A mixture of 6-chloro-2-(methylsulfanyl)pyrimidin-4-amine (50 g, 285 mmol), KCN (37.1 g, 569 mmol), Pd$_2$(dba)$_3$ (15.6 g, 17.1 mmol), DPPF (12.6 g, 22.8 mmol) and tributyl(chloro)stannane (5.56 g, 17.1 mmol) in ACN (500 mL) was stirred at 15° C. for 30 min, and then heated to 80° C. for 16 h. The mixture was cooled to room temperature, poured into water (2.0 L) and extracted with EtOAc (1.5 L). The organic layer was washed with water (1.5 L), dried over sodium sulfate, filtered and concentrated. Purification by flash chromatography on silica (PE/EtOAc/DCM, gradient from 8/1/0 to 4/1/1, with 0.1% NH$_4$OH) afforded the title compound as an off-white solid (28.6 g, 53%). $^1$H NMR (400 MHz DMSO-d$_6$): 7.62 (brs, 2H), 6.63 (s, 1H), 2.40 (s, 3H).

Step 2: 6-amino-5-bromo-2-(methylsulfanyl)pyrimidine-4-carbonitrile

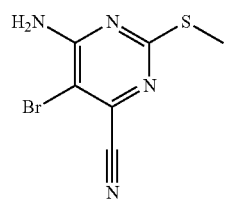

NBS (11.2 g, 62.9 mmol) was added portion-wise to a solution of 6-amino-2-(methylsulfanyl)pyrimidine-4-carbonitrile (10.0 g, 60.2 mmol) in DMF (90 mL) maintained at 5° C. The reaction mixture was then stirred at the same temperature for 1 h. It was poured into water (300 mL) and extracted with EtOAc (300 mL). The organic layer was washed with 0.5M NaHCO$_3$ solution (300 mL×2), dried over sodium sulfate, filtered and concentrated to give the title compound as a yellow solid (7.78 g, 52.7%).

Step 3: 6-amino-5-(2,3-dichlorophenyl)-2-(methylsulfanyl)pyrimidine-4-carbonitrile

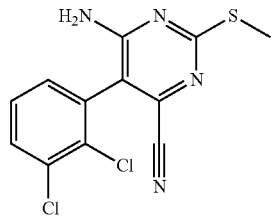 [SMILES: CSc1nc(N)c(-c2cccc(Cl)c2Cl)c(C#N)n1]

A mixture of 6-amino-5-bromo-2-(methylsulfanyl)pyrimidine-4-carbonitrile (1.55 g, 6.32 mmol), 2,3-dichlorophenyl)boronic acid (3.02 g, 15.8 mmol), XPhos Palladacycle Gen 3 (267 mg, 316 umol) and K$_3$PO$_4$ (4.03 g, 18.9 mmol) in 1,4-dioxane (15 mL) and H$_2$O (3 mL) was stirred under nitrogen at 95° C. for 16 h. The mixture was cooled to room temperature, diluted with DCM (20 mL) and filtered. The filtrate was concentrated under vacuum and purified by RP-MPLC (TFA condition) to give the title compound as a yellow solid (1.01 g, 48%) $^1$H NMR (400 MHz, CDCl$_3$): 7.65 (dd, J=1.2, 8.0 Hz, 1H), 7.41 (t, J=7.6 Hz, 1H), 7.29 (dd, J=7.6, 8.0 Hz, 1H), 5.04 (br, 2H), 2.57 (s, 3H). LC/MS (M+1): 311.1.

Step 4: 6-Amino-5-(2,3-dichloro-phenyl)-2-methanesulfonyl-pyrimidine-4-carbonitrile

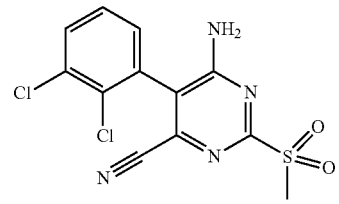 [SMILES: CS(=O)(=O)c1nc(N)c(-c2cccc(Cl)c2Cl)c(C#N)n1]

A solution of mCPBA (2.83 g; 12.65 mmol) in DCM (40 mL) was added to a solution of 6-amino-5-(2,3-dichlorophenyl)-2-(methylsulfanyl)pyrimidine-4-carbonitrile (1.97 g; 6.32 mmol) in DCM (40 mL) maintained at 0° C. The reaction mixture was stirred at RT for 2 h, then cooled down to 0° C. before the ad dilution of another solution of mCPBA (1.42 g; 6.32 mmol) in DCM (20 mL) to obtain complete conversion.

Reaction mixture was stirred at RT for another 2 h. It was then filtered to remove the white precipitate. Filtrate was concentrated, dissolved again in DCM, filtered and concentrated. Purification by flash chromatography on silica (hexane:EtOAc, gradient from 60:40 to 80:20) afforded the title compound as a white solid (1.5 g, 69%). 1H NMR (400 MHz, DMSO-d6) δ 8.73 (s, 1H), 7.85 (dd, J=6.1, 3.5 Hz, 1H), 7.70 (s, 1H), 7.63-7.55 (m, 2H), 3.37 (s, 3H). LC/MS (M+1): 342.9.

Intermediate 5: {1-[4-Amino-6-cyano-5-(2,3-dichloro-phenyl)-pyrimidin-2-yl]-4-methyl-piperidin-4-yl}-carbamic Acid Tert-Butyl Ester

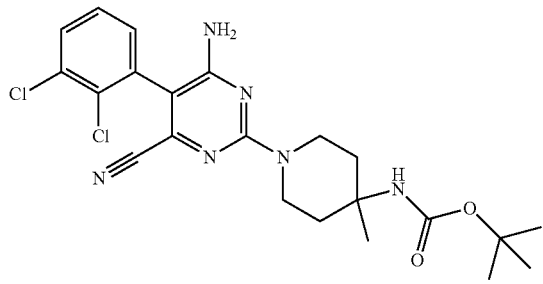 [SMILES: CC1(NC(=O)OC(C)(C)C)CCN(c2nc(N)c(-c3cccc(Cl)c3Cl)c(C#N)n2)CC1]

A solution of tert-butyl (4-methylpiperidin-4-yl)carbamate (Synthonix; 62 mg; 0.29 mmol) and potassium carbonate (101 mg; 0.73 mmol) in ACN (0.50 mL) and DMF (0.50 mL) was stirred at room for 10 min before the addition of 6-Amino-5-(2,3-dichloro-phenyl)-2-methanesulfonyl-pyrimidine-4-carbonitrile (Intermediate 4; 50 mg; 0.15 mmol). The reaction mixture was then heated at 100° C. for 66 h. It was diluted with EtOAc (40 mL) and washed with water (2×10 mL) and brine (10 mL). Organic layer was dried over sodium sulfate, filtered and concentrated. Purification by flash chromatography on silica (hexane: EtOAc, gradient from 95:5 to 40:60) afforded the title compound as a white foam 1H NMR (400 MHz, DMSO-d6) 7.72 (dd, J=8.0, 1.6 Hz, 1H), 7.45 (t, J=7.8 Hz, 1H), 7.38 (dd, J=7.7, 1.6 Hz, 1H), 6.56 (s, 2H), 4.08-3.93 (m, 2H), 3.40-3.24 (m, 2H), 2.04 (d, J=13.5 Hz, 2H), 1.46-1.32 (m, 11H), 1.26 (s, 3H).

Intermediate 6: 6-Amino-2-(4-amino-4-methyl-piperidin-1-yl)-5-(2,3-dichlorophenyl)-pyrimidine-4-carboxylic Acid

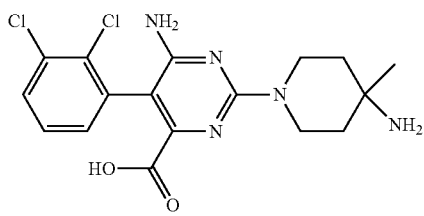 [SMILES: CC1(N)CCN(c2nc(N)c(-c3cccc(Cl)c3Cl)c(C(=O)O)n2)CC1]

A solution of tert-butyl N-[1-[4-amino-6-cyano-5-(2,3-dichlorophenyl)pyrimidin-2-yl]-4-methylpiperidin-4-yl]carbamate (intermediate 5; 370 mg, 0.628 mmol) and NaOH (132 mg, 3.139 mmol) in water (5 mL) was stirred for 16 h at 100° C. in an oil bath. The pH was adjusted to 4 by addition of a 1M HCl solution and the solution was concentrated under reduced pressure. The residue was dissolved in MeOH (10 mL) and purified by flash chromatography C18 silica gel (ACN: water—0.5% HCl), gradient from 10% to 50% in 10 min) to afford the title compound as a yellow solid (250 mg, 94%). mp: 179-181° C. 1H NMR (400 MHz, DMSO-d6) 8.18 (s, 3H), 7.63-7.57 (m, 1H), 7.39-7.31 (m, 2H), 7.22 (s, 1H), 7.15 (d, J=7.5 Hz, 1H), 7.09 (s, 1H), 4.27 (d, J=13.9 Hz, 1H), 2.55 (s, OH), 1.71 (s, 4H), 1.39 (s, 3H). LC/MS (M+1): 396.1.

Intermediate 7: 6-amino-2-(4-{[(tert-butoxy)carbonyl]amino}-4-methylpiperidin-1-yl)-5-(2,3-dichlorophenyl)pyrimidine-4-carboxylic Acid

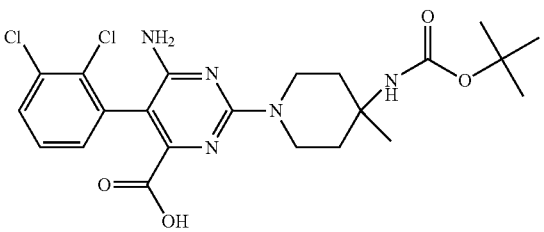 [SMILES: CC1(NC(=O)OC(C)(C)C)CCN(c2nc(N)c(-c3cccc(Cl)c3Cl)c(C(=O)O)n2)CC1]

A solution of tert-butyl N-[1-[4-amino-6-cyano-5-(2,3-dichlorophenyl)pyrimidin-2-yl]-4-methylpiperidin-4-yl]carbamate (Intermediate 5, 200 mg, 0.34 mmol) in aq. NaOH (1N solution, 4 mL) and EtOH (2 mL) was heated at 100° C. for 16 h. It was then diluted with water and extracted with EtOAc (3×20 mL). Combined organic layers were then washed with brine, dried over magnesium sulfate, filtered and concentrated. Purification by flash chromatography on silica (EtOAc:MeOH, 70:30) afforded the title compound as a white solid (140 mg, 69%). LC/MS (M+1): 496.1.

Intermediate 8: tert-butyl N-[1-(5-bromo-4-cyano-6-methylpyrimidin-2-yl)-4-methylpiperidin-4-yl]carbamate Step 1: tert-butyl N-[1-(4-cyano-6-methylpyrimidin-2-yl)-4-methylpiperidin-4-yl]carbamate

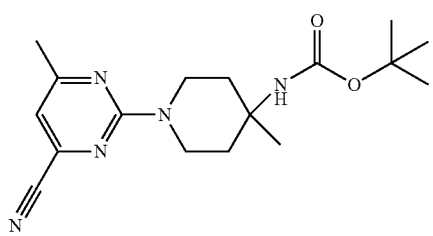 [SMILES: Cc1cc(C#N)nc(N2CCC(C)(NC(=O)OC(C)(C)C)CC2)n1]

A solution of 2-chloro-6-methylpyrimidine-4-carbonitrile (1 g, 6.2 mmol), tert-butyl N-(4-methylpiperidin-4-yl)carbamate (1.7 g, 7.4 mmol) and TEA (0.1 mL) in ACN (15 mL) was heated at 80° C. for 2 h. The solvent was removed under reduced pressure and the crude was purified by flash chromatography (PE:EtOAc, gradient from 100:0 to 50:50) to afford the title compound as a yellow solid (1.9 g, 92%). LC/MS (M+1): 332.2.

Step 2: tert-butyl N-[1-(5-bromo-4-cyano-6-methylpyrimidin-2-yl)-4-methylpiperidin-4-yl]carbamate

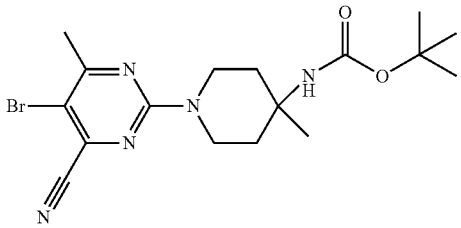 [SMILES: Cc1nc(N2CCC(C)(NC(=O)OC(C)(C)C)CC2)nc(C#N)c1Br]

A solution of tert-butyl N-[1-(4-cyano-6-methylpyrimidin-2-yl)-4-methylpiperidin-4-yl]carbamate (1.9 g, 5.7 mmol) and NBS (1.6 g, 8.5 mmol) in DMF (10 mL) was stirred at room temperature for 1 h. The reaction mixture was then diluted with water (200 mL) and extracted with EtOAc (3×200 mL). Combined organic layers were washed with brine, dried over anhydrous sodium sulfate, filtered and concentrated to give the title compound as a yellow solid (2.3 g, 96%). LC/MS (M+1): 410.2.

Intermediate 9: 7-chloro-6-(4,4,5,5-tetramethyl-1,3,2-dioxaborolan-2-yl)-1H-indazole

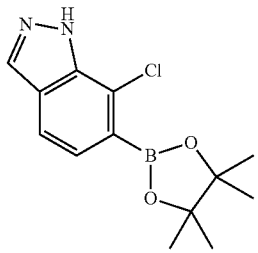 [SMILES: CC1(C)OB(c2ccc3cn[nH]c3c2Cl)OC1(C)C]

A mixture of 6-bromo-7-chloro-1H-indazole (300 mg, 1.23 mmol), Pd(dppf)Cl$_2$.DCM (53 mg, 0.062 mmol), BPD (497 mg, 1.859 mmol) and KOAc (381 mg, 3.7 mmol) in dioxane (5 mL) flushed with nitrogen was heated at 120° C. for 2 h in a sealed tube. Solvent was then removed under reduced pressure and the residue was purified by flash chromatography on silica (PE: EtOAc, 50:50) to afford the title compound as a yellow oil (300 mg, 44%). LC/MS (M+1): 279.2.

Intermediate 10: 6-amino-5-(7-chloro-1H-indazol-6-yl)-2-methanesulfonyl-pyrimidine-4-carbonitrile

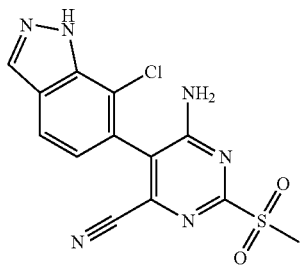 [SMILES: CS(=O)(=O)c1nc(N)c(-c2ccc3cn[nH]c3c2Cl)c(C#N)n1]

The title compound was obtained following a procedure similar to the one described for intermediate 4 but starting from 7-chloro-6-(4,4,5,5-tetramethyl-1,3,2-dioxaborolan-2-yl)-1H-indazole (intermediate 9) as a yellow oil. LC/MS (M+1): 349.0.

Intermediate 11: tert-butyl N-[(3S,4S)-8-(5-bromo-4-cyano-6-methylpyrimidin-2-yl)-3-methyl-2-oxa-8-azaspiro[4.5]decan-4-yl]carbamate Step 1: tert-butyl N-[(3S,4S)-8-(4-cyano-6-methylpyrimidin-2-yl)-3-methyl-2-oxa-8-azaspiro[4.5]decan-4-yl]carbamate

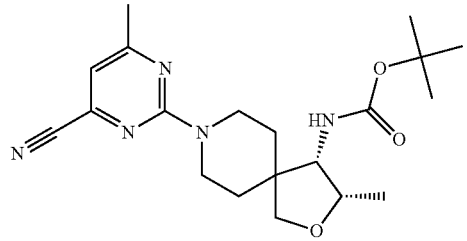 [SMILES: Cc1cc(C#N)nc(N2CCC3(CC2)CO[C@@H](C)[C@H]3NC(=O)OC(C)(C)C)n1]

A solution of 2-chloro-6-methylpyrimidine-4-carbonitrile (106 mg; 0.69 mmol), tert-butyl N-[(3S,4S)-3-methyl-2-oxa-8-azaspiro[4.5]decan-4-yl]carbamate (125 mg; 0.46 mmol) and DIEA (0.4 mL, 2.31 mmol) in anhydrous DMSO (2.5 mL) was stirred for 24 h at 70° C. The reaction mixture was diluted with water (10 mL) and EtOAc (25 mL). Organic layer was washed with water (2×) and brine, dried over sodium sulfate, filtered and concentrated. Purification by flash chromatography on silica (Hexane:EtOAc, gradient from 95:5 to 20:80) afforded the title compound as a yellow foam (175 mg, 98%). 1H NMR (Bruker 400 MHz, DMSO-d6): 7.03 (s, 1H), 6.98 (d, J=10.4 Hz, 1H), 4.23-4.11 (m, 1H), 3.88 (dd, J=10.5, 5.1 Hz, 1H), 3.85-3.78 (m, 1H), 3.78-3.63 (m, 3H), 3.63-3.53 (m, 1H), 3.50 (d, J=8.4 Hz, 1H), 2.34 (s, 3H), 1.69-1.51 (m, 3H), 1.51-1.42 (m, 1H), 1.39 (s, 9H), 1.02 (d, J=6.3 Hz, 3H); LC/MS (M+1): 388.2.

Step 2: tert-butyl N-[(3S,4S)-8-(5-bromo-4-cyano-6-methylpyrimidin-2-yl)-3-methyl-2-oxa-8-azaspiro[4.5]decan-4-yl]carbamate

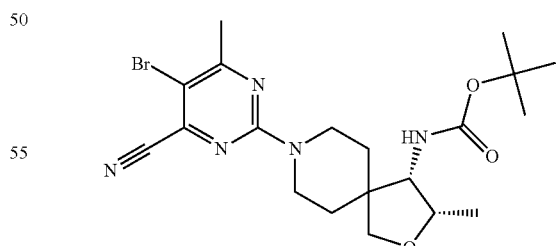

A solution of N-Bromosuccinimide (121 mg; 0.68 mmol) in DMF (1.75 mL) was added slowly to a solution of tert-butyl N-[(3S,4S)-8-(4-cyano-6-methylpyrimidin-2-yl)-3-methyl-2-oxa-8-azaspiro[4.5]decan-4-yl]carbamate (175 mg; 0.45 mmol) in DMF (1.75 mL) maintained at 0° C. The reaction mixture was stirred at RT for 2 h. It was then diluted with EtOAc (50 mL) and washed with water (2×25 mL) and brine (25 mL), dried over sodium sulfate, filtered and concentrated. Purification by flash chromatography on silica (Hexane:EtOAc; gradient from 95:5 to 50:50) to afford the title compound as a white foam (158 mg, 75%). 1H NMR (Bruker 400 MHz, DMSO-d6): 6.99 (d, J=10.5 Hz, 1H), 4.22-4.12 (m, 1H), 3.88 (dd, J=10.5, 5.1 Hz, 1H), 3.85-3.76 (m, 1H), 3.76-3.63 (m, 3H), 3.60-3.47 (m, 2H), 2.48 (s, 3H), 1.69-1.52 (m, 3H), 1.52-1.43 (m, 1H), 1.40 (s, 9H), 1.03 (d, J=6.3 Hz, 3H); LC/MS (M+1): 466.1, 468.1.

Intermediate 12: tert-butyl N-[(1R)-8-(4-cyano-6-methylpyrimidin-2-yl)-3,3-difluoro-8-azaspiro[4.5]decan-1-yl]carbamate Step 1: tert-butyl N-[(1R)-8-(4-cyano-6-methylpyrimidin-2-yl)-3,3-difluoro-8-azaspiro[4.5]decan-1-yl]carbamate

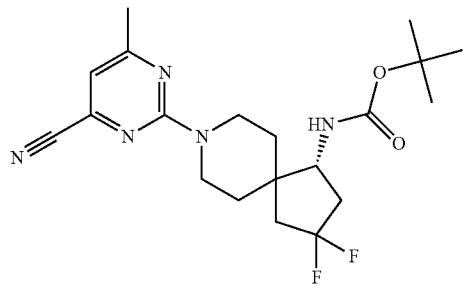 [SMILES: Cc1cc(C#N)nc(N2CCC3(CC2)CC(F)(F)C[C@H]3NC(=O)OC(C)(C)C)n1]

The title compound was obtained following procedure described for intermediate 12, step 1 but starting from 2-chloro-6-methylpyrimidine-4-carbonitrile (99 mg; 0.65 mmol) and tert-butyl N-[(1R)-3,3-difluoro-8-azaspiro[4.5]decan-1-yl]carbamate (125 mg; 0.43 mmol) as a yellow foam (172 mg, 98%).1H NMR (400 MHz, DMSO-d6): 7.09-7.00 (m, 2H), 4.51-4.26 (m, 2H), 3.85 (q, J=9.3 Hz, 1H), 3.18-2.94 (m, 2H), 2.48-2.36 (m, 2H), 2.34 (s, 3H), 2.31-1.95 (m, 2H), 1.62-1.38 (m, 4H), 1.34 (s, 9H), LC/MS (M+1): 408.1

Step 2: tert-butyl N-[(1R)-8-(5-bromo-4-cyano-6-methylpyrimidin-2-yl)-3,3-difluoro-8-azaspiro[4.5]decan-1-yl]carbamate

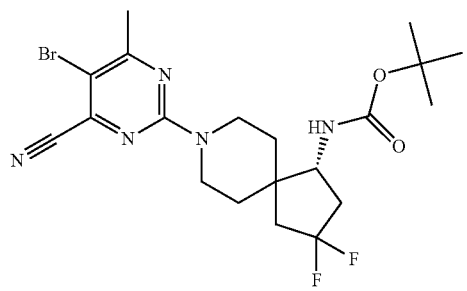 [SMILES: Cc1nc(N2CCC3(CC2)CC(F)(F)C[C@H]3NC(=O)OC(C)(C)C)nc(C#N)c1Br]

The title compound was obtained following procedure described for intermediate 12, step 2 but starting from tert-butyl N-[(1R)-8-(4-cyano-6-methylpyrimidin-2-yl)-3,3-difluoro-8-azaspiro[4.5]decan-1-yl]carbamate (170.00 mg; 0.42 mmol) as a yellow solid (150 mg, 74%). LC/MS (M+1): 486.1, 488.1.

Intermediate 13: tert-butyl N-[(1R)-8-(5-bromo-4-cyano-6-methylpyrimidin-2-yl)-8-azaspiro[4.5]decan-1-yl]carbamate Step 1: tert-butyl N-[(1R)-8-(4-cyano-6-methylpyrimidin-2-yl)-8-azaspiro[4.5]decan-1-yl]carbamate

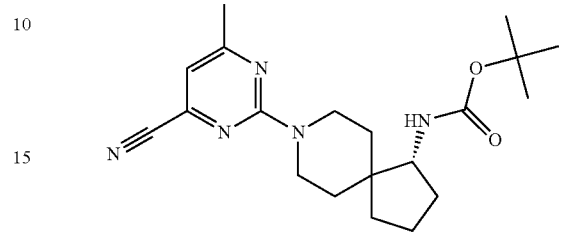

The title compound was obtained following procedure described for intermediate 12, step 1 but starting from 2-chloro-6-methylpyrimidine-4-carbonitrile (258 mg; 1.68 mmol) and tert-butyl N-[(1R)-8-azaspiro[4.5]decan-1-yl]carbamate (214 mg; 0.84 mmol) as a yellow foam (295 mg, 94%). 1H NMR (Bruker 400 MHz, DMSO-d6): 7.00 (s, 1H), 6.73 (d, J=9.3 Hz, 1H), 4.45-4.13 (m, 2H), 3.57 (q, J=8.3 Hz, 1H), 3.24-3.06 (m, 2H), 2.34 (s, 3H), 1.93-1.78 (m, 1H), 1.78-1.58 (m, 2H), 1.58-1.40 (m, 4H), 1.41-1.20 (m, 12H). LC/MS (M+1): 372.0.

Step 2: tert-butyl N-[(1R)-8-(5-bromo-4-cyano-6-methylpyrimidin-2-yl)-8-azaspiro[4.5]decan-1-yl]carbamate

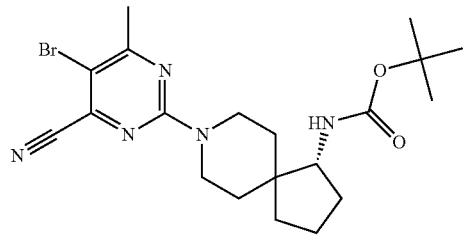 [SMILES: Cc1nc(N2CCC3(CCC[C@H]3NC(=O)OC(C)(C)C)CC2)nc(C#N)c1Br]

The title compound was obtained following procedure described for intermediate 12, step 2 but starting from tert-butyl N-[(1R)-8-(4-cyano-6-methylpyrimidin-2-yl)-8-azaspiro[4.5]decan-1-yl]carbamate (295 mg; 0.79 mmol) as a yellow foam (270 mg, 75%). LC/MS: 450.0, 452.0.

Intermediate 14: (3R)-3H-spiro[1-benzofuran-2,4'-piperidin]-3-amine Hydrochloride Step 1: 2-(2-fluorophenyl)-1,3-dithiane

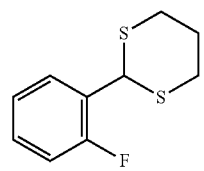 [SMILES: Fc1ccccc1C1SCCCS1]

BF$_3$.Et$_2$O (25 mL, 197 mmol) was added to a solution of 2-fluoro-benzaldehyde (10.0 g, 76.5 mmol) and 1,3-propanedithiol (17.4 g, 153.1 mmol) in DCM (100 mL) at 25° C. The resulting mixture was stirred for 16 h at 25° C. It was then concentrated under vacuum and purified by flash chromatography on silica (PE:EtOAc, 5:1) to afford the title compound as an off-white solid (16.0 g, 95%). LC/MS (M+1): 215

Step 2: 4-(2-fluorobenzoyl)piperidin-4-ol

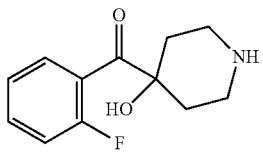 [SMILES: O=C(c1ccccc1F)C1(O)CCNCC1]

A solution of 2-(2-fluorophenyl)-1,3-dithiane (10.0 g, 40.7 mmol) in THF (5 mL) was added to a solution of LDA in THF (41 mL, 2M) maintained at −78° C. under nitrogen atmosphere. The resulting mixture was stirred at −20° C. for 30 min. Then a solution of tert-butyl 4-oxopiperidine-1-carboxylate (12.8 g, 61.1 mmol) in THF (5 mL) was added dropwise at −78° C. After stirring for 1 h at −78° C., the reaction mixture was poured into a saturated solution of NH$_4$Cl (100 mL) and extracted with EtOAc (3×100 mL). Combined organic layers were washed with brine (1×100 ml), dried over anhydrous Na$_2$SO$_4$, filtered and concentrated. Purification by flash chromatography on silica (PE:EtOAc, 1:1) afforded tert-butyl 4-[2-(2-fluorophenyl)-1,3-dithian-2-yl]-4-hydroxypiperidine-1-carboxylate as an off-white solid (15.0 g, 78%), LC/MS (M+1): 314.

A solution of tert-butyl 4-[2-(2-fluorophenyl)-1,3-dithian-2-yl]-4-hydroxypiperidine-1-carboxylate (15.0 g, 47.9 mmol), TBAB (4.63 g, 14.4 mmol), Pyridine hydrobromide (15.3 g, 95.8 mmol) and pyridine (7.7 mL, 95.8 mmol) in DCM (200 mL) and H$_2$O (40 mL) was stirred for 16 h at 25° C. The resulting mixture was concentrated under reduced pressure and purified by flash chromatography on silica (DCM:MeOH, 1;1) to afford the title compound as a brown oil (10.4 g, 97%). LC/MS (M+1): 224.

Step 3: Spiro[1-benzofuran-2,4'-piperidin]-3-one

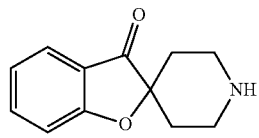 [SMILES: O=C1c2ccccc2OC12CCNCC2]

A solution of 4-(2-fluorobenzoyl)piperidin-4-ol (10.0 g, 40.3 mmol), t-BuOK (9.52 g, 80.6 mmol) and dioxane (100 mL) was stirred for 2 h at 120° C. The reaction mixture was cooled to room temperature, filtered and concentrated under vacuum. The residue was purified by flash chromatography on silica (DCM:MeOH, 1:1) to afford the title compound as a brown solid (8.0 g, 96%). LC/MS (Ml): 204.

Step 4: (S)-2-methyl-N-[1'-[(S)-2-methylpropane-2-sulfinyl]spiro[1-benzofuran-2,4'-piperidin]-3-ylidene]propane-2-sulfinamide

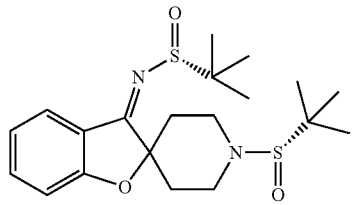 [SMILES: CC(C)(C)[S@](=O)N1CCC2(CC1)Oc1ccccc1/C2=N/[S@](=O)C(C)(C)C]

A mixture of Ti(OEt)$_4$ (50 mL), (R)-2-methylpropane-2-sulfinamide (18.0 g, 140.7 mmol) and spiro[1-benzofuran-2,4'-piperidin]-3-one (5.00 g, 23.4 mmol) was stirred for 16 h at 90° C. it was then diluted with water (1 20 mL) and extracted with EtOAc (3×120 mL). The combined organic layers were washed with brine (1×100 mL), dried over anhydrous Na$_2$SO$_4$, filtered and concentrated. Purification by flash chromatography on silica (PE:EtOAc, 1:1) afforded the title compound as a yellow solid (6.0 g, 60%). LC/MS (M+1): 411.

Step 5: (S)-2-methyl-N-[(3S)-1'-[(S)-2-methylpropane-2-sulfinyl]-3H-spiro[1-benzofuran-2,4'-piperidin]-3-yl]propane-2-sulfinamide

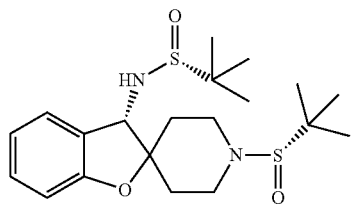 [SMILES: CC(C)(C)[S@](=O)N1CCC2(CC1)Oc1ccccc1[C@@H]2N[S@](=O)C(C)(C)C]

NaBH$_4$ (1.87 g, 46.9 mmol) was added to a solution of (S)-2-methyl-N-[1-[(S)-2-methylpropane-2-sulfinyl]spiro[1-benzofuran-2,4'-piperidin]-3-ylidene]propane-2-sulfinamide (4.00 g, 9.38 mmol) in THF (100 mL) and H$_2$O (2.00 mL) at −50° C. The resulting mixture was stirred for 2 h at 25° C. It was then quenched with saturated NH$_4$Cl aqueous at 0° C. and extracted with EtOAc (3×100 mL). Combined organic layers were washed with brine (1×100 mL), dried over anhydrous Na$_2$SO$_4$, filtered and concentrated. Purification by flash chromatography on silica (PE: EtOAc, 1;1) afforded the title compound as a yellow solid (2 g, 52%). LC/MS (M+1): 413.

Step 6: (3R)-3H-spiro[1-benzofuran-2,4'-piperidin]-3-amine Hydrochloride

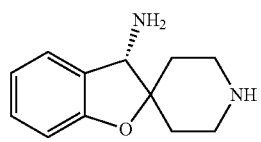 [SMILES: N[C@H]1c2ccccc2OC12CCNCC2]

A mixture of HCl/MeOH (10 mL, 6M) and (S)-2-methyl-N-[(3S)-1-[(S)-2-methylpropane-2-sulfinyl]-3H-spiro[1-benzofuran-2,4-piperidin]-3-yl]propane-2-sulfinamide (700 mg, 1.70 mmol) was stirred for 2 h at 25° C. The resulting mixture was concentrated under reduced pressure. The solids were collected by filtration and washed with Et₂O (3×10 mL) to give the title compound as an off-white solid (300 mg, 85%). LC/MS (M+1): 205.

Intermediate 15: 3H-spiro[furo[2,3-b]pyridine-2,4'-piperidin]-3-amine

Step 1: 3-(1,3-dithian-2-yl)-2-fluoropyridine

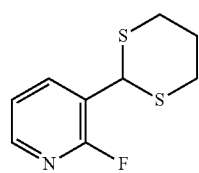 [SMILES: Fc1ncccc1C1SCCCS1]

To a solution of 2-fluoropyridine-3-carbaldehyde (46.0 g, 349.3 mmol) and 1,3-propanedithiol (43.8 g, 384.2 mmol) in DCM (500 mL) was added BF₃.Et₂O (29 mL, 107.6 mmol, 0.31 equiv, 47%) dropwise at room temperature. The resulting mixture was stirred for 16 h at room temperature. The reaction was quenched with saturated NaHCO₃ (200 mL) and extracted with EtOAc (3×200 mL). The combined organic layers were dried over anhydrous Na₂SO₄, filtered and concentrated. Purification by flash chromatography on silica (PE:EtOAc, 10:1) afforded the title compound as a white solid (59 g, 63%). LC/MS (M+1): 216.

Step 2: Tert-butyl 4-[2-(2-fluoropyridin-3-yl)-1,3-dithian-2-yl]-4-hydroxypiperidine-1-carboxylate

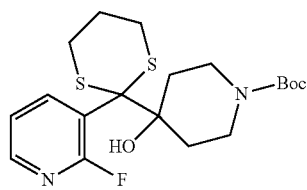 [SMILES: CC(C)(C)OC(=O)N1CCC(O)(C2(c3cccnc3F)SCCCS2)CC1]

A solution of LDA (240 mL, 2M in THF) was added dropwise to a solution of 3-(1,3-dithian-2-yl)-2-fluoropyridine (59.0 g, 220.3 mmol) in THF (150 mL) maintained at −78° C. The resulting mixture was then stirred for 60 min at −20° C. before the addition of a solution of tert-butyl 4-oxopiperidine-1-carboxylate (92.4 g, 440.6 mmol) in THF (30 mL) at −78° C. The resulting mixture was stirred for an additional 1 h at −78C and quenched with saturated NH₄Cl (500 mL) at 0° C. It was extracted with EtOAc (3×300 mL). The combined organic layers were dried over anhydrous Na₂SO₄, filtered and concentrated. Purification by flash chromatography on silica (PE:EtOAc, 5:1) afforded the title compound as a white solid ((80 g, 87%). LC/MS: 359 (M+H−56)

Step 3: Tert-butyl 4-(2-fluoropyridine-3-carbonyl)-4-hydroxypiperidine-1-carboxylate

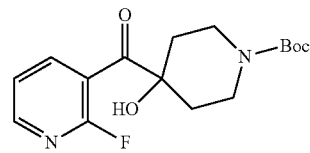 [SMILES: CC(C)(C)OC(=O)N1CCC(O)(C(=O)c2cccnc2F)CC1]

A solution of tert-butyl 4-[2-(2-fluoropyridin-3-yl)-1,3-dithian-2-yl]-4-hydroxypiperidine-1-carboxylate (90.0 g, 213.6 mmol), TBAB (21.7 g, 64.1 mmol), 2I˙[2]-tribromane.pyridine (143.8 g, 427.2 mmol) and pyridine (27.2 mL, 320.4 mmol, 1.50 equiv) in DCM (1 L) and H₂O (200 mL) was stirred for 10 h at room temperature. The reaction mixture was then extracted with DCM (3×300 mL). The combined organic layers were dried over anhydrous Na₂SO₄, filtered and concentrated. Purification by flash chromatography on silica (PE:EtOAc, 2:1) afforded the title compound as a yellow solid (50.0 g, 71%). LC/MS: 269 (M+H−56).

Step 4: Tert-butyl 3-oxospiro[furo[2,3-b]pyridine-2,4-piperidine]-1-carboxylate

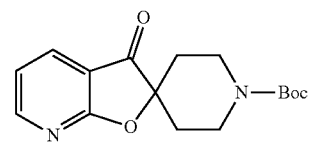 [SMILES: CC(C)(C)OC(=O)N1CCC2(CC1)Oc1ncccc1C2=O]

t-BuOK (6.51 g, 55.1 mmol) was added to a solution of tert-butyl 4-(2-fluoropyridine-3-carbonyl)-4-hydroxypiperidine-1-carboxylate (17.0 g, 50.1 mmol) in dioxane (170 mL) at room temperature. After stirring for 2 h, the resulting mixture was poured into water (200 mL) and extracted with EtOAc (3×200 mL). The combined organic layers were dried over anhydrous Na₂SO₄, filtered and concentrated. Purification by flash chromatography on silica (PE:EtOAc 5:1) afforded the title compound as a white solid (8.5 g, 53%). LC/MS: 249 (M+H−56).

Step 5: Tert-butyl 3-[[(R)-2-methylpropane-2-sulfinyl]imino]spiro[furo[2,3-b]pyridine-2,4'-piperidine]-1'-carboxylate

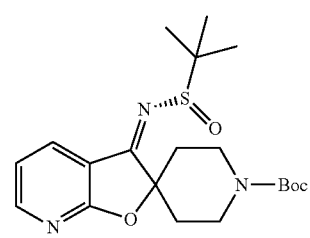

A mixture of tert-butyl 3-oxospiro[furo[2,3-b]pyridine-2,4-piperidine]-1-carboxylate (8.50 g, 26.8 mmol), (R)-2-methylpropane-2-sulfinamide (20.5 g, 160.7 mmol) and Ti(OEt)₄ (60 mL) was stirred for 2 h at 90° C. The resulting mixture was cooled to room temperature and poured into with H₂O (150 mL). it was filtered, and the filtrate was extracted with EtOAc (3×150 mL). The combined organic layers were dried over anhydrous Na₂SO₄, filtered and concentrated. Purification by flash chromatography on silica (PE: EtOAc, 5:1) afforded the title compound as a yellow solid (11 g, 96%). LC/MS (M+1): 408.0.

Step 6: Tert-butyl-3-[[(S)-2-methylpropane-2-sulfinyl]amino]-3H-spiro[furo[2,3-b]pyridine-2,4'-piperidine]-1'-carboxylate

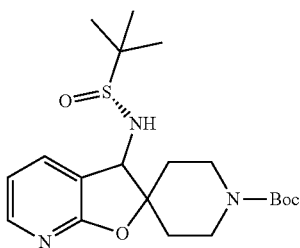 [SMILES: CC(C)(C)OC(=O)N1CCC2(CC1)Oc1ncccc1C2N[S@](=O)C(C)(C)C]

Sodium borohydride (4.66 g, 117 mmol) was added in portions to a stirred solution of tert-butyl 3-[[(R)-2-methylpropane-2-sulfinyl]imino]spiro[furo[2,3-b]pyridine-2,4-piperidine]-1-carboxylate(10.0 g, 23.4 mmol) in THF (100 mL) and MeOH (100 mL) at −50° C. The resulting mixture was stirred for 1 h at −50° C. and quenched with water (10 mL). Solvent was removed under reduced pressure, the mixture was diluted with water (100 mL) and extracted with ethyl acetate (3×100 mL). The combined organic layers were washed with brine (100 mL), dried over anhydrous sodium sulfate, filtered and concentrated to afford the title compound as a yellow solid (10 g, 62%). LC/MS (M+1): 410.0.

Step 7: 3H-spiro[furo[2,3-b]pyridine-2,4'-piperidin]-3-amine

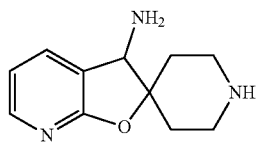 [SMILES: NC1c2cccnc2OC12CCNCC2]

A solution of HCl (gas) in 1,4-dioxane (100 mL) was added dropwise to a solution of tert-butyl-3-[[(S)-2-methylpropane-2-sulfinyl]amino]-3H-spiro[furo[2,3-b]pyridine-2,4'-piperidine]-1'-carboxylate (10.0 g, 24.4 mmol) in DCM (60 mL) maintained at 0° C. After stirring for 1 h at room temperature, the resulting mixture was concentrated under reduced pressure. The resulting HCl salt was loaded onto the SiliaBond Propylsulfonic Acid (SCX-2) resin, which was pre-wetted with methanol, eluting with methanol until no HCl was detected. Then the free amine was washed out with 7M NH₃ in methanol. The eluent was concentrated under vacuum to give the title compound as an orange oil (4.0 g, 77.7%). LC/MS (M+1): 206.

Intermediate 16: (4S)-4,6-dihydrospiro[cyclopenta[d][1,3]thiazole-5,4'-piperidin]-4-amine Step 1: tert-butyl (4Z)-2-chloro-4-{[(R)-2-methylpropane-2-sulfinyl]imino}-4,6-dihydrospiro[cyclopenta[d][1,3]thiazole-5,4'-piperidine]-1'-carboxylate

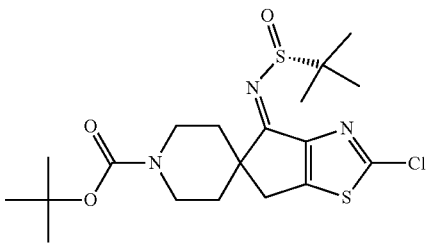 [SMILES: CC(C)(C)OC(=O)N1CCC2(CC1)Cc1sc(Cl)nc1/C2=N\[S@](=O)C(C)(C)C]

A mixture of tert-butyl 2-chloro-4-oxo-6H-spiro[cyclopenta[d][1,3]thiazole-5,4-piperidine]-1-carboxylate (300 mg, 0.845 mmol) and (R)-2-methylpropane-2-sulfinamide (647 mg, 5.07 mmol) in Ti(OEt)₄ (3.39 g, 14.1) was stirred for 19 h at 90° C. under nitrogen atmosphere. The reaction was then quenched by the addition water (50 mL) and filtered. The filtrate was extracted with EtOAc (3×150 mL). Combined organic layers were dried over sodium sulfate, filtered and concentrated. Purification by flash chromatography on silica (PE: EtOAc, gradient from 1:0 to 1:1) afforded the title compound as a yellow solid (280 mg, 74%). LC/MS (M+1): 446.1.

Step 2: tert-butyl (4S)-2-chloro-4-{[(R)-2-methylpropane-2-sulfinyl]amino}-4,6-dihydrospiro [cyclopenta[d][1,3]thiazole-5,4'-piperidine]-1'-carboxylate

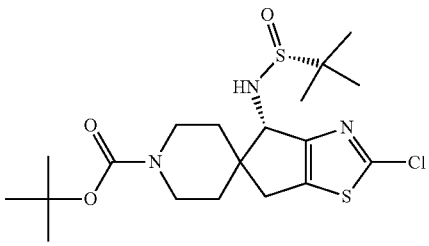 [SMILES: CC(C)(C)OC(=O)N1CCC2(CC1)Cc1sc(Cl)nc1[C@H]2N[S@](=O)C(C)(C)C]

Sodium borohydride (70 mg, 1.78 mmol) was added portion-wise to a solution of tert-butyl-(4Z)-2-chloro-4-[[(R)-2-ethylpropane-2-lfinyl]imino]-6H-spiro[cyclopenta[d][1,3]thiazole-5,4-piperidine]-1-carboxylate (400 mg, 0.892 mmol) in THF (4.4 mL) and water (1.3 mL) maintained at −50° C. under argon atmosphere. The resulting mixture was stirred for 2 h at −50° C. under argon atmosphere, quenched by the addition of water (50 mL) and filtered. The filtrate was extracted with EtOAc (3×50 mL). Combined organic layers were dried over sodium sulfate, filtered and concentrated. Purification by flash chromatography on silica (PE:EtOAc, gradient from 1:0 to 0:1) afforded the title compound as a yellow solid (200 mg, 50%), LC/MS (M+1): 448.1.

Step 3: tert-butyl (4S)-4-{[(R)-2-methylpropane-2-sulfinyl]amino}-4,6-dihydrospiro [cyclopenta[d][1,3]thiazole-5,4'-piperidine]-1'-carboxylate

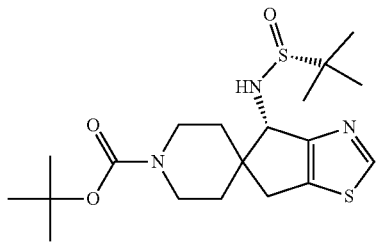 [SMILES: CC(C)(C)OC(=O)N1CCC2(CC1)Cc1scnc1[C@H]2N[S@](=O)C(C)(C)C]

A suspension of tert-butyl (4S)-2-chloro-4-[[(R)-2-methylpropane-2-sulfinyl]amino]-4,6-dihydrospiro[cyclopenta[d][1,3] thiazole-5,4-piperidine]-1-carboxylate (0.20 g, 0.446 mmol), Pd/C (0.10 g, 0.094 mmol, 10%) in MeOH (10 mL) under $H_2$ atmosphere was stirred for 12 h at 100° C. The mixture was filtered through a celite pad and the filtrate was concentrated to give the title compound as a yellow sold (130 mg, 66%). LC/MS (M+1):414.2.

Step 4: (4S)-4,6-dihydrospiro[cyclopenta[d][1,3]thiazole-5,4'-piperidin]-4-amine

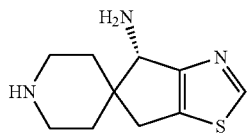

A solution of tert-butyl (4S)-4-[[(R)-2-methylpropane-2-sulfinyl]amino]-4,6-dihydrospiro [cyclopenta[d][1,3]thiazole-5,4-piperidine]-1-carboxylate (150 mg, 0.337 mmol) in MeOH/HCl (4 mL, 26 mmol, 20%) was stirred for 30 min at room temperature. The solvent was removed under reduced pressure and the residue was loaded onto SiliaBond Propylsulfonic Acid (SCX-2) resin, pre-wetted with methanol. The resin was eluted with MeOH and the free amine was released with MeOH/$NH_3$ (7M). MeOH was removed under reduced pressure to afford the title compound as an off-white solid (65 mg, 89%). LC/MS (M+1): 210.1.

Compound 1: 2-(4-amino-4-methylpiperidin-1-yl)-5-(2,3-dichlorophenyl)pyrimidine-4-carboxamide Step 1: Synthesis of tert-butyl (1-(4-cyano-5-(2,3-dichlorophenyl)pyrimidin-2-yl)-4-methylpiperidin-4-yl)carbamate

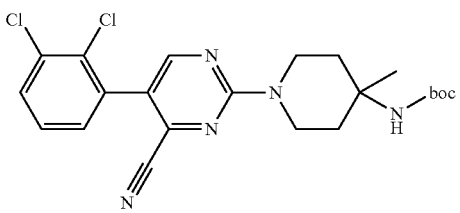

A solution of tert-butyl (1-(5-bromo-4-cyanopyrimidin-2-yl)-4-methylpiperidin-4-yl)carbamate (Intermediate 1, 2 g, 5.06 mmol), 2,3-dichlorophenyl boronic acid (0.967 g, 5.06 mmol) and cesium carbonate (4.1 g, 12.6 mmol) in dioxane/water mixture (15:5 mL) was degassed with nitrogen for 3 min. $Pd(PPh_3)_4$ (0.58 g, 0.51 mmol) was added and the reaction mixture was heated overnight at 100° C. under inert atmosphere. The reaction mixture was dissolved in EtOAc (50 mL) and washed with water (30 mL) and brine solution (30 mL). Organic layer was dried over sodium sulphate, filtered and concentrated. Purification by flash chromatography on silica (PE: AcOEt, gradient from 100:0 to 80:20) afforded the title compound as a white solid (1.6 g, 70%). 1H NMR (400 MHz, DMSO-d6): 8.68 (s, 1H), 8.80 (dd, J=2.0, 7.6 Hz, 1H), 4.56 (m, 2H), 6.69 (brs, 1H), 4.06 (m, 2H), 3.45 (m, 2H), 2.12 (m, 2H), 1.48 (m. 2H), 1.40 (s, 9H), 1.27 (s, 3H).

Step 2: tert-butyl N-{1-[4-carbamoyl-5-(2,3-dichlorophenyl)pyrimidin-2-yl]-4-methylpiperidin-4-yl}carbamate

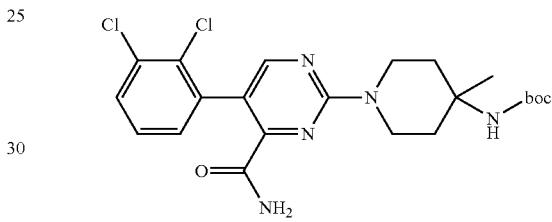

To a solution of tert-butyl (1-(4-cyano-5-(2,3-dichlorophenyl)pyrimidin-2-yl)-4-methylpiperidin-4-yl)carbamate (0.2 g, 0.432 mmol) in DMSO (8 mL) was added hydrogen peroxide (0.4 mL, 30% in water) and potassium carbonate (0.119 g, 0.86 mmol) at 0° C. The reaction mixture was stirred at room temperature for 1 h, then quenched with water and extracted with ethyl acetate (2×20 mL). Combined organic layers were dried over anhydrous sodium sulfate, filtered and concentrated to afford the title compound (0.18 g, 87%). LC/MS (M+1): 480.2.

Step 3: 2-(4-amino-4-methylpiperidin-1-yl)-5-(2,3-dichlorophenyl)pyrimidine-4-carboxamide hydrochloride

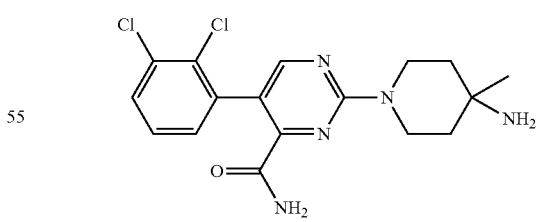

A solution of HCl (2 mL of a 4M solution in dioxane) was added to a solution of tert-butyl N-{1-[4-carbamoyl-5-(2,3-dichlorophenyl)pyrimidin-2-yl]-4-methylpiperidin-4-yl}carbamate (180 mg, 0.375 mmol) in anhydrous dichloromethane (5 mL) maintained at 0° C. The reaction mixture was stirred at room temperature for 1 h. It was then concentrated under reduced pressure to give the title compound as a white solid (75 mg, 50%). 1H NMR (400 MHz, DMSO-d6): 8.36 (s, 1H), 8.14 (m, 4H), 7.59 (m, 2H), 7.37 (t, J=9.2 Hz, 1H), 7.26 (d, J=7.2 Hz, 1H), 4.40 (m, 2H), 3.52 (m, 2H), 1.76 (m, 4H), 1.41 (s, 3H).

Compound 2: 6-Amino-2-(4-amino-4-methyl-piperidin-1-yl)-5-(3-chlorophenyl)-pyrimidine-4-carboxylic Acid Amide Step 1: tert-butyl N-{1-[4-amino-6-carbamoyl-5-(3-chlorophenyl)pyrimidin-2-yl]-4-methylpiperidin-4-yl}carbamate

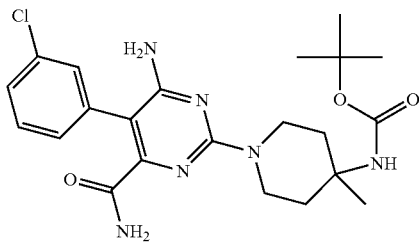 [SMILES: CC1(NC(=O)OC(C)(C)C)CCN(c2nc(N)c(-c3cccc(Cl)c3)c(C(N)=O)n2)CC1]

A mixture of tert-butyl N-[1-(4-amino-5-bromo-6-carbamoylpyrimidin-2-yl)-4-methylpiperidin-4-yl]carbamate (Intermediate 2, 250 mg, 0.41 mmol), (3-chlorophenyl) boronic acid (137 mg, 0.83 mmol), Pd(PPh₃)₄ (34 mg, 0.03 mmol) and sodium carbonate (84 mg, 0.75 mmol) in water (2 mL) and dioxane (6 mL) was heated for 30 min at 130° C. under inert atmosphere. Solvent was then removed under reduced pressure and the crude was purified by flash chromatography on silica (PE:EtOAc, 50:50) to give the title compound as a yellow solid (110 mg, 47%). LC/MS (M+1): 461.2.

Step 2: 6-Amino-2-(4-amino-4-methyl-piperidin-1-yl)-5-(3-chloro-phenyl)-pyrimidine-4-carboxylic Acid Amide

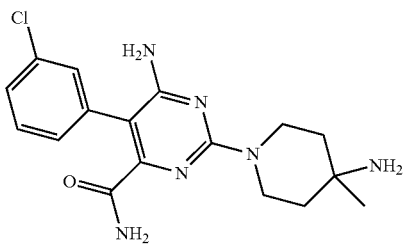 [SMILES: CC1(N)CCN(c2nc(N)c(-c3cccc(Cl)c3)c(C(N)=O)n2)CC1]

A solution of tert-butyl N-[1-[4-amino-6-carbamoyl-5-(3-chlorophenyl)pyrimidin-2-yl]-4-methylpiperidin-4-yl]carbamate (200 mg, 0.37 mmol) and HCl (0.6 mL of a 1.25 M solution in MeOH) in MeOH (6 mL) was stirred at room temperature for 2 h. Solvent was removed under reduced pressure and the crude was purified by preparative HPLC (XBridge Prep C18 OBD Column, 5 μm, 19*150 mm; mobile phase, Water (10 mM NH₄HCO₃+0.1% NH₄OH) and ACN (gradient from 18% ACN up to 48% in 8 min) to afford the title compound as a white solid (31 mg, 23%). mp: 118-120° C. 1H NMR (300 MHz, CD₃OD); 7.43-7.27 (m, 2H), 7.28-7.20 (m, 1H), 7.16 (m, 1H), 4.07-3.95 (m, 2H), 3.70 (m, 2H), 1.58 (m, 4H), 1.25 (d, J=1.3 Hz, 3H). LC/MS (M+1): 361.3.

Compound 3: 6-Amino-2-(4-amino-4-methyl-piperidin-1-yl)-5-(2,3-dichlorophenyl)-pyrimidine-4-carboxylic Acid Amide Step 1: 6-Amino-2-(4-amino-4-methyl-piperidin-1-yl)-5-(2,3-dichloro-phenyl)pyrimidine-4-carbonitrile bis-trifluoroacetate

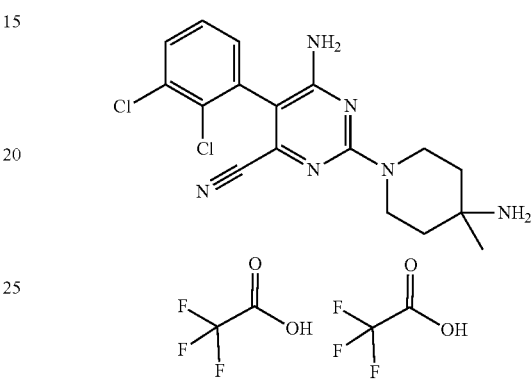

A solution of {1-[4-Amino-6-cyano-5-(2,3-dichloro-phenyl)-pyrimidin-2-yl]-4-methylpiperidin-4-yl}-carbamic acid tert-butyl ester (intermediate 5; 34 mg; 0.07 mmol) and TFA (0.34 mL) in DCM (0.68 mL) was stirred for 1 h at room temperature. Solvent was then removed under reduced pressure and excess TFA was removed by coevaporation with toluene to give the title compound a white foam (42 mg, 97%).
LC/MS (M+1): 377.1

Step 2: 6-Amino-2-(4-amino-4-methyl-piperidin-1-yl)-5-(2,3-dichloro-phenyl)-pyrimidine-4-carboxylic Acid Amide

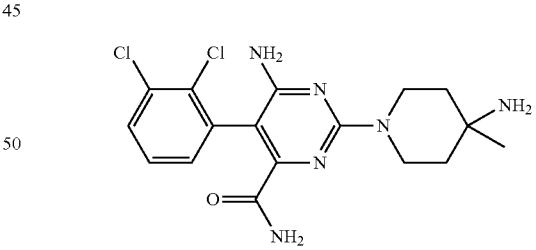

A solution of 6-Amino-2-(4-amino-4-methyl-piperidin-1-yl)-5-(2,3-dichloro-phenyl)pyrimidine-4-carbonitrile bis-trifluoroacetate (35 mg; 0.06 mmol), sodium hydroxide (0.1 mL of a 6M aqueous solution, 0.58 mmol) and hydrogen peroxide (30% weight, 70 ul; 0.58 mmol) in DMF (1.40 mL) was heated in a microwave reactor at 100° C. for 1 h. Hydrogen peroxide and sodium hydroxide were added twice (same amount) and the reaction mixture heated at 100° C. again to obtain full conversion. Reaction mixture was filtered through a celite pad before purification by preparative HPLC (XBridge Prep C-18 OBD 10 uM, 30×250. Water (0.1% Ammonium Hydroxide) and ACN, gradient from 30 to 80% in 15 minutes) to afford the title compound as a white amorphous foam (mixture of two atropisomers, 12 mg, 48%). 1H NMR (400 MHz, DMSO-d6) 7.70 (s, 1H), 7.51 (dd, J=8.1, 1.6 Hz, 1H), 7.28 (t, J=7.8 Hz, 1H), 7.14 (s, 1H), 7.10 (dd, J=7.6, 1.6 Hz, 1H), 6.05 (s, 2H), 3.99-3.87 (m, 2H), 3.68-3.54 (m, 2H), 1.47-1.31 (m, 4H), 1.08 (s, 3H). LC/MS (M+1): 395.2.

Compound 26 and 27: (4M)-6-Amino-2-(4-amino-4-methyl-piperidin-1-yl)-5-(2,3-dichloro-phenyl)-pyrimidine-4-carboxylic acid amide and (4P)-6-Amino-2-(4-amino-4-methyl-piperidin-1-yl)-5-(2,3-dichloro-phenyl)-pyrimidine-4-carboxylic Acid Amide

26

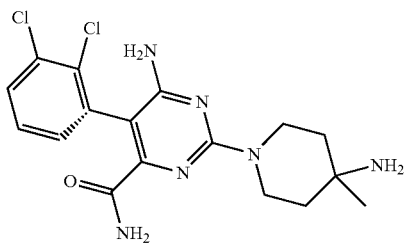

27

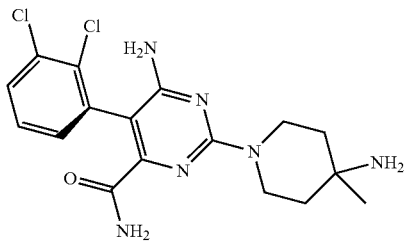

A mixture of atropisomers 3 (200 mg) was separated by SFC ((R,R)WHELK-01 4.6×150 mm, 5 um, EtOH+0.1% DEA:CO₂, 10-50%).

First eluting isomer (compound 26): white solid, 76 mg, RT=3.42 min, ed=99.7%, 1H NMR (300 MHz, DMSO-d6): 7.75-7.68 (m, 1H), 7.49 (dd, J=8.0, 1.6 Hz, 1H), 7.27 (t, J=7.8 Hz, 1H), 7.15 (s, 1H), 7.08 (dd, J=7.7, 1.6 Hz, 1H), 6.07 (s, 2H), 3.96-3.85 (m, 2H), 3.68-3.53 (m, 2H), 1.59 (brs, 1H), 1.37 (q, J=4.9, 4.4 Hz, 4H), 1.07 (s, 3H), mp: 126-128° C.

Second eluting isomer (compound 27): white solid, 76 mg, RT=3.79 min, ed=98.2%, 1H NMR (300 MHz, DMSO-d6) 7.71 (s, 1H), 7.49 (dd, J=8.1, 1.5 Hz, 1H), 7.27 (t, J=7.8 Hz, 1H), 7.16 (s, 1H), 7.08 (dd, J=7.7, 1.6 Hz, 1H), 3.91 (d, J=13.6 Hz, 2H), 3.61 (dt, J=13.1, 6.4 Hz, 2H), 1.61 (brs, 2H), 1.46-1.34 (m, 4H), 1.07 (s, 3H), mp: 130-132° C.

Compound 4: 6-Amino-2-(4-amino-4-methyl-piperidin-1-yl)-5-(3-fluoro-phenyl)pyrimidine-4-carboxylic Acid Amide

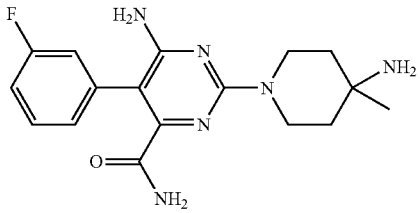

The title compound was obtained following procedure described above but starting from tert-butyl N-[1-(4-amino-5-bromo-6-carbamoylpyrimidin-2-yl)-4-methylpiperidin-4-yl]carbamate (Intermediate 2, 500 mg, 1.1 mmol) and (3-fluorophenyl)boronic acid (243 mg, 1.7 mmol) as an off-white solid. 1H NMR (400 Mz, DMSO-d6) 7.61 (s, 1H), 7.37 (q, J=7.6 Hz, 1H), 7.16 (s, 1H), 7.09 (t, J=8.6 Hz, 1H), 7.03-6.94 (m, 2H), 6.00 (brs, 2H), 3.90-3.90 (m, 2H), 3.62-3.45 (m, 2H), 1.75 (brs, 1H), 1.39-1.36 (m, 4H), 1.09 (s, 3H). LC/MS (M+1): 345.2.

Compound 5: 6-amino-2-[(3S,4S)-4-amino-3-methyl-2-oxa-8-azaspiro[4.5]decan-8-yl]-5-(2,3-dichlorophenyl)pyrimidine-4-carboxamide

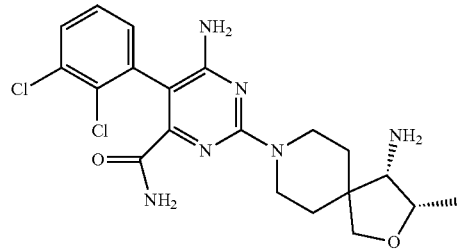 [SMILES: C[C@@H]1OCC2(CCN(c3nc(N)c(-c4cccc(Cl)c4Cl)c(C(N)=O)n3)CC2)[C@@H]1N]

The title compound was obtained following procedure described above but starting from ((3S,4S)-3-Methyl-2-oxa-8-aza-spiro[4.5]dec-4-yl)-carbamic acid tert-butyl ester (WUXI, 130 mg, 0.5 mmol) and 6-Amino-5-(2,3-dichlorophenyl)-2-methanesulfonyl-pyrimidine-4-carbonitrile (Intermediate 5, 110 mg, 0.3 mmol) as a white powder (30 mg, 20%, 3 steps). 1H NMR (400 MHz, DMSO-d6) 7.71 (s, 1H), 7.51 (dd, J=8.0, 1.5 Hz, 1H), 7.28 (t, J=7.8 Hz, 1H), 7.15 (s, 1H), 7.10 (dd, J=7.6, 1.5 Hz, 1H), 6.08 (s, 2H), 4.12 (m, 3H), 3.68 (d, J=8.4 Hz, 1H), 3.49 (d, J=8.4 Hz, 1H), 3.47-3.32 (m, 2H), 2.89 (d, J=5.2 Hz, 1H), 1.75-1.63 (m, 1H), 1.63-1.52 (m, 1H), 1.52-1.38 (m, 2H), 1.38-1.20 (m, 2H), 1.08 (d, J=6.4 Hz, 3H). LC/MS (M+1): 451.1.

Compound 6: 6-amino-2-{9-amino-3-azabicyclo[3.3.1]nonan-3-yl}-5-(2,3-dichlorophenyl)pyrimidine-4-carboxamide

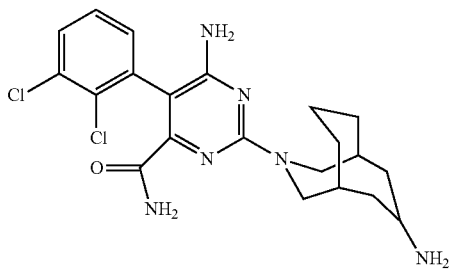 [SMILES: NC(=O)c1nc(N2CC3CCCC(CC(N)C3)C2)nc(N)c1-c1cccc(Cl)c1Cl]

The title compound was obtained following procedure described above but starting from tert-butyl N-(3-azabicyclo[3.3.1]nonan-9-yl)carbamate (Achemblock) and 6-Amino-5-(2,3-dichloro-phenyl)-2-methanesulfonyl-pyrimidine-4-carbonitrile (Intermediate 4) as a white powder (mixture of isomers—1:1). LC/MS (M+1): 421.3.

Compound 7: 6-amino-2-[(1R)-1-amino-8-azaspiro[4.5]decan-8-yl]-5-(2,3-dichlorophenyl)pyrimidine-4-carboxamide

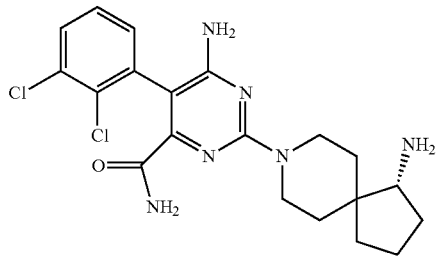 [SMILES: NC(=O)c1nc(N2CCC3(CCC[C@H]3N)CC2)nc(N)c1-c1cccc(Cl)c1Cl]

The title compound was obtained following procedure described above but starting from (R)-(8-Aza-spiro[4.5]dec-1-yl)-carbamic acid tert-butyl ester (WUXI) and 6-Amino-5-(2,3-dichloro-phenyl)-2-methanesulfonyl-pyrimidine-4-carbonitrile (Intermediate 4) as a white powder. 1H NMR (400 MHz, DMSO-d6) 7.50 (dd, J=8.1, 1.6 Hz, 1H), 7.28 (t, J=7.9 Hz, 1H), 7.09 (dd, J=7.6, 1.5 Hz, 1H), 4.44 (t, J=12.2 Hz, 2H), 3.00 (q, J=10.4 Hz, 2H), 2.65 (t, J=7.3 Hz, 1H), 1.91-1.71 (m, 2H), 1.69-1.56 (m, 1H), 1.56-1.42 (m, 3H), 1.42-1.25 (m, 2H), 1.25-1.08 (m, 2H). LC/MS (M+1): 435.1.

Compound 8: 6-amino-2-[(1R)-1-amino-3,3-difluoro-8-azaspiro[4.5]decan-8-yl]-5-(2,3-dichlorophenyl)pyrimidine-4-carboxamide

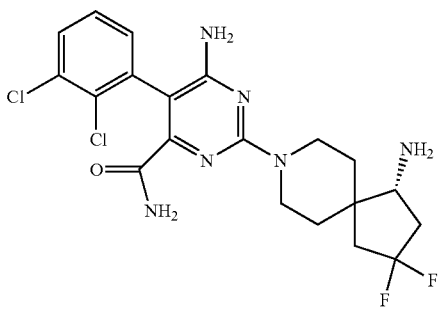 [SMILES: NC(=O)c1nc(N2CCC3(CC2)CC(F)(F)C[C@H]3N)nc(N)c1-c1cccc(Cl)c1Cl]

The title compound was obtained following procedure described above but starting from ((R)-3,3-Difluoro-8-aza-spiro[4.5]dec-1-yl)-carbamic acid tert-butyl ester (WUXI) and 6-Amino-5-(2,3-dichloro-phenyl)-2-methanesulfonyl-pyrimidine-4-carbonitrile (Intermediate 4) as a white powder. 1H NMR (400 MHz, DMSO-d6) δ 7.72 (s, 1H), 7.51 (dd, J=8.0, 1.5 Hz, 1H), 7.28 (t, J=7.8 Hz, 1H), 7.20-7.13 (m, 1H), 7.10 (dt, J=7.6, 1.4 Hz, 1H), 6.09 (s, 2H), 4.54 (t, J=16.4 Hz, 2H), 3.13-2.84 (m, 3H), 2.47-2.28 (m, 2H), 2.14-1.85 (m, 2H), 1.74-1.43 (m, 4H), 1.30 (dd, J=27.6, 13.3 Hz, 2H). LC/MS (M+1): 471.1.

Compound 9: 6-Amino-2-(4-amino-4-methyl-piperidin-1-yl)-5-(2,3-dichlorophenyl)-pyrimidine-4-carboxylic Acid Methylamide

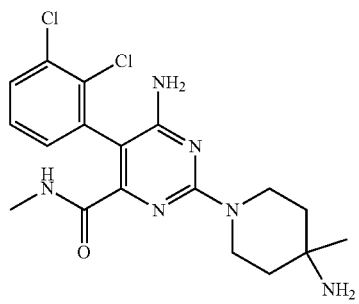

A solution of 6-amino-2-(4-amino-4-methylpiperidin-1-yl)-5-(2,3-dichlorophenyl)pyrimidine-4-carboxylic acid (Intermediate 6, 110 mg, 0.27 mmol) and SO$_2$Cl$_2$ (0.5 mL) in MeOH (5 mL) was heated at 80° C. for 4 h under nitrogen atmosphere. Solvent was removed under reduced pressure and the residue was redissolved in a 2M methyl amine solution in THF (2 mL) and heated at 90° C. for 16 h in a sealed reactor. Solvent was removed under reduced pressure and the crude was purified by preparative HPLC (XBridge Shield RP18 OBD Column, 5 μm, 19*150 mm; Water (10 mM NH$_4$HCO$_3$): ACN gradient from 38% to 68% in 8 min) to afford the title compound as a white solid (12 mg, 24%). mp: 147-149° C.; δ 1H NMR (300 MHz, DMSO-d6) 8.32 (d, J=5.0 Hz, 1H), 7.49 (dd, J=8.1, 1.5 Hz, 1H), 7.26 (t, J=7.9 Hz, 1H), 7.05 (dd, J=7.6, 1.6 Hz, 1H), 6.07 (s, 2H), 4.02-3.92 (m, 2H), 3.64-3.53 (m, 2H), 2.71 (d, J=1.5 Hz, 3H), 1.44-1.39 (m, 6H), 1.07 (s, 3H). LC/MS (M+1): 409.1.

Compound 10: 6-amino-2-[6-amino-7-hydroxy-1-(propan-2-yl)-2-azaspiro[3.4]octan-2-yl]-5-(2,3-dichlorophenyl)pyrimidine-4-carboxamide

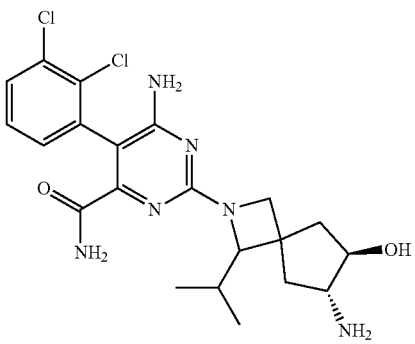 [SMILES: CC(C)C1N(c2nc(N)c(-c3cccc(Cl)c3Cl)c(C(N)=O)n2)CC12C[C@@H](N)[C@H](O)C2]

The title compound was obtained following procedure described above but starting from rac-tert-butyl n-[(6r,7r)-7-hydroxy-1-(propan-2-yl)-2-azaspiro[3.4]octan-6-yl]carbamate hydrochloride (Enamine) and 6-Amino-5-(2,3-dichloro-phenyl)-2-methanesulfonyl-pyrimidine-4-carbonitrile (Intermediate 4) as a white powder (mixture of two diastereoisomers). LC/MS (M+1): 465.2.

Compound 11: 6-amino-2-[8-(aminomethyl)-6-azaspiro[3.4]octan-6-yl]-5-(2,3-dichlorophenyl)pyrimidine-4-carboxamide

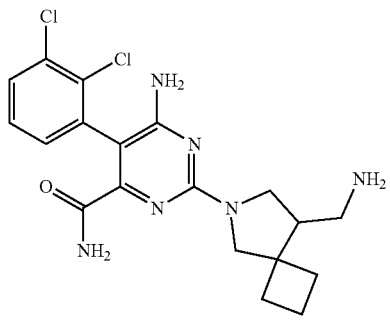 [SMILES: NCC1CN(c2nc(N)c(-c3cccc(Cl)c3Cl)c(C(N)=O)n2)CC12CCC2]

The title compound was obtained following procedure described above but starting from tert-butyl n-((6-azaspiro[3.4]octan-8-yl)methyl)carbamate (Enamine) and 6-Amino-5-(2,3-dichloro-phenyl)-2-methanesulfonyl-pyrimidine-4-carbonitrile (Intermediate 4) as a white powder (mixture of isomers). 1H NMR (400 MHz, DMSO-d6) δ 7.70 (s, 1H), 7.54-7.47 (m, 1H), 7.32-7.23 (m, 1H), 7.17 (s, 1H), 7.13-7.05 (m, 1H), 6.03 (s, 2H), 3.76-3.38 (m, 4H), 2.84 (d, J=12.0 Hz, 1H), 2.41-2.29 (m, 1H), 2.28-1.64 (m, 7H). LC/MS (M+1): 421.2.

Compound 12: 6-amino-2-[3-(aminomethyl)-8-azabicyclo[3.2.1]octan-8-yl]-5-(2,3-dichlorophenyl)pyrimidine-4-carboxamide

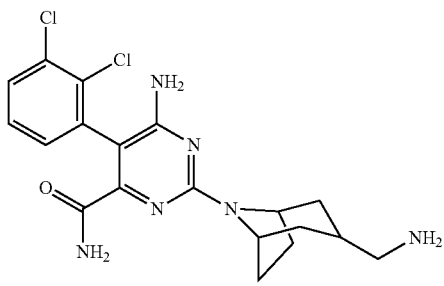 [SMILES: NCC1CC2CCC(C1)N2c1nc(N)c(-c2cccc(Cl)c2Cl)c(C(N)=O)n1]

The title compound was obtained following procedure described above but starting from tert-butyl n-((8-azabicyclo[3.2.1]octan-3-yl)methyl)carbamate (Enamine) and 6-Amino-5-(2,3-dichloro-phenyl)-2-methanesulfonyl-pyrimidine-4-carbonitrile (Intermediate 4) as a white powder. 1H NMR (400 MHz, Methanol-d4) δ 7.49 (dd, J=8.0, 1.6 Hz, 1H), 7.29 (t, J=7.8 Hz, 1H), 7.16 (dd, J=7.6, 1.6 Hz, 1H), 4.80-4.74 (m, 2H), 2.48 (d, J=6.7 Hz, 2H), 2.15-1.95 (m, 3H), 1.84 (d, J=7.5 Hz, 2H), 1.73-1.62 (m, 2H), 1.48 (td, J=13.5, 2.9 Hz, 2H). LC/MS (M+1): 421.2.

Compounds 13 and 14: 6-amino-5-(2,3-dichlorophenyl)-2-[(1R,7S,11s)-11-amino-9-azabicyclo[5.3.1]undecan-9-yl]pyrimidine-4-carboxamide and 6-amino-5-(2,3-dichlorophenyl)-2-[(1R,7S,11r)-11-amino-9-azabicyclo[5.3.1]undecan-9-yl]pyrimidine-4-carboxamide

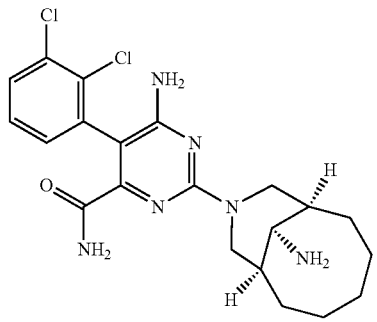

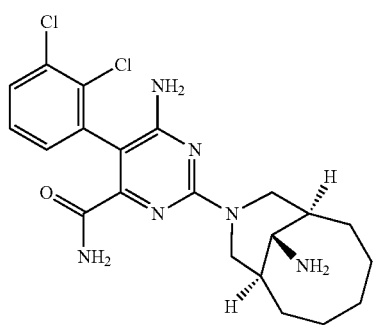

The title compounds were obtained following procedure described above but starting from tert-butyl n-(9-azabicyclo[5.3.1]undecan-11-yl)carbamate oxalic acid (Enamine) and 6-Amino-5-(2,3-dichloro-phenyl)-2-methanesulfonyl-pyrimidine-4-carbonitrile (Intermediate 4) as a mixture of two diastereoisomers. The two isomers were separated by preparative-HPLC (XBridge Prep C-18 OBD 10 uM, 30×250. 30-80% ACN/Water/(0.1% Ammonium Hydroxide)/ACN gradient from 30% to 80% in 15 min).

First eluting isomer (arbitrarily assigned): 6-amino-5-(2,3-dichlorophenyl)-2-[(1R,7S,11 s)-1-amino-9-azabicyclo[5.3.1]undecan-9-yl]pyrimidine-4-carboxamide; white powder (8.2 mg, 17%), 1H NMR (400 MHz, DMSO-d6) 7.66 (s, 1H), 7.51 (dd, J=8.0, 1.5 Hz, 1H), 7.28 (t, J=7.8 Hz, 1H), 7.23-7.08 (m, 2H), 6.10 (s, 2H), 4.81 (dd, J=13.3, 6.3 Hz, 2H), 3.09 (t, J=6.0 Hz, 1H), 2.85 (dd, J=13.5, 4.5 Hz, 2H), 2.02 (d, J=3.1 Hz, 1H), 1.95-1.73 (m, 3H), 1.73-1.56 (m, 3H), 1.51 (dt, J=14.9, 7.5 Hz, 2H), 1.29 (q, J=12.9, 12.5 Hz, 2H), 1.19-1.00 (m, 1H). LC/MS (M+1): 449.5.

Second eluting isomer (arbitrarily assigned): 6-amino-5-(2,3-dichlorophenyl)-2-[(1R,7S,11r)-11-amino-9-azabicyclo[5.3.1]undecan-9-yl]pyrimidine-4-carboxamide, white powder (4.7 mg, 10%), 1H NMR (400 MHz, Methanol-d4) 7.48 (dd, J=8.0, 1.6 Hz, 1H), 7.29 (t, J=7.8 Hz, 1H), 7.17 (dd, J=7.6, 1.6 Hz, 1H), 4.59-4.52 (m, 2H), 3.47-3.42 (m, 1H), 3.28-3.24 (m, 1H), 2.01-1.90 (m, 2H), 1.88-1.71 (m, 4H), 1.61-1.39 (m, 4H), 1.37-1.19 (m, 2H). LC/MS: 449.2.

Compound 15: 2-(4-amino-4-methylpiperidin-1-yl)-5-(2,3-dichlorophenyl)-6-hydroxypyrimidine-4-carboxamide Step 1: tert-butyl N-{1-[4-amino-6-carbamoyl-5-(2,3-dichlorophenyl)pyrimidin-2-yl]-4-methylpiperidin-4-yl}carbamate

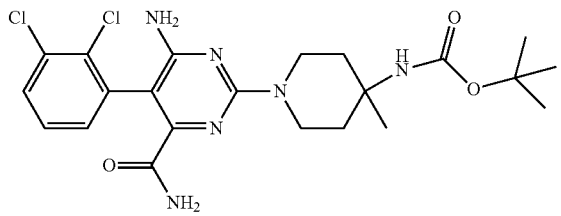 [SMILES: CC1(NC(=O)OC(C)(C)C)CCN(c2nc(N)c(-c3cccc(Cl)c3Cl)c(C(N)=O)n2)CC1]

A solution of tert-butyl N-[1-[4-amino-6-cyano-5-(2,3-dichlorophenyl)pyrimidin-2-yl]-4-methylpiperidin-4-yl]carbamate (intermediate 5, 371 mg, 0.78 mmol) in EtOH (5 mL) and aq. NaOH (0.8 mL of a 2.2 M solution) was heated at 100° C. for 16 h. The reaction mixture was cooled down to RT and pH was adjusted 7 by addition of a 3M HCl solution. The resulting solution was extracted with EtOAc (30 mL) and combined organic layers were washed with brine, dried over sodium sulfate, filtered and concentrated. Purification by flash chromatography on silica (EtOAc: MeOH, gradient from 100:0 to 80:20) afforded the title compound as an off-white solid (180 mg, 49%). LC/MS: 495.1.

Step 2: 2-(4-amino-4-methylpiperidin-1-yl)-5-(2,3-dichlorophenyl)-6-hydroxypyrimidine-4-carboxamide

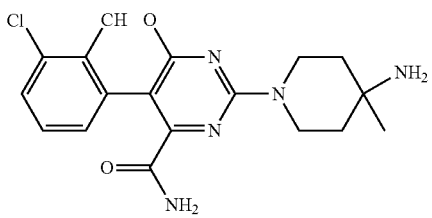 [SMILES: Cc1c(Cl)cccc1-c1c(O)nc(N2CCC(C)(N)CC2)nc1C(N)=O]

A solution of tert-butyl N-[1-[4-amino-6-carbamoyl-5-(2,3-dichlorophenyl)pyrimidin-2-yl]-4-methylpiperidin-4-yl]carbamate (60 mg, 0.122 mmol) and NaNO$_2$ (88 mg, 1.3 mmol) in THF (5 mL), water (3 mL) and conc. HCl (1 mL) was stirred at 0° C. for 4 h. The solvent was removed under reduced pressure and the residue was diluted with aq HCl (5 M, 2 mL) and stirred at room temperature for 30 min. It was then poured onto ice and extracted with EtOAc (3×30 mL). Combined organic layers were washed with brine, dried over magnesium sulfate, filtered and concentrated. Purification by preparative HPLC (XBridge OBD C18 Column, 19*250 mm, 5 um; Water (10 mM NH$_4$HCO$_3$) and ACN, gradient from 58% to 80% in 8 min) to give the title compound as a yellow solid (4 mg, 8%). 1H NMR (400 MHz, Methanol-d4) 7.48-7.47 (m, 1H), 7.45-7.44 (m, 1H), 7.28-7.23 (m, 1H), 4.41-4.20 (m, 2H), 3.51-3.38 (m, 2H), 1.92-1.81 (m, 4H), 1.54-1.50 (m, 3H), LC/MS (M+1): 396.1.

Compound 16: 2-(4-Amino-4-methyl-piperidin-1-yl)-6-chloro-5-(2,3-dichlorophenyl)-pyrimidine-4-carboxylic Acid Amide

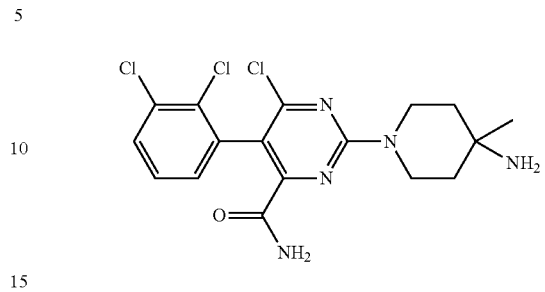

A solution of NaNO$_2$ (197 mg, 2.7 mmol) in water (1 mL) was added to a solution of tert-butyl N-[1-[4-amino-6-cyano-5-(2,3-dichlorophenyl)pyrimidin-2-yl]-4-methylpiperidin-4-yl]carbamate (intermediate 5, 440 mg, 0.90 mmol) in aq. HCl (6M solution, 5 mL, 29.6 mmol) maintained at 0° C. The reaction mixture was stirred at 0° C. for 30 min, then at room temperature for 4 h. The reaction mixture was poured into ice and pH was adjusted to 9 by addition of aq. NaOH (2M). It was extracted with EtOAc (3×30 mL). Combined organic layers were washed with brine, dried over magnesium sulfate, filtered and concentrated. Purification by flash chromatography on silica (PE:EtOAc, 50:50) afforded a yellow solid (210 mg) which was redissolved in ACN (4 mL) and aq. NaOH (0.5 M, 4 mL). The reaction mixture was heated at 70° C. for 1 h. It was then diluted with water (15 mL) and extracted with EtOAc (3×30 mL). Combined organic layers were dried over magnesium sulfate, filtered and concentrated. Purification by flash chromatography (PE:EtOAc, 50:50) afforded the title compound as a yellow solid (80 mg, 51%). 1H NMR (400 MHz, Methanol-d4) 7.53 (dd, J=8.0, 1.6 Hz, 1H), 7.30 (t, J=7.9 Hz, 1H), 7.17 (dd, J=7.6, 1.6 Hz, 1H), 4.09-4.01 (m, 2H), 3.89 (d, J=5.5 Hz, 2H), 1.65 (qdd, J=13.2, 7.5, 4.3 Hz, 4H), 1.27 (s, 3H). LC/MS (M+1): 415.0.

Compound 17: 6-Amino-2-(4-amino-4-methyl-piperidin-1-yl)-5-(2,3-dichlorophenyl)-pyrimidine-4-carboxylic acid (2-hydroxy-ethyl)-amide

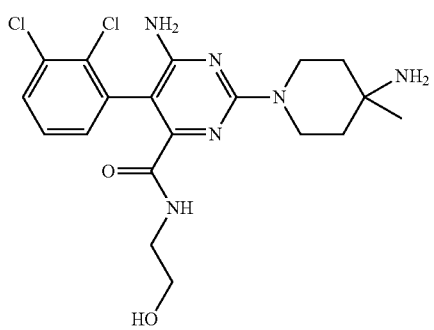 [SMILES: CC1(N)CCN(c2nc(N)c(-c3cccc(Cl)c3Cl)c(C(=O)NCCO)n2)CC1]

The title compound was obtained following procedure described above but starting from 6-amino-2-(4-[[(tert-butoxy)carbonyl]amino]-4-methylpiperidin-1-yl)-5-(2,3-dichlorophenyl)pyrimidine-4-carboxylic acid (intermediate 7) and 2-aminoethan-1-ol as a white solid. mp: 125-127° C. 1H NMR (400 MHz, M ethanol-d4) 7.54-7.47 (m, 1H), 7.31 (t, J=7.8 Hz, 1H), 7.18-7.12 (m, 1H), 4.08-3.97 (m, 2H), 3.82-3.71 (m, 2H), 3.62-3.55 (m, 2H), 3.30 (d, J=5.6 Hz, 2H), 1.68-1.53 (m, 3H), 1.25 (s, 3H). LC/MS (M+1): 439.2.

Compound 18: 2-(4-Amino-4-methyl-piperidin-1-yl)-5-(2,3-dichloro-phenyl)-6-methyl-pyrimidine-4-carboxylic Acid Amide Step 1: tert-butyl N-{1-[4-cyano-5-(2,3-dichlorophenyl)-6-methylpyrimidin-2-yl]-4-methylpiperidin-4-yl}carbamate

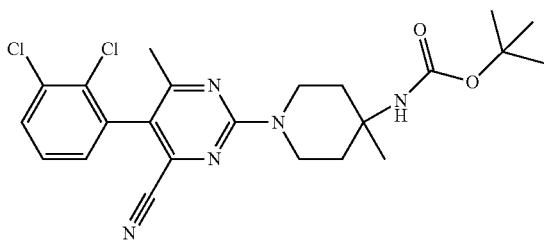 [SMILES: Cc1nc(N2CCC(C)(NC(=O)OC(C)(C)C)CC2)nc(C#N)c1-c1cccc(Cl)c1Cl]

A mixture of tert-butyl N-[1-(5-bromo-4-cyano-6-methylpyrimidin-2-yl)-4-methylpiperidin-4-yl]carbamate (Intermediate 8, 2.3 g, 5.5 mmol), (2,3-dichlorophenyl)boronic acid (2.2 g, 11 mmol), Pd(PPh₃)₄ (1.34 g, 1.1 mmol) and NaHCO₃ (2.43 g, 27.4 mmol) in dioxane (9 mL) and water (3 mL) was heated at 110° C. for 2 h under nitrogen atmosphere in a sealed reactor. The solvent was removed under reduced pressure and the crude was purified by flash chromatography on silica (PE:EtOAc, gradient from 100:0 to 50:50) to afford the title compound as a yellow solid (3 g, 100%). LC/MS (M+1): 476.4.

Step 2: 2-(4-Amino-4-methyl-piperidin-1-yl)-5-(2,3-dichloro-phenyl)-6-methylpyrimidine-4-carboxylic Acid Amide

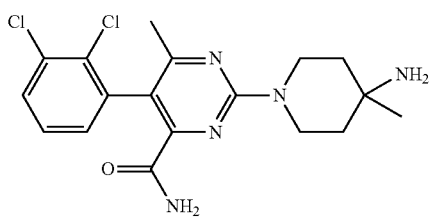 [SMILES: Cc1nc(N2CCC(C)(N)CC2)nc(C(N)=O)c1-c1cccc(Cl)c1Cl]

A solution of tert-butyl N-[1-[4-cyano-5-(2,3-dichlorophenyl)-6-methylpyrimidin-2-yl]-4-methylpiperidin-4-yl]carbamate (100 mg, 0.199 mmol) in conc. HCl (3 mL) was stirred at room temperature under nitrogen atmosphere for 16 h. The crude mixture was directly purified by preparative HPLC (XBridge Prep OBD C18 Column, 30*150 mm 5 um; Water (10 mM NH₄HCO₃) and ACN gradient from 32% to 62% in 8 min). The title compound was isolated as a yellow solid (25 mg, 31%). mp: 103-105° C. 1H NMR (400 MHz, Methanol-d4) 9.38 (s, 1H), 8.07 (d, J=1.5 Hz, 1H), 7.77 (d, J=3.1 Hz, 1H), 7.72 (d, J=3.1 Hz, 1H), 7.64 (d, J=1.8 Hz, 1H), 4.46 (d, J=12.7 Hz, 2H), 3.67 (s, 2H), 2.03 (d, J=13.7 Hz, 4H), 1.58 (s, 3H). LC/MS (M+1): 394.1.

Compound 30 and 31: (4M)-2-(4-amino-4-methylpiperidin-1-yl)-5-(2,3-dichlorophenyl)-6-methylpyrimidine-4-carboxamide and (4P)-2-(4-amino-4-methylpiperidin-1-yl)-5-(2,3-dichlorophenyl)-6-methylpyrimidine-4-carboxamide

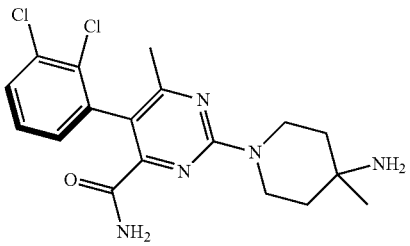

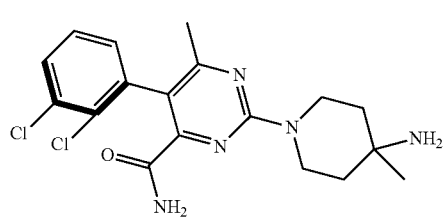

A mixture of atropisomers from compound 18 (250 mg) was separated by preparative HPLC (Column: CHIRALPAK IG, 2×25 cm, 5 um, Hexane+8 mmol/L NH3.MeOH: EtOH-50%).

First eluting isomer (compound 30): white solid, 60 mg, RT=6.96 min, 1H NMR (300 MHz, DMSO-d6): 7.91 (s, 1H), 7.56 (dd, J=8.0, 1.6 Hz, 1H), 7.40-7.28 (m, 2H), 7.18 (dd, J=7.6, 1.6 Hz, 1H), 4.01 (d, J=13.7 Hz, 2H), 3.70 (dt, J=12.8, 6.3 Hz, 2H), 1.98 (s, 4H), 1.42 (d, J=5.4 Hz, 4H), 1.10 (s, 3H); LC/MS (M+1): 394.1, mp: 160-162° C.

Second eluting isomer (compound 31): white solid, 40 mg, RT=14.5 min, 1H NMR (300 MHz, DMSO-d6): 7.91 (s, 1H), 7.56 (dd, J=8.0, 1.6 Hz, 1H), 7.40-7.29 (m, 2H), 7.18 (dd, J=7.6, 1.6 Hz, 1H), 4.03 (d, J=13.4 Hz, 2H), 3.68 (dt, J=13.1, 6.4 Hz, 2H), 1.98 (s, 3H), 1.78 (d, J=9.2 Hz, 2H), 1.41 (d, J=5.3 Hz, 4H), 1.09 (s, 4H). LC/MS (M+1): 394.1, mp: 190-192° C.

Compound 19: 2-(4-Amino-4-methyl-piperidin-1-yl)-6-chloro-5-(3-fluorophenyl)-pyrimidine-4-carboxylic Acid Amide Step 1: tert-butyl N-{1-[4-amino-6-carbamoyl-5-(3-fluorophenyl)pyrimidin-2-yl]-4-methylpiperidin-4-yl}carbamate

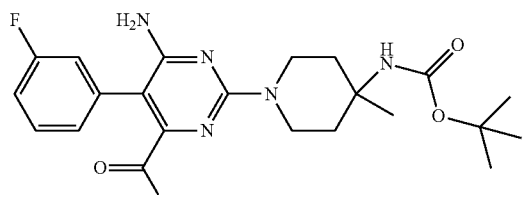

The title compound was obtained following procedure described for compound 2 but starting from tert-butyl N-[1-

(4-amino-5-bromo-6-carbamoylpyrimidin-2-yl)-4-methylpiperidin-4-yl]carbamate (Intermediate 2) and (3-fluorophenyl)boronic acid as a brown solid. LC/MS (M+1): 445.2.

Step 2: 2-(4-Amino-4-methyl-piperidin-1-yl)-6-chloro-5-(3-fluoro-phenyl)-pyrimidine-4-carboxylic Acid Amide

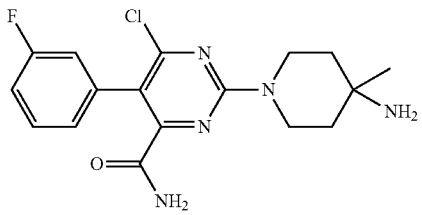 [SMILES: CC1(N)CCN(c2nc(Cl)c(-c3cccc(F)c3)c(C(N)=O)n2)CC1]

The title compound was obtained following a procedure similar to the one described for compound 16 but starting from tert-butyl N-[1-[4-amino-6-carbamoyl-5-(3-fluorophenyl)pyrimidin-2-yl]-4-methylpiperidin-4-yl]carbamate. The title compound was isolated as a white solid. mp: 110-112° C. 1H NM R (400 MHz, Methanol-d4) 7.53-7.39 (m, 1H), 7.42-7.36 (m, 1H), 7.16-6.99 (m, 5H), 4.55-4.45 (m, 3H), 3.54 (ddd, J=14.1, 9.7, 3.9 Hz, 3H), 2.05 (s, 1H), 2.00-1.87 (m, 1H), 1.85 (ddd, J=18.0, 8.3, 3.8 Hz, H), 1.54 (s, 4H). LC/MS (M+1): 364.0.

Compound 20: 6-Amino-2-(4-amino-4-methyl-piperidin-1-yl)-5-(2,3-dichlorophenyl)-pyrimidine-4-carboxylic Acid Hydroxyamide

Step 1: methyl 6-amino-2-(4-amino-4-methylpiperidin-1-yl)-5-(2,3-dichlorophenyl)pyrimidine-4-carboxylate

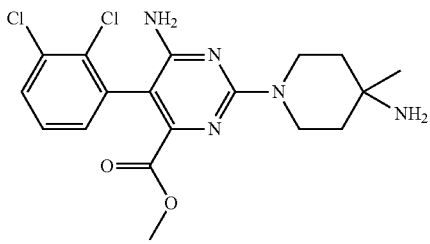 [SMILES: COC(=O)c1nc(N2CCC(C)(N)CC2)nc(N)c1-c1cccc(Cl)c1Cl]

A solution of 6-amino-2-(4-[[(tert-butoxy)carbonyl]amino]-4-methylpiperidin-1-yl)-5-(2,3-dichlorophenyl)pyrimidine-4-carboxylic acid (Intermediate 7, 40 mg, 0.073 mmol) and SOCl$_2$ (1 mL, 13.1 mmol) in MeOH (4 mL) was stirred at 70° C. for 2 h. Solvent was then removed under reduced pressure to afford the title compound as a brown solid (38 mg, 96%). LC/MS (M+1): 410.2.

Step 2: 6-Amino-2-(4-amino-4-methyl-piperidin-1-yl)-5-(2,3-dichloro-phenyl)pyrimidine-4-carboxylic Acid Hydroxyamide

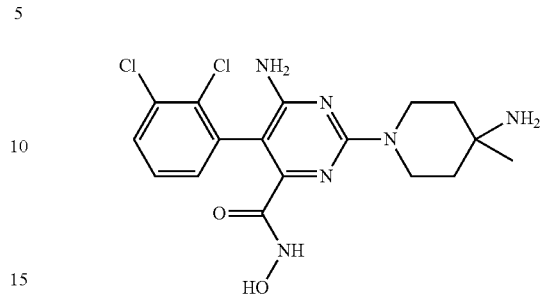

A solution of methyl 6-amino-2-(4-amino-4-methylpiperidin-1-yl)-5-(2,3-dichlorophenyl)pyrimidine-4-carboxylate (33 mg, 0.1 mmol), NH$_2$OH (20 µl, 50% in water) in MeOH (1 mL) was stirred at room temperature for 16 h. The solvent was removed under reduced pressure and the crude was purified by preparative HPLC (XBridge Shield RP18 OBD Column, 5 um, 19*150 mm; Water (10 mM NH$_4$HCO$_3$) and ACN gradient from 25% to 55% in 8 min) to give the title compound as a white solid (9 mg, 33%). 1H NMR (400 MHz, DMSO-d6) 7.56-7.49 (m, 2H), 7.29 (t, J=7.9 Hz, 2H), 7.12 (s, 1H), 7.12 (d, J=7.8 Hz, 1H), 6.10 (s, 4H), 3.91 (d, J=12.6 Hz, 4H), 3.64 (s, 5H), 1.39 (d, J=9.5 Hz, 10H), 1.24 (s, 1H), 1.09 (s, 6H). LC/MS (M+1): 411.1.

Compound 21: 6-Amino-2-(4-amino-4-methyl-piperidin-1-yl)-5-(2,3-dichlorophenyl)-pyrimidine-4-carboxylic Acid Hydrazide

Step 1: tert-butyl N-{1-[4-amino-5-(2,3-dichlorophenyl)-6-(hydrazinocarbonyl)-pyrimidin-2-yl]-4-methylpiperidin-4-yl}carbamate

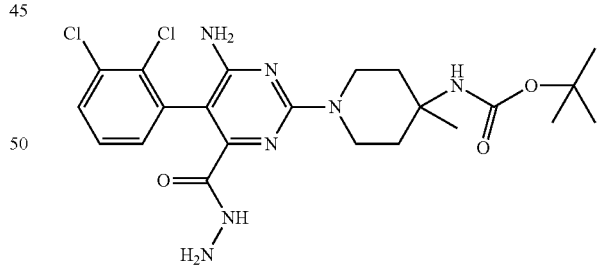

A solution of 6-amino-2-(4-{[(tert-butoxy)carbonyl]amino}-4-methylpiperidin-1-yl)-5-(2,3-dichlorophenyl)pyrimidine-4-carboxylic acid (intermediate 7, 50 mg, 0.084 mmol), HATU (50 mg, 0.126 mmol), DIEA (34 mg, 0.25 mmol) and hydrazine (6 ul) in DMF (5.0 mL) was stirred at 80° C. for 24 h. The reaction mixture was then diluted with water/ice (25 mL) and extracted with EtOAc (3×30 mL). Combined organic layers were washed with brine, dried over magnesium sulfate, filtered and concentrated. Purification by flash chromatography on silica (PE:EtOAc, 90:10) afforded the title compound as a yellow solid (40 mg, 88%).

Step 2: 6-Amino-2-(4-amino-4-methyl-piperidin-1-yl)-5-(2,3-dichloro-phenyl)pyrimidine-4-carboxylic Acid Hydrazide

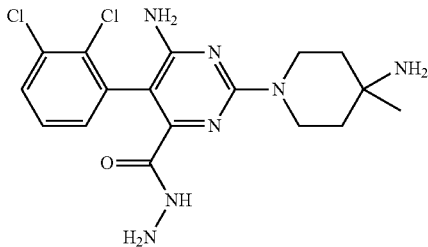 [SMILES: CC1(N)CCN(c2nc(N)c(-c3cccc(Cl)c3Cl)c(C(=O)NN)n2)CC1]

A solution of tert-butyl N-[1-[4-amino-5-(2,3-dichloro-phenyl)-6-(hydrazinecarbonyl)pyrimidin-2-yl]-4-methylpiperidin-4-yl]carbamate (40 mg, 0.074 mmol) in HCl (2 mL of a 4N solution in dioxane) was stirred at room temperature for 4 h. The solvent was then removed under reduced pressure and the crude was purified by preparative HPLC (XBridge Prep OBD C18 Column, 30×150 mm 5 um; Water (10 mM NH$_4$HCO$_3$) and ACN gradient from 30% to 60% in 8 min). The title compound was isolated as a white solid (4.3 mg, 13%). mp: 171-173° C. 1H NMR (300 MHz, Methanol-d4) 7.50 (d, J=7.8 Hz, 1H), 7.30 (t, J=7.8 Hz, 1H), 7.15 (d, J=7.5 Hz, 1H), 4.05 (dt, J=13.9, 5.2 Hz, 2H), 3.69 (ddd, J=13.1, 7.7, 4.3 Hz, 2H), 1.69-1.50 (m, 4H), 1.26 (s, 3H). LC/MS (M+1): 410.1.

Compound 22: 2-(4-Amino-4-methyl-piperidin-1-yl)-6-fluoro-5-(3-fluorophenyl)-pyrimidine-4-carboxylic Acid Amide

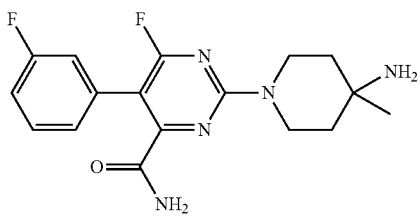

A mixture of tert-butyl N-[1-[4-amino-6-carbamoyl-5-(3-fluorophenyl)pyrimidin-2-yl]-4-methylpiperidin-4-yl]carbamate (prepared in step 1 from compound 4, 179 mg, 0.396 mmol), phenylboronic acid (3.0 mL), NaNO$_2$ (139 mg, 1.9 mmol) and KF (117 mg, 1.9 mmol) was stirred for 1 h at 0° C. The reaction was then quenched by addition of aq. NH$_4$Cl (10 mL) and extracted with EtOAc (3×30 mL). Combined organic layers were washed with brine, dried over magnesium sulfate, filtered and concentrated. The crude product (50 mg) was purified by preparative HPLC (XBridge Prep OBD C18 Column, 19×250 mm, 5 um; Water (10 mM NH$_4$HCO$_3$) and ACN, gradient from 30% to 45% in 8 min) to afford the title compound as a white solid (8 mg, 5%). mp: 90-92° C. 1H NMR (400 MHz, Methanol-d4) 7.45-7.35 (m, 1H), 7.17-7.05 (m, 3H), 4.03 (s, 2H), 3.85 (s, 2H), 1.72-1.55 (m, 4H), 1.28 (s, 3H). LC/MS (M+1): 348.1.

Compound 23: 6-amino-2-[4-(aminomethyl)-8-oxa-2-azaspiro[4.5]decan-2-yl]-5-(2,3-dichlorophenyl)pyrimidine-4-carboxamide

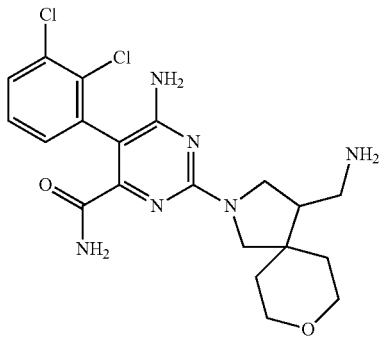 [SMILES: NCC1CN(c2nc(N)c(-c3cccc(Cl)c3Cl)c(C(N)=O)n2)CC12CCOCC2]

The title compound was obtained following procedure described above but starting from 6-Amino-5-(2,3-dichloro-phenyl)-2-methanesulfonyl-pyrimidine-4-carbonitrile (intermediate 4) and tert-butyl n-((8-oxa-2-azaspiro[4.5]decan-4-yl)methyl)carbamate (enamine) as a white powder. 1H NMR (400 MHz, DMSO-d6) 7.78 (s, 1H), 7.51 (dd, J=8.1, 1.6 Hz, 1H), 7.28 (t, J=7.8 Hz, 1H), 7.18 (s, 1H), 7.10 (dt, J=7.6, 1.5 Hz, 1H), 6.04 (s, 2H), 3.84-3.64 (m, 4H), 2.72-2.61 (m, 2H), 1.98-1.84 (m, 2H), 1.77 (dd, J=18.1, 6.4 Hz, 2H), 1.55 (t, J=10.6 Hz, 2H), 1.36 (t, J=16.2 Hz, 3H). LC/MS (M+1): 451.3

Compound 24: 2-[3a-(aminomethyl)-octahydro-1H-isoindol-2-yl]-6-amino-5-(2,3-dichlorophenyl)pyrimidine-4-carboxamide

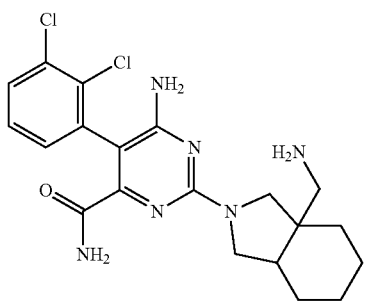 [SMILES: NCC12CCCCC1CN(c1nc(N)c(-c3cccc(Cl)c3Cl)c(C(N)=O)n1)C2]

The title compound was obtained following procedure described above but starting from 6-Amino-5-(2,3-dichloro-phenyl)-2-methanesulfonyl-pyrimidine-4-carbonitrile (intermediate 4) and tert-butyl n-(octahydro-1 h-isoindol-3a-ylmethyl)-carbamate (Enamine) as a white powder (mixture of isomers). 1H NMR (400 MHz, DMSO-d6) 7.68 (s, 1H), 7.51 (dd, J=8.1, 1.6 Hz, 1H), 7.28 (t, J=7.8 Hz, 1H), 7.16 (s, 1H), 7.13-7.07 (m, 1H), 6.00 (s, 2H), 3.71-3.35 (m, 4H), 2.64 (s, 1H), 2.10-1.99 (m, 1H), 1.66-1.22 (m, 9H). LC/MS (M+1): 435.

Compound 25: 2-(4-amino-4-methylpiperidin-1-yl)-5-(3-fluorophenyl)-6-hydroxypyrimidine-4-carboxamide hydrochloride

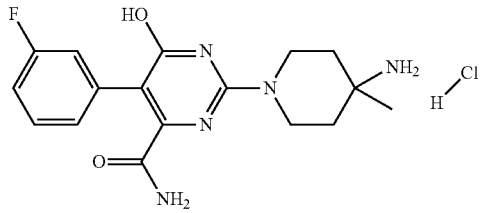

A solution of 2-(4-amino-4-methylpiperidin-1-yl)-6-fluoro-5-(3-fluorophenyl)pyrimidine-4-carboxamide (example 36, 50 mg, 0.072 mmol) in conc. HCl (1.0 mL) and water (2.0 mL) was stirred at 50° C. for 2 h. The resulting mixture was concentrated under reduced pressure and directly purified by preparative HPLC (XBridge Prep OBD C18 Column, 19*250 mm, 5 um; Water (10 mM NH$_4$HCO$_3$ and ACN (gradient from 58% to 80% in 8 min) to give the title compound as a white solid (8.6 mg, 31%). 1H NMR (400 MHz, DMSO-d6) 7.63 (s, 1H), 7.33-7.23 (m, 2H), 7.12-7.02 (m, 2H), 7.04-6.96 (m, 1H), 4.06 (s, 1H), 3.81 (s, 2H), 3.61 (s, 2H), 1.48 (s, 4H), 1.17 (s, 3H). LC/MS (M+1): 346.1

Compounds 66 and 67: (5P)-6-amino-2-[(3S,4S)-4-amino-3-methyl-2-oxa-8-azaspiro[4.5]decan-8-yl]-5-(2,3-dichlorophenyl)pyrimidine-4-carboxamide and (5M)-6-amino-2-[(3S,4S)-4-amino-3-methyl-2-oxa-8-azaspiro[4.5]decan-8-yl]-5-(2,3-dichlorophenyl)pyrimidine-4-carboxamide Step 1: tert-butyl N-[(3S,4S)-8-[4-amino-6-cyano-5-(2,3-dichlorophenyl)pyrimidin-2-yl]-3-methyl-2-oxa-8-azaspiro[4.5]decan-4-yl]carbamate

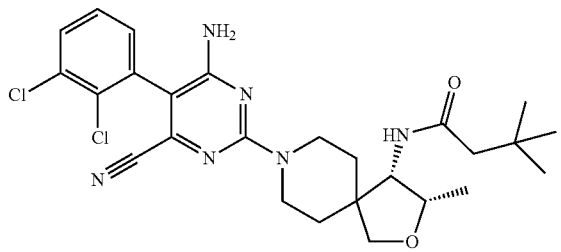 [SMILES: C[C@@H]1OCC2(CCN(c3nc(N)c(-c4cccc(Cl)c4Cl)c(C#N)n3)CC2)[C@@H]1NC(=O)CC(C)(C)C]

A solution of 6-Amino-5-(2,3-dichloro-phenyl)-2-methanesulfonyl-pyrimidine-4-carbonitrile (Intermediate 4, 1.50 g; 4.37 mmol), tert-butyl N-[(3S,4S)-3-methyl-2-oxa-8-azaspiro[4.5]decan-4-yl]carbamate (WUXI; 1.77 g; 6.56 mmol) DIEA (2.27 mL) in anhydrous DMSO (60 mL) was stirred for 6 h at 70° C. The reaction mixture was then diluted with water (300 mL) and EtOAc (800 mL). Organic layer was washed with water (2×300 mL) and brine (300 mL), dried over sodium sulfate, filtered and concentrated. Purification by flash chromatography on silica (hexane: EtOAc, gradient from 95:5 t 20:80) afforded the title compound as a white solid (2.07 g, 89%). 1H NMR (400 MHz, DMSO-d6): 7.72 (dd, J=8.0, 1.6 Hz, 1H), 7.45 (t, J=7.8 Hz, 1H), 7.39 (dd, J=7.7, 1.7 Hz, 1H), 6.97 (d, J=10.5 Hz, 1H), 4.17 (p, J=6.2 Hz, 1H), 3.89 (dd, J=10.6, 5.1 Hz, 1H), 3.86-3.75 (m, 1H), 3.75-3.61 (m, 3H), 3.57-3.43 (m, 2H), 1.68-1.50 (m, 3H), 1.50-1.31 (m, 10H), 1.03 (d, J=6.3 Hz, 3H); LC/MS (M+1): 533.1

Step 2: tert-butyl N-[(3S,4S)-8-[4-amino-6-carbamoyl-5-(2,3-dichlorophenyl)pyrimidin-2-yl]-3-methyl-2-oxa-8-azaspiro[4.5]decan-4-yl]carbamate

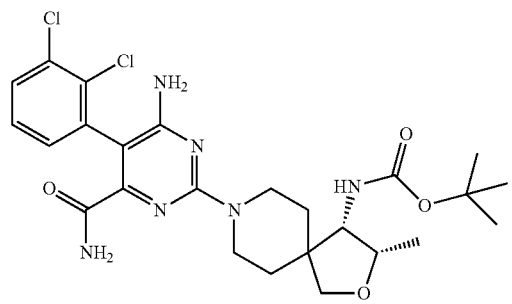 [SMILES: C[C@@H]1OCC2(CCN(c3nc(N)c(-c4cccc(Cl)c4Cl)c(C(N)=O)n3)CC2)[C@@H]1NC(=O)OC(C)(C)C]

A solution of tert-butyl N-[(3S,4S)-8-[4-amino-6-cyano-5-(2,3-dichlorophenyl)pyrimidin-2-yl]-3-methyl-2-oxa-8-azaspiro[4.5]decan-4-yl]carbamate (Intermediate 4; 2.0 g; 3.75 mmol), potassium carbonate (2.59 g; 18.75 mmol) and hydrogen peroxide, 30% weight (7.65 ml; 67.49 mmol) in DMSO (50 mL) was stirred at 50° C. for 4.5 h. The reaction mixture was diluted with EtOAc (800 mL) and washed with a solution of sodium thiosulfate pentahydrate (50.25 g; 202.46 mmol) in water (500 mL). The organic layer was washed with water (2×400 mL) and brine (400 mL), dried over sodium sulfate, filtered and concentrated to give the title compound as a white solid (2.2 g, 95.8%). 1H NMR (Bruker 400 MHz, DMSO-d6): 7.73 (s, 1H), 7.51 (dd, J=8.0, 1.5 Hz, 1H), 7.28 (t, J=7.8 Hz, 1H), 7.14 (s, 1H), 7.10 (dd, J=7.4, 1.2 Hz, 1H), 6.97 (d, J=10.5 Hz, 1H), 6.08 (s, 2H), 4.22-4.11 (m, 1H), 3.96-3.78 (m, 2H), 3.78-3.64 (m, 3H), 3.61-3.47 (m, 2H), 1.69-1.50 (m, 4H), 1.40 (s, 9H), 1.03 (d, J=6.3 Hz, 3H). LC/MS (M+1): 551.2.

Step 3: (5P)-6-amino-2-[(3S,4S)-4-amino-3-methyl-2-oxa-8-azaspiro[4.5]decan-8-yl]-5-(2,3-dichlorophenyl)pyrimidine-4-carboxamide and (5M)-6-amino-2-[(3S,4S)-4-amino-3-methyl-2-oxa-8-azaspiro[4.5]decan-8-yl]-5-(2,3-dichlorophenyl)pyrimidine-4-carboxamide

66

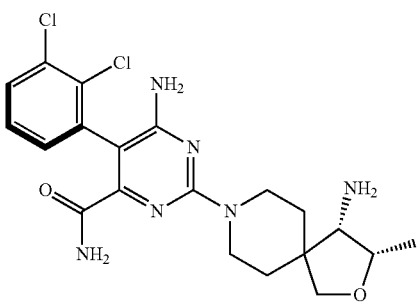

-continued

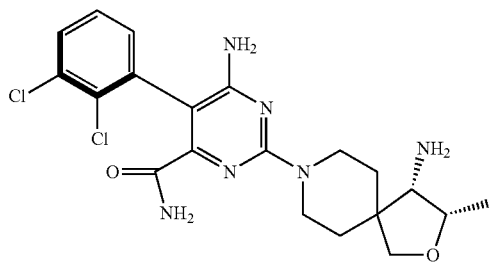

A solution of tert-butyl N-[(3S,4S)-8-[4-amino-6-carbamoyl-5-(2,3-dichlorophenyl)pyrimidin-2-yl]-3-methyl-2-oxa-8-azaspiro[4.5]decan-4-yl]carbamate (2.20 g; 3.59 mmol; 1.00 eq.) in Dichloromethane (44 mL) and TFA (22 mL) was stirred for 1 hour at room temperature. Toluene was added and the mixture was concentrated under reduced pressure. This operation was repeated twice. The crude residue (3.3 g) was purified by preparative SFC (column Amylose2, 250× 21 mm, 5 micron, Methanol+20 mM NH$_4$OH:CO$_2$; 45-55).

First eluting fraction (compound 67) (5M)-6-amino-2-[(3S,4S)-4-amino-3-methyl-2-oxa-8-azaspiro[4.5]decan-8-yl]-5-(2,3-dichlorophenyl)pyrimidine-4-carboxamide: white amorphous solid; 637 mg (40%). RT=4.04 min; ed=100%; 1H NMR (400 MHz, DMSO-d6): 7.71 (s, 1H), 7.51 (dd, J=8.1, 1.5 Hz, 1H), 7.28 (t, J=7.8 Hz, 1H), 7.15 (s, 1H), 7.10 (dd, J=7.6, 1.5 Hz, 1H), 6.08 (s, 2H), 4.16-3.99 (m, 3H), 3.68 (d, J=8.4 Hz, 1H), 3.50 (d, J=8.4 Hz, 1H), 3.48-3.25 (m, 4H), 2.91 (d, J=5.1 Hz, 1H), 1.77-1.34 (m, 6H), 1.09 (d, J=6.4 Hz, 3H); LC/MS (M+1): 451.0.

Second eluting fraction (compound 66) (5P)-6-amino-2-[(3S,4S)-4-amino-3-methyl-2-oxa-8-azaspiro[4.5]decan-8-yl]-5-(2,3-dichlorophenyl)pyrimidine-4-carboxamide: white solid; 603 mg (37%). RT=4.53 min; ed=95%; 1H NMR (Bruker 400 MHz, DMSO-d6): 7.72 (s, 1H), 7.51 (dd, J=8.0, 1.6 Hz, 1H), 7.28 (t, J=7.8 Hz, 1H), 7.15 (s, 1H), 7.10 (dd, J=7.7, 1.6 Hz, 1H), 6.08 (s, 2H), 4.15-3.99 (m, 3H), 3.68 (d, J=8.4 Hz, 1H), 3.50 (d, J=8.4 Hz, 1H), 3.48-3.34 (m, 4H), 2.90 (d, J=5.2 Hz, 1H), 1.75-1.63 (m, 1H), 1.63-1.53 (m, 1H), 1.53-1.29 (m, 4H), 1.08 (d, J=6.4 Hz, 3H). LC/MS (M+1): 451.0.

Compound 85: 2-[(3S,4S)-4-amino-3-methyl-2-oxa-8-azaspiro[4.5]decan-8-yl]-5-(2,3-dichlorophenyl)-6-methylpyrimidine-4-carboxamide Step 1: tert-butyl N-[(3S,4S)-8-[4-cyano-5-(2,3-dichlorophenyl)-6-methylpyrimidin-2-yl]-3-methyl-2-oxa-8-azaspiro[4.5]decan-4-yl]carbamate

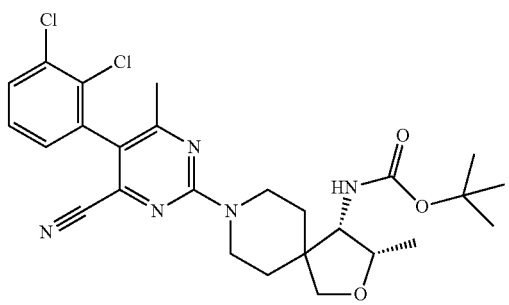 [SMILES: Cc1nc(N2CCC3(CC2)CO[C@@H](C)[C@H]3NC(=O)OC(C)(C)C)nc(C#N)c1-c1cccc(Cl)c1Cl]

Under an atmosphere on N$_2$, tert-butyl N-[(3S,4S)-8-(5-bromo-4-cyano-6-methylpyrimidin-2-yl)-3-methyl-2-oxa-8-azaspiro[4.5]decan-4-yl]carbamate (108 mg; 0.23 mmol) was combined with 2,3-dichlorophenylboronic acid (66 mg; 0.35 mmol) and cesium carbonate (151 mg; 0.46 mmol) in 1,4-dioxane (2.2 mL) and water (0.54 mL). The mixture was degassed for 10 min before the addition of tetrakis(triphenylphosphine)palladium(0) (53 mg; 0.05 mmol) and stirred at 100° C. for 2 h. The reaction mixture was cooled at room temperature and diluted with EtOAc (10 mL). It was filtered through a celite pad which was rinsed with EtOAc (10 mL). Filtrate was concentrated and purified by flash chromatography on silica (hexane:EtOAc, gradient from 95:5 to 20:80) to afford the title compound as a white solid (72 mg, 58%). 1H NMR (Bruker 400 MHz, DMSO-d6): 7.80 (dd, J=6.4, 3.2 Hz, 1H), 7.60-7.47 (m, 2H), 7.01 (d, J=10.5 Hz, 1H), 4.18 (p, J=6.2 Hz, 1H), 3.96-3.84 (m, 2H), 3.84-3.73 (m, 2H), 3.70 (d, J=8.5 Hz, 1H), 3.66-3.58 (m, 1H), 3.54 (d, J=8.2 Hz, 1H), 2.12 (s, 3H), 1.75-1.44 (m, 4H), 1.40 (s, 9H), 1.03 (d, J=6.3 Hz, 3H). LC/MS (M+1): 532.2.

Step 2: tert-butyl N-[(3S,4S)-8-[4-carbamoyl-5-(2,3-dichlorophenyl)-6-methylpyrimidin-2-yl]-3-methyl-2-oxa-8-azaspiro[4.5]decan-4-yl]carbamate

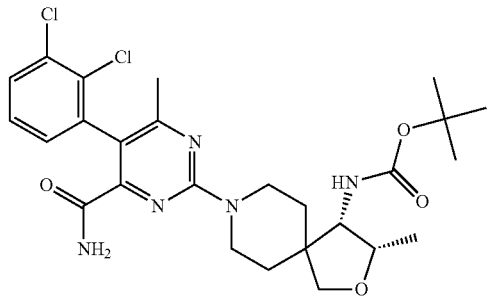 [SMILES: Cc1nc(N2CCC3(CC2)CO[C@@H](C)[C@H]3NC(=O)OC(C)(C)C)nc(C(N)=O)c1-c1cccc(Cl)c1Cl]

A solution of tert-butyl N-[(3S,4S)-8-[4-cyano-5-(2,3-dichlorophenyl)-6-methylpyrimidin-2-yl]-3-methyl-2-oxa-8-azaspiro[4.5]decan-4-yl]carbamate (100 mg; 0.19 mmol), potassium carbonate (130 mg; 0.94 mmol) and hydrogen peroxide, 30% weight (0.38 mL; 3.38 mmol) in DMSO (2.5 mL) was stirred at 50° C. for 6 h. The reaction mixture was diluted with EtOAc (50 mL) and washed with a solution of sodium thiosulfate pentahydrate (2.52 g; 10.1 mmol) in water (25 mL). The organic layer was washed with water (2×25 mL) and brine (25 mL), dried over sodium sulfate, filtered and concentrated to give the title compound as a white solid (103 mg, 94%). LC/MS (M+1): 550.2

Step 3: 2-[(3S,4S)-4-amino-3-methyl-2-oxa-8-azaspiro[4.5]decan-8-yl]-5-(2,3-dichlorophenyl)-6-methylpyrimidine-4-carboxamide

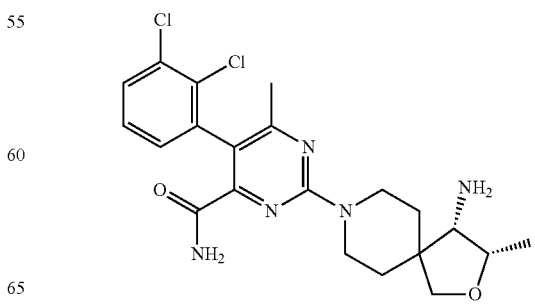

A solution of tert-butyl N-[(3S,4S)-8-[4-carbamoyl-5-(2,3-dichlorophenyl)-6-methylpyrimidin-2-yl]-3-methyl-2-oxa-8-azaspiro[4.5]decan-4-yl]carbamate (100.00 mg; 0.18 mmol; 1.00 eq.) in dichloromethane (2 mL) and TFA (1 mL) was stirred for 1 hour at room temperature. Toluene was added and the mixture was concentrated under reduced pressure. This operation was repeated twice. The crude was then purified by preparative HPLC (XBridge Prep C-18 OBD 10 uM, 30×250; ACN:Water with 0.1% Ammonium Hydroxide, gradient from 20 to 60% in 15 minutes) to afford the title compound as a white powder (70 mg, 86%). 1H NMR (Bruker 400 MHz, DMSO-d6): 7.93 (s, 1H), 7.58 (dd, J=8.0, 1.6 Hz, 1H), 7.43-7.29 (m, 2H), 7.20 (dd, J=7.7, 1.6 Hz, 1H), 4.23-4.10 (m, 2H), 4.08 (dd, J=6.5, 5.2 Hz, 1H), 3.70 (d, J=8.4 Hz, 1H), 3.61-3.42 (m, 3H), 2.93 (d, J=5.2 Hz, 1H), 2.00 (s, 3H), 1.77-1.68 (m, 1H), 1.68-1.42 (m, 5H), 1.09 (d, J=6.4 Hz, 3H); LC/MS (M+1): 450.1.

Compound 94 and 95: (5P)-2-[(3S,4S)-4-amino-3-methyl-2-oxa-8-azaspiro[4.5]decan-8-yl]-5-(2,3-dichlorophenyl)-6-methylpyrimidine-4-carboxamide and (5M)-2-[(3S,4S)-4-amino-3-methyl-2-oxa-8-azaspiro[4.5]decan-8-yl]-5-(2,3-dichlorophenyl)-6-methylpyrimidine-4-carboxamide

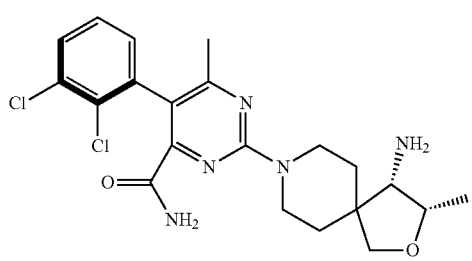

94

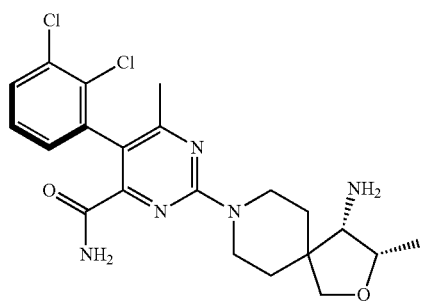

95

The two atropisomers from compound 85 were separated by preparative SFC (column IA, 250×21 mm, 5 micron, Methanol+20 mM NH$_4$OH:CO$_2$, 30-70).

First eluting isomer (compound 94): white amorphous solid, 24 mg, RT=3.32 min, ed=100%, 1H NMR (Bruker 400 MHz, DMSO-d6): 7.93 (s, 1H), 7.58 (dd, J=8.0, 1.5 Hz, 1H), 7.42-7.29 (m, 2H), 7.20 (dd, J=7.6, 1.6 Hz, 1H), 4.24-4.02 (m, 3H), 3.70 (d, J=8.4 Hz, 1H), 3.62-3.41 (m, 3H), 2.92 (d, J=5.2 Hz, 1H), 2.00 (s, 3H), 1.80-1.33 (m, 6H), 1.09 (d, J=6.4 Hz, 3H). LC/MS (M+1): 450.2.

Second eluting isomer (Compound 95): white solid, 22 mg, RT=3.67 min, ed=100%, 1H NMR (400 MHz, DMSO-d6): 7.93 (s, 1H), 7.58 (dd, J=8.0, 1.6 Hz, 1H), 7.41-7.30 (m, 2H), 7.20 (dd, J=7.7, 1.6 Hz, 1H), 4.27-3.99 (m, 3H), 3.71 (d, J=8.5 Hz, 1H), 3.65-3.39 (m, 3H), 2.94 (d, J=5.2 Hz, 1H), 2.00 (s, 3H), 1.81-1.35 (m, 5H), 1.35-1.17 (m, 1H), 1.09 (d, J=6.4 Hz, 3H), LC/MS (M+1): 450.2.

Compound 96 and 97: (5M)-2-[(1R)-1-amino-3,3-difluoro-8-azaspiro[4.5]decan-8-yl]-5-(2,3-dichlorophenyl)-6-methylpyrimidine-4-carboxamide and (5P)-2-[(1R)-1-amino-3,3-difluoro-8-azaspiro[4.5]decan-8-yl]-5-(2,3-dichlorophenyl)-6-methylpyrimidine-4-carboxamide

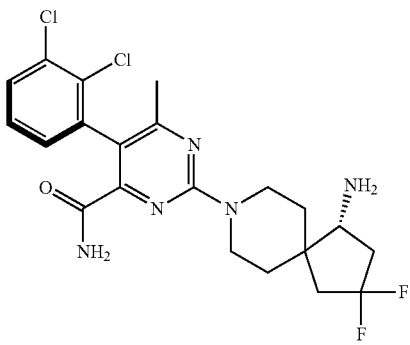

96

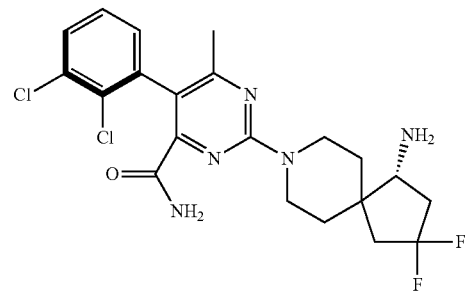

97

The title compounds were obtained following procedure described for compound 85 but starting from tert-butyl N-[(1R)-8-(5-bromo-4-cyano-6-methylpyrimidin-2-yl)-3,3-difluoro-8-azaspiro[4.5]decan-1-yl]carbamate (150.00 mg; 0.31 mmol) and 2,3-dichlorophenylboronic acid (88.28 mg; 0.46 mmol) as a white powder (65 mg, 44% for three steps, mixture of the two atropisomers).

The two atropisomers were separated by preparative SFC (column Cel4, 250×21 mm, 5 micron, Methanol+20 mM NH$_4$OH:CO2)

First eluting isomer (compound 96): white solid, 31 mg, RT=, ed=, 1H NMR (Bruker 400 MHz, DMSO-d6): 7.93 (s, 1H), 7.58 (d, J=8.0 Hz, 1H), 7.42-7.28 (m, 2H), 7.20 (d, J=7.6 Hz, 1H), 4.61 (dd, J=17.5, 13.3 Hz, 2H), 3.18-2.94 (m, 3H), 2.46-2.29 (m, 2H), 2.12-1.91 (m, 5H), 1.78-1.54 (m, 4H), 1.36 (dd, J=26.1, 13.4 Hz, 2H), LC/MS (M+1): 470.2.

Second eluting isomer (compound 97): white solid, 25 mg, RT=, ed=, 1H NMR (Bruker 400 MHz, DMSO-d6): 7.93 (s, 1H), 7.58 (dd, J=8.0, 1.5 Hz, 1H), 7.41-7.29 (m, 2H), 7.20 (dd, J=7.6, 1.6 Hz, 1H), 4.61 (dd, J=19.0, 14.6 Hz, 2H), 3.17-2.95 (m, 3H), 2.47-2.29 (m, 2H), 2.12-1.92 (m, 5H), 1.86-1.51 (m, 4H), 1.44-1.28 (m, 2H), LC/MS (M+1): 470.2.

Compounds 98, 104, 99, 105: (5P)-2-[(3aR,6aS)-3a-(aminomethyl)octahydrocyclopenta[c]pyrrol-2-yl]-6-amino-5-(2,3-dichlorophenyl)pyrimidine-4-carboxamide, (5P)-2-[(3aS,6aR)-3a-(aminomethyl)octahydrocyclopenta[c]pyrrol-2-yl]-6-amino-5-(2,3-dichlorophenyl)pyrimidine-4-carboxamide, (5M)-2-[(3aR,6aS)-3a-(aminomethyl)octahydrocyclopenta[c]pyrrol-2-yl]-6-amino-5-(2,3-dichlorophenyl)pyrimidine-4-carboxamide, (5M)-2-[(3aS,6aR)-3a-(aminomethyl)octahydrocyclopenta[c]pyrrol-2-yl]-6-amino-5-(2,3-dichlorophenyl)pyrimidine-4-carboxamide Step 1: rac-2-[(3aS,6aR)-3a-(aminomethyl)-octahydrocyclopenta[c]pyrrol-2-yl]-6-amino-5-(2,3-dichlorophenyl)pyrimidine-4-carboxamide

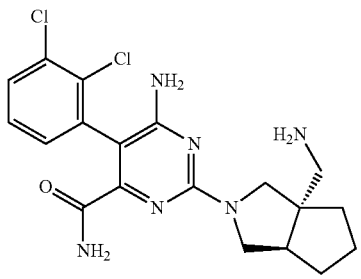 [SMILES: NC[C@]12CCC[C@H]1CN(c1nc(N)c(-c3cccc(Cl)c3Cl)c(C(N)=O)n1)C2]

The title compound was obtained following procedure described for compound 85 but starting from 6-amino-2-chloropyrimidine-4-carbonitrile (250 mg, 1.6 mmol) and rac-tert-butyl n-([(3ar,6ar)-octahydrocyclopenta[c]pyrrol-3a-yl]methyl)carbamate hydrochloride (Enamine, 895 mg, 3.2 mmol as a white amorphous solid (179 mg, 25%, 5 steps). 1H NMR (400 MHz, DMSO-d6) δ 7.69 (s, 1H), 7.51 (d, J=8.0 Hz, 1H), 7.28 (t, J=7.8 Hz, 1H), 7.21-7.04 (m, 2H), 6.02 (s, 2H), 3.80-3.36 (m, 4H), 3.06 (d, J=6.1 Hz, 2H), 2.56 (s, 2H), 2.35 (ddq, J=12.8, 8.4, 4.6, 4.1 Hz, 1H), 1.95-1.37 (m, 6H); LC/MS (M+1): 421.1.

Step 2: Separation of the Four Isomers

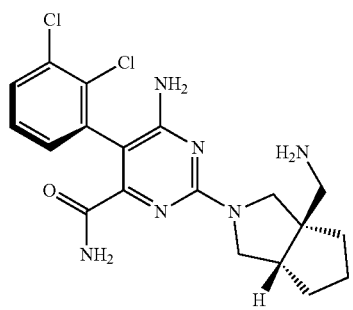
98

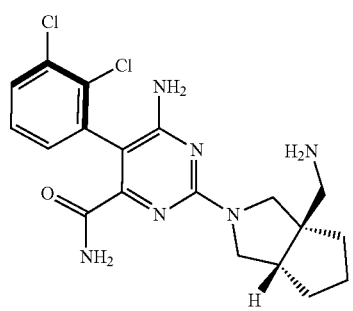
99

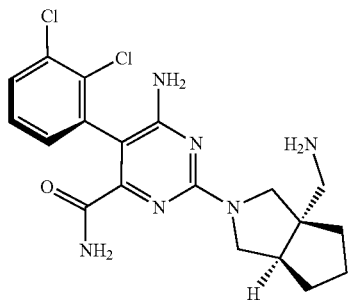
104

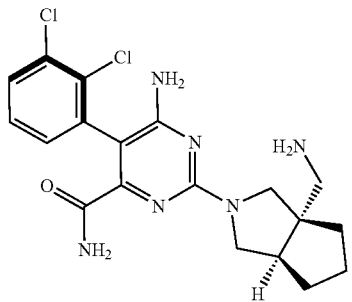
105

The isomers of rac-2-[(3aS,6aR)-3a-(aminomethyl)-octahydrocyclopenta[c]pyrrol-2-yl]-6-amino-5-(2,3-dichlorophenyl)pyrimidine-4-carboxamide were separated by preparative SFC (column: IG, 250×21 mm, 5 micron, Methanol+20 mM NH4OH:CO2, 30:70%).

Stereochemistry was assigned arbitrarily. Enantiomer purity was assessed by SFC using a chiral column IC (Methanol+20 mM NH4OH).

First eluting fraction (Compound 98): white amorphous solid, 26 mg, RT=3.76 min, ed=95.9%, 1H NMR (400 MHz, DMSO-d6) δ 7.68 (s, 1H), 7.51 (dd, J=8.1, 1.6 Hz, 1H), 7.28 (t, J=7.8 Hz, 1H), 7.21-7.04 (m, 2H), 6.03 (s, 2H), 3.65 (ddd, J=35.0, 11.5, 6.8 Hz, 2H), 3.26-3.19 (m, 1H), 2.42-2.26 (m, 1H), 1.93-1.40 (m, 8H), 1.24 (d, J=3.0 Hz, 2H), 0.87 (dt, J=13.4, 7.2 Hz, 1H), LC/MS (M+1): 421.1

Second eluting fraction (Compound 104): white amorphous solid, 35 mg, RT=3.82 min, ed=97.3%, 1H NMR (400 MHz, DMSO-d6) δ 7.69 (s, 1H), 7.51 (dd, J=8.1, 1.6 Hz, 1H), 7.28 (t, J=7.8 Hz, 1H), 7.16 (s, 1H), 7.09 (dd, J=7.6, 1.6 Hz, 1H), 6.02 (s, 2H), 3.81-3.54 (m, 2H), 2.56 (s, 2H), 2.43-2.19 (m, 2H), 1.95-1.36 (m, 8H), 1.36-1.13 (m, 1H); LC/MS (M+1): 421.0

Third eluting fraction (Compound 99): white amorphous solid, 46 mg, RT=4.14 min, ed=95.1%, 1H NMR (400 MHz, DMSO-d6) δ 7.69 (s, 1H), 7.51 (dd, J=8.1, 1.6 Hz, 1H), 7.28 (t, J=7.8 Hz, 1H), 7.16 (s, 1H), 7.09 (dd, J=7.6, 1.6 Hz, 1H), 6.02 (s, 2H), 3.81-3.54 (m, 2H), 2.56 (s, 2H), 2.43-2.19 (m, 2H), 1.95-1.36 (m, 8H), 1.36-1.13 (m, 1H); LC/MS (M+1): 421.0

Fourth eluting fraction (Compound 105): white amorphous solid, 29 mg, RT=4.2 min, ed=95.4%, 1H NMR (400 MHz, DMSO-d6) δ 7.69 (s, 1H), 7.51 (dd, J=8.1, 1.5 Hz, 1H), 7.28 (t, J=7.8 Hz, 1H), 7.16 (s, 1H), 7.10 (dd, J=7.6, 1.6 Hz, 1H), 6.02 (s, 2H), 3.77-3.54 (m, 2H), 2.56 (s, 2H), 2.43-2.22 (m, 2H), 1.94-1.41 (m, 8H), 1.24 (s, 1H).); LC/MS (M+1): 421.1

Compounds 100, 101, 102, 103: (5P)-2-[(3aR,7aS)-3a-(aminomethyl)octahydro-1H-isoindol-2-yl]-6-amino-5-(2,3-dichlorophenyl)pyrimidine-4-carboxamide, (5P)-2-[(3aS,7aR)-3a-(aminomethyl)-octahydro-1H-isoindol-2-yl]-6-amino-5-(2,3-dichlorophenyl)pyrimidine-4-carboxamide, (5M)-2-[(3aR,7aS)-3a-(aminomethyl)-octahydro-1H-isoindol-2-yl]-6-amino-5-(2,3-dichlorophenyl)pyrimidine-4-carboxamide, (5M)-2-[(3aS,7aR)-3a-(aminomethyl)-octahydro-1H-isoindol-2-yl]-6-amino-5-(2,3-dichlorophenyl)pyrimidine-4-carboxamide Step 1: 2-[3a-(aminomethyl)-octahydro-1H-isoindol-2-yl]-6-amino-5-(2,3-dichlorophenyl)pyrimidine-4-carboxamide

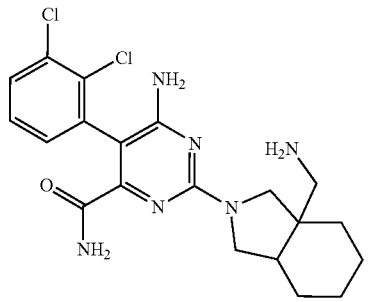 [SMILES: NCC12CCCCC1CN(c1nc(N)c(-c3cccc(Cl)c3Cl)c(C(N)=O)n1)C2]

The title compound was obtained following procedure described for compound 85 but starting from 6-amino-2-chloropyrimidine-4-carbonitrile (250 mg, 1.6 mmol) and tert-butyl n-(octahydro-1 h-isoindol-3a-ylmethyl)carbamate (Enamine, 823 mg, 3.2 mmol as a white amorphous solid (128 mg, 19%, 5 steps). 1H NMR (400 MHz, DMSO-d6) δ 7.68 (s, 1H), 7.50 (d, 1H), 7.28 (t, J=7.8 Hz, 1H), 7.23-7.04 (m, 2H), 6.00 (s, 2H), 3.70-3.34 (m, 4H), 2.63 (q, J=5.8 Hz, 1H), 2.05 (dd, J=11.5, 5.8 Hz, 2H), 1.72-1.20 (m, 8H); LC/MS (M+1): 435.1.

Step 2: Separation of the Four Isomers

100

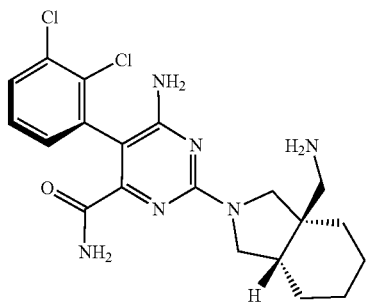

101

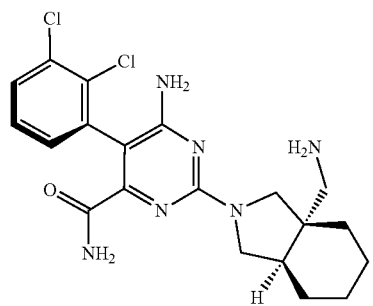

102

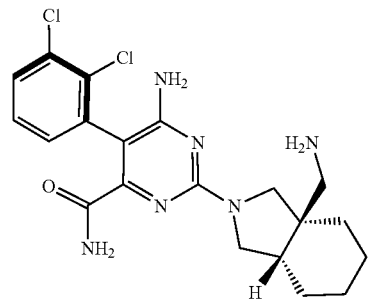

103

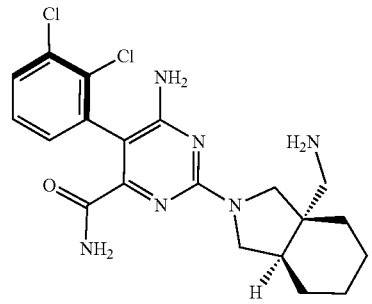

The isomers of 2-[3a-(aminomethyl)-octahydro-1H-isoindol-2-yl]-6-amino-5-(2,3-dichlorophenyl)pyrimidine-4-carboxamide were separated by preparative SFC (column: IG, 250×21 mm, 5 micron, Methanol+20 mM NH4OH:CO2, 30:70%). Stereochemistry was assigned arbitrarily. Enantiomer purity was assessed by SFC using a chiral column IG (Methanol+20 mM NH4OH).

First eluting fraction (Compound 100): white amorphous solid, 20 mg, RT=3.67 min, ed=95.0%, 1H NMR (400 MHz, DMSO-d6): 7.68 (s, 1H), 7.51 (dd, J=8.0, 1.5 Hz, 1H), 7.28 (t, J=7.8 Hz, 1H), 7.22-7.05 (m, 2H), 6.00 (s, 2H), 3.77-3.48 (m, 2H), 2.62 (d, J=14.0 Hz, 2H), 2.04 (s, 2H), 1.69-1.17 (m, 10H), 0.95-0.74 (m, 1H), LC/MS (M+1): 435.0

Second eluting fraction (Compound 101): white amorphous solid, 19 mg, RT=3.59 min, ed=93.4%, 1H NMR (400 MHz, DMSO-d6): 7.76-7.59 (m, 1H), 7.51 (dd, J=8.1, 1.6 Hz, 1H), 7.28 (t, J=7.8 Hz, 1H), 7.22-7.04 (m, 2H), 6.00 (s, 2H), 3.73-3.43 (m, 2H), 2.64 (d, J=14.3 Hz, 1H), 2.15-1.89 (m, 2H), 1.40 (t, J=56.6 Hz, 9H), 0.96-0.72 (m, 1H); LC/MS (M+1): 435.0

Third eluting fraction (Compound 102): white amorphous solid, 20 mg, RT=3.85 min, ed=91.3%, 1H NMR (400 MHz, DMSO-d6): 7.68 (s, 1H), 7.51 (dd, J=8.0, 1.6 Hz, 1H), 7.28 (t, J=7.8 Hz, 1H), 7.22-7.01 (m, 2H), 6.00 (s, 2H), 3.73-3.43 (m, 2H), 2.64 (s, 2H), 2.03 (dt, J=15.3, 7.2 Hz, 2H), 1.78-0.97 (m, 1 OH), 0.97-0.68 (m, 1H). LC/MS (M+1): 435.0

Fourth eluting fraction (Compound 103): white amorphous solid, 16 mg, RT=4.02 min, ed=94.2%, 1H NMR (400

MHz, DMSO-d6): 7.68 (s, 1H), 7.51 (d, J=7.8 Hz, 1H), 7.28 (q, J=7.0, 6.3 Hz, 1H), 7.22-7.00 (m, 2H), 6.00 (s, 2H), 3.51 (s, 2H), 2.04 (s, 2H), 1.34 (d, J=77.2 Hz, 11H), 0.85 (s, 2H); LC/MS (M+1): 435.1

Compound 113 and 114: (5P)-2-[(1R)-1-amino-8-azaspiro[4.5]decan-8-yl]-5-(2,3-dichlorophenyl)-6-methylpyrimidine-4-carboxamide and (5M)-2-[(1R)-1-amino-8-azaspiro[4.5]decan-8-yl]-5-(2,3-dichlorophenyl)-6-methyl pyrimidine-4-carboxamide

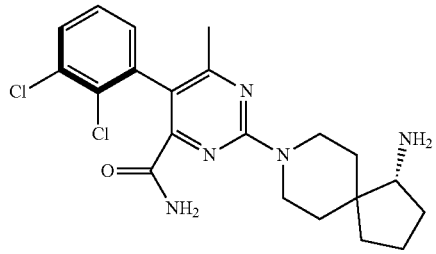

113

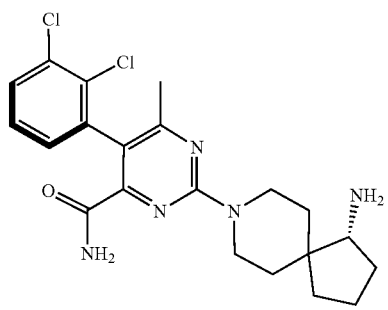

114

The title compounds were obtained following procedure described for compound 85 but starting from tert-butyl N-[(1R)-8-(5-bromo-4-cyano-6-methylpyrimidin-2-yl)-8-azaspiro[4.5]decan-1-yl]carbamate (intermediate 13, 100 mg; 0.22 mmol) and 2,3-dichlorophenylboronic acid (64 mg; 0.33 mmol) as a white powder (43 mg, 31% for three steps, mixture of the two atropisomers).

The two atropisomers were separated by preparative SFC (column Whelk-O, 250×21 mm, 5 micron, Methanol+20 mM NH4OH:CO2, 5-45).

First eluting isomer (compound 113): white solid, 9 mg, RT=3.51 min, ed=100%, 1H NMR (400 MHz, DMSO-d6): 7.91 (s, 1H), 7.58 (dd, J=8.0, 1.5 Hz, 1H), 7.43-7.29 (m, 2H), 7.20 (dd, J=7.6, 1.6 Hz, 1H), 4.55 (t, J=13.0 Hz, 2H), 3.15-3.05 (m, 2H), 2.78 (t, J=7.4 Hz, 1H), 2.00 (s, 3H), 1.96-1.72 (m, 3H), 1.73-1.29 (m, 7H), 1.29-1.14 (m, 2H), LC/MS (M+1): 434.0.

Second eluting isomer (compound 114): white solid, 9 mg, RT=4.03 min, ed=94.3%, 1H NMR (400 MHz, DMSO-d6): 7.90 (s, 1H), 7.58 (dd, J=8.1, 1.6 Hz, 1H), 7.40-7.30 (m, 2H), 7.20 (dd, J=7.6, 1.6 Hz, 1H), 4.54 (td, J=9.5, 5.1 Hz, 2H), 3.20-3.05 (m, 2H), 2.73 (t, J=7.4 Hz, 1H), 2.00 (s, 3H), 1.94-1.76 (m, 2H), 1.75-1.47 (m, 5H), 1.46-1.31 (m, 2H), 1.31-1.13 (m, 3H), LC/MS (M+1): 434.0.

Compounds 117 and 118: (5P)-6-amino-2-[(1S)-1-amino-1,3-dihydrospiro[indene-2,4'-piperidin]-1'-yl]-5-(2,3-dichlorophenyl)pyrimidine-4-carboxamide and (5M)-6-amino-2-[(1S)-1-amino-1,3-dihydrospiro[indene-2,4'-piperidin]-1'-yl]-5-(2,3-dichlorophenyl)pyrimidine-4-carboxamide Step 1: 6-amino-2-[(1S)-1-amino-1,3-dihydrospiro[indene-2,4'-piperidin]-1'-yl]-5-(2,3-dichlorophenyl)pyrimidine-4-carbonitrile

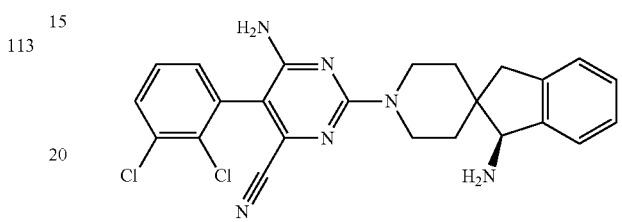

A solution of 6-Amino-5-(2,3-dichloro-phenyl)-2-methanesulfonyl-pyrimidine-4-carbonitrile (75 mg; 0.22 mmol; 1.00 eq.), (3S)-1,3-dihydrospiro[indene-2,4'-piperidin]-3-amine dihydrochloride (Pharmablock, 90 mg; 0.33 mmol; 1.50 eq.) and potassium carbonate (151 mg; 1.09 mmol; 5.00 eq.) in MeCN (1.50 ml; 20.00 V) and N,N-Dimethylformamide (0.75 ml; 10.00 V) was stirred at 100° C. for 18 hrs. The reaction mixture was diluted with EtOAc (40 mL) and was washed with water (2×10 mL) and brine (10 mL). The organic layer was dried over sodium sulfate, filtered and concentrated. Purification by flash chromatography on silica (EtOAc:MeOH, gradient from 99:1 to 90:10) afforded the title compound as a white solid (76 mg, 75%).

1H NMR (Bruker 400 MHz, DMSO-d6): 7.72 (dd, J=8.0, 1.7 Hz, 1H), 7.45 (t, J=7.8 Hz, 1H), 7.39 (dd, J=7.6, 1.6 Hz, 1H), 7.30 (dd, J=6.6, 1.7 Hz, 1H), 7.22-7.10 (m, 3H), 7.00-6.57 (m, 2H), 4.44 (t, J=14.2 Hz, 2H), 3.83 (s, 1H), 3.21-3.02 (m, 3H), 2.62 (d, J=15.6 Hz, 1H), 1.93-1.78 (m, 2H), 1.78-1.67 (m, 1H), 1.59 (td, J=12.6, 4.3 Hz, 1H), 1.48 (d, J=13.2 Hz, 1H), 1.07 (d, J=13.3 Hz, 1H). LC/MS (M+1): 465.2.

Step 2: (5P)-6-amino-2-[(1S)-1-amino-1,3-dihydrospiro[indene-2,4'-piperidin]-1'-yl]-5-(2,3-dichlorophenyl)pyrimidine-4-carboxamide and (5M)-6-amino-2-[(1S)-1-amino-1,3-dihydrospiro[indene-2,4'-piperidin]-1'-yl]-5-(2,3-dichlorophenyl)pyrimidine-4-carboxamide

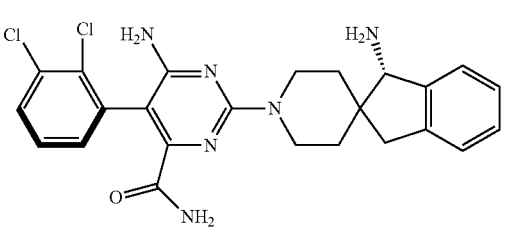

117

189

-continued

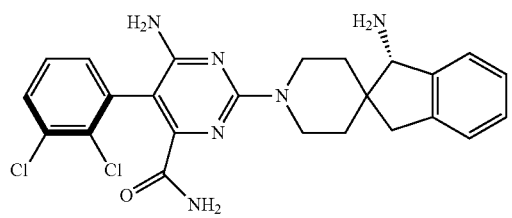

118

A solution of 6-amino-2-[(1S)-1-amino-1,3-dihydrospiro[indene-2,4'-piperidin]-1'-yl]-5-(2,3-dichlorophenyl)pyrimidine-4-carbonitrile (936 mg; 2.01 mmol), potassium carbonate (1.39 g; 10.1 mmol) and hydrogen peroxide, 30% weight (4.1 ml; 36.2 mmol) in DMSO (23 mL) was stirred at 50° C. for 4 h. The reaction mixture was diluted with EtOAc (800 mL) and washed with a solution of sodium thiosulfate pentahydrate (27 g; 109 mmol) in water (230 mL). The organic layer was washed with water (2×400 mL) and brine (400 mL), dried over sodium sulfate, filtered and concentrated to give the title compound as a white solid (970 mg).

The two atropisomers were separated by preparative SFC (column IC, 250×21 mm, 5 micron; methanol+20 mM NH$_4$OH:CO$_2$, 45-55)

First eluting isomer (compound 117): white solid, 309 mg, RT=6.62 min, ed=100%, LC/MS (M+1) 483.1.

Second eluting isomer (compound 118): white solid, 328 mg, RT=7.98 min, ed=99.4%, 1H NMR (400 MHz, DMSO-d6): 7.74 (s, 1H), 7.53-7.50 (m, 1H), 7.37-7.25 (m, 2H), 7.25-7.15 (m, 4H), 7.12-7.10 (m, 1H), 6.12 (s, 2H), 4.54 (d, J=13.7 Hz, 2H), 3.90 (s, 1H), 3.16-3.01 (m, 3H), 2.67 (d, J=15.6 Hz, 1H), 1.79-1.68 (m, 1H), 1.64 ? 1.58 (m, 1H), 1.47 (d, J=13.0 Hz, 1H), 1.12 (d, J=13.0 Hz, 1H); LC/MS (M+1) 483.1.

Compound 119 and 120: (M)-2-[(1S)-1-amino-1,3-dihydrospiro[indene-2,4'-piperidin]-1'-yl]-5-(2,3-dichlorophenyl)-6-methylpyrimidine-4-carboxamide and (P)-2-[(1S)-1-amino-1,3-dihydrospiro[indene-2,4'-piperidin]-1'-yl]-5-(2,3-dichlorophenyl)-6-methylpyrimidine-4-carboxamide Step 1: 6-methyl-2-{1-oxo-1,3-dihydrospiro[indene-2,4'-piperidin]-1'-yl}pyrimidine-4-carbonitrile

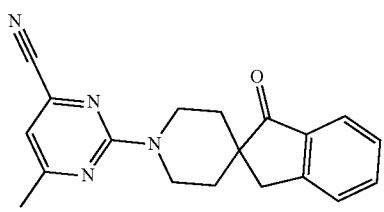 [SMILES: Cc1cc(C#N)nc(N2CCC3(CC2)Cc2ccccc2C3=O)n1]

A solution of 2-chloro-6-methylpyrimidine-4-carbonitrile (120 mg, 0.742 mmol), 1H-spiro[indene-2,4-piperidin]-3-one hydrochloride (Pharmablock, 279 mg, 1.114 mmol) and DIEA (303 mg, 2.23 mmol) in MeCN (5.0 mL was stirred for 2 h at 80° C. under nitrogen atmosphere. The resulting mixture was concentrated under vacuum and purified by flash chromatography on silica (PE:EtOAC, 1:1) to afford the title compound as a white solid (200 mg, 84%); LC/MS (M+1): 319.0.

190

Step 2: 5-bromo-6-methyl-2-{1-oxo-1,3-dihydrospiro[indene-2,4'-piperidin]-1'-yl}pyrimidine-4-carbonitrile

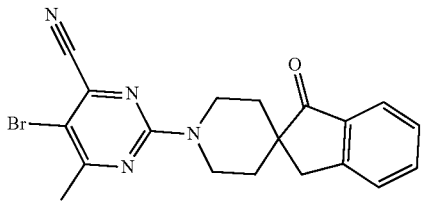 [SMILES: Cc1nc(N2CCC3(CC2)Cc2ccccc2C3=O)nc(C#N)c1Br]

A solution of 6-methyl-2-[3-oxo-1H-spiro[indene-2,4-piperidin]-1-yl]pyrimidine-4-carbonitrile (180 mg, 0.565 mmol) and NBS (158 mg, 0.847) in DMF (5.0 mL) was stirred for 1 h at room temperature. The reaction was quenched with Water and extracted with EtOAc (3×30 mL). The combined organic layers were washed with brine (1×30 mL), dried over anhydrous sodium sulfate, filtered and concentrated. Purification by flash chromatography on silica (PE: EtOAc, 5:1) afforded the title compound as a yellow solid (220 mg, 96.38%). LC/MS (M+1): 396.9.

Step 3: 5-(2,3-dichlorophenyl)-6-methyl-2-{3-oxo-1,3-dihydrospiro[indene-2,4'-piperidin]-1'-yl}pyrimidine-4-carbonitrile

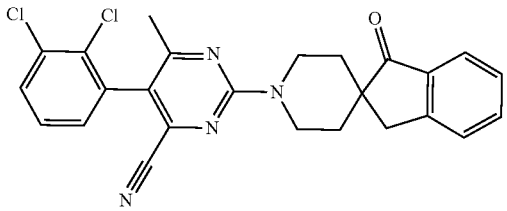 [SMILES: Cc1nc(N2CCC3(CC2)Cc2ccccc2C3=O)nc(C#N)c1-c1cccc(Cl)c1Cl]

A mixture of 5-bromo-6-methyl-2-[3-oxo-1H-spiro[indene-2,4-piperidin]-1-yl]pyrimidine-4-carbonitrile (590 mg, 1.46 mmol), 2,3-dichlorophenylboronic acid (880 mg, 4.38 mmol), K$_3$PO$_4$ (978 mg, 4.38 mmol), XPhos Pd G3 (130 mg, 0.146 mmol) and XPhos (73 mg, 0.146 mmol) in 1,4-dioxane (5 mL) and water (3 mL) was stirred for 2 h at 100° C. under a nitrogen atmosphere. The resulting mixture was concentrated under reduced pressure and purified by Prep-TLC on silica (PE:EtOAc, 1:1) to afford the title compound as a yellow solid (820 mg, 81%). LC/MS (M+1): 463.2.

Step 4: (R)—N-{1'-[4-cyano-5-(2,3-dichlorophenyl)-6-methylpyrimidin-2-yl]-1,3-dihydrospiro[indene-2,4'-piperidin]-3-ylidene}-2-methylpropane-2-sulfinamide

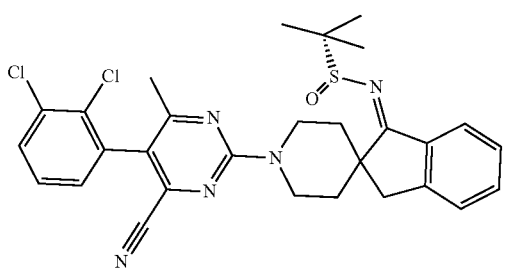

A mixture of 5-(2,3-dichlorophenyl)-6-methyl-2-[3-oxo-1H-spiro[indene-2,4-piperidin]-1-yl]pyrimidine-4-carbonitrile (780 mg, 1.34 mmol) and (R)-2-methylpropane-2-sulfinamide (681 mg, 5.340 mmol) in Ti(OEt)$_4$ (12.3 g, 53.5 mmol) was stirred for 2 h at 90° C. under nitrogen atmosphere. The reaction mixture was then diluted with water and EtOAc and filtered. The filter cake was washed with EtOAc (100 mL) and the filtrate was concentrated under reduced pressure. The aqueous layer was extracted with EtOAc (3×120 mL). Combined organic layers were dried over sodium sulfate, filtered and concentrated. Purification by flash chromatography on silica (PE:EtOAc, 1:1) afforded the title compound as a yellow solid (800 mg, 64%). LC/MS (M+1):566.2.

Step 5: (R)—N-[(3S)-1'-[4-cyano-5-(2,3-dichlorophenyl)-6-methylpyrimidin-2-yl]-1,3-dihydrospiro[indene-2,4'-piperidin]-3-yl]-2-methylpropane-2-sulfinamide

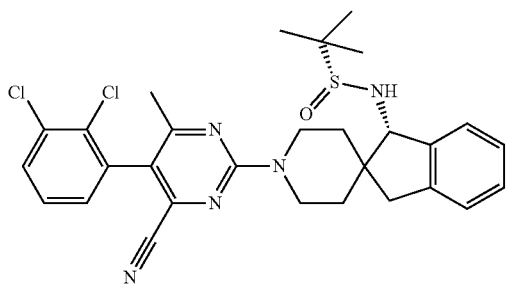 [SMILES: Cc1nc(N2CCC3(CC2)Cc2ccccc2[C@H]3N[S@](=O)C(C)(C)C)nc(C#N)c1-c1cccc(Cl)c1Cl]

A solution of NaBH$_4$ (93 mg, 2.34 mmol) in water (1.3 mL) was slowly added to a solution of (R)—N-[1-[4-cyano-5-(2,3-dichlorophenyl)-6-methylpyrimidin-2-yl]-1H-spiro[indene-2,4-piperidin]-3-ylidene]-2-methylpropane-2-sulfinamide (440 mg, 0.468 mmol) in THF (8.8 mL) maintained at −50° C. The resulting mixture was stirred for 1 h at 25° C. under N$_2$ atmosphere. The reaction was quenched by the addition of Water/Ice (30 mL) and the aqueous layer was extracted with EtOAc (3×50 mL). Combined organic layers were dried over sodium sulfate, filtered and concentrated to give the title compound as a yellow oil (320 mg, 63%). LC/MS (M+1): 568.2.

Step 6: 5-(2,3-dichlorophenyl)-6-methyl-2-[(3S)-3-{[(R)-2-methylpropane-2-sulfinyl]amino}-1,3-dihydrospiro[indene-2,4'-piperidin]-1'-yl]pyrimidine-4-carboxamide

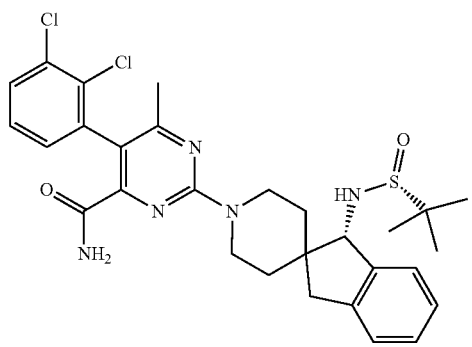 [SMILES: Cc1nc(N2CCC3(CC2)Cc2ccccc2[C@H]3N[S@](=O)C(C)(C)C)nc(C(N)=O)c1-c1cccc(Cl)c1Cl]

Into a 30 mL sealed tube were added A mixture of (R)—N-[(3S)-1-[4-cyano-5-(2,3-dichlorophenyl)-6-methylpyrimidin-2-yl]-1,3-dihydrospiro[indene-2,4-piperidin]-3-yl]-2-methylpropane-2-sulfinamide (300 mg, 0.275 mmol) and NaOH (200 mg, 4.750 mmol) in EtOH (5.00 mL) and water (5 mL) was stirred for 1 h at 70° C. under nitrogen atmosphere in a sealed tube. The reaction mixture was then extracted with EtOAc (3×30 mL). Combined organic layers were dried over sodium sulfate, filtered and concentrated to give the title compound as a yellow solid (400 mg, 88%). LC/MS (M+1): 586.2.

Step 7: 2-[(1S)-1-amino-1,3-dihydrospiro[indene-2,4'-piperidin]-1'-yl]-5-(2,3-dichlorophenyl)-6-methylpyrimidine-4-carboxamide

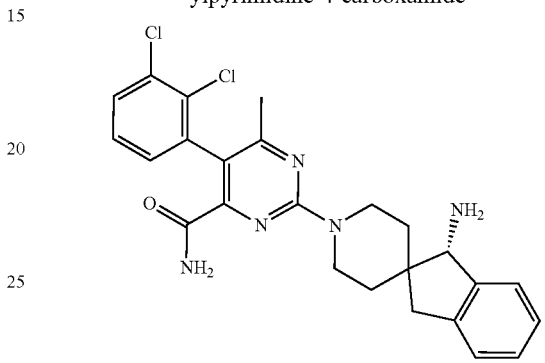

A solution of 5-(2,3-dichlorophenyl)-6-methyl-2-[(1S)-1-[[(R)-2-methylpropane-2-sulfinyl]amino]-1,3-dihydrospiro[indene-2,4-piperidin]-1-yl]pyrimidine-4-carboxamide (100 mg, 0.17 mmol) and HCl(gas) in 1,4-dioxane (2.00 mL, 7.9 mmol, 12%) was stirred for 1 h at 25@$^1$ under nitrogen atmosphere. The solvent was removed under reduced pressure and the residue was purified by reverse flash chromatography on C18 silica gel (ACN: water+NH$_4$OH, gradient from 0:100 to 50:50) to give the title compound as a white solid (50 mg, 60%). 1H NMR (400 MHz, DMSO-d6): 7.94 (s, 1H), 7.58 (d, J=7.9 Hz, 1H), 7.41-7.29 (m, 3H), 7.24-7.14 (m, 4H), 4.62 (t, J=15.0 Hz, 2H), 3.86 (s, 1H), 3.17 (s, 1H), 3.10 (d, J=15.7 Hz, 1H), 2.66 (d, J=15.5 Hz, 1H), 2.01 (s, 3H), 1.82-1.71 (m, 1H), 1.64 (dd, J=13.7, 9.4 Hz, 1H), 1.52 (d, J=13.1 Hz, 1H), 1.13 (d, J=13.4 Hz, 1H). LC/MS (M+1): 482.2.

Step 8: atropisomers separation: (5M)-2-[(1S)-1-amino-1,3-dihydrospiro[indene-2,4'-piperidin]-1'-yl]-5-(2,3-dichlorophenyl)-6-methylpyrimidine-4-carboxamide and (5P)-2-[(1S)-1-amino-1,3-dihydrospiro[indene-2,4'-piperidin]-1'-yl]-5-(2,3-dichlorophenyl)-6-methylpyrimidine-4-carboxamide

119

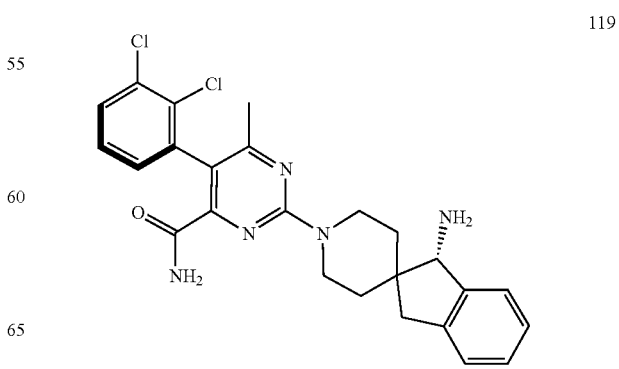

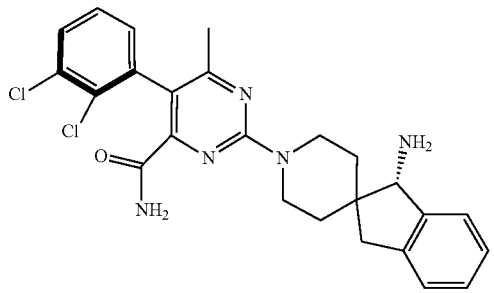

The atropisomers from 2-[(1S)-1-amino-1,3-dihydrospiro[indene-2,4'-piperidin]-1'-yl]-5-(2,3-dichlorophenyl)-6-methylpyrimidine-4-carboxamide were separated by preparative HPLC (column (R,R)whelk-O1, 4.6*50 mm, 3.5 um, Hexane+0.1% DEA:EtOH, 50:50).

First eluting isomer (compound 119): 29 mg, RT=1.1 min, ed=97.9; 1H NMR (400 MHz, DMSO-d6): 7.94 (s, 1H), 7.58 (dd, J=8.1, 1.5 Hz, 1H), 7.41-7.29 (m, 3H), 7.19 (ddd, J=15.5, 7.2, 2.8 Hz, 4H), 4.62 (t, J=16.3 Hz, 2H), 3.86 (s, 1H), 3.25-3.15 (m, 1H), 3.11 (d, J=15.7 Hz, 1H), 2.66 (d, J=15.4 Hz, 1H), 2.01 (s, 3H), 1.77 (t, J=11.3 Hz, 1H), 1.62 (d, J=11.9 Hz, 1H), 1.52 (d, J=12.9 Hz, 1H), 1.13 (d, J=13.0 Hz, 1H). LC/MS (M+1): 481.2, mp: 114-115° C.

Second eluting isomer (compound 120): 19 mg, RT=6.9 min, ed=98.5, LC/MS (M+1): 481.2, mp: 121-123° C.

Compound 121: 6-amino-2-[(4S)-4-amino-4,6-dihydrospiro[cyclopenta[d][1,3]thiazole-5,4'-piperidin]-1'-yl]-5-(2,3-dichlorophenyl)pyrimidine-4-carboxamide Step 1: 6-amino-2-[(4S)-4-amino-4,6-dihydrospiro[cyclopenta[d][1,3]thiazole-5,4'-piperidin]-1'-yl]-5-(2,3-dichlorophenyl)pyrimidine-4-carbonitrile

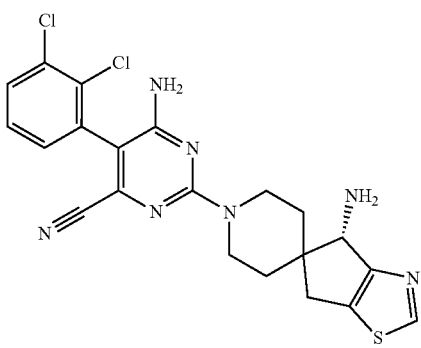 [SMILES: N#Cc1nc(N2CCC3(CC2)Cc2scnc2[C@H]3N)nc(N)c1-c1cccc(Cl)c1Cl]

A mixture of (4S)-4,6-dihydrospiro[cyclopenta[d][1,3]thiazole-5,4'-piperidin]-4-amine(Intermediate 16, 100 mg, 0.430 mmol), 6-amino-5-(2,3-dichlorophenyl)-2-methanesulfonylpyrimidine-4-carbonitrile (220 mg, 0.439 mmol) and K₂CO₃ (10 mg, 0.069 mmol) in ACN (4.0 mL) was stirred for 12 h at RT under nitrogen atmosphere. Solvent was removed under reduced pressure and the residue was purified by chromatography on silica (PE:EtOAc, 1:9) to afford the title compound as a yellow solid (60 mg, 24%). LC/MS (M+1): 472.1.

Step 2: 6-amino-2-[(4S)-4-amino-4,6-dihydrospiro[cyclopenta[d][1,3]thiazole-5,4'-piperidin]-1'-yl]-5-(2,3-dichlorophenyl)pyrimidine-4-carboxamide

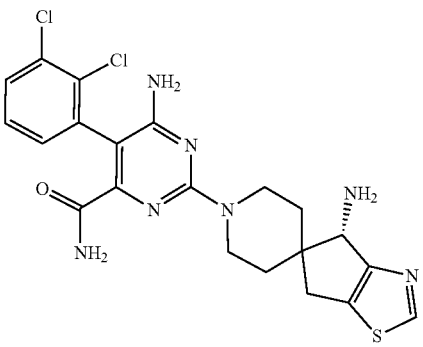 [SMILES: NC(=O)c1nc(N2CCC3(CC2)Cc2scnc2[C@H]3N)nc(N)c1-c1cccc(Cl)c1Cl]

A solution of 6-amino-2-[(4S)-4-amino-4,6-dihydrospiro[cyclopenta[d][1,3]thiazole-5,4-piperidin]-1-yl]-5-(2,3-dichlorophenyl)pyrimidine-4-carbonitrile (40 mg, 0.070 mmol), NaOH (73 mg, 1.73 mmol) in water (1 mL) and EtOH (1 mL) was stirred for 1 h at 50° C. Solvent was removed under reduced pressure and the residue was purified by preparative HPLC (column XBridge, Prep C18 OBD, 19×150 mm, 5 um, Water+10 mmol NH₄HCO₃):ACN; Gradient from 70:30 to 50:50 in 8 min) to give the title compound as an off-white solid (5.6 mg, 16%). 1H NMR (400 MHz, DMSO-d6): 8.96 (s, 1H), 7.74 (s, 1H), 7.52 (dd, J=8.0, 1.5 Hz, 1H), 7.29 (t, J=7.8 Hz, 1H), 7.16 (s, 1H), 7.11 (d, J=7.5 Hz, 1H), 6.11 (s, 1H), 4.44 (dd, J=21.6, 14.3 Hz, 2H), 3.98 (s, 1H), 3.25 ? 3.17 (m, 2H), 2.87 (d, J=15.3 Hz, 1H), 2.75 (d, J=15.3 Hz, 1H), 1.82-1.71 (m, 1H), 1.68-1.50 (m, 3H), 1.24 (s, 1H), LC/MS (M+1): 490.1.

Compound 122: 2-((S)-3-amino-3H-spiro[benzofuran-2,4'-piperidin]-1'-yl)-5-(2,3-dichlorophenyl)-6-methylpyrimidine-4-carboxamide Step 1: 6-methyl-2-[3-oxospiro[1-benzofuran-2,4-piperidin]-1-yl]pyrimidine-4-carbonitrile

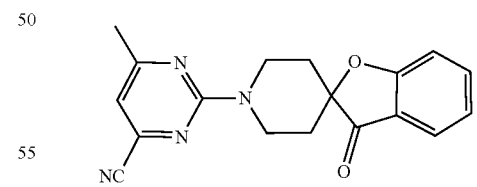

A solution of 2-chloro-6-methylpyrimidine-4-carbonitrile (100 mg, 0.619 mmol), spiro[1-benzofuran-2,4-piperidin]-3-one (140 mg, 0.682 mmol) and DIEA (0.215 mL, 1.24 mmol, 2 equiv) in CAN (4.0 mL) was stirred for 2 h at 80° C. The resulting mixture was cooled down to room temperature and concentrated under vacuum. The residue was purified by silica gel column chromatography (PE/EtOAc, 1:1) to afford the title compound as a yellow solid (120 mg, 54%). LC/MS (M+1): 321

Step 2: 5-bromo-6-methyl-2-[3-oxospiro[1-benzo-furan-2,4'-piperidin]-1'-yl]pyrimidine-4-carbonitrile

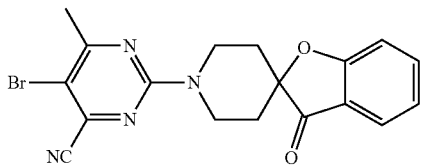 [SMILES: Cc1nc(N2CCC3(CC2)Oc2ccccc2C3=O)nc(C#N)c1Br]

NBS (105 mg, 0.563 mmol) was added to a solution of 6-methyl-2-[3-oxospiro[1-benzofuran-2,4-piperidin]-1-yl]pyrimidine-4-carbonitrile (100 mg, 0.281 mmol) in DMF (5.0 mL) at 25° C. The resulting mixture was stirred for 2 h at 25° C. It was then diluted with water (40 mL) and extracted with EtOAc (3×45 mL). Combined organic layers were washed with brine (1×100 mL), dried over anhydrous sodium sulfate, filtered and concentrated to give the title compound as a yellow solid (110 mg, 85% yield). LC/MS (M+1): 399, 401.

Step 3: 5-(2,3-dichlorophenyl)-6-methyl-2-{3-oxo-3H-spiro[1-benzofuran-2,4'-piperidin]-1'-yl}pyrimidine-4-carbonitrile

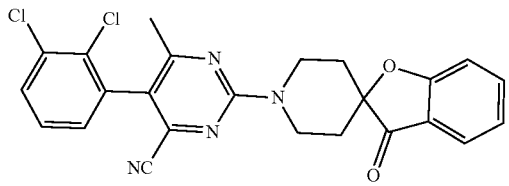 [SMILES: Cc1nc(N2CCC3(CC2)Oc2ccccc2C3=O)nc(C#N)c1-c1cccc(Cl)c1Cl]

A solution of 5-bromo-6-methyl-2-[3-oxospiro[1-benzofuran-2,4-piperidin]-1-yl]pyrimidine-4-carbonitrile (100 mg, 0.216 mmol), 2,3-dichlorophenylboronic acid (87 mg, 0.432 mmol), K₃PO₄ (145 mg, 0.648 mmol), XPhos (22 mg, 0.043 mmol) and XPhos Pd G3 (39 mg, 0.043 mmol) in 1,4-dioxane (2 mL) and water (0.5 mL) was stirred for 2 h at 100° C. The resulting mixture was cooled down to room temperature, and then concentrated under reduced pressure. The residue was diluted with DCM (5 mL), filtered and the filtrate was concentrated under vacuum. The residue was purified by flash chromatography on silica (PE/EtOAc, 1:1) to afford the title compound as a yellow solid (95 mg, 78%). LC/MS (M+1): 465.

Step 4: (S)-N-((E)-1'-(4-cyano-5-(2,3-dichlorophenyl)-6-methylpyrimidin-2-yl)-3H-spiro[benzofuran-2,4'-piperidin]-3-ylidene)-2-methylpropane-2-sulfinamide

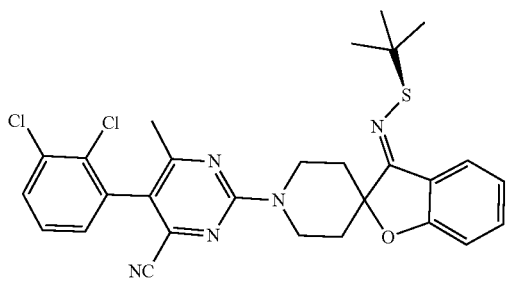

A mixture of 5-(2,3-dichlorophenyl)-6-methyl-2-[3-oxospiro[1-benzofuran-2,4-piperidin]-1-yl]pyrimidine-4-carbonitrile (90 mg, 0.18 mmol), (S)-2-methylpropane-2-sulfinamide (138 mg, 1.08 mmol) and Ti(OEt)₄ (1 mL) was stirred for 4 h at 90° C. The resulting mixture was cooled to room temperature, poured into a mixture of water (20 mL) and EtOAc (20 mL) and filtered. The two layers from the filtrate were separated and the aqueous phase was extracted with EtOAc (3×20 mL). Combined organic layers were dried over anhydrous sodium sulfate, filtered and concentrated. Purification by flash chromatography on silica (PE/EtOAc, 1:1) afforded the title compound as an off-white solid (180 mg, 100% yield). LC/MS (M+1): 568.2.

Step 5: 2-((S)-3-((tert-butylthio)amino)-3H-spiro[benzofuran-2,4'-piperidin]-1'-yl)-5-(2,3-dichlorophenyl)-6-methylpyrimidine-4-carbonitrile

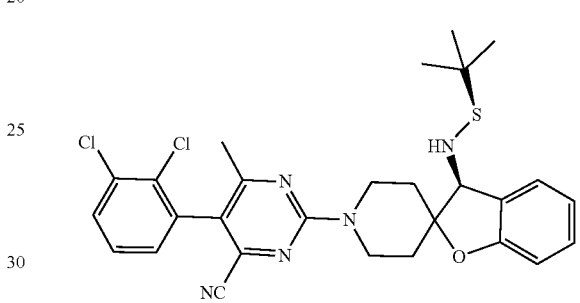

NaBH₄ (31 mg, 0.782 mmol) was added to a solution of (S)-N-[1-[4-cyano-5-(2,3-dichlorophenyl)-6-methylpyrimidin-2-yl]spiro[1-benzofuran-2,4-piperidin]-3-ylidene]-2-methylpropane-2-sulfinamide (160 mg, 0.156 mmol) in THF (4.0 mL) and H₂O (1.0 mL) maintained at −50° C. under nitrogen atmosphere. The resulting mixture was stirred for 1 h at 25° C. It was then poured into water (10 mL) and extracted with EtOAc (3×10 mL). Combined organic layers were washed with brine (1×30 mL), dried over anhydrous sodium sulfate, filtered and concentrated to give the title compound as a yellow solid (130 mg, 94% yield). LC/MS (M+1): 554, 556.

Step 6: 2-((S)-3-((tert-butylthio)amino)-3H-spiro[benzofuran-2,4'-piperidin]-1'-yl)-5-(2,3-dichlorophenyl)-6-methylpyrimidine-4-carboxamide

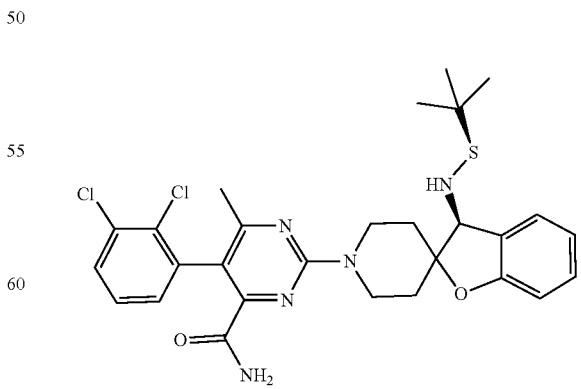

A mixture of (S)-N-[(3S)-1-[4-cyano-5-(2,3-dichlorophenyl)-6-methylpyrimidin-2-yl]-3H-spiro[1-benzofuran-2,4- piperidin]-3-yl]-2-methylpropane-2-sulfinamide (130 mg, 0.142 mmol), NaOH aqueous (1.5 mL, 2M) and EtOH (3.0 mL) was stirred for 1 h at 70° C. The mixture was cooled down to room temperature and the solvent removed under reduced pressure. The residual aqueous layer was extracted with EtOAc (3×5 mL). Combined organic layers were dried over sodium sulfate, filtered and concentrated. Purification by flash chromatography on silica (PE:EtOAc, 1:1) afforded the title compound as a yellow solid (120 mg, 94% yield) as a yellow solid. LC/MS (M+1): 572, 574.

Step 7: 2-((S)-3-amino-3H-spiro[benzofuran-2,4'-piperidin]-1'-yl)-5-(2,3-dichlorophenyl)-6-methylpyrimidine-4-carboxamide

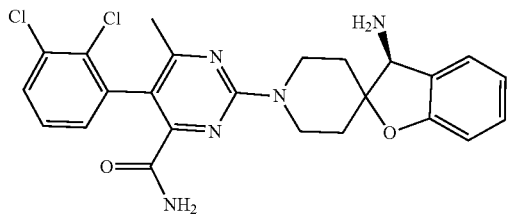 [SMILES: Cc1nc(N2CCC3(CC2)Oc2ccccc2[C@@H]3N)nc(C(N)=O)c1-c1cccc(Cl)c1Cl]

A mixture of 5-(2,3-dichlorophenyl)-6-methyl-2-[(3S)-3-[[(S)-2-methylpropane-2-sulfinyl]amino]-3H-spiro[1-benzofuran-2,4-piperidin]-1-yl]pyrimidine-4-carboxamide (70 mg, 0.113 mmol) and HCl/1,4-dioxane (7 mL of a 4M solution) was stirred for 2 h at 25° C. The resulting mixture was concentrated under vacuum and purified by reverse phase chromatography (Column: C18 silica gel; water+10 mmol/L NH₄HCO₃: ACN, gradient from 0% to 70% in 40 min) to give the title compound as an off-white solid (45.7 mg, 84%) ¹H-NMR (400 MHz, DMSO-d₆): 8.00 (brs, 1H), 7.59 (dd, J=8.0, 1.2 Hz, 1H), 7.41-7.33 (m, 3H), 7.22-7.14 (m, 2H), 6.88 (t, J=7.2 Hz, 1H), 6.80 (d, J=7.6 Hz, 1H), 4.68-4.57 (m, 2H), 4.13 (s, 1H), 3.49-3.33 (m, 2H), 2.03 (s, 3H), 1.94-1.70 (m, 4H). LC/MS (M+1): m/z=484.1

Compound 123: 6-amino-2-((R)-3-amino-3H-spiro[benzofuran-2,4'-piperidin]-1'-yl)-5-(2,3-dichlorophenyl)pyrimidine-4-carboxamide di-hydrochloride Step 1: 6-amino-2-[(3S)-3-amino-3H-spiro[1-benzofuran-2,4'-piperidin]-1'-yl]-5-(2,3-dichlorophenyl)pyrimidine-4-carbonitrile

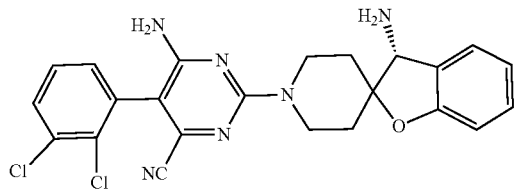 [SMILES: N#Cc1nc(N2CCC3(CC2)Oc2ccccc2[C@H]3N)nc(N)c1-c1cccc(Cl)c1Cl]

A solution of 6-amino-5-(2,3-dichlorophenyl)-2-methanesulfonylpyrimidine-4-carbonitrile (192 mg, 0.492 mmol), (3R)-3H-spiro[1-benzofuran-2,4'-piperidin]-3-amine (intermediate 14, 204 mg, 0.985 mmol) and K₂CO₃ (143 mg, 0.985 mmol) in DMF (10 mL) was stirred for 2 h at 100° C. The reaction mixture was cooled down to room temperature, poured into water (50 mL) and extracted with EtOAc (3×50 mL). Combined organic layers were dried over anhydrous sodium sulfate, filtered and concentrated. Purification by flash chromatography on silica (DCM: MeOH, 10:1) afforded the title compound as a yellow solid (100 mg, 29% yield) as a yellow solid. LC/MS: 467.

Step 2: 6-amino-2-((R)-3-amino-3H-spiro[benzofuran-2,4'-piperidin]-1'-yl)-5-(2,3-dichlorophenyl) pyrimidine-4-carboxamide di-hydrochloride

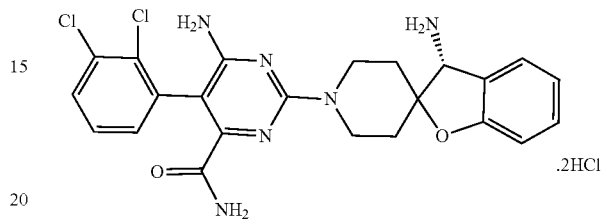

A mixture of 6-amino-2-[(3R)-3-amino-3H-spiro[1-benzofuran-2,4-piperidin]-1-yl]-5-(2,3-dichlorophenyl)pyrimidine-4-carbonitrile (30 mg, 0.043 mmol), NaOH aqueous (0.5 mL, 2M) and EtOH (0.50 mL) was stirred for 30 min at 70° C. The resulting mixture was cooled to room temperature, concentrated and purified by reverse phase chromatography (Column: C18 silica gel; water+0.05% HCl: CH₃CN, Gradient from 0% to 70% in 40 min) to give the title compound as an off-white solid (6.6 mg, 26%). ¹H-NMR (400 MHz, DMSO-d₆): 7.78 (s, 1H), 7.52 (dd, J=8.0, 1.6 Hz, 1H), 7.33-7.27 (m, 2H), 7.18-7.10 (m, 3H), 6.86 (t, J=7.6 Hz, 1H), 6.78 (d, J=8.0 Hz, 1H), 6.16 (br s, 2H), 4.57-4.47 (m, 2H), 4.08 (s, 1H), 3.25-3.20 (m, 2H), 1.90-1.80 (m, 1H), 1.78-1.68 (m, 3H), LC/MS (M+1): 485.2.

Compounds 124, 125, 126, 127: (4M)-2-[(3R)-3-amino-3H-spiro[furo[2,3-b]pyridine-2,4'-piperidin]-1'-yl]-5-(2,3-dichlorophenyl)-6-methylpyrimidine-4-carboxamide, (4M)-2-[(3S)-3-amino-3H-spiro[furo[2,3-b]pyridine-2,4'-piperidin]-1'-yl]-5-(2,3-dichlorophenyl)-6-methylpyrimidine-4-carboxamide, (4P)-2-[(3R)-3-amino-3H-spiro[furo[2,3-b]pyridine-2,4'-piperidin]-1'-yl]-5-(2,3-dichlorophenyl)-6-methylpyrimidine-4-carboxamide, (4P)-2-[(3S)-3-amino-3H-spiro[furo[2,3-b]pyridine-2,4'-piperidin]-1'-yl]-5-(2,3-dichlorophenyl)-6-methylpyrimidine-4-carboxamide Step 1: 2-[3-amino-3H-spiro[furo[2,3-b]pyridine-2,4'-piperidin]-1'-yl]-5-(2,3-dichlorophenyl)-6-methylpyrimidine-4-carbonitrile

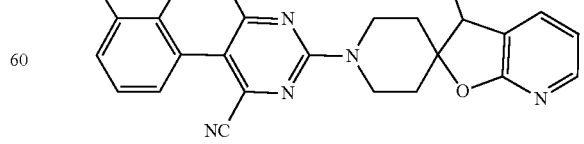

A solution of 2-chloro-5-(2,3-dichlorophenyl)-6-methylpyrimidine-4-carbonitrile (1.10 g, 3.65 mmol), 3H-spiro[furo[2,3-b]pyridine-2,4-piperidin]-3-amine(Intermediate 15, 1.15 g, 5.47 mmol) and DIEA (1.81 mL, 11.0 mmol) in ACN (12 mL) was stirred for 0.5 h at 80° C. The resulting mixture was concentrated under reduced pressure and purified by flash chromatography on silica (PE:EtOAc, 1:1) to afford the title compound as a yellow solid (1.4 g, 81%). LC/MS (M+1): 467.1.

Step 2: 2-[3-amino-3H-spiro[furo[2,3-b]pyridine-2, 4'-piperidin]-1'-yl]-5-(2,3-dichlorophenyl)-6-methylpyrimidine-4-carboxamide

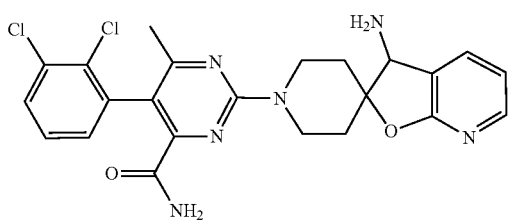 [SMILES: Cc1nc(N2CCC3(CC2)Oc2ncccc2C3N)nc(C(N)=O)c1-c1cccc(Cl)c1Cl]

A mixture of 2-[3-amino-3H-spiro[furo[2,3-b]pyridine-2, 4-piperidin]-1-yl]-5-(2,3-dichlorophenyl)-6-methylpyrimidine-4-carbonitrile (0.80 g, 1.70 mmol), NaOH (0.16 g, 3.80 mmol), EtOH (4 mL) and H$_2$O (4 mL) was stirred for 0.5 h at 70° C. The mixture cooled down to room temperature and neutralized to pH 7 by addition of 6M HCl. The resulting mixture was concentrated under reduced pressure and purified by reverse phase chromatography (Column: C18 silica gel; water+containing 10 mmol/L NH$_4$HCO$_3$: ACN; Gradient from 10% to 50% in 30 min) to afford 2-[3-amino-3H-spiro[furo[2,3-b]pyridine-2,4-piperidin]-1-yl]-5-(2,3-dichlorophenyl)-6-methylpyrimidine-4-carboxamide (700 mg, 79%) as white solid. LC/MS (M+1): 485.

Step 3: Isomers Separation

124

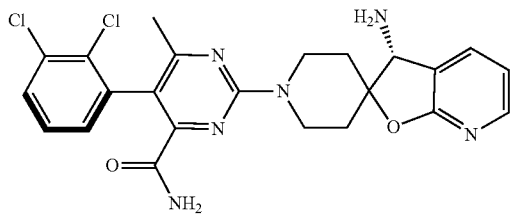

125

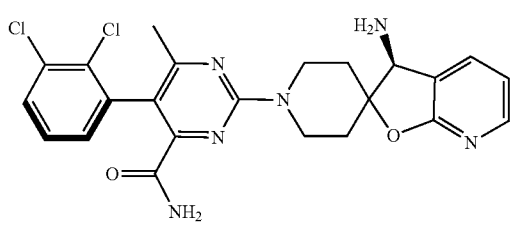

126

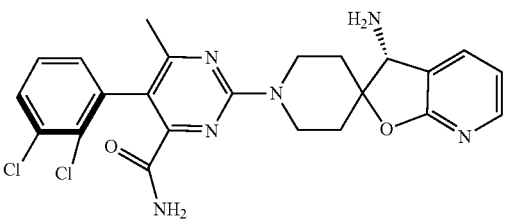

127

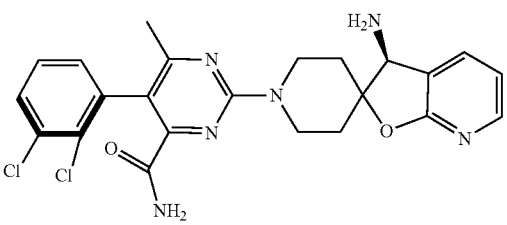

A first separation by preparative HPLC (Column CHIRALPAK IC, 3×25 cm, 5 um, Hexane+8 mmol/L NH$_3$.MeOH: EtOH; 50%) afforded two fractions: Fraction A (130 mg) (RT: 9.6 min) and Fraction B (300 mg) (RT: 14.64 min).

Isomers from fraction A were separated by preparative HPLC (Column CHIRALPAK IA, 3×25 cm, 5 um, MTBE+ 10 mM NH$_3$-MEOH:EtOH, 20%).

First eluting isomer (124): 56 mg, RT: 11 min, $^1$H NMR (400 MHz, DMSO-d$_6$) δ8.00 (s, 2H), 7.72 (d, J=7.2, 1H), 7.59 (dd, J=8.0, 1.6 Hz, 1H), 7.43-7.33 (m, 2H), 7.21 (dd, J=8.0, 1.6 Hz, 1H), 6.92 (dd, J=7.2, 5.2 Hz, 1H), 4.71-4.61 (m, 2H), 4.14 (s, 1H), 3.51-3.39 (m, 2H), 2.20 (brs, 2H), 2.03 (s, 3H), 1.94-1.77 (m, 4H); LC/MS (M+1): 485.1; RT=1.82 min (analytical column—chiral pack IA, MtBE+0.1% DEA: EtOH, 80:20), purity: 100%.

Second eluting isomer (125): 60 mg, RT: 12.9 min, $^1$H NMR (400 MHz, DMSO-d$_6$): 8.01-8.00 (m, 2H), 7.72 (d, J=6.8 Hz, 1H), 7.59 (dd, J=8.0, 1.2 Hz, 1H), 7.40-7.34 (m, 2H), 7.22 (dd, J=7.6, 1.6 Hz, 1H), 6.92 (dd, J=7.2, 5.2 Hz, 1H), 4.72-4.61 (m, 2H), 4.14 (s, 1H), 3.51-3.39 (m, 2H), 2.20 (brs, 2H), 2.03 (s, 3H), 1.96-1.76 (m, 4H); LC/MS (M+1): 485.1; RT=2.26 min (analytical column—chiral pack IA, MtBE+0.1% DEA:EtOH, 80:20); purity: 99.5%.

Isomers from fraction B were separated by preparative HPLC (CHIRALPAK ID, 3×25 cm, 5 um, MTBE+10 mM NH$_3$-MEOH:EtOH, 15%).

First eluting isomer (126): 92 mg, RT: 12.0 min; $^1$H NMR (400 MHz, DMSO-d$_6$): 8.01-8.00 (m, 2H), 7.72 (d, J=6.4, 1H), 7.59 (dd, J=8.0, 1.6 Hz, 1H), 7.41-7.34 (m, 2H), 7.22 (dd, J=7.6, 1.6 Hz, 1H), 6.91 (dd, J=7.2, 5.2 Hz, 1H), 4.72-4.61 (m, 2H), 4.14 (s, 1H), 3.49-3.39 (m, 2H), 2.15 (brs, 2H), 2.03 (s, 3H), 1.93-1.77 (m, 4H), RT=2.33 min (analytical column—chiral pack AD, MtBE+0.1% DEA: EtOH, 85:15); purity: 100%.

Second eluting isomer (127): 111 mg, RT: 15.5 min, ed=99.1%, $^1$H NMR (400 MHz, DMSO-d$_6$): 8.01-8.00 (m, 2H), 7.71 (d, J=6.8 Hz, 1H), 7.59 (dd, J=8.0, 1.2 Hz, 1H), 7.40-7.34 (m, 2H), 7.22 (dd, J=7.6, 1.2 Hz, 1H), 6.92 (dd, J=6.8, 4.8 Hz, 1H), 4.71-4.61 (m, 2H), 4.14 (s, 1H), 3.49-3.39 (m, 2H), 2.19 (br s, 2H), 2.03 (s, 3H), 1.91-1.77 (m, 4H); LC/MS (M+1): 485.1; RT=3.17 min (analytical column Chiralpak ID, MtB+0.1% DEA:EtOH, 85:15). purity: 99.1.

Compounds 128, 129, 130, 131: (4P)-6-amino-2-[(3R)-3-amino-3H-spiro[furo[2,3-b]pyridine-2,4-piperidin]-1-yl]-5-(2,3-dichlorophenyl)pyrimidine-4-carboxamide, (4P)-6-amino-2-[(3S)-3-amino-3H-spiro[furo[2,3-b]pyridine-2,4-piperidin]-1-yl]-5-(2,3-dichlorophenyl)pyrimidine-4-carboxamide, (4M)-6-amino-2-[(3R)-3-amino-3H-spiro[furo[2,3-b]pyridine-2,4-piperidin]-1-yl]-5-(2,3-dichlorophenyl)pyrimidine-4-carboxamide; (4M)-6-amino-2-[(3S)-3-amino-3H-spiro[furo[2,3-b]pyridine-2,4-piperidin]-1-yl]-5-(2,3-dichlorophenyl)pyrimidine-4-carboxamide Step 1: 6-amino-2-[3-amino-3H-spiro[furo[2,3-b]pyridine-2,4-piperidin]-1-yl]-5-(2,3-dichlorophenyl)pyrimidine-4-carbonitrile

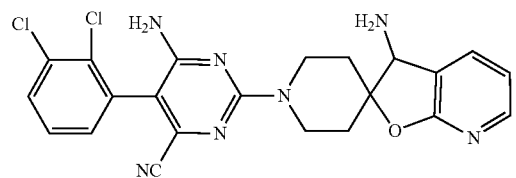 [SMILES: N#Cc1nc(N2CCC3(CC2)Oc2ncccc2C3N)nc(N)c1-c1cccc(Cl)c1Cl]

A solution of DIEA (1.06 mL, 6.13 mmol, 2.00 equiv), 6-amino-5-(2,3-dichlorophenyl)-2-methanesulfonylpyrimidine-4-carbonitrile (intermediate 4, 1.04 g, 3.06 mmol) and 3H-spiro[furo[2,3-b]pyridine-2,4-piperidin]-3-amine (0.84 g, 3.89 mmol) in EtOH (12 mL) was stirred for 4 h at 60° C. The resulting mixture was concentrated under vacuum and purified by flash chromatography on silica (PE:EtOAc, 1:9) to afford the title compound as a yellow solid (900 mg, 47% yield). LC/MS (M+1): 468.

Step 2: 6-amino-2-[3-amino-3H-spiro[furo[2,3-b]pyridine-2,4-piperidin]-1-yl]-5-(2,3-dichlorophenyl)pyrimidine-4-carboxamide

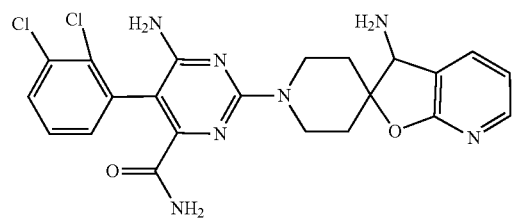 [SMILES: NC(=O)c1nc(N2CCC3(CC2)Oc2ncccc2C3N)nc(N)c1-c1cccc(Cl)c1Cl]

The title compound was obtained following a similar procedure as described for compounds 124-127, step 2, but starting from 6-amino-2-[3-amino-3H-spiro[furo[2,3-b]pyridine-2,4-piperidin]-1-yl]-5-(2,3-dichlorophenyl)pyrimidine-4-carbonitrile (0.90 g, 1.47 mmol) as an off-white solid (600 mg, 83%). LC/MS (M+1): 486.

Step 3: Isomers Separation

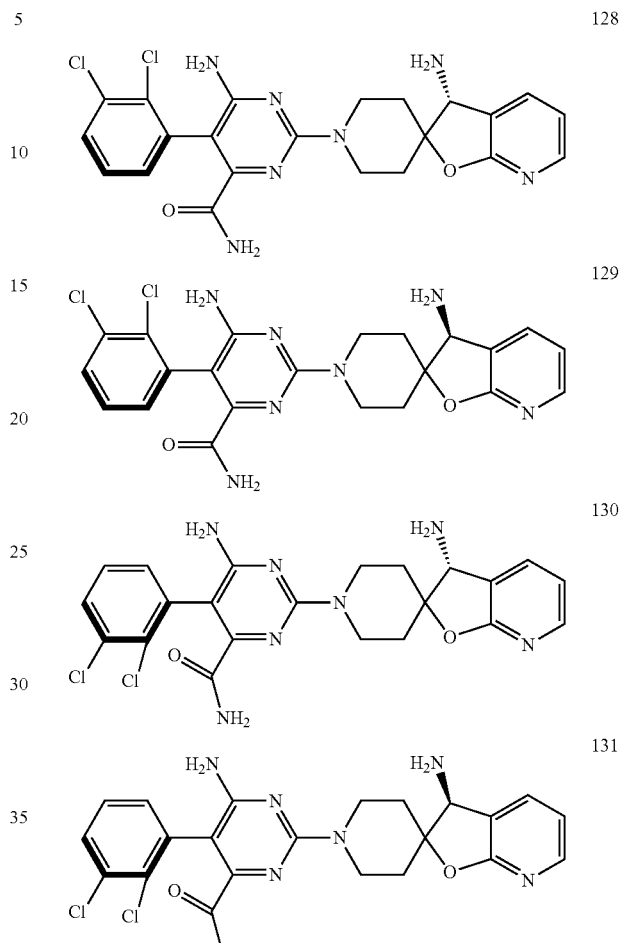

A first separation by preparative HPLC (Column: CHIRALPAK IA, 3×25 cm, 5 um; MTBE+10 mM NH$_3$-MEOH):EtOH, 15%) afforded three fractions:

First eluting fraction: 150 mg of a mixture of two isomers.
Second eluting fraction (128): white solid, 68 mg, RT=7.22 min, $^1$H NMR (400 MHz, DMSO-d6): 8.00 (dd, J=4.8, 1.2 Hz, 1H), 7.78 (s, 1H), 7.71 (d, J=6.8 Hz, 1H), 7.52 (dd, J=8.0, 1.2 Hz, 1H), 7.29 (t, J=7.6 Hz, 1H), 7.18 (s, 1H), 7.12 (dd, J=7.6, 1.6 Hz, 1H), 6.91 (dd, J=7.2, 5.2 Hz, 1H), 6.17 (brs, 2H), 4.58-4.52 (m, 2H), 4.13 (s, 1H), 3.40-3.31 (m, 2H), 2.32 (br s, 2H), 1.95-1.85 (m, 1H), 1.79-1.72 (m, 3H). RT (analytical column—chiral pack IA, MtBE+0.1% DEA:EtOH=85:15)=1.98 min; purity: 95.1%.
Third eluting fraction (129): white solid, 62 mg, RT=9.57 min, $^1$H NMR (400 MHz, DMSO-d6) δ8.00 (dd, J=4.8, 1.2 Hz, 1H), 7.78 (s, 1H), 7.70 (d, J=6.8 Hz, 1H), 7.52 (dd, J=8.0, 1.2 Hz, 1H), 7.29 (t, J=8.0 Hz, 1H), 7.18 (s, 1H), 7.12 (dd, J=7.6, 1.6 Hz, 1H), 6.91 (dd, J=7.2, 5.2 Hz, 1H), 6.17 (brs, 2H), 4.58-4.51 (m, 2H), 4.12 (s, 1H), 3.40-3.31 (m, 2H), 2.32 (brs, 1H), 1.95-1.85 (m, 1H), 1.79-1.72 (m, 3H). RT (analytical column—chiral pack IA, MtBE+0.1% DEA: EtOH=85:15)=2.45 min; purity: 92.7%.
The isomers from first eluting fraction were separated by preparative HPLC (CHIRALPAK IA, 3×25 cm, 5 um:Hex: DCM=3:1+10 mM NH$_3$-MEOH): EtOH, 15%).

First eluting isomer (130): white solid, 46 mg, RT=7.22 min, ¹H NMR (400 MHz, DMSO-d6) δ7.99 (d, J=5.6 Hz, 1H), 7.78 (s, 1H), 7.70 (d, J=6.8 Hz, 1H), 7.52 (dd, J=8.0, 1.6 Hz, 1H), 7.29 (t, J=8.0 Hz, 1H), 7.18 (s, 1H), 7.11 (dd, J=7.0, 1.6 Hz, 1H), 6.90 (dd, J=7.2, 5.2 Hz, 1H), 6.17 (br s, 1H), 4.62-4.51 (m, 2H), 4.12 (s, 1H), 3.39-3.31 (m, 2H), 1.95-1.86 (m, 1H), 1.79-1.74 (m, 3H). RT=2.81 min (analytical column—chiral pack IA, Hex:DCM=3:1+0.1% DEA: EtOH=85:15); purity: 92.3%.

Second eluting isomer (131): white solid, 39 mg, Rt=13.8 min, ¹H NMR (400 MHz, DMSO-d6): 7.99 (d, J=3.6 Hz, 1H), 7.78 (s, 1H), 7.70 (d, J=7.6 Hz, 1H), 7.52 (dd, J=8.0, 1.2 Hz, 1H), 7.29 (t, J=8.0 Hz, 1H), 7.18 (s, 1H), 7.11 (d, J=7.6, 1H), 6.90 (dd, J=7.2, 5.2 Hz, 1H), 6.17 (brs, 1H), 4.62-4.51 (m, 2H), 4.11 (s, 1H), 3.35-3.31 (m, 2H), 2.10 (brs, 1H), 1.95-1.86 (m, 1H), 1.78-1.71 (m, 3H). RT=2.42 min (analytical column—chiral pack IA, Hex:DCM=3:1+ 0.1% DEA:EtOH=85:15); purity: 99.9%.

Compounds from table 3 have been prepared following similar synthetic routes as the ones described above:

TABLE 3

| Compound | Analytic description |
| --- | --- |
| 28 | white solid; 1H NMR (400 MHz, DMSO-d6) δ: 7.84 (s, 2H), 7.59 (dd, J = 8.1, 1.6 Hz, 2H), 7.41 (s, 4H), 7.36 (t, J = 7.8 Hz, 2H), 7.23 (d, J = 7.5 Hz, 3H), 4.27 (s, 2H), 3.87 (s, 1H), 3.12 (s, 2H), 2.68 (s, 1H), 1.98 (s, 9H), 1.89-1.80 (m, 1H), 1.72 (s, 0H), 1.68 (s, 6H), 1.56 (d, J = 11.3 Hz, 5H), 1.26 (d, J = 14.2 Hz, 2H), 1.10 (dd, J = 25.8, 13.0 Hz, 1H); LC/MS: [M + 1]: 394.2 |
| 29 | white amorphous solid; 1H NMR (400 MHz, DMSO-d6) δ 7.73-7.67 (m, 1H), 7.50 (d, J = 8.0 Hz, 1H), 7.28 (t, J = 7.8 Hz, 1H), 7.16-7.08 (m, 2H), 6.04 (s, 2H), 4.57 (s, 1H), 4.26 (d, J = 13.0 Hz, 2H), 3.38-3.34 (m, 2H), 3.18-3.12 (m, 2H), 1.53-1.40 (m, 2H), 1.36 (s, 2H), 1.26 (d, J = 14.1 Hz, 2H). LC/MS: [M + 1]: 411 |
| 31 | White solid; 1H NMR (300 MHz, DMSO-d6) δ 7.91 (s, 1H), 7.56 (dd, J = 8.0, 1.6 Hz, 1H), 7.40-7.29 (m, 2H), 7.18 (dd, J = 7.6, 1.6 Hz, 1H), 4.03 (d, J = 13.4 Hz, 2H), 3.68 (dt, J = 13.1, 6.4 Hz, 2H), 1.98 (s, 3H), 1.78 (d, J = 9.2 Hz, 2H), 1.41 (d, J = 5.3 Hz, 4H), 1.09 (s, 4H). LC/MS: [M + 1]: 394.0. |
| 32 | yellow solid, 1H NMR (300 MHz, DMSO-d6): 7.90 (s, 1H), 7.59 (dt, J = 8.0, 1.3 Hz, 1H), 7.44-7.31 (m, 2H), 7.21 (dd, J = 7.6, 1.6 Hz, 1H), 4.63 (s, 1H), 3.06 (d, J = 17.5 Hz, 3H), 2.56 (d, J = 3.8 Hz, 1H), 2.01 (d, J = 1.3 Hz, 3H), 1.84 (d, J = 12.5 Hz, 2H), 1.63 (s, 4H), 1.41-1.15 (m, 2H), LC/MS (M + 1): 408.1 |
| 33 | off-white solid, 1H NMR (300 MHz, DMSO-d6) ? 8.08 (s, 0H), 8.02 (s, 2H), 7.54 (dd, J = 8.1, 1.5 Hz, 1H), 7.41-7.26 (m, 2H), 7.13 (dd, J = 7.7, 1.5 Hz, 1H), 4.91 (s, 1H), 4.76 (s, 1H), 4.37 (s, 8H), 3.90 (dt, J = 11.4, 4.2 Hz, 2H), 3.63 (t, J = 10.4 Hz, 2H), 2.18 (dd, J = 13.2, 6.5 Hz, 2H), 1.99 (s, 3H), 1.70 (d, J = 11.7 Hz, 2H), LC/MS (M + 1): 422.3 |
| 34 | orange solid, 1H NMR (400 MHz, Methanol-d4) d 7.54 (d, J = 7.9 Hz, 1H), 7.39-7.29 (m, 1H), 7.20 (d, J = 8.2 Hz, 1H), 4.14-3.50 (m, 8H), 3.50-3.20 (m, 4H), 2.86-2.74 (m, 1H), 2.22 (s, 2H), 1.36 (s, 2H), LC/MS (M + 1): 423.1 |
| 35 | white solid; 1H NMR (300 MHz, DMSO-d6) δ 7.88 (s, 1H), 7.59 (dd, J = 8.0, 1.5 Hz, 1H), 7.40 (s, 1H), 7.35 (t, J = 7.8 Hz, 1H), 7.23-7.17 (m, 1H), 3.77-3.70 (m, 1H), 3.52 (s, 2H), 3.40 (s, 1H), 2.99 (t, J = 6.5 Hz, 1H), 2.08-2.00 (m, 4H), 1.96-1.83 (m, 1H), 1.75-1.67 (m, 2H), 1.61-1.50 (m, 3H), 1.39-1.30 (m, 1H), LC/MS: [M + 1]: 420.1. |
| 36 | off-white solid; 1H NMR (300 MHz, DMSO-d6) δ 7.79 (s, 1H), 7.57 (dd, J = 8.0, 1.6 Hz, 1H), 7.52 (s, 1H), 7.40-7.27 (m, 2H), 7.20 (d, J = 7.5 Hz, 1H), 4.28 (s, 1H), 1.95 (s, 4H), 1.63 (q, J = 7.9, 7.4 Hz, 1H), 1.50 (s, 1H), 1.28-1.08 (m, 1H), LC/MS: [M + 1]: 394.2. |
| 37 | white solid; 1H NMR (300 MHz, DMSO-d6) δ 7.88 (s, 1H), 7.59 (dd, J = 8.0, 1.5 Hz, 1H), 7.41 (s, 1H), 7.35 (t, J = 7.8 Hz, 1H), 7.21-7.09 (m, 1H), 3.65-3.61 (m, 2H), 3.53 (s, 1H), 2.97 (t, J = 6.7 Hz, 1H), 2.00 (s, 3H), 1.92-1.88 (m, 2H), 1.73-1.64 (m, 4H), 1.54-1.50 (m, 2H), 1.37-1.21 (m, 1H). LC/MS: [M + 1]: 420.1. |
| 38 | Amorphous white solid; 1H NMR (400 MHz, DMSO-d6) δ 7.71 (s, 1H), 7.52 (d, J = 7.9 Hz, 1H), 7.29 (t, J = 8.1 Hz, 1H), 7.21-7.05 (m, 2H), 6.08 (s, 2H), 4.25 (d, J = 12.8 Hz, 2H), 3.69 (d, J = 10.5 Hz, 2H), 3.58 (d, J = 12.3 Hz, 2H), 2.91 (s, 2H), 2.06 (d, J = 13.9 Hz, 2H), 1.69 (t, J = 14.5 Hz, 2H), 1.52 (d, J = 5.9 Hz, 2H), 1.36 (t, J = 12.7 Hz, 1H), 1.16 (d, J = 13.2 Hz, 1H), 1.00 (t, J = 12.2 Hz, 1H), LC/MS: [M + 1]: 451 |
| 39 | Amorphous white solid; 1H NMR (400 MHz, DMSO-d6) δ 7.71 (s, 1H), 7.52 (d, J = 8.0 Hz, 1H), 7.30 (t, J = 7.8 Hz, 1H), 7.23-7.06 (m, 2H), 6.07 (s, 2H), 5.08-4.47 (m, 2H), 3.82 (d, J = 11.0 Hz, 1H), 3.26-2.97 (m, 3H), 2.88-2.65 (m, 3H), 2.11 (t, J = 12.1 Hz, 1H), 1.89 (d, J = 12.5 Hz, 1H), 1.75-1.39 (m, 6H), 1.39-1.24 (m, 2H), 1.24-1.05 (m, 1H), LC/MS: [M + 1]: 465 |
| 40 | Amorphous white solid; 1H NMR (400 MHz, DMSO-d6) δ 7.74 (s, 1H), 7.54 (d, J = 8.1 Hz, 1H), 7.31 (td, J = 8.1, 2.0 Hz, 1H), 7.21-7.09 (m, 2H), 6.12 (s, 2H), 4.01-3.77 (m, 4H), 3.74-3.51 (m, 4H), 2.67-2.61 (m, 2H), 1.99-1.87 (m, 2H), 1.55 (s, 4H), 1.51-1.40 (m, 1H), LC/MS: [M + 1]: 451 |
| 41 | Amorphous white solid; 1H NMR (400 MHz, DMSO-d6) δ 7.70 (s, 1H), 7.51 (d, J = 7.9 Hz, 1H), 7.35-7.23 (m, 1H), 7.21-7.04 (m, 2H), |

TABLE 3-continued

| Compound | Analytic description |
|---|---|
| | 6.04 (s, 2H), 4.18-3.94 (m, 2H), 3.45 (s, 2H), 3.03-2.78 (m, 2H), 2.41 (s, 2H), 1.40 (t, J = 11.4 Hz, 2H), 1.25 (d, J = 13.1 Hz, 2H), 0.92 (d, J = 9.8 Hz, 3H), LC/MS: [M + 1]: 409.1 |
| 42 | Yellow solid; 1H NMR (300 MHz, DMSO-d6) δ 8.33 (d, J = 20.3 Hz, 3H), 7.90 (s, 1H), 7.61-7.58 (m, 1H), 7.46 (s, 1H), 7.36 (t, J = 7.9 Hz, 1H), 7.22-7.18 (m, 1H), 3.79-3.34 (m, 5H), 3.05-3.00 (m, 1H), 2.85-2.79 (m, 1H), 2.11-2.09 (m, 1H), 2.02-1.93 (m, 4H), 1.76-1.74 (m, 1H), 1.55-1.51 (m, 1H). LC/MS: [M + 1]: 406.0 |
| 43 | White solid; 1H NMR (300 MHz, DMSO-d6) δ 8.05-7.65 (m, 1H), 7.58 (d, J = 7.9 Hz, 1H), 7.36 (dd, J = 14.3, 6.6 Hz, 2H), 7.23 (dd, J = 7.4, 4.5 Hz, 1H), 4.27 (d, J = 116.1 Hz, 2H), 2.65 (d, J = 12.5, 5.1 Hz, 1H), 1.98 (d, J = 5.6 Hz, 4H), 1.90-1.43 (m, 5H), 1.34 (dd, J = 11.4, 7.5 Hz, 1H). LC/MS: [M + 1]: 394.1 |
| 44 | White solid; 1H NMR (300 MHz, DMSO-d6) δ 7.95-7.83 (m, 1H), 7.59 (dd, J = 8.0, 1.6 Hz, 1H), 7.45 (s, 1H), 7.35 (t, J = 7.8 Hz, 1H), 7.20 (dd, J = 7.7, 1.6 Hz, 1H), 4.29 (ddt, J = 18.7, 10.6, 1.3 Hz, 2H), 4.10 (dd, J = 20.9, 10.6 Hz, 2H), 2.96 (s, 1H), 2.89 (s, 1H), 2.01 (s, 3H), 1.73 (s, 2H). LC/MS: [M + 1]: 384.1 |
| 45 | White solid; 1H NMR (300 MHz, DMSO-d6) δ 7.87 (s, 1H), 7.59 (dd, J = 8.0, 1.6 Hz, 1H), 7.48-7.30 (m, 2H), 7.23 (s, 1H), 4.03-3.54 (m, 4H), 2.01 (s, 4H), 1.84-1.18 (m, 8H), 1.07 (s, 3H), LC/MS: [M + 1]: 408.0. |
| 43 | White solid; 1H NMR (300 MHz, DMSO-d6) δ 7.80 (s, 1H), 7.60 (dd, J = 8.0, 1.6 Hz, 1H), 7.44 (s, 1H), 7.36 (t, J = 7.8 Hz, 1H), 7.20 (d, J = 7.5 Hz, 1H), 4.41 (s, 1H), 4.01-3.94 (m, 2H), 3.03-2.89 (m, 2H), 2.32-2.29 (m, 1H), 2.23-2.20 (m, 2H), 1.99 (s, 3H). LC/MS: [M + 1]: 365.9. |
| 47 | White solid; 1H NMR (300 MHz, DMSO-d6) δ 8.19 (s, 4H), 7.59 (dd, J = 8.1, 1.5 Hz, 1H), 7.49 (s, 1H), 7.37 (t, J = 7.8 Hz, 1H), 7.21 (dd, J = 7.6, 1.5 Hz, 1H), 5.06 (s, 1H), 4.61 (d, J = 13.7 Hz, 1H), 4.01 (d, J = 12.0 Hz, 1H), 3.92 (d, J = 10.8 Hz, 1H), 3.59-3.55 (m, 1H), 3.45 (t, J = 11.5 Hz, 1H), 3.34-3.22 (m, 3H), 2.05 (s, 3H), LC/MS: [M + 1]: 396.0. |
| 48 | White solid; 1H NMR (300 MHz, DMSO-d6) δ 8.23 (s, 4H), 7.60 (dd, J = 8.1, 1.5 Hz, 1H), 7.50 (s, 1H), 7.36 (t, J = 7.8 Hz, 1H), 7.17-7.11 (m, 1H), 4.93 (s, 1H), 4.60 (s, 1H), 4.02 (d, J = 12.0 Hz, 1H), 3.92 (d, J = 11.1 Hz, 1H), 3.59 (dd, J = 12.2, 3.2 Hz, 1H), 3.47 (d, J = 12.0 Hz, 1H), 3.33-3.21 (m, 3H), 2.05 (s, 3H), LC/MS: [M + 1]: 396.0. |
| 49 | Amorphous white solid; 1H NMR (400 MHz, DMSO-d6) δ 7.67 (s, 1H), 7.52 (d, J = 8.0 Hz, 1H), 7.30 (t, J = 8.1 Hz, 1H), 7.23-7.09 (m, 2H), 6.02 (s, 2H), 4.02-3.59 (m, 4H), 3.50 (s, 1H), 1.88 (s, 2H), 1.82-1.25 (m, 6H), LC/MS: [M + 1]: 395 |
| 50 | Amorphous white solid; 1H NMR (400 MHz, DMSO-d6) δ 7.69 (s, 1H), 7.57-7.46 (m, 1H), 7.37-7.24 (m, 1H), 7.24-7.03 (m, 2H), 6.01 (s, 2H), 3.67-3.48 (m, 2H), 3.48-3.33 (m, 2H), 3.05-2.90 (m, 1H), 2.20-2.05 (m, 1H), 1.83-1.31 (m, 6H), 1.32-0.92 (m, 3H), LC/MS: [M + 1]: 421 |
| 51 | White solid; 1H NMR (400 MHz, DMSO-d6) δ 7.72 (s, 1H), 7.51 (dd, J = 8.0, 1.6 Hz, 1H), 7.43-7.14 (m, 7H), 7.13-7.06 (m, 1H), 6.06 (s, 2H), 4.23-3.80 (m, 2H), 3.57-3.43 (m, 1H), 3.34 (d, J = 28.3 Hz, 2H), 3.17 (q, J = 8.9 Hz, 1H), 2.64 (d, J = 4.1 Hz, 1H), 2.38 (s, 1H), 2.23-1.56 (m, 2H), LC/MS: [M + 1]: 457 |
| 52 | White amorphous solid; LC/MS: [M + 1]: 477. |
| 53 | White amorphous solid; 1H NMR (400 MHz, DMSO-d6) δ 7.70 (s, 1H), 7.51 (dd, J = 8.1, 1.6 Hz, 1H), 7.28 (t, J = 7.8 Hz, 1H), 7.14 (s, 1H), 7.10 (dd, J = 7.6, 1.6 Hz, 1H), 6.04 (s, 2H), 4.25-4.08 (m, 2H), 3.51-3.36 (m, 2H), 1.50-1.08 (m, 10H), 0.89 (t, J = 6.6 Hz, 3H), LC/MS: [M + 1]: 423 |
| 54 | White amorphous solid; 1H NMR (400 MHz, DMSO-d6) δ 7.64 (s, 1H), 7.51 (d, J = 7.9 Hz, 1H), 7.28 (t, J = 7.8 Hz, 1H), 7.22-7.05 (m, 2H), 6.17 (s, 2H), 4.91 (s, 1H), 3.87 (d, J = 8.7 Hz, 2H), 3.63 (d, J = 8.7 Hz, 2H), 3.07 (s, 2H), 2.55 (s, 2H), LC/MS: [M + 1]: 383 |
| 55 | White amorphous solid; 1H NMR (400 MHz, DMSO-d6) δ 7.63 (s, 1H), 7.53 (d, J = 8.3 Hz, 1H), 7.30 (dd, J = 9.1, 6.6 Hz, 1H), 7.18 (s, 1H), 7.13 (t, J = 6.4 Hz, 1H), 6.17 (s, 2H), 3.86 (dd, J = 23.9, 8.5 Hz, 2H), 3.57 (t, J = 8.9 Hz, 2H), 3.12 (d, J = 6.0 Hz, 2H), 2.67 (s, 2H), 1.25 (s, 3H), LC/MS: [M + 1]: 381 |
| 56 | Off-white solid; 1H NMR (300 MHz, DMSO-d6) δ 7.88 (s, 1H), 7.57 (dd, J = 8.0, 1.6 Hz, 1H), 7.42-7.28 (m, 2H), 7.18 (dd, J = 7.6, 1.6 Hz, 1H), 3.74 (dd, J = 11.6, 7.9 Hz, 2H), 3.58-3.47 (m, 2H), 2.93-2.83 (m, 2H), 2.55-2.42 (m, 4H), 2.20 (s, 3H), 1.98 (s, 3H), LC/MS: [M + 1]: 406.3. |
| 57 | Off-white solid; 1H NMR (300 MHz, DMSO-d6) δ 7.82 (s, 1H), 7.58 (dd, J = 8.0, 1.6 Hz, 1H), 7.40 (s, 1H), 7.34 (t, J = 7.8 Hz, 1H), 7.18 (dd, J = 7.7, 1.6 Hz, 1H), 5.00 (s, 1H), 4.00 (d, J = 8.8 Hz, 2H), 3.72 (d, J = 8.8 Hz, 2H), 3.43 (s, 2H), 1.97 (s, 3H), LC/MS: [M + 1]: 382.3 |
| 58 | Yellow solid; 1H NMR (400 MHz, DMSO-d6) δ 8.62 (d, J = 48.3 Hz, 3H), 7.86 (d, J = 47.1 Hz, 1H), 7.60 (ddd, J = 8.1, 3.2, 1.5 Hz, 1H), 7.44 (s, 1H), 7.37 (td, J = 7.9, 2.7 Hz, 1H), 7.26-7.17 (m, 1H), 3.74 (d, J = |

TABLE 3-continued

| Compound | Analytic description |
|---|---|
| | 41.5 Hz, 4H), 2.92-2.63 (m, 1H), 2.36-1.86 (m, 5H), 1.09 (p, J = 6.3 Hz, 2H), LC/MS: [M + 1]: 392 |
| 60 | Yellow solid; 1H NMR (400 MHz, DMSO-d6) δ 8.64 (s, 1H), 8.16 (s, 1H), 7.90 (s, 1H), 7.50 (s, 1H), 7.43 (s, 1H), 7.18 (t, J = 7.5 Hz, 1H), 4.05 (d, J = 13.0 Hz, 2H), 3.71 (ddd, J = 13.1, 8.0, 5.0 Hz, 2H), 1.45 (q, J = 4.9, 4.3 Hz, 4H), 1.12 (s, 3H), LC/MS: [M + 1]: 352 |
| 61 | Yellow solid; 1H NMR (400 MHz, DMSO-d6) δ 8.58 (s, 1H), 8.15 (s, 1H), 7.95 (d, J = 9.1 Hz, 1H), 7.64 (dd, J = 9.1, 6.6 Hz, 1H), 7.57 (s, 1H), 7.43 (d, J = 6.6 Hz, 1H), 4.08-4.05 (m, 2H), 3.82-3.77 (m, 2H), 1.52-1.40 (m, 4H), 1.14 (s, 3H). LC/MS: [M + 1]: 354.2. |
| 62 | Yellow oil; 1H NMR (400 MHz, Methanol-d4) δ 8.55-8.15 (m, 1H), 7.75-7.73 (m, 1H), 7.02-7.00 (m, 1H), 4.01-3.71 (m, 6H), 1.72-1.61 (m, 4H), 1.41-1.21 (m, 7H), 0.93-0.78 (m, 1H). LC/MS: [M + 1]: 401.0. |
| 64 | White amorphous solid; 1H NMR (400 MHz, DMSO-d6 + D2O) δ 7.50 (dd, J = 8.1, 1.5 Hz, 1H), 7.29 (t, J = 7.9 Hz, 1H), 7.10 (dd, J = 7.7, 1.6 Hz, 1H), 4.70 (d, J = 50.7 Hz, 1H), 4.20-3.85 (m, 1H), 3.20-2.84 (m, 2H), 2.81-2.56 (m, 2H), 1.76-1.47 (m, 2H), LC/MS: [M + 1]: 399 |
| 65 | White amorphous solid; 1H NMR (400 MHz, DMSO-d6) δ 7.64 (s, 1H), 7.51 (d, J = 8.0 Hz, 1H), 7.29 (t, J = 7.9 Hz, 1H), 7.21-7.06 (m, 2H), 6.21 (s, 1H), 6.00 (s, 2H), 3.92 (s, 1H), 3.01 (d, J = 4.1 Hz, 1H), 1.59 (dt, J = 33.1, 11.9 Hz, 6H), 1.29 (d, J = 9.0 Hz, 2H), LC/MS: [M + 1]: 395 |
| 68 | White solid; 1H NMR (300 MHz, DMSO-d6) δ 7.87 (s, 1H), 7.58 (dd, J = 8.0, 1.6 Hz, 1H), 7.44-7.30 (m, 2H), 7.22 (d, J = 21.9 Hz, 1H), 4.56 (d, J = 13.4 Hz, 1H), 4.18 (d, J = 14.8 Hz, 1H), 3.65-3.43 (m, 3H), 3.13 (s, 1H), 2.91 (s, 1H), 1.99 (s, 3H), 1.94-1.67 (m, 3H), 1.63-1.59 (m, 2H), 1.22-1.12 (t, J = 14.9 Hz, 1H), LC/MS: [M + 1]: 406.1. |
| 69 | White amorphous solid; 1H NMR (400 MHz, DMSO-d6) δ 7.63 (s, 1H), 7.52 (ddd, J = 8.0, 3.2, 1.6 Hz, 1H), 7.29 (td, J = 7.9, 2.2 Hz, 1H), 7.18 (d, J = 10.6 Hz, 1H), 7.10 (dt, J = 7.6, 2.0 Hz, 1H), 6.18 (s, 2H), 4.34 (q, J = 6.7 Hz, 1H), 4.21 ? 4.08 (m, 2H), 3.74 (ddd, J = 14.7, 7.8, 3.6 Hz, 2H), 3.63 (dd, J = 8.7, 5.6 Hz, 2H), LC/MS: [M + 1]: 353 |
| 70 | White amorphous solid; 1H NMR (400 MHz, DMSO-d6) δ 7.67 (s, 1H), 7.51 (dd, J = 8.1, 1.6 Hz, 1H), 7.28 (t, J = 7.9 Hz, 1H), 7.16 (s, 1H), 7.09 (dd, J = 7.6, 1.5 Hz, 1H), 6.08 (s, 2H), 3.84 (d, J = 11.2 Hz, 2H), 3.41 (d, J = 10.6 Hz, 3H), 2.61 (d, J = 6.9 Hz, 1H), 1.58 (s, 2H), 0.78 ? 0.68 (m, 1H), LC/MS: [M + 1]: 393 |
| 71 | White amorphous solid; 1H NMR (400 MHz, DMSO-d6) δ 7.67 (s, 1H), 7.50 (d, J = 8.1 Hz, 1H), 7.28 (t, J = 7.9 Hz, 1H), 7.15 (s, 1H), 7.09 (d, J = 7.6 Hz, 1H), 6.01 (s, 2H), 3.60 (s, 2H), 3.50 (s, 2H), 3.16 (d, J = 10.3 Hz, 1H), 2.54 (s, 2H), 2.00 (dt, J = 12.6, 6.5 Hz, 1H), 1.65 (dd, J = 12.6, 6.4 Hz, 1H), LC/MS: [M + 1]: 367 |
| 72 | White solid; 1H NMR (300 MHz, DMSO-d6) δ 7.88 (s, 1H), 7.59 (dd, J = 8.0, 1.5 Hz, 1H), 7.45-7.31 (m, 2H), 7.20 (dd, J = 7.6, 1.6 Hz, 1H), 3.80-3.67 (m, 2H), 3.60-3.42 (m, 3H), 2.74 (s, 2H), 2.00 (s, 3H), 1.90-1.69 (m, 2H), 1.55-1.39 (m, 2H), LC/MS: [M + 1]: 406.1. |
| 73 | White solid; 1H NMR (300 MHz, DMSO-d6) δ 7.88 (s, 1H), 7.59 (dd, J = 8.0, 1.6 Hz, 1H), 7.46-7.31 (m, 2H), 7.20 (dd, J = 7.6, 1.6 Hz, 1H), 3.81-3.69 (m, 2H), 3.56-3.44 (m, 3H), 2.79-2.66 (m, 2H), 2.00 (s, 3H), 1.89-1.70 (m, 2H), 1.53-1.39 (m, 2H), LC/MS: [M + 1]: 406.1. |
| 74 | White solid; 1H NMR (300 MHz, DMSO-d6) δ 7.88 (s, 1H), 7.59 (dd, J = 8.0, 1.6 Hz, 1H), 7.46-7.32 (m, 2H), 7.20 (dd, J = 7.7, 1.6 Hz, 1H), 3.81-3.67 (m, 2H), 3.61-3.44 (m, 3H), 2.83-2.68 (m, 2H), 2.00 (s, 3H), 1.89-1.70 (m, 2H), 1.59-1.38 (m, 2H), LC/MS: [M + 1]: 406.1. |
| 75 | White solid; 1H NMR (300 MHz, DMSO-d6) δ 7.88 (s, 1H), 7.59 (dd, J = 8.1, 1.6 Hz, 1H), 7.45-7.31 (m, 2H), 7.20 (dd, J = 7.7, 1.5 Hz, 1H), 3.78-3.59 (m, 3H), 3.46-3.44 (m, 1H), 3.05-3.03 (m, 1H), 2.89-2.78 (m, 1H), 2.40-2.31 (m, 1H), 2.07-1.86 (s, 5H), 1.42-1.39 (m, 2H), LC/MS: [M + 1]: 406.1. |
| 76 | White solid; 1H NMR (300 MHz, DMSO-d6) δ 7.88 (s, 1H), 7.59 (dd, J = 8.0, 1.6 Hz, 1H), 7.45-7.30 (m, 2H), 7.20 (dd, J = 7.6, 1.6 Hz, 1H), 3.79-3.57 (m, 3H), 3.51-3.38 (m, 1H), 3.06-3.01 (m, 1H), 2.88-2.79 (m, 1H), 2.38-2.27 (m, 1H), 2.08-2.00 (m, 4H), 1.95-1.83 (m, 1H), 1.50-1.31 (m, 2H), LC/MS: [M + 1]: 406.1. |
| 77 | White solid; 1H NMR (300 MHz, DMSO-d6) δ 7.90 (s, 1H), 7.60 (dd, J = 8.0, 1.6 Hz, 1H), 7.46-7.33 (m, 2H), 7.21 (dd, J = 7.6, 1.6 Hz, 1H), 3.80-3.59 (m, 3H), 3.49-3.42 (m, 1H), 3.10-3.02 (m, 1H), 2.91-2.81 (m, 1H), 2.42-2.32 (m, 1H), 2.11-1.87 (m, 6H), 1.51-1.35 (m, 2H), LC/MS: [M + 1]: 406.1. |
| 78 | White solid; 1H NMR (300 MHz, DMSO-d6) δ 8.06 (s, 1H), 7.60 (dd, J = 8.1, 1.6 Hz, 1H), 7.55 (s, 1H), 7.35 (t, J = 7.8 Hz, 1H), 7.23 (dd, J = 7.6, 1.6 Hz, 1H), 4.09-3.82 (m, 4H), 1.51 (brs, 4H), 1.21 (s, 3H), LC/MS: [M + 1]: 414.0 |
| 79 | White solid; 1H NMR (300 MHz, DMSO-d6) δ 8.03 (s, 1H), 7.60-7.58 (m, 1H), 7.52 (s, 1H), 7.35 (t, J = 7.9 Hz, 1H), 7.24-7.22(m, 1H), 4.03 (brs, 2H), 3.66 (brs, 2H), 1.43-1.41 (m, 4H), 1.09 (s, 3H), LC/MS: [M + 1]: 414.3 |

TABLE 3-continued

| Compound | Analytic description |
|---|---|
| 80 | White solid; 1H NMR (300 MHz, DMSO-d6) δ 7.85 (s, 1H), 7.57 (dd, J = 8.1, 1.6 Hz, 1H), 7.43-7.30 (m, 2H), 7.18 (d, J = 7.6 Hz, 1H), 5.06 (s, 1H), 3.91 (s, 1H), 3.82-3.60 (m, 2H), 3.48-3.35 (m, 3H), 2.16-1.99 (m, 5H), LC/MS: [M + 1]: 382.0 |
| 81 | Off-White solid; 1H NMR (400 MHz, Methanol-d4) δ 8.29 (d, J = 4.9 Hz, 1H), 7.25 (d, J = 4.9 Hz, 1H), 4.15 (s, 1H), 4.20-4.10 (m, 2H), 3.86 (ddd, J = 13.2, 7.8, 4.1 Hz, 2H), 2.11 (s, 3H), 1.65 (tdd, J = 13.1, 10.4, 4.2 Hz, 4H), 1.30 (s, 3H), LC/MS: [M + 1]: 395.0 |
| 82 | White solid; 1H NMR (400 MHz, DMSO-d6) δ 7.91 (s, 1H), 7.48 (dd, J = 8.9, 2.5 Hz, 1H), 7.37 (s, 1H), 7.32-7.19 (m, 2H), 3.99-3.77 (m, 4H), 2.01 (s, 3H), 1.50 (t, J = 5.8 Hz, 4H), 1.17 (s, 3H), LC/MS: [M + 1]: 378.0 |
| 83 | Off-White solid; 1H NMR (400 MHz, Methanol-d4) δ 8.60 (s, 1H), 8.46 (d, J = 5.0 Hz, 1H), 7.30 (d, J = 4.9 Hz, 1H), 4.12 (ddd, J = 13.8, 7.2, 4.2 Hz, 2H), 3.88 (ddd, J = 13.8, 7.7, 4.1 Hz, 2H), 2.11 (s, 3H), 1.64 (th, J = 13.0, 4.2 Hz, 4H), 1.28 (s, 3H), LC/MS: [M + 1]: 361.0 |
| 84 | White solid; 1H NMR (300 MHz, DMSO-d6) δ 7.85 (s, 1H), 7.57 (dd, J = 8.1, 1.6 Hz, 1H), 7.43-7.29 (m, 2H), 7.17 (d, J = 7.6 Hz, 1H), 5.08 (s, 1H), 4.03 (s, 1H), 3.84-3.54 (m, 3H), 3.43-3.35 (m, 1H), 3.22-3.09 (m, 1H), 2.17-1.98 (s, 4H), LC/MS: [M + 1]: 382.0 |
| 86 | Yellow solid; 1H NMR (300 MHz, DMSO-d6) δ 8.56-8.48 (m, 2H), 7.88 (s, 1H), 7.41 (s, 1H), 7.25-7.17 (m, 2H), 4.00 (d, J = 13.2 Hz, 2H), 3.66 (dt, J = 12.9, 6.3 Hz, 2H), 2.09 (s, 4H), 1.39 (d, J = 5.6 Hz, 4H), 1.08 (s, 3H), LC/MS: [M + 1]: 327.2 |
| 87 | LC/MS: [M + 1]: 394.1. |
| 88 | White solid; 1H NMR (400 MHz, DMSO-d6) 7.81-7.73(m, 1H), 7.58 (dd, J = 8.1, 1.6 Hz, 1H), 7.40-7.30 (m, 3H), 7.22 (d, J = 7.6 Hz, 1H), 3.88 (brs, 1H), 2.75 (s, 1H), 2.05-1.96 (m, 4H), 1.86-1.77 (m, 1H), 1.74-1.69 (m, 2H), 1.34-1.23 (m, 2H), 1.08-0.83 (m, 1H). LC/MS: [M + 1]: 394.0. |
| 89 | White solid; 1H NMR (300 MHz, Methanol-d4) δ 7.50 (dd, J = 8.1, 1.6 Hz, 1H), 7.29 (t, J = 7.9 Hz, 1H), 7.14 (dd, J = 7.7, 1.6 Hz, 1H), 4.03-3.89 (m, 1H), 3.00-2.93 (m, 1H), 2.68 (s, 1H), 2.46 (s, 2H), 2.45-2.33 (m, 1H), 2.06 (s, 4H), 2.00-1.83 (m, 2H), 1.55-1.40 (m, 1H), 1.31-1.16 (m, 4H), LC/MS: [M + 1]: 394.0. |
| 90 | White solid; 1H NMR (300 MHz, Methanol-d4) δ 7.50 (dd, J = 8.1, 1.6 Hz, 1H), 7.29 (t, J = 7.9 Hz, 1H), 7.14 (dd, J = 7.7, 1.6 Hz, 1H), 4.03-3.89 (m, 1H), 3.00-2.93 (m, 1H), 2.68 (s, 1H), 2.46 (s, 2H), 2.45-2.33 (m, 1H), 2.06 (s, 4H), 2.00-1.83 (m, 2H), 1.55-1.40 (m, 1H), 1.31-1.16 (m, 4H), LC/MS: [M + 1]: 394.0. |
| 91 | White solid; 1H NMR (300 MHz, Methanol-d4) δ 7.50 (dd, J = 8.1, 1.6 Hz, 1H), 7.29 (t, J = 7.9 Hz, 1H), 7.14 (dd, J = 7.7, 1.6 Hz, 1H), 4.03-3.89 (m, 1H), 3.00-2.93 (m, 1H), 2.68 (s, 1H), 2.46 (s, 2H), 2.45-2.33 (m, 1H), 2.06 (s, 4H), 2.00-1.83 (m, 2H), 1.55-1.40 (m, 1H), 1.31-1.16 (m, 4H), LC/MS: [M + 1]: 394.0. |
| 92 | White solid; 1H NMR (300 MHz, DMSO-d6) δ 7.65 (s, 1H), 7.49 (dd, J = 8.1, 1.6 Hz, 1H), 7.38-7.21 (m, 2H), 7.19-7.05 (m, 1H), 6.01 (s, 2H), 3.76 (s, 2H), 3.59 (s, 2H), 1.91 (s, 1H), 1.57-1.33 (m, 7H), 1.03 (d, J = 12.8 Hz, 3H), LC/MS: [M + 1]: 409.2 |
| 93 | White solid; 1H NMR (300 MHz, DMSO-d6) δ 7.77 (s, 1H), 7.57 (d, J = 8.1 Hz, 1H), 7.40-7.28 (m, 2H), 7.21 (d, J = 6.6 Hz, 2H), 4.00-3.86 (m, 1H), 2.85-2.78 (s, 1H), 1.96 (s, 3H), 1.83-1.67 (m, 2H), 1.58-1.44 (m, 6H), LC/MS: [M + 1]: 394 |
| 106 | Yellow powder; 1H NMR (400 MHz, Methanol-d4) δ 7.53 (dd, J = 8.1, 1.5 Hz, 1H), 7.33 (t, J = 7.8 Hz, 1H), 7.20 (dd, J = 7.6, 1.5 Hz, 1H), 5.63 (t, J = 56.9 Hz, 1H), 4.61 (dt, J = 13.7, 3.9 Hz, 2H), 1.76 (td, J = 12.8, 4.7 Hz, 2H), 1.55 (d, J = 13.5 Hz, 2H), 1.43-0.73 (m, 2H), LC/MS: [M + 1]: 431 |
| 107 | Yellow powder; 1H NMR (400 MHz, Methanol-d4) δ 7.53 (dd, J = 8.1, 1.6 Hz, 1H), 7.33 (t, J = 7.8 Hz, 1H), 7.20 (dd, J = 7.6, 1.5 Hz, 1H), 5.64 (t, J = 56.9 Hz, 1H), 4.62 (dt, J = 13.6, 4.0 Hz, 2H), 1.76 (ddd, J = 13.5, 11.9, 4.7 Hz, 2H), 1.60-1.45 (m, 2H), 1.41-0.76 (m, 2H), LC/MS: [M + 1]: 431 |
| 108 | Off-white solid; 1H NMR (400 MHz, Methanol-d4) δ 7.50 (dd, J = 8.1, 1.6 Hz, 1H), 7.30 (t, J = 7.8 Hz, 1H), 7.16 (dd, J = 7.6, 1.6 Hz, 1H), 3.93-3.68 (m, 4H), 1.98-1.78 (m, 4H), 1.65 (t, J = 6.0 Hz, 2H), 1.21 (s, 3H), LC/MS: [M + 1]: 409.2. |
| 109 | Off-white solid; 1H NMR (400 MHz, Methanol-d4) δ7.50 (dd, J = 8.1, 1.6 Hz, 1H), 7.30 (t, J = 7.8 Hz, 1H), 7.16 (dd, J = 7.6, 1.6 Hz, 1H), 3.93-3.68 (m, 4H), 1.98-1.78 (m, 4H), 1.65 (t, J = 6.0 Hz, 2H), 1.21 (s, 3H), LC/MS: [M + 1]: 409.2. |
| 110 | Off-white solid; 1H NMR (400 MHz, Methanol-d4) δ 7.50 (dd, J = 8.1, 1.6 Hz, 1H), 7.30 (t, J = 7.8 Hz, 1H), 7.16 (dd, J = 7.6, 1.6 Hz, 1H), 3.93-3.68 (m, 4H), 1.98-1.78 (m, 4H), 1.65 (t, J = 6.0 Hz, 2H), 1.21 (s, 3H), LC/MS: [M + 1]:409.2. |
| 111 | Off-white solid; 1H NMR (400 MHz, Methanol-d4) δ 7.50 (dd, J = 8.1, 1.6 Hz, 1H), 7.30 (t, J = 7.8 Hz, 1H), 7.16 (dd, J = 7.6, 1.6 Hz, 1H), |

TABLE 3-continued

| Compound | Analytic description |
|---|---|
|  | 3.93-3.68 (m, 4H), 1.98-1.78 (m, 4H), 1.65 (t, J = 6.0 Hz, 2H), 1.21 (s, 3H), LC/MS: [M + 1]: 428.2 |
| 112 | White solid; 1H NMR (300 MHz, DMSO-d6) δ 7.68 (s, 1H), 7.49 (dd, J = 8.1, 1.5 Hz, 1H), 7.27 (t, J = 7.8 Hz, 1H), 7.15 (s, 1H), 7.08 (dd, J = 7.7, 1.6 Hz, 1H), 6.01 (s, 1H), 4.54 (d, J = 11.6 Hz, 1H), 3.70-3.48(m, 1H), 3.09 (brs, 1H), 2.98 (s, 3H), 2.52 (s, 1H), 1.95 (d, J = 11.3 Hz, 2H), 1.59 (d, J = 14.7 Hz, 4H), 1.31 (d, J = 13.1 Hz, 2H), LC/MS: [M + 1]: 409.1 |
| 115 | White solid; 1H NMR (400 MHz, Chloroform-d) δ 7.51 (s, 1H), 7.06-6.95 (m, 1H), 6.83-6.74 (m, 1H), 5.41-5.35 (m, 1H), 4.12-3.95 (m, 4H), 3.92-3.76 (m, 2H), 2.13 (s, 3H), 1.74-1.53 (m, 4H), 1.28 (s, 5H), LC/MS: [M + 1]: 408.1. |
| 116 | White solid; 1H NMR (400 MHz, Chloroform-d) δ 7.52 (s, 1H), 7.06-6.94 (m, 1H), 6.83-6.74 (m, 1H), 5.58 (s, 1H), 4.07-3.88 (m, 6H), 2.13 (s, 3H), 1.77-1.62 (m, 4H), 1.30-1.28 (m, 5H), LC/MS: [M + 1]: 408.1. |

Example 3: Testing Compounds of the Present Invention for Inhibitory Activities Against SHP2 and ERK1 2

SHP2 Biochemical Assay:

The inhibition of SHP2 by compounds of the invention was monitored using the surrogate substrate DiFMUP after protein activation by a peptide bearing two appropriately spaced phosphotyrosine. Full length SHP2 protein (Recombinant HumanSHP-2, E. coli derived Ser2Arg593, N-terminal 6His tag from R&D systems; 0.0.24 nM) was incubated with activating peptide, IRSI_2pY (New England Peptide, 140 nM) and DiFMUP (molecular probes, 80 uM) at RT in buffer (HEPES pH 7.2 60 mM, DDT 5 mM, KCl 75 mM, NaCl 75 mM, EDTA 1 mM, Tween 20 0.05%) in presence of compound (10 concentrations range, top concentration 50 µM) for 60 min. The generation of the DiFMU product by activated SHP2 was monitored through Fluorescence measurement with a PerkinElmer Envision reader.

The inhibitor dose response curves were analyzed with Genedata Screener. $IC_{50}$ ranges for compounds of the invention are shown in table 4 below.

p-Erk Cellular Assay in MDA-MB-468 and KYSE520:

The effect of SHP2 inhibitors on pERK level was assessed using phospho-specific antibody using Mesoscale quantification platform. For measuring change in pERK levels using mesoscale, 30,000 cells of MDA MB468 and KYSE520 cells were plated in 96-well tissue culture treated plate in 175 ul volume of media. After an overnight incubation at 37° C., various SHP2 inhibitors were added in different concentration to each well maintaining duplicate wells across plates and incubated with compounds for 2 h at 37° C. followed by a wash with ice cold PBS buffer. The cells were then lysed in lysis buffer and processed and analyzed for p-ERK/ERK as per manufacturer's instructions (Mesoscale discovery, cat No. K15107D-3). $IC_{50}$ ranges for compounds of the invention are shown in table 4 below.

TABLE 4

| Compound | SHP-2 Biochemical assay $IC_{50}$ (uM) | pERK1/2 in KYSE520 $IC_{50}$ (uM) | pERK1/2 in MDA-MB-468 $IC_{50}$ (uM) |
|---|---|---|---|
| 1 | 3.700 | NT | 12 |
| 2 | 2.100 | NT | 3.085 |
| 3 | 0.160 | 0.754 | 0.346 |
| 4 | 3.700 | NT | NT |
| 5 | 0.072 | 1.094 | 1.009 |
| 6 | 2.700 | NT | NT |
| 7 | 0.120 | 1.373 | 0.606 |
| 8 | 0.200 | 1.512 | 2.184 |
| 9 | 1.100 | 6.437 | 1.497 |
| 10 | 9.600 | NT | NT |
| 11 | 0.590 | 10.223 | 1.833 |
| 12 | 1.600 | NT | NT |
| 13 | >10 | NT | NT |
| 14 | 8.800 | NT | NT |
| 15 | ND | NT | NT |
| 16 | 0.060 | 1.140 | 0.516 |
| 17 | 12.000 | NT | NT |
| 18 | 0.104 | 2.396 | 0.231 |
| 19 | 87.000 | NT | NT |
| 20 | 0.150 | 8.452 | 0.492 |
| 21 | 1.600 | NT | NT |
| 22 | 21.000 | NT | NT |
| 23 | 4.700 | NT | NT |
| 24 | 0.270 | 7.646 | 2.347 |
| 25 | >10 | NT | NT |
| 26 | >10 | >10 | 8.185 |
| 27 | 0.082 | 1.467 | 0.342 |
| 28 | 0.360 | 11.489 | 1.631 |
| 29 | 0.260 | 7.700 | 1.166 |
| 30 | 0.110 | NT | 0.475 |
| 31 | 7.900 | NT | NT |
| 32 | 0.200 | 3.608 | 0.736 |
| 33 | 2.400 | NT | NT |
| 34 | 1.100 | NT | NT |
| 35 | 1.100 | NT | NT |
| 36 | 13.000 | NT | NT |
| 37 | 1.100 | NT | NT |
| 38 | 7.600 | NT | NT |
| 39 | 6.300 | NT | NT |
| 40 | 3.900 | NT | NT |
| 41 | 0.310 | 2.993 | 0.908 |
| 42 | 4.800 | NT | NT |
| 43 | 3.100 | NT | NT |
| 44 | 11.000 | NT | NT |
| 45 | 0.170 | 2.098 | 0.646 |
| 46 | 5.500 | NT | NT |
| 47 | >10 | NT | NT |
| 48 | >10 | NT | NT |
| 49 | 0.120 | 2.538 | 0.683 |
| 50 | 10.000 | NT | NT |
| 51 | 1.500 | NT | NT |
| 52 | >10 | NT | NT |
| 53 | 0.200 | 1.300 | 0.652 |
| 54 | 7.700 | NT | NT |
| 55 | 1.700 | NT | NT |
| 56 | 0.960 | NT | NT |
| 57 | >10 | NT | NT |
| 58 | 4.400 | NT | NT |

TABLE 4-continued

| Compound | SHP-2 Biochemical assay IC$_{50}$ (uM) | pERK1/2 in KYSE520 IC$_{50}$ (uM) | pERK1/2 in MDA-MB-468 IC$_{50}$ (uM) |
|---|---|---|---|
| 60 | >10 | NT | NT |
| 61 | >10 | NT | NT |
| 62 | >10 | NT | NT |
| 64 | 10.000 | NT | NT |
| 65 | 3.700 | NT | NT |
| 66 | 0.052 | 0.863 | 0.503 |
| 67 | 16.000 | NT | NT |
| 68 | 6.200 | NT | NT |
| 69 | 5.600 | NT | NT |
| 70 | 5.300 | NT | NT |
| 71 | 1.300 | NT | NT |
| 72 | 6.700 | NT | NT |
| 73 | 5.200 | NT | NT |
| 74 | >10 | NT | NT |
| 75 | 2.100 | NT | NT |
| 76 | 1.000 | NT | NT |
| 77 | >10 | NT | NT |
| 78 | 1.400 | NT | NT |
| 79 | 0.030 | 0.837 | 0.177 |
| 80 | 5.300 | NT | NT |
| 81 | 0.720 | 11.345 | 1.715 |
| 82 | 2.000 | NT | NT |
| 83 | 14.000 | NT | NT |
| 84 | 6.300 | NT | NT |
| 85 | 0.048 | 1.241 | 0.407 |
| 86 | >10 | NT | NT |
| 87 | 1.200 | NT | NT |
| 88 | 0.410 | 4.250 | NT |
| 89 | 13.000 | NT | NT |
| 90 | >10 | NT | NT |
| 91 | 0.100 | 2.600 | NT |
| 93 | 2.3 | NT | NT |
| 94 | 2.600 | NT | NT |
| 95 | 0.022 | 0.486 | 0.497 |
| 96 | 0.062 | 0.993 | NT |
| 97 | 4.400 | NT | NT |
| 98 | 0.049 | 1.2 | 0.395 |
| 99 | 3.7 | NT | NT |
| 100 | 0.5 | 12.8 | |
| 101 | 0.075 | 0.390 | 0.445 |
| 102 | 17.000 | NT | NT |
| 103 | 5.600 | NT | NT |
| 104 | 0.120 | 2.249 | NT |
| 105 | 10.000 | NT | NT |
| 106 | 15.000 | NT | NT |
| 107 | 3.200 | NT | NT |
| 108 | 1.300 | NT | NT |
| 109 | 0.071 | 0.468 | 0.42 |
| 110 | 4.400 | NT | NT |
| 111 | 0.530 | 4.700 | NT |
| 112 | 0.066 | 0.596 | 0.67 |
| 113 | 0.660 | NT | NT |
| 114 | 0.045 | 0.284 | 0.316 |
| 115 | 0.570 | NT | NT |
| 116 | >10 | NT | NT |
| 117 | 0.001 | 0.001 | NT |
| 118 | 0.041 | 0.114 | NT |
| 119 | 0.001 | 0.021 | NT |
| 120 | 0.270 | NT | NT |
| 121 | 0.002 | 0.016 | NT |
| 122 | 0.017 | 0.048 | NT |
| 123 | 0.015 | 0.058 | NT |
| 124 | 0.006 | 0.268 | NT |
| 125 | 0.530 | NT | NT |
| 126 | 1.200 | NT | NT |
| 127 | >10 | NT | NT |
| 128 | 0.006 | 0.161 | NT |
| 129 | 0.330 | NT | NT |
| 130 | 0.077 | 2.245 | NT |
| 131 | 7.000 | NT | NT |

Example 4: In-Vitro Safety Profile—Testing the Selectivity Over hErg

Inhibition of the ion channel hErg (or Kv11.1) current causes QT interval prolongation resulting in potentially fatal ventricular tachyarrhythmia called Torsade de Pointes. This is one of the major causes of cardiotoxicity and hErg channel activity is usually evaluated early in the drug development process to mitigate cardiotoxicity risk.

hERG ion channel activity was assessed using a patch clamp technique in stable Kv11.1 (hERG) transfected human embryonic kidney cell line (HEK293). Whole cell recordings were carried out with an automated patch clamp device Patchliner™ from Nanion Technologies, Munich following manufacturer recommendation. Different concentrations of the test compound or reference, quinidine, were applied to whole cells suspension and current was measured using a pulse pattern with fixed amplitudes. The effect on Kv11.1 (hERG) ion channel activity was judged from the tail current amplitude and Changes in Kv11.1 (hERG) ion channel activity between control value (defined as 100%) and test compound and reported as percent change of control value of COI.

TABLE 5

In-vitro safety profile

| Structure | No. | Split between hErg and cell activity Ki(patch Clamp)/ IC50 (KYSE) |
|---|---|---|
| 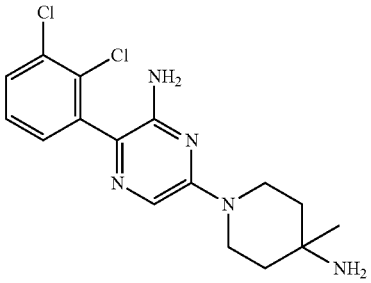 [SMILES: CC1(N)CCN(c2cnc(-c3cccc(Cl)c3Cl)c(N)n2)CC1] | SHP-099 (example 7 of WO2015/107493) | 2.5 |

TABLE 5-continued
| | | In-vitro safety profile |
|---|---|---|
| Structure | No. | Split between hErg and cell activity Ki(patch Clamp)/ IC50 (KYSE) |
| 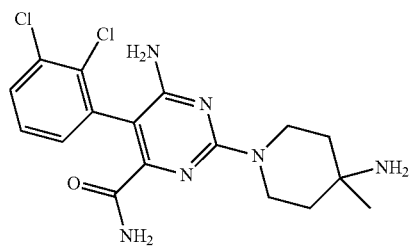 [SMILES: CC1(N)CCN(c2nc(N)c(-c3cccc(Cl)c3Cl)c(C(N)=O)n2)CC1] | Compound No. 3 | >14 |
| 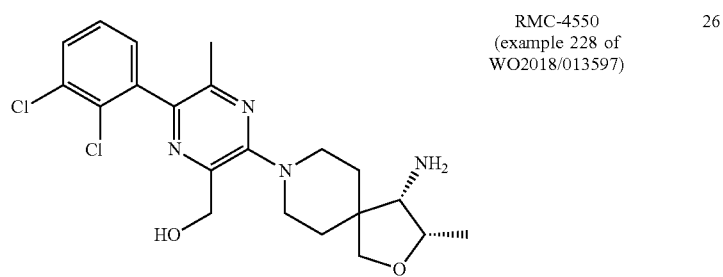 | RMC-4550 (example 228 of WO2018/013597) | 26 |
| 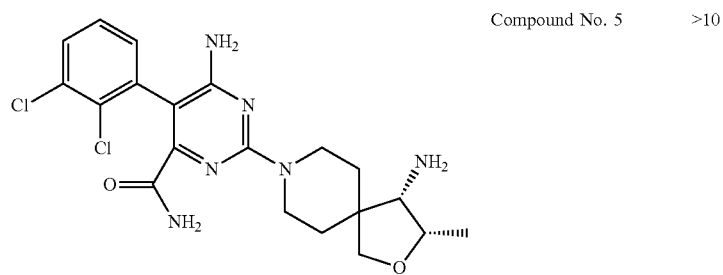 | Compound No. 5 | >10 |
| 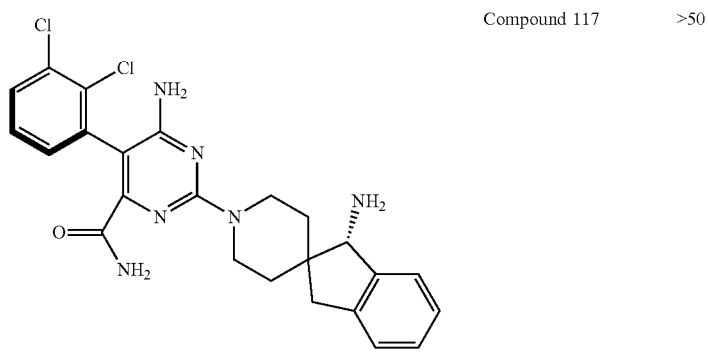 | Compound 117 | >50 |

TABLE 5-continued

| | In-vitro safety profile | |
|---|---|---|
| Structure | No. | Split between hErg and cell activity Ki(patch Clamp)/ IC50 (KYSE) |
| (structure) | Compound 119 | 97 |
| (structure) | Compound 121 | >600 |
| (structure) | Compound 122 | >50 |
| (structure) | Compound 123 | >100 |

219

Result

The compounds of the present invention show a much better split between hErg activity (Ki in patch clamp assay) and cell activity (IC50 in KYSE) as compared to known SHP2 inhibitors SHP-099 and RMC-4550. This should translate to less likelihood of cardio toxicity when administered to subjects.

Example 5: Testing the Pharmacokinetic Properties of the Compounds of the Present Invention in Mouse Female CD1 mice (N=3) received a single oral (gavage) or a single intravenous (bolus) injection of compound. Dosing vehicles were typically given by oral gavage as 0.5% Methocel K4M/0.25% Tween20 in sodium citrate buffer, 0.1M, pH 3.0 or, for IV administration, as a solution in 10% Kolliphor HS15 in Na acetate buffer, 0.01M, pH 4.5. Consecutive blood samples were taken sub-lingually under isofluorane inhalation from animals after 0.083 (IV), 0.25, 0.5, 1, 2, 4, 6 and 24 h and were further processed to obtain plasma. Samples were protein precipitated and analyzed by LC/MS/MS.

TABLE 6

PK data in mouse

| Name, No. | Clearance L/h/kg | AUC ng/ml*h (normalized 1 mpk) | Vd ss (L/kg) | Cmax ng/mL Normalized to 1 mgk) |
|---|---|---|---|---|
| SHP-099 | 5.7 | 129 | 5 | 48 |
| Compound 27 | 2.24 | 230 | 8.7 | 48 |
| Compound 95 | 0.77 | 1214 | 3.99 | 150 |

Result

In mouse PK, the compounds of the present invention (No. 27 and 95) shows a lower clearance and higher exposure as compared to the reference compound SHP-099.

Example 6: Testing Compounds of the Present Invention for Inhibitory Activities Against SHP2 Active Mutant E76K with and without an Activating Peptide A selection of compounds has been tested in a biochemical assay using same conditions as described in example 3, but with an auto-activated mutant protein SHP2 E76K with and without the addition of the activating peptide IRSI_2pY (New England Peptide, 140 nM).

TABLE 7

| Compound | SHP-2 IC$_{50}$ (µM) peptide | SHP-2 E76Z IC$_{50}$ (µM) No peptide | SHP-2 E76Z IC$_{50}$ (µM) peptide |
|---|---|---|---|
| SHP-099 (example 7 of WO2015/107493) | 47 nM | 34 uM * | 250 uM * (+10 uM ppIRS-1) |
| Compound 117 | 0.4 nM | 0.5 nM | 1.1 nM |

* From LaRochelle J. R. et al., *Nature comm.*, 2018, 9: 4508, 1-10

In strongly SHP2 activating conditions, our compound retains a nM range potency while known inhibitor SHP099 losses several logs in similar conditions. This can be an advantage for treating cancer with strongly activating SHP2 mutations.

220

Example 6: Activity in U937 Cells

Selected compounds were tested in a cytokine release assay in monocytic cells (U937) to test their anti-inflammatory properties. Cells were plated in a 96-well cell culture plate using serum-free media. The cells were treated with indicated concentrations of SHP-2 inhibitors for 30 minutes followed by overnight stimulation with recombinant IL-6 (50 ng/ml). The MCP-1 production was measured in the culture supernatant using a MCP-1 AlphaLISA kit (Perkin Elmer).

The mixture of compounds (117+118) suppressed MCP-1 production in U937 cells stimulated with IL-6 with an IC$_{50}$=67 nM (see FIG. 1). This result indicates that compounds of the present invention should be useful for treatment of hyperproliferative disorders associated with the immune system, as described herein.

Example 7: Injection Vials

A solution of 100 g of a compound of the present invention and 5 g of disodium hydrogenphosphate in 3 L of bidistilled water is adjusted to pH 6.5 using 2 N hydrochloric acid, filtered under sterile conditions, transferred into injection vials, lyophilised under sterile conditions and sealed under sterile conditions. Each injection vial contains 5 mg of a compound of the present invention.

Example 8: Solution

A solution is prepared from 1 g of a compound of the present invention, 9.38 g of NaH$_2$PO$_4$ 2 H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 L and sterilised by irradiation.

Example 9: Ampoules

A solution of 1 kg of a compound of the present invention in 60 L of bidistilled water is filtered under sterile conditions, transferred into ampoules, lyophilised under sterile conditions and sealed under sterile conditions. Each ampoule contains 10 mg of a compound of the present invention.

The invention claimed is:

1. A compound according to formula (I):

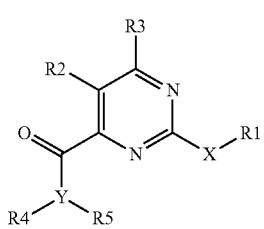

or a pharmaceutically acceptable salt thereof, wherein

X is —N— or —N(Me)— when R1 is cyclohexyl, cyclopentyl, or piperidinyl, each optionally substituted with 1 or two groups selected from —F, —NH$_2$, and —CH$_2$NH$_2$; or X is a bond when R1 is

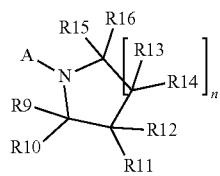

R2 is an aryl or heteroaryl which is substituted with 1-3 groups selected from —F, —Cl, —CF$_3$, C$_1$-C$_3$ alkoxy and C$_1$-C$_3$ alkyl;

R3 is —H, —NH$_2$, —OH, —Cl, —F, —Br, or —CH$_3$;

Y is —N—;

R4 and R5 are independently —H, —NH$_2$, —OH, C$_1$-C$_3$ alkyl, or C$_1$-C$_3$ hydroxyalkyl, n is 0, 1, 2, or 3; and each of R9, R10, R11, R12, R13, R14, R15 and R16, when present, are independently selected from —H, C$_1$-C$_3$ alkyl, —NH$_2$, —OH, —Cl, —F, —Br, C$_1$-C$_3$ aminoalkyl, C$_1$-C$_3$ hydroxyalkyl, C$_1$-C$_3$ alkoxy, and phenyl; or two of R9, R11, R13 and R16 are taken together to form a bridged bicyclic heterocyclic system which is optionally substituted with 1-3 substituents selected from C$_1$-C$_3$ alkyl, —NH$_2$, —OH, —Cl, —F, —Br, C$_1$-C$_3$ aminoalkyl, C$_1$-C$_3$ hydroxyalkyl, C$_1$-C$_3$ alkoxy, and phenyl; or two of R9, R10, R11, R12, R13, R14, R15, and R16, which are attached to the same carbon atom, are taken together to form a monocyclic or bicyclic spirocyclyl, which is optionally substituted with 1-3 substituents selected from C$_1$-C$_3$ alkyl, —NH$_2$, —OH, —Cl, —F, —Br, C$_1$-C$_3$ aminoalkyl, C$_1$-C$_3$ hydroxyalkyl, C$_1$-C$_3$ alkoxy, and phenyl; or two of R9, R10, R11, R12, R13, R14, R15, and R16, which are attached to adjacent carbon atoms, are taken together to form a fused carbocyclyl or heterocyclyl, which is optionally substituted with 1-3 substituents selected from C$_1$-C$_3$ alkyl, —NH$_2$, —OH, —Cl, —F, —Br, C$_1$-C$_3$ aminoalkyl, C$_1$-C$_3$ hydroxyalkyl, C$_1$-C$_3$, alkoxy, and phenyl.

2. The compound of claim 1, or a pharmaceutically acceptable salt thereof, wherein R2 is selected from phenyl, pyridine, indole, 2,1,3-benzoxadiazole and 1,3-benzodiazole, each of which is optionally and independently substituted with 1 to 3 groups selected from —F, —Cl, —CF$_3$, —OCH$_3$ and —CH$_3$.

3. The compound of claim 1, or a pharmaceutically acceptable salt thereof, wherein R2 is selected from phenyl and pyridine, each of which is optionally and independently substituted with 1-3 groups selected from —Cl, —F, —CF$_3$ and —OCH$_3$.

4. The compound of claim 1, or a pharmaceutically acceptable salt thereof, wherein one of R4 and R5 is —H and the other is —OH.

5. A compound according to claim 1, as shown by Formula (Ia):

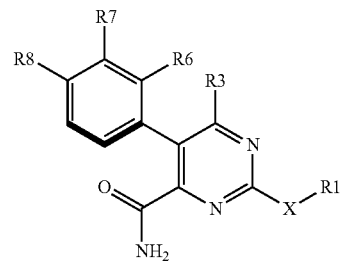

or a pharmaceutically acceptable salt thereof, wherein each of R6, R7 and R8 are independently selected from —H, —F, —Cl, —CF$_3$, C$_1$-C$_3$ alkoxy and C$_1$-C$_3$ alkyl.

6. The compound according to claim 1, or a pharmaceutically acceptable salt thereof, wherein X is a bond.

7. The compound of claim 1, or a pharmaceutically acceptable salt thereof, wherein X—R1 is

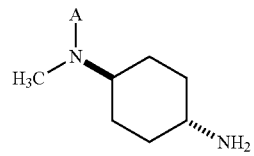

wherein A is the point of attachment to the pyrimidine ring.

8. The compound according to claim 1, or a pharmaceutically acceptable salt thereof, wherein X is —N— or —N(Me)— and R1 is a cyclopentyl substituted with one —CH$_2$NH$_2$, a cyclohexyl substituted with one —NH$_2$, or a piperidine substituted with one —F.

9. The compound according to claim 1, as shown by Formula (Ib):

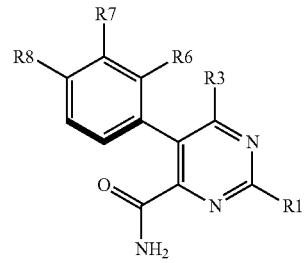

or a pharmaceutically acceptable salt thereof, wherein R1 is

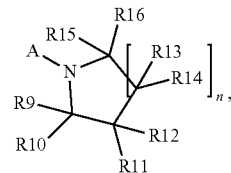

when A is the point of attachment to the pyrimidine ring of Formula Ib;

each of R6, R7 and R8 are independently selected from —H, —F, —Cl, —CF$_3$, C$_1$-C$_3$ alkoxy and C$_1$-C$_3$ alkyl;

n is 0, 1, 2, or 3; and each of R9, R10, R11, R12, R13, R14, R15 and R16, when present, are independently selected from —H, $C_1$-$C_3$ alkyl, —$NH_2$, —OH, —Cl, —F, —Br, $C_1$-$C_3$ aminoalkyl, $C_1$-$C_3$ hydroxyalkyl, $C_1$-$C_3$ alkoxy, and phenyl; or two of R9, R11, R13 and R16 are taken together to form a bridged bicyclic heterocyclic system which is optionally substituted with 1-3 substituents selected from $C_1$-$C_3$ alkyl, —$NH_2$, —OH, —Cl, —F, —Br, $C_1$-$C_3$ aminoalkyl, $C_1$-$C_3$ hydroxyalkyl, $C_1$-$C_3$ alkoxy, and phenyl; or two of R9, R10, R11, R12, R13, R14, R15, and R16, which are attached to the same carbon atom, are taken together to form a monocyclic or bicyclic spirocyclyl, which is optionally substituted with 1-3 substituents selected from $C_1$-$C_3$ alkyl, —$NH_2$, —OH, —Cl, —F, —Br, $C_1$-$C_3$ aminoalkyl, $C_1$-$C_3$ hydroxyalkyl, $C_1$-$C_3$ alkoxy, and phenyl; or two of R9, R10, R11, R12, R13, R14, R15, and R16, which are attached to adjacent carbon atoms, are taken together to form a fused carbocyclyl or heterocyclyl, which is optionally substituted with 1-3 substituents selected from $C_1$-$C_3$ alkyl, —$NH_2$, —OH, —Cl, —F, —Br, $C_1$-$C_3$ aminoalkyl, $C_1$-$C_3$ hydroxyalkyl, $C_1$-$C_3$ alkoxy, and phenyl.

10. The compound of claim 9, or a pharmaceutically acceptable salt thereof, wherein R1 is selected from the group consisting of:

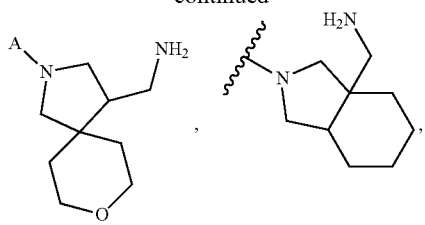
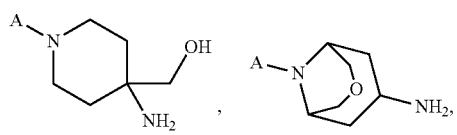
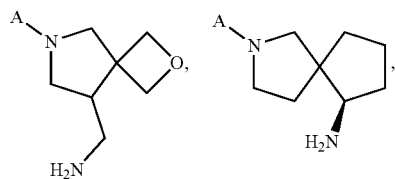
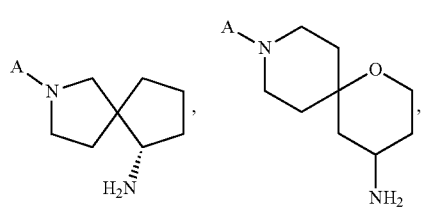
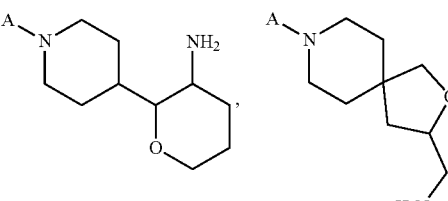
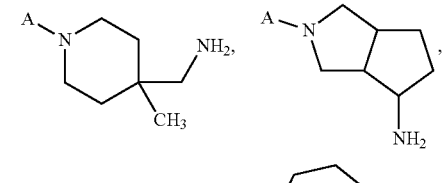
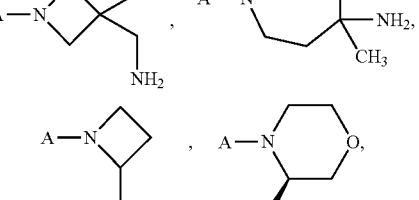
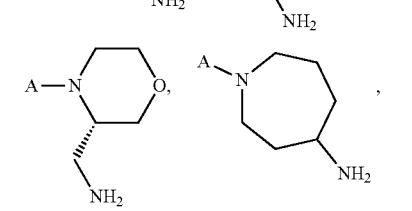
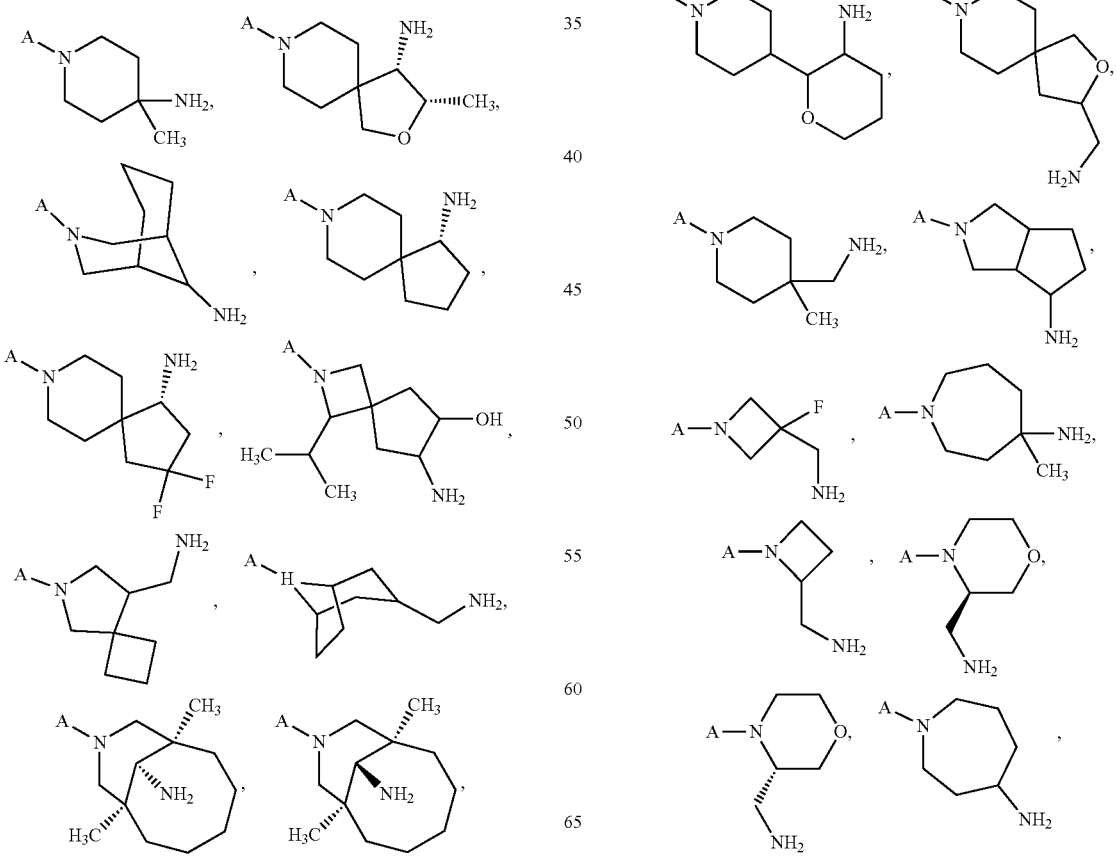

-continued
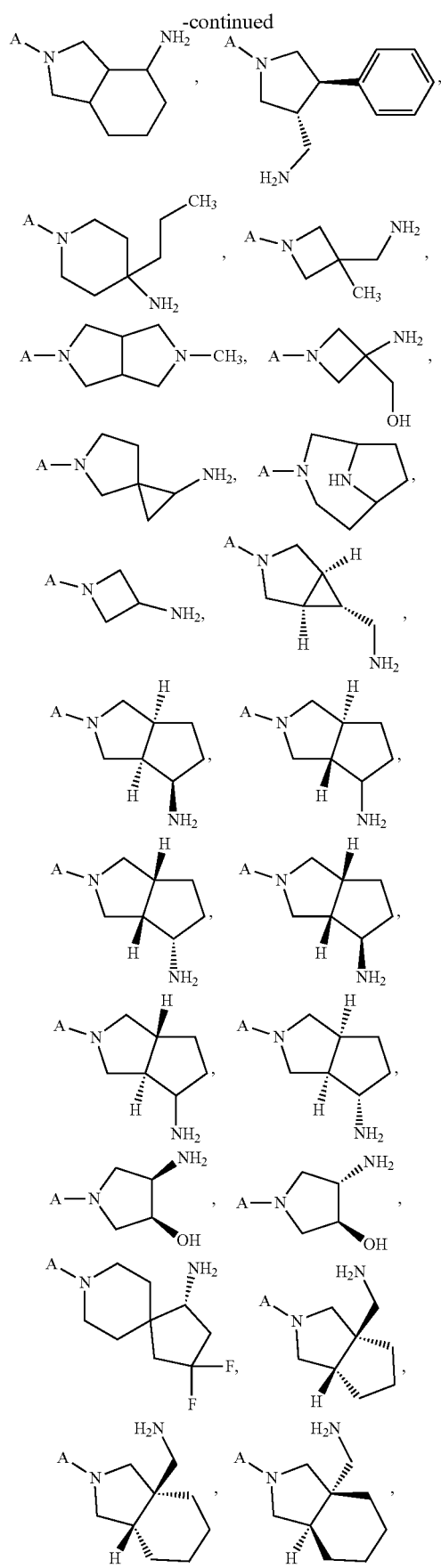
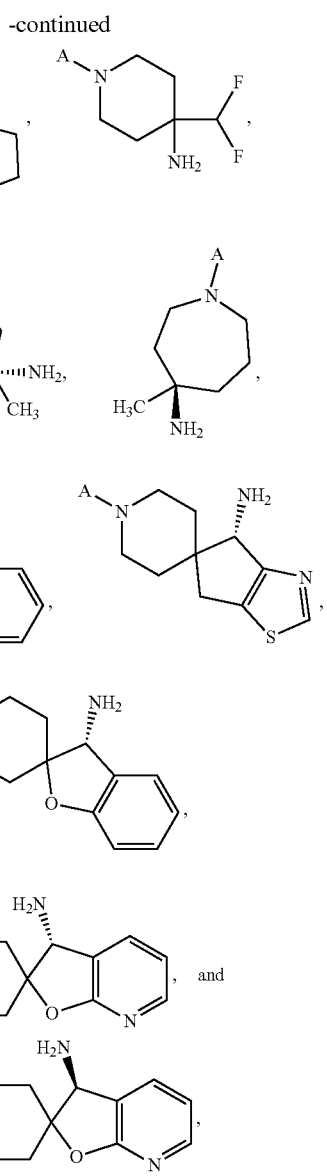
wherein A represents the point of attachment to the pyrimidine ring.
11. The compound of claim 9, or a pharmaceutically acceptable salt thereof, according to the Formula Ic:
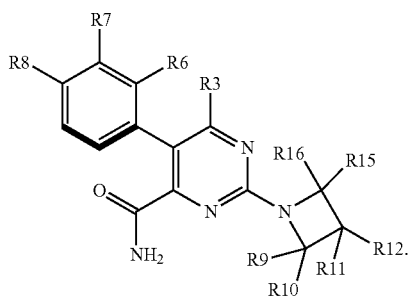
12. The compound of claim 9, or a pharmaceutically acceptable salt thereof, according to the Formula Id:

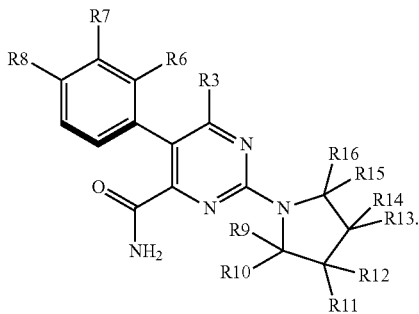

13. The compound of claim 12, or a pharmaceutically acceptable salt thereof, wherein the

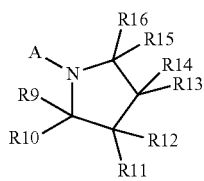

substituent is selected from the group consisting of:

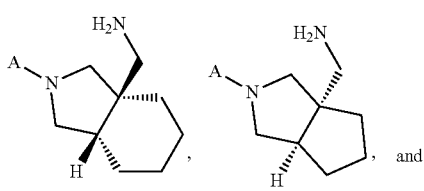

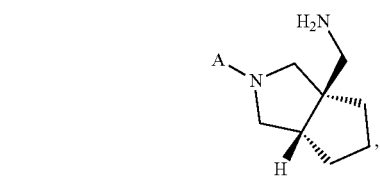

wherein A represents the point of attachment to the pyrimidine ring.

14. The compound of claim 9, or a pharmaceutically acceptable salt thereof, according to the Formula Ie:

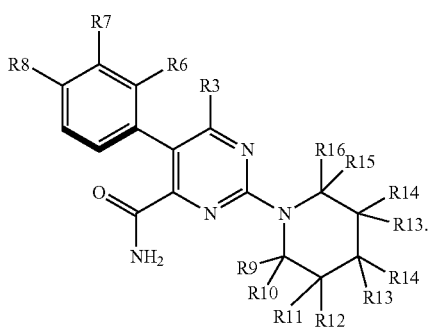

15. The compound of claim 14, or a pharmaceutically acceptable salt thereof, wherein the

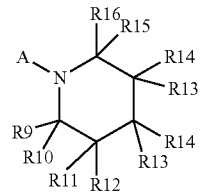

substituent is selected from the group consisting of:

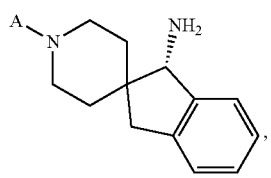

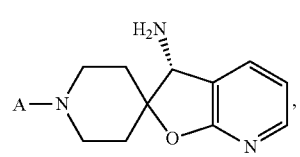

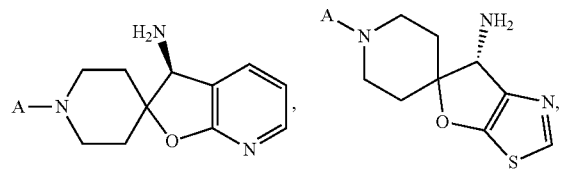

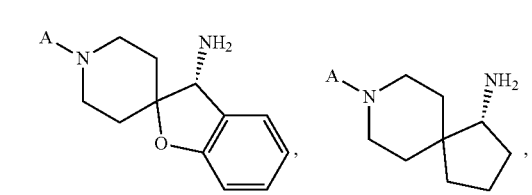

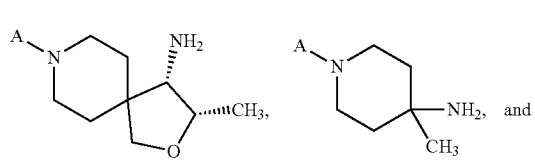

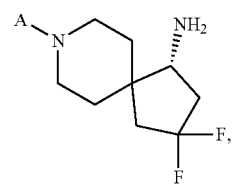

wherein A represents the point of attachment to the pyrimidine ring.

16. The compound of claim 9, or a pharmaceutically acceptable salt thereof, according to the Formula If:

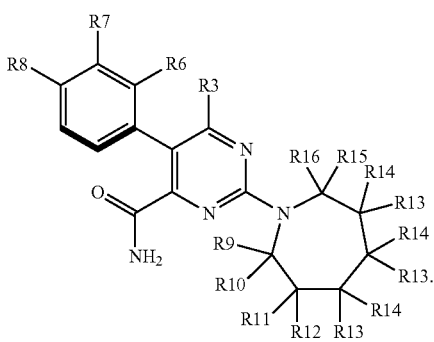

17. The compound of claim 16, or a pharmaceutically acceptable salt thereof,
wherein the

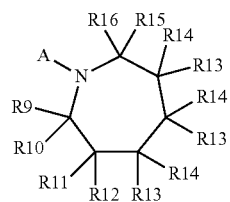

substituent is selected from the group consisting of:

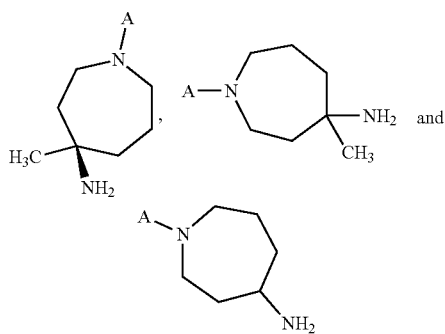

wherein A represents the point of attachment to the pyrimidine ring.

18. The compound according to claim 1, wherein $R^3$ is —CH$_3$.

19. The compound according to claim 1, wherein $R^3$ is —NH$_2$.

20. The compound according to claim 1, wherein $R^3$ is —H.

21. The compound according to claim 1, wherein $R^3$ is —Cl.

22. The compound according to claim 9, wherein $R^8$ is —H and both of $R^6$ and $R^7$ are —Cl.

23. The compound according to claim 1, selected from the group consisting of:
  2-(4-amino-4-methylpiperidin-1-yl)-5-(2,3-dichloro-phenyl)-pyrimidine-4-carboxamide;
  6-Amino-2-(4-amino-4-methyl-piperidin-1-yl)-5-(3-chloro-phenyl)-pyrimidine-4-carboxylic acid amide;
  6-Amino-2-(4-amino-4-methyl-piperidin-1-yl)-5-(2,3-di-chloro-phenyl)-pyrimidine-4-carboxylic acid amide;
  6-Amino-2-(4-amino-4-methyl-piperidin-1-yl)-5-(3-fluoro-phenyl)-pyrimidine-4-carboxylic acid amide;
  6-amino-2-[(3S,4S)-4-amino-3-methyl-2-oxa-8-azaspiro-[4.5]decan-8-yl]-5-(2,3-dichlorophenyl)pyrimidine-4-carboxamide;
  6-amino-2-{9-amino-3-azabicyclo[3.3.1]nonan-3-yl}-5-(2,3-dichlorophenyl)pyrimidine-4-carboxamide;
  6-amino-2-[(1R)-1-amino-8-azaspiro[4.5]decan-8-yl]-5-(2,3-dichlorophenyl)pyrimidine-4-carboxamide;
  6-amino-2-[(1R)-1-amino-3,3-difluoro-8-azaspiro[4.5]decan-8-yl]-5-(2,3-dichlorophenyl)pyrimidine-4-carboxamide;
  6-Amino-2-(4-amino-4-methyl-piperidin-1-yl)-5-(2,3-di-chloro-phenyl)-pyrimidine-4-carboxylic acid methylamide;
  6-amino-2-[6-amino-7-hydroxy-1-(propan-2-yl)-2-azaspiro[3.4]octan-2-yl]-5-(2,3-dichlorophenyl)pyrimidine-4-carboxamide;
  6-amino-2-[8-(aminomethyl)-6-azaspiro[3.4]octan-6-yl]-5-(2,3-dichlorophenyl)pyrimidine-4-carboxamide;
  6-amino-2-[3-(aminomethyl)-8-azabicyclo[3.2.1]octan-8-yl]-5-(2,3-dichlorophenyl)pyrimidine-4-carboxamide;
  6-amino-5-(2,3-dichlorophenyl)-2-[(1R,7S,11s)-11-amino-1,7-dimethyl-9-azabicyclo[5.3.1]undecan-9-yl]pyrimidine-4-carboxamide;
  6-amino-5-(2,3-dichlorophenyl)-2-[(1R,7S,11r)-11-amino-1,7-dimethyl-9-azabicyclo[5.3.1]undecan-9-yl]pyrimidine-4-carboxamide;
  2-(4-Amino-4-methyl-piperidin-1-yl)-5-(2,3-dichloro-phenyl)-6-hydroxy-pyrimidine-4-carboxylic acid amide;
  2-(4-Amino-4-methyl-piperidin-1-yl)-6-chloro-5-(2,3-di-chloro-phenyl)-pyrimidine-4-carboxylic acid amide;
  6-Amino-2-(4-amino-4-methyl-piperidin-1-yl)-5-(2,3-di-chloro-phenyl)-pyrimidine-4-carboxylic acid (2-hy-droxy-ethyl)-amide;
  2-(4-Amino-4-methyl-piperidin-1-yl)-5-(2,3-dichloro-phenyl)-6-methyl-pyrimidine-4-carboxylic acid amide;
  2-(4-Amino-4-methyl-piperidin-1-yl)-6-chloro-5-(3-fluoro-phenyl)-pyrimidine-4-carboxylic acid amide;
  6-Amino-2-(4-amino-4-methyl-piperidin-1-yl)-5-(2,3-di-chloro-phenyl)-pyrimidine-4-carboxylic acid hydroxyamide;
  6-Amino-2-(4-amino-4-methyl-piperidin-1-yl)-5-(2,3-di-chloro-phenyl)-pyrimidine-4-carboxylic acid hydrazide;
  2-(4-Amino-4-methyl-piperidin-1-yl)-6-fluoro-5-(3-fluoro-phenyl)-pyrimidine-4-carboxylic acid amide;
  6-amino-2-[4-(aminomethyl)-8-oxa-2-azaspiro[4.5]decan-2-yl]-5-(2,3-dichlorophenyl)pyrimidine-4-carboxamide;
  2-[3a-(aminomethyl)-octahydro-1H-isoindol-2-yl]-6-amino-5-(2,3-dichlorophenyl)pyrimidine-4-carboxamide;
  2-(4-Amino-4-methyl-piperidin-1-yl)-5-(3-fluoro-phenyl)-6-hydroxy-pyrimidine-4-carboxylic acid amide;
  (4P)-6-amino-2-(4-amino-4-methylpiperidin-1-yl)-5-(2,3-dichlorophenyl)pyrimidine-4-carboxamide;
  (4M)-6-amino-2-(4-amino-4-methylpiperidin-1-yl)-5-(2,3-dichlorophenyl)pyrimidine-4-carboxamide;
  2-(3-Amino-cyclohexylamino)-5-(2,3-dichloro-phenyl)-6-methyl-pyrimidine-4-carboxylic acid amide;
  6-amino-2-[4-amino-4-(hydroxymethyl)piperidin-1-yl]-5-(2,3-dichlorophenyl)pyrimidine-4-carboxamide;
  (4M)-2-(4-amino-4-methylpiperidin-1-yl)-5-(2,3-dichlo-rophenyl)-6-methylpyrimidine-4-carboxamide;
  (4P)-2-(4-amino-4-methylpiperidin-1-yl)-5-(2,3-dichlo-rophenyl)-6-methylpyrimidine-4-carboxamide;

2-[(4-Amino-cyclohexyl)-methyl-amino]-5-(2,3-dichloro-phenyl)-6-methyl-pyrimidine-4-carboxylic acid amide;
2-(7-Amino-3-oxa-9-aza-bicyclo[3.3.1]non-9-yl)-5-(2,3-dichloro-phenyl)-6-methyl-pyrimidine-4-carboxylic acid amide;
6-amino-2-[4-(aminomethyl)-2-oxa-6-azaspiro[3.4]octan-6-yl]-5-(2,3-dichlorophenyl)pyrimidine-4-carboxamide;
2-((R)-6-Amino-2-aza-spiro[4.4]non-2-yl)-5-(2,3-dichloro-phenyl)-6-methyl-pyrimidine-4-carboxylic acid amide;
2-(3-Aminomethyl-cyclopentylamino)-5-(2,3-dichloro-phenyl)-6-methyl-pyrimidine-4-carboxylic acid amide;
2-((S)-6-Amino-2-aza-spiro[4.4]non-2-yl)-5-(2,3-dichloro-phenyl)-6-methyl-pyrimidine-4-carboxylic acid amide;
6-amino-2-{4-amino-1-oxa-9-azaspiro[5.5]undecan-9-yl}-5-(2,3-dichlorophenyl)pyrimidine-4-carboxamide;
6-amino-2-[4-(3-aminooxan-2-yl)piperidin-1-yl]-5-(2,3-dichlorophenyl)pyrimidine-4-carboxamide;
6-amino-2-[3-(aminomethyl)-2-oxa-8-azaspiro[4.5]decan-8-yl]-5-(2,3-dichlorophenyl)pyrimidine-4-carboxamide;
6-amino-2-[4-(aminomethyl)-4-methylpiperidin-1-yl]-5-(2,3-dichlorophenyl)pyrimidine-4-carboxamide;
2-(4-Amino-hexahydro-cyclopenta[c]pyrrol-2-yl)-5-(2,3-dichloro-phenyl)-6-methyl-pyrimidine-4-carboxylic acid amide hydrochloride;
2-(2-Aminomethyl-cyclopentylamino)-5-(2,3-dichloro-phenyl)-6-methyl-pyrimidine-4-carboxylic acid amide;
2-(3-Aminomethyl-3-fluoro-azetidin-1-yl)-5-(2,3-dichloro-phenyl)-6-methyl-pyrimidine-4-carboxylic acid amide;
2-(4-Amino-4-methyl-azepan-1-yl)-5-(2,3-dichloro-phenyl)-6-methyl-pyrimidine-4-carboxylic acid amide;
2-(2-Aminomethyl-azetidin-1-yl)-5-(2,3-dichloro-phenyl)-6-methyl-pyrimidine-4-carboxylic acid amide;
(4P)-2-[(3R)-3-(aminomethyl)morpholin-4-yl]-5-(2,3-dichlorophenyl)-6-methylpyrimidine-4-carboxamide hydrochloride;
(4P)-2-[(3 S)-3-(aminomethyl)morpholin-4-yl]-5-(2,3-dichlorophenyl)-6-methylpyrimidine-4-carboxamide hydrochloride;
6-amino-2-(4-aminoazepan-1-yl)-5-(2,3-dichlorophenyl)-pyrimidine-4-carboxamide;
6-amino-2-(4-amino-octahydro-1H-isoindol-2-yl)-5-(2,3-dichlorophenyl)pyrimidine-4-carboxamide;
6-amino-2-[(3R,4R)-3-(aminomethyl)-4-phenylpyrrolidin-1-yl]-5-(2,3-dichlorophenyl)pyrimidine-4-carboxamide;
6-amino-2-({4-azaspiro[bicyclo[2.2.2]octane-2,2'-oxan]-4'-yl}amino)-5-(2,3-dichlorophenyl)pyrimidine-4-carboxamide;
6-amino-2-(4-amino-4-propylpiperidin-1-yl)-5-(2,3-dichloro-phenyl)pyrimidine-4-carboxamide;
6-amino-2-[3-(aminomethyl)-3-hydroxyazetidin-1-yl]-5-(2,3-dichlorophenyl)pyrimidine-4-carboxamide;
6-amino-2-[3-(aminomethyl)-3-methylazetidin-1-yl]-5-(2,3-dichlorophenyl)pyrimidine-4-carboxamide;
5-(2,3-Dichloro-phenyl)-6-methyl-2-(5-methyl-hexahydro-pyrrolo[3,4-c]pyrrol-2-yl)-pyrimidine-4-carboxylic acid amide;
2-(3-Amino-3-hydroxymethyl-azetidin-1-yl)-5-(2,3-dichloro-phenyl)-6-methyl-pyrimidine-4-carboxylic acid amide;
2-(1-Amino-5-aza-spiro[2.4]hept-5-yl)-5-(2,3-dichloro-phenyl)-6-methyl-pyrimidine-4-carboxylic acid amide;
2-(4-Amino-4-methyl-piperidin-1-yl)-5-(1H-benzoimidazol-4-yl)-pyrimidine-4-carboxylic acid amide;
2-(4-Amino-4-methyl-piperidin-1-yl)-5-benzo[1,2,5]-oxadiazol-4-yl-pyrimidine-4-carboxylic acid amide;
6-Amino-2-(4-amino-4-methyl-piperidin-1-yl)-5-(7-chloro-1H-indazol-6-yl)-pyrimidine-4-carboxylic acid amide;
5-(2,3-Dichloro-phenyl)-6-methyl-2-(5-methyl-hexahydro-pyrrolo[3,4-c]pyrrol-2-yl)-pyrimidine-4-carboxylic acid amide;
(5M)-6-amino-5-(2,3-dichlorophenyl)-2-{[(3S,4R)-3-fluoropiperidin-4-yl]amino}-pyrimidine-4-carboxamide;
6-amino-2-{[(1R,2S)-2-aminocyclohexyl]amino}-5-(2,3-dichlorophenyl)-pyrimidine-4-carboxamide;
(5P)-6-amino-2-[(3 S,4S)-4-amino-3-methyl-2-oxa-8-azaspiro[4.5]decan-8-yl]-5-(2,3-dichlorophenyl)-pyrimidine-4-carboxamide;
(5M)-6-amino-2-[(3 S,4S)-4-amino-3-methyl-2-oxa-8-azaspiro[4.5]decan-8-yl]-5-(2,3-dichlorophenyl)-pyrimidine-4-carboxamide;
2-(3,9-Diaza-bicyclo[4.2.1]-non-3-yl)-5-(2,3-dichloro-phenyl)-6-methyl-pyrimidine-4-carboxylic acid amide;
6-amino-2-(3-aminoazetidin-1-yl)-5-(2,3-dichlorophenyl)-pyrimidine-4-carboxamide;
6-amino-2-[(1R,5S,6R)-6-(aminomethyl)-3-azabicyclo-[3.1.0]hexan-3-yl]-5-(2,3-dichlorophenyl)pyrimidine-4-carboxamide;
6-amino-2[2-(aminomethyl)-azetidin-1-yl]-5-(2,3-dichlorophenyl)pyrimidine-4-carboxamide;
2-((3aR,4R,6aS)-4-Amino-hexahydro-cyclopenta-[c]pyrrol-2-yl)-5-(2,3-dichloro-phenyl)-6-methyl-pyrimidine-4-carboxylic acid amide;
2-((3aS,6aS)-4-Amino-hexahydro-cyclopenta-[c]pyrrol-2-yl)-5-(2,3-dichloro-phenyl)-6-methyl-pyrimidine-4-carboxylic acid amide;
2-((3aS,4S,6aR)-4-Amino-hexahydro-cyclopenta-[c]pyrrol-2-yl)-5-(2,3-dichloro-phenyl)-6-methyl-pyrimidine-4-carboxylic acid amide;
2-((3aS,4R,6aR)-4-Amino-hexahydro-cyclopenta[c]pyrrol-2-yl)-5-(2,3-dichloro-phenyl)-6-methyl-pyrimidine-4-carboxylic acid amide;
2-((3aR,6aR)-4-Amino-hexahydro-cyclopenta-[c]pyrrol-2-yl)-5-(2,3-dichloro-phenyl)-6-methyl-pyrimidine-4-carboxylic acid amide;
2-((3aR,4S,6aS)-4-Amino-hexahydro-cyclopenta-[c]pyrrol-2-yl)-5-(2,3-dichloro-phenyl)-6-methyl-pyrimidine-4-carboxylic acid amide;
(4M)-2-(4-amino-4-methylpiperidin-1-yl)-6-chloro-5-(2,3-dichlorophenyl)-pyrimidine-4-carboxamide;
(4P)-2-(4-amino-4-methylpiperidin-1-yl)-6-chloro-5-(2,3-dichlorophenyl)-pyrimidine-4-carboxamide;
2-((3R,4S)-3-Amino-4-hydroxy-pyrrolidin-1-yl)-5-(2,3-dichloro-phenyl)-6-methyl-pyrimidine-4-carboxylic acid amide;
2-(4-Amino-4-methyl-piperidin-1-yl)-5-(2,3-dichloro-pyridin-4-yl)-6-methyl-pyrimidine-4-carboxylic acid amide;
2-(4-Amino-4-methyl-piperidin-1-yl)-5-(2-chloro-4-fluoro-phenyl)-6-methyl-pyrimidine-4-carboxylic acid amide;
2-(4-Amino-4-methyl-piperidin-1-yl)-5-(4-chloro-pyridin-3-yl)-6-methyl-pyrimidine-4-carboxylic acid amide;

2-((3S,4S)-3-Amino-4-hydroxy-pyrrolidin-1-yl)-5-(2,3-dichloro-phenyl)-6-methyl-pyrimidine-4-carboxylic acid amide;

2-[(3S,4S)-4-amino-3-methyl-2-oxa-8-azaspiro[4.5]decan-8-yl]-5-(2,3-dichlorophenyl)-6-methylpyrimidine-4-carboxamide;

2-(4-Amino-4-methyl-piperidin-1-yl)-6-methyl-5-pyridin-4-yl-pyrimidine-4-carboxylic acid amide;

(4M)-2-{[(1S,3R)-3-aminocyclohexyl]amino}-5-(2,3-dichlorophenyl)-6-methylpyrimidine-4-carboxamide;

(4M)-2-{[(1R,3S)-3-aminocyclohexyl]amino}-5-(2,3-dichlorophenyl)-6-methylpyrimidine-4-carboxamide;

(4P)-2-{[(1R,3S)-3-aminocyclohexyl]amino}-5-(2,3-dichlorophenyl)-6-methylpyrimidine-4-carboxamide;

(4P)-2-{[(1S,3R)-3-aminocyclohexyl]amino}-5-(2,3-dichlorophenyl)-6-methylpyrimidine-4-carboxamide;

6-Amino-2-(4-amino-4-methyl-azepan-1-yl)-5-(2,3-dichloro-phenyl)-pyrimidine-4-carboxylic acid amide;

2-(4-Amino-4-methyl-piperidin-1-yl)-5-(1H-indol-3-yl)-6-methyl-pyrimidine-4-carboxylic acid amide;

2-(4-Amino-cyclohexyl-amino)-5-(2,3-dichloro-phenyl)-6-methyl-pyrimidine-4-carboxylic acid amide;

(5M)-2-[(3S,4S)-4-amino-3-methyl-2-oxa-8-azaspiro[4.5]-decan-8-yl]-5-(2,3-dichloro-phenyl)-6-methylpyrimidine-4-carboxamide;

(5P)-2-[(3S,4S)-4-amino-3-methyl-2-oxa-8-azaspiro[4.5]-decan-8-yl]-5-(2,3-dichloro-phenyl)-6-methylpyrimidine-4-carboxamide;

(5M)-2-[(1R)-1-amino-3,3-difluoro-8-azaspiro[4.5]-decan-8-yl]-5-(2,3-dichloro-phenyl)-6-methylpyrimidine-4-carboxamide;

(5P)-2-[(1R)-1-amino-3,3-difluoro-8-azaspiro[4.5]-decan-8-yl]-5-(2,3-dichlorophenyl)-6-methylpyrimidine-4-carboxamide;

(5P)-2-[(3aR,6aS)-3a-(aminomethyl)-octahydro-cyclopenta[c]pyrrol-2-yl]-6-amino-5-(2,3-dichlorophenyl)-pyrimidine-4-carboxamide;

(5M)-2-[(3aR,6aS)-3a-(aminomethyl)-octahydro-cyclopenta[c]pyrrol-2-yl]-6-amino-5-(2,3-dichlorophenyl)-pyrimidine-4-carboxamide;

(5P)-2-[(3aR,7aS)-3a-(aminomethyl)-octahydro-1H-isoindol-2-yl]-6-amino-5-(2,3-dichlorophenyl)pyrimidine-4-carboxamide;

(5P)-2-[(3aS,7aR)-3a-(aminomethyl)-octahydro-1H-isoindol-2-yl]-6-amino-5-(2,3-dichlorophenyl)pyrimidine-4-carboxamide;

(5M)-2-[(3aR,7aS)-3a-(aminomethyl)-octahydro-1H-isoindol-2-yl]-6-amino-5-(2,3-dichlorophenyl)pyrimidine-4-carboxamide;

(5M)-2-[(3aS,7aR)-3a-(aminomethyl)-octahydro-1H-isoindol-2-yl]-6-amino-5-(2,3-dichlorophenyl)pyrimidine-4-carboxamide;

(5P)-2-[(3aS,6aR)-3a-(aminomethyl)-octahydro-cyclopenta[c]pyrrol-2-yl]-6-amino-5-(2,3-dichlorophenyl)-pyrimidine-4-carboxamide;

(5M)-2-[(3 aS,6aR)-3a-(aminomethyl)-octahydro-cyclopenta[c]pyrrol-2-yl]-6-amino-5-(2,3-dichlorophenyl)-pyrimidine-4-carboxamide;

(5P)-6-amino-2[4-amino-4-(difluoromethyl)piperidin-1-yl]-5-(2,3-dichlorophenyl)-pyrimidine-4-carboxamide;

(5M)-6-amino-2[4-amino-4-(difluoromethyl)piperidin-1-yl]-5-(2,3-dichlorophenyl)-pyrimidine-4-carboxamide;

(5P)-6-amino-2-[(4S)-4-amino-4-methylazepan-1-yl]-5-(2,3-dichlorophenyl)-pyrimidine-4-carboxamide;

(5P)-6-amino-2-[(4R)-4-amino-4-methylazepan-1-yl]-5-(2,3-dichlorophenyl)-pyrimidine-4-carboxamide;

(5M)-6-amino-2-[(4S)-4-amino-4-methylazepan-1-yl]-5-(2,3-dichlorophenyl)-pyrimidine-4-carboxamide;

2-(4-Amino-4-methyl-piperidin-1-yl)-5-(2-chloro-3-trifluoromethyl-phenyl)-6-methyl-pyrimidine-4-carboxylic acid amide;

6-Amino-2-[(4-amino-cyclohexyl)-methyl-amino]-5-(2,3-dichloro-phenyl)-pyrimidine-4-carboxylic acid amide;

(5M)-2-[(1R)-1-amino-8-azaspiro[4.5]decan-8-yl]-5-(2,3-dichlorophenyl)-6-methylpyrimidine-4-carboxamide;

(5P)-2-[(1R)-1-amino-8-azaspiro[4.5]decan-8-yl]-5-(2,3-dichlorophenyl)-6-methylpyrimidine-4-carboxamide;

(4M)-2-(4-amino-4-methylpiperidin-1-yl)-5-(2-chloro-4-fluoro-3-methoxyphenyl)-6-methylpyrimidine-4-carboxamide;

(4P)-2-(4-amino-4-methylpiperidin-1-yl)-5-(2-chloro-4-fluoro-3-methoxyphenyl)-6-methylpyrimidine-4-carboxamide;

(5P)-6-amino-2-[(1S)-1-amino-1,3-dihydrospiro[indene-2,4'-piperidin]-1'-yl]-5-(2,3-dichlorophenyl)pyrimidine-4-carboxamide;

(5M)-6-amino-2-[(1S)-1-amino-1,3-dihydrospiro[indene-2,4'-piperidin]-1'-yl]-5-(2,3-dichlorophenyl)pyrimidine-4-carboxamide;

(5M)-2-[(1S)-1-amino-1,3-dihydrospiro[indene-2,4'-piperidin]-1'-yl]-5-(2,3-dichlorophenyl)-6-methylpyrimidine-4-carboxamide;

(5P)-2-[(1S)-1-amino-1,3-dihydrospiro[indene-2,4'-piperidin]-1'-yl]-5-(2,3-dichlorophenyl)-6-methylpyrimidine-4-carboxamide;

6-amino-2-[(4 S)-4-amino-4,6-dihydrospiro[cyclopenta[d][1,3]thiazole-5,4'-piperidin]-1'-yl]-5-(2,3-dichlorophenyl)pyrimidine-4-carboxamide;

2-[(3R)-3-amino-3H-spiro[1-benzofuran-2,4'-piperidin]-1'-yl]-5-(2,3-dichlorophenyl)-6-methylpyrimidine-4-carboxamide;

6-amino-2-[(3R)-3-amino-3H-spiro[1-benzofuran-2,4'-piperidin]-1'-yl]-5-(2,3-dichlorophenyl)pyrimidine-4-carboxamide;

(4M)-2-[(3R)-3-amino-3H-spiro[furo[2,3-b]pyridine-2,4'-piperidin]-1'-yl]-5-(2,3-dichlorophenyl)-6-methylpyrimidine-4-carboxamide;

(4M)-2-[(3S)-3-amino-3H-spiro[furo[2,3-b]pyridine-2,4'-piperidin]-1'-yl]-5-(2,3-dichlorophenyl)-6-methylpyrimidine-4-carboxamide;

(4P)-2-[(3R)-3-amino-3H-spiro[furo[2,3-b]pyridine-2,4'-piperidin]-1'-yl]-5-(2,3-dichlorophenyl)-6-methylpyrimidine-4-carboxamide;

(4P)-2-[(3S)-3-amino-3H-spiro[furo[2,3-b]pyridine-2,4'-piperidin]-1'-yl]-5-(2,3-dichlorophenyl)-6-methylpyrimidine-4-carboxamide;

(4P)-6-amino-2-[(3R)-3-amino-3H-spiro[furo[2,3-b]pyridine-2,4'-piperidin]-1'-yl]-5-(2,3-dichlorophenyl)pyrimidine-4-carboxamide;

(4P)-6-amino-2-[(3 S)-3-amino-3H-spiro[furo[2,3-b]pyridine-2,4'-piperidin]-1'-yl]-5-(2,3-dichlorophenyl)pyrimidine-4-carboxamide;

(4M)-6-amino-2-[(3R)-3-amino-3H-spiro[furo[2,3-b]pyridine-2,4'-piperidin]-1'-yl]-5-(2,3-dichlorophenyl)pyrimidine-4-carboxamide; and (4M)-6-amino-2-[(3 S)-3-amino-3H-spiro[furo[2,3-b]pyridine-2,4'-piperidin]-1'-yl]-5-(2,3-dichlorophenyl)pyrimidine-4-carboxamide;

or a pharmaceutically acceptable salt thereof.

24. A pharmaceutical composition comprising a compound according to claim 1 together with a pharmaceutically acceptable carrier, adjuvant and/or excipient.

* * * * *